US012428480B2

(12) United States Patent
Baeuerle et al.

(10) Patent No.: US 12,428,480 B2
(45) Date of Patent: Sep. 30, 2025

(54) ANTI-CD19 ANTIBODIES AND MULTI-SPECIFIC BINDING PROTEINS

(71) Applicant: CULLINAN THERAPEUTICS, INC., Cambridge, MA (US)

(72) Inventors: Patrick A. Baeuerle, Cambridge, MA (US); Jennifer Michaelson, Cambridge, MA (US); Bochong Li, Boston, MA (US); Naveen Mehta, Cambridge, MA (US)

(73) Assignee: Cullinan Therapeutics, Inc., Cambridge, MA (US)

( * ) Notice: Subject to any disclaimer, the term of this patent is extended or adjusted under 35 U.S.C. 154(b) by 744 days.

(21) Appl. No.: 17/784,988

(22) PCT Filed: Dec. 11, 2020

(86) PCT No.: PCT/US2020/064706
§ 371 (c)(1),
(2) Date: Jun. 13, 2022

(87) PCT Pub. No.: WO2021/119551
PCT Pub. Date: Jun. 17, 2021

(65) Prior Publication Data
US 2023/0037815 A1    Feb. 9, 2023

Related U.S. Application Data

(60) Provisional application No. 62/946,931, filed on Dec. 11, 2019.

(51) Int. Cl.
*C07K 16/28* (2006.01)
*A61K 39/00* (2006.01)
*A61P 31/04* (2006.01)

(52) U.S. Cl.
CPC .......... *C07K 16/2803* (2013.01); *A61P 31/04* (2018.01); *C07K 16/2809* (2013.01); *A61K 2039/505* (2013.01); *C07K 2317/31* (2013.01); *C07K 2317/569* (2013.01); *C07K 2317/622* (2013.01); *C07K 2317/73* (2013.01); *C07K 2317/92* (2013.01); *C07K 2317/94* (2013.01)

(58) Field of Classification Search
CPC ............ C07K 16/2803; C07K 16/2809; C07K 2317/31; C07K 2317/569; C07K 2317/622; C07K 2317/73; A61K 2039/505
See application file for complete search history.

(56) References Cited

U.S. PATENT DOCUMENTS

| | | |
|---|---|---|
| 2009/0291072 A1 | 11/2009 | Baeuerle et al. |
| 2016/0340444 A1 | 11/2016 | Baeuerle et al. |
| 2019/0218515 A1 | 7/2019 | Ballesteros et al. |
| 2021/0238286 A1 | 8/2021 | Baeuerle et al. |
| 2023/0032087 A1 | 2/2023 | Baeuerle et al. |

FOREIGN PATENT DOCUMENTS

| | | | |
|---|---|---|---|
| CN | 101128487 A | 2/2008 | |
| CN | 105399832 A | 3/2016 | |
| CN | 107406507 A | 11/2017 | |
| CN | 107849148 A | 3/2018 | |
| CN | 108026177 A | 5/2018 | |
| DE | 602008049817.3 | 4/2017 | |
| DE | 602008049910.3 | 4/2017 | |
| EP | 2139918 B1 | 4/2017 | |
| EP | 2559702 B1 | 4/2017 | |
| JP | 2017-512814 A | 5/2017 | |
| WO | WO 2005/052004 A2 | 6/2005 | |
| WO | WO 2007/068354 A1 | 6/2007 | |
| WO | WO-2009052431 A2 * | 4/2009 | ....... A61K 39/39566 |
| WO | WO 2012/109624 A2 | 8/2012 | |
| WO | WO 2012/131078 A1 | 10/2012 | |
| WO | WO 2013/013700 A1 | 1/2013 | |
| WO | WO 2013/024059 A2 | 2/2013 | |
| WO | WO 2014/012082 A2 | 1/2014 | |
| WO | WO 2014/012085 A2 | 1/2014 | |
| WO | WO 2015/157286 A1 | 10/2015 | |
| WO | WO 2016/016412 A1 | 2/2016 | |
| WO | WO 2016/116626 A1 | 7/2016 | |
| WO | WO 2016/180982 A1 | 11/2016 | |
| WO | WO 2016/187594 A1 | 11/2016 | |
| WO | 2017008169 A1 | 1/2017 | |
| WO | WO 2017/040344 A2 | 3/2017 | |
| WO | WO 2017/055328 A1 | 4/2017 | |
| WO | WO-2017085172 A2 * | 5/2017 | ............. C07K 16/18 |
| WO | WO 2017/178572 A1 | 10/2017 | |

(Continued)

OTHER PUBLICATIONS

Text of WO2018208864. * Image file will not upload to OC* (Year: 2018).*
Canadian Intellectual Property Office, "Office Action," regarding Application No. 3161283, 5 pages, dated Feb. 8, 2024.
European Patent Office, "Extended European Search Report," regarding Application No. 20899414.5, 10 pages, dated Mar. 15, 2024.
Liu, L., et al., "MGD011, a CD19 x CD3 Dual-Affinity Retargeting Bi-specific Molecule Incorporating Extended Circulating Half-life for the Treatment of B-cell Malignancies," Clin Cancer Res; 23(6), 14 pages, dated Mar. 15, 2017.

(Continued)

*Primary Examiner* — Janet L Andres
*Assistant Examiner* — Brian Hartnett
(74) *Attorney, Agent, or Firm* — Lathrop GPM LLP; Malaika O.D. Tyson

(57) ABSTRACT

Provided herein are anti-CD 19 antibodies and multi-specific binding proteins that bind CD 19, CD3, and serum albumin. Also provided are pharmaceutical compositions comprising these antibodies or multi-specific binding proteins, expression vectors and host cells for making these antibodies or multi-specific binding proteins, and methods of use of these antibodies or multi-specific binding proteins in treating cancers.

11 Claims, 7 Drawing Sheets
Specification includes a Sequence Listing.

(56) References Cited

FOREIGN PATENT DOCUMENTS

| WO | WO 2017/194438 A1 | 11/2017 |
|---|---|---|
| WO | WO 2018/098356 A1 | 5/2018 |
| WO | 201907706 A1 | 4/2019 |
| WO | WO 2019/077062 A1 | 4/2019 |
| WO | WO 2019/237081 A1 | 12/2019 |
| WO | WO 2020/069028 A1 | 4/2020 |
| WO | WO 2021/119531 A1 | 6/2021 |
| WO | WO 2021/119551 A1 | 6/2021 |

OTHER PUBLICATIONS

Speiss, C., et al., "Alternative molecular formats and therapeutic applications for bispecific antibodies," Molecular Immunology 67 (2015), 12 pages, dated Jan. 27, 2015.

Suurs, F., et al., "A review of bispecific antibodies and antibody constructs in oncology and clinical challenges," Pharmacology & Thmpeutics 201 (2019), 17 pages, dated Apr. 24, 2019.

Asaadi et al., "A comprehensive comparison between camelid nanobodies and single chain variable fragments", Biomarker Res., Dec. 4, 2021, 9(1): 87.

Australian Examination Report in Australian Patent Application No. 2019282836, 6 pages, dated Mar. 27, 2025.

Casset et al., "A peptide mimetic of an anti-CD4 monoclonal antibody by rational design", Biochem. Biophys. Res. Commun., Jul. 18, 2003, 307(1): 198-205.

Chinese Office Action for Chinese Patent Application No. 201980050411.2, dated Aug. 29, 2024, including English translation.

Chinese Office Action for Chinese Patent Application No. 202080096427.X, dated Apr. 12, 2025, including English translation.

Dubel, Handbook of Therapeutic Antibodies, 2007, Ch. 5.2-5.3, pp. 100-101.

Feng et al., "Construction and next-generation sequencing analysis of a large phage-displayed VNAR single-domain antibody library from six naïve nurse sharks", Antibody Therapeutics, Jan. 2019, 2(1): 1-11. Epub Nov. 7, 2018.

International Search Report and Written Opinion for International Patent Application No. PCT/US2019/036177, mailed Aug. 29, 2019.

International Search Report and Written Opinion for PCT International Application No. PCT/US2020/064672, mailed Mar. 18, 2021.

Japanese Office Action for Japanese Patent Application No. 2021-518060, dated Apr. 26, 2023, including English translation.

Johnson and WU, "The Kabat Database and a Bioinformatics Example", Methods in Molecular Biology, Antibody Engineering: Methods and Protocols, 2004, vol. 248, pp. 11-25.

MacCallum et al., "Antibody-antigen interactions: contact analysis and binding site topography", J. Mol. Biol., Oct. 11, 1996, 262(5): 732-745.

Muller et al., "Improved pharmacokinetics of recombinant bispecific antibody molecules by fusion to human serum albumin", J. Biol. Chem., Apr. 27, 2007, 282(17): 12650-12660, Epublished Mar. 8, 2007.

Nguyen et al., "The pharmacokinetics of an albumin-binding Fab (AB.Fab) can be modulated as a function of for albumin", Comparative Study, Protein Eng Des Sel., Jul. 2006, 19(7): 291-297, Epublished Apr. 18, 2006.

Paul, "Immunoglobulins: Structure and Function", Fundamental Immunology, Aug. 2003, 5th Edition, Chapter 3, pp. 109-147.

Robinson et al., "A CD19/CD3 bispecific antibody for effective immunotherapy of chronic lymphocytic leukemia in the ibrutinib era", Lymphoid Neoplasia, Aug. 2, 2018, 132(5): 521-532.

Rudikoff et al., "Single amino acid substitution altering antigen-binding specificity", Pnas USA, Mar. 1982, 79(6): 1979-1983.

Sela-Culang et al., "The structural basis of antibody-antigen recognition", Front. Immunol., Oct. 8, 2013, 4: 302.

Supplemental European Search Report for European Patent Applciation No. 20899790.8, dated Mar. 19, 2024.

Tjink et al., "Improved tumor targeting of anti-epidermal growth factor receptor Nanobodies through albumin binding: taking advantage of modular Nanobody technology", Mol Cancer Ther., Aug. 2008, 7(8): 2288-2297.

Vajdos et al., "Comprehensive functional maps of the antigen-binding site of an anti-ErbB2 antibody obtained with shotgun scanning mutagenesis", J. Mol. Biol., Jul. 5, 2002, 320(2): 415-428.

Ward et al., "Binding activities of a repertoire of single immunoglobulin variable domains secreted from Escherichia coli", Oct. 12, 1989, Nature, 341: 544-546.

Yau et al., "Affinity maturation of a VHH by mutational hotspot randomization", Journal of Immunological Methods, Feb. 2005, 297(1-2): 213-224.

International Search Report and Written Opinion for PCT International Patent Application No. PCT/US2020/064706, dated Mar. 18, 2021.

Löffler et al., "A recombinant bispecific single-chain antibody, CD19 x CD3, induces rapid and high lymphoma-directed cytotoxicity by unstimulated T lymphocytes", Blood, Mar. 15, 2000, 95(6): 2098-2103.

\* cited by examiner

ANTI-CD19 ANTIBODIES AND MULTI-SPECIFIC BINDING PROTEINS

CROSS-REFERENCE TO RELATED APPLICATIONS

This application claims the benefit of and priority to U.S. Provisional Patent Application No. 62/946,931, filed on Dec. 11, 2019, the disclosure of which is hereby incorporated by reference in its entirety for all purposes.

FIELD OF THE INVENTION

The invention relates to anti-CD19 antibodies and multi-specific binding proteins that bind CD19, CD3, and optionally serum albumin. In addition, the invention relates to pharmaceutical compositions comprising these antibodies or multi-specific binding proteins, expression vectors and host cells for making these antibodies or multi-specific binding proteins, and methods of use of these antibodies or multi-specific binding proteins in treating cancers.

BACKGROUND

Bispecific molecules such as BiTE® (bispecific T-cell engager) constructs are recombinant protein constructs made from two flexibly linked antibody-derived binding domains. One binding domain of BiTE® constructs is specific for a selected tumor-associated surface antigen on target cells, and the second binding domain is specific for CD3, a subunit of the T cell receptor complex on T cells. By this design, BiTE® constructs can transiently connect T cells with target cells and, at the same time, potently activate the inherent cytolytic potential of T cells against target cells.

The CD3 receptor complex is a protein complex composed of four polypeptide chains. In mammals, the complex contains a CD3γ (gamma) chain, a CD3δ (delta) chain, and two CD3ε (epsilon) chains. The CD3γ (gamma), CD3δ (delta), and CD3ε (epsilon) chains are highly related cell-surface proteins of the immunoglobulin superfamily containing a single extracellular immunoglobulin domain. These chains associate with the T cell receptor (TCR) to form a TCR-CD3 complex and to generate an activation signal in T lymphocytes upon antigen engagement. About 95% of T cells express αβ TCR, which contains an α (alpha) chain and a β (beta) chain. Two TCRξ (zeta) chains are also present in the TCR-CD3 complex. The αβ TCR is responsible for recognizing antigens presented by a major histocompatibility complex (MHC). When the TCR engages with antigenic peptide and MHC complex, the T lymphocyte is activated through a series of biochemical events mediated by associated enzymes, co-receptors, specialized adaptor molecules, and activated or released transcription factors.

CD19, also known as B-cell surface antigen B4 or Leu-12, is a transmembrane protein expressed on B lymphocytes and follicular dendritic cells. CD19 is a co-receptor for the B-cell antigen receptor complex on B lymphocytes (see, Carter et al. (2002) Science, 256: 105-07; van Zelm et al. (2006) N. Eng. J. Med., 354: 1901-12). Together with the B cell receptor (BCR), CD19 modulates intrinsic and antigen receptor-induced signaling thresholds critical for clonal expansion of B cells and humoral immunity. CD19 is a human B-cell surface marker that is expressed from early stages of pre-B cell development through terminal differentiation into plasma cells. It is also expressed on many non-Hodgkin lymphoma (NHL) cells and certain leukemias. Antibodies that bind CD19 have been developed and tested in clinical studies against cancers of lymphoid origin such as B-cell malignancies (see, e.g., Hekman et al. (1991) Cancer Immunol. Immunother., 32: 364-72; Vlasfeld et al. (1995) Cancer Immunol. Immunother., 40: 37-47; Corny et al. (1995) J. Immunother. Emphasis Tumor Immunol., 18: 231-41; and Manzke et al. (2001) Int. J. Cancer, 91: 516-22). Furthermore, a BiTE® construct called blinatumomab has been developed for clinical use.

BiTE® constructs are believed to suffer from rapid clearance from the body. Therefore, whilst they are able to rapidly penetrate many areas of the body, and are quick to produce and easier to handle, their in vivo applications may be limited by their brief persistence in vivo. Prolonged administration by continuous intravenous infusions may be required to achieve therapeutic effects of blinatumomab and solitomab because of their short in vivo half-life. However, such continuous intravenous infusions are inconvenient for patients and may increase the costs of treatment.

Although significant developments have been made in constructing anti-CD19 antibodies and multi-specific binding proteins, there remains a need for new and useful proteins for treating cancer that have adequate therapeutic efficacy, a format straightforward to manufacture, and favorable pharmacokinetic properties such as a longer half-life.

SUMMARY OF THE INVENTION

The present invention is based, in part, upon the development of new antibodies that bind CD19. Also provided are multi-specific binding proteins comprising a first domain that binds CD19 (e.g., human CD19), a second domain that binds CD3 (e.g., human CD3), and optionally a half-life extension domain, which can be a third domain that binds serum albumin (e.g., human serum albumin), wherein the first domain is derived from these new antibodies. These domains are linked in certain manners for favorable therapeutic efficacy and in vivo half-life. The anti-CD19 antibodies and multi-specific binding proteins are useful for treating diseases and disorders associated with aberrant cells expressing CD19, such as certain B-cell hematologic malignancies.

Accordingly, in one aspect, the present disclosure provides a multi-specific binding protein comprising: (a) a first antigen-binding site that binds human CD19 with a $K_D$ within the range of 5 pM to 1 nM; and (b) a second antigen-binding site that binds human CD3 with a $K_D$ within the range of 0.5 nM to 20 nM.

In certain embodiments, the multi-specific binding protein is a fusion protein comprising the first and second antigen binding sites. In certain embodiments, the multi-specific binding protein further comprises a half-life extension domain. In certain embodiments, the half-life extension domain comprises a third antigen-binding site that binds human serum albumin. In certain embodiments, the half-life extension domain is not disposed between the first antigen-binding site and the second antigen-binding site in a polypeptide chain.

In certain embodiments, each $K_D$ is measured by surface plasmon resonance. In certain embodiments, the first antigen-binding site binds human CD19 with a $K_D$ within the range of 5 pM to 0.1 nM, and the second antigen-binding site binds human CD3 with a $K_D$ within the range of 0.5 nM to 10 nM. In certain embodiments, the ratio of the $K_D$ with which the second antigen-binding site binds human CD3 to the $K_D$ with which the first antigen-binding site binds human CD19 is within the range of 10:1 to 1,000:1.

In certain embodiments, each $K_D$ is measured by bio-layer interferometry. In certain embodiments, the first antigen-binding site binds human CD19 with a $K_D$ within the range of 50 pM to 1 nM, and the second antigen-binding site binds human CD3 with a $K_D$ within the range of 1 nM to 20 nM. In certain embodiments, the ratio of the $K_D$ with which the second antigen-binding site binds human CD3 to the $K_D$ with which the first antigen-binding site binds human CD19 is within the range of 10:1 to 100:1.

In another aspect, the present disclosure provides an antigen-binding site that binds human CD19, the antibody comprising a heavy chain variable domain (VH) comprising complementarity determining regions HCDR1, HCDR2, and HCDR3 and a light chain variable domain (VL) comprising complementarity determining regions LCDR1, LCDR2, and LCDR3, wherein the HCDR1, HCDR2, HCDR3, LCDR1, LCDR2, and LCDR3 comprise the amino acid sequences of SEQ ID NOs: 110, 111, 113, 114, 115, and 71, respectively, but not 93, 87, 68, 80, 70, and 71, respectively.

In certain embodiments, the HCDR1, HCDR2, HCDR3, LCDR1, LCDR2, and LCDR3 comprise the amino acid sequences of SEQ ID NOs: 110, 117, 119, 114, 120, and 71, respectively, but not 93, 87, 68, 80, 70, and 71, respectively. In certain embodiments, the HCDR1, HCDR2, HCDR3, LCDR1, LCDR2, and LCDR3 comprise the amino acid sequences of SEQ ID NOs: 65, 66, 68, 69, 70, and 71, respectively. In certain embodiments, the VH comprises an amino acid sequence at least 85%, at least 90%, at least 95%, at least 99%, or 100% identical to SEQ ID NO: 62, and the VL comprises an amino acid sequence at least 85%, at least 90%, at least 95%, at least 99%, or 100% identical to SEQ ID NO: 63. In certain embodiments, the antigen-binding site comprises the amino acid sequence of SEQ ID NO: 72. In certain embodiments, the antigen-binding site binds human CD19 with a $K_D$ lower than or equal to 1 nM.

In another aspect, the present disclosure provides an antigen-binding site that binds human CD19, the antibody comprising a VH comprising complementarity determining regions HCDR1, HCDR2, and HCDR3 and a VL comprising complementarity determining regions LCDR1, LCDR2, and LCDR3, wherein the HCDR1, HCDR2, HCDR3, LCDR1, LCDR2, and LCDR3 comprise the amino acid sequences of SEQ ID NOs: 53, 54, 56, 57, 58, and 59, respectively, but not SEQ ID NOs: 4, 23, 17, 18, 19, and 10, respectively. In certain embodiments, the HCDR1, HCDR2, HCDR3, LCDR1, LCDR2, and LCDR3 comprise the amino acid sequences of SEQ ID NOs: 53, 54, 56, 57, 60, and 59, respectively, but not SEQ ID NOs: 4, 23, 17, 18, 19, and 10, respectively. In certain embodiments, the HCDR1, HCDR2, HCDR3, LCDR1, LCDR2, and LCDR3 comprise the amino acid sequences of SEQ ID NOs: 53, 61, 56, 57, 60, and 59, respectively, but not SEQ ID NOs: 4, 23, 17, 18, 19, and 10, respectively. In certain embodiments, the HCDR1, HCDR2, HCDR3, LCDR1, LCDR2, and LCDR3 comprise the amino acid sequences of SEQ ID NOs: 4, 5, 7, 8, 9, and 10, respectively. In certain embodiments, the VH comprises an amino acid sequence at least 85%, at least 90%, at least 95%, at least 99%, or 100% identical to SEQ ID NO: 1, and the VL comprises an amino acid sequence at least 85%, at least 90%, at least 95%, at least 99%, or 100% identical to SEQ ID NO: 2. In certain embodiments, the antigen-binding site comprises the amino acid sequence of SEQ ID NO: 11. In certain embodiments, the antigen-binding site binds human CD19 with a $K_D$ lower than or equal to 0.3 nM.

In another aspect, the present disclosure provides an antibody comprising an antigen-binding site that binds CD19 as disclosed herein.

In another aspect, the present disclosure provides a multi-specific binding protein comprising: (a) a first antigen-binding site that binds human CD19 as disclosed herein; and (b) a second antigen-binding site that binds human CD3.

In certain embodiments, the multi-specific binding protein further comprises a half-life extension domain. In certain embodiments, the half-life extension domain comprises a third antigen-binding site that binds human serum albumin.

In certain embodiments, the third antigen-binding site comprises a VH comprising complementarity determining regions HCDR1, HCDR2, and HCDR3, wherein the HCDR1, HCDR2, and HCDR3 comprise the amino acid sequences of SEQ ID NOs: 184, 409, and 411, respectively, but not SEQ ID NOs: 129, 133, and 135, respectively.

In certain embodiments, the HCDR1, HCDR2, and HCDR3 of the third antigen-binding site comprise the amino acid sequences of SEQ ID NOs: 184, 185, and 187, respectively, but not SEQ ID NOs: 129, 133, and 135, respectively. In certain embodiments, the HCDR1, HCDR2, and HCDR3 of the third antigen-binding site comprise the amino acid sequences of SEQ ID NOs: 189, 190, and 192, respectively, but not SEQ ID NOs: 129, 133, and 135, respectively. In certain embodiments, the HCDR1, HCDR2, and HCDR3 of the third antigen-binding site comprise the amino acid sequences of SEQ ID NOs: 189, 193, and 195, respectively, but not SEQ ID NOs: 129, 133, and 135, respectively. In certain embodiments, the HCDR1, HCDR2, and HCDR3 of the third antigen-binding site comprise the amino acid sequences of SEQ ID NOs: 123, 124, and 126, respectively. In certain embodiments, the VH of the third antigen-binding site comprises an amino acid sequence at least 85%, at least 90%, at least 95%, at least 99%, or 100% identical to SEQ ID NO: 121. In certain embodiments, the third antigen-binding site binds human serum albumin with a $K_D$ lower than or equal to 10 nM. In certain embodiments, the third antigen-binding site binds protein A with a $K_D$ lower than or equal to 2 nM. In certain embodiments, the third antigen-binding site has a melting temperature greater than or equal to 60° C.

In certain embodiments, the multi-specific binding protein comprises a single polypeptide chain. In certain embodiments, the third antigen-binding site is not positioned between the first antigen-binding site and the second antigen-binding site in the polypeptide chain.

In certain embodiments, the third antigen-binding site is positioned N-terminal to both the first antigen-binding site and the second antigen-binding site in the polypeptide chain. In certain embodiments, the third antigen-binding site is positioned N-terminal to the first antigen-binding site, and the first antigen-binding site is positioned N-terminal to the second antigen-binding site in the polypeptide chain. In certain embodiments, the third antigen-binding site is positioned N-terminal to the second antigen-binding site, and the second antigen-binding site is positioned N-terminal to the first antigen-binding site in the polypeptide chain.

In certain embodiments, the third antigen-binding site is positioned C-terminal to both the first antigen-binding site and the second antigen-binding site in the polypeptide chain. In certain embodiments, the first antigen-binding site is positioned N-terminal to the second antigen-binding site, and the second antigen-binding site is positioned N-terminal to the third antigen-binding site in the polypeptide chain. In certain embodiments, the second antigen-binding site is positioned N-terminal to the first antigen-binding site, and the first antigen-binding site is positioned N-terminal of the third antigen-binding site in the polypeptide chain.

In certain embodiments, the first antigen-binding site is positioned N-terminal to the third antigen-binding site, and the third antigen-binding site is positioned N-terminal to the second antigen-binding site in the polypeptide chain. In other embodiments, the second antigen-binding site is positioned N-terminal to the third antigen-binding site, and the third antigen-binding site is positioned N-terminal binding protein the first antigen-binding site in the polypeptide chain.

In certain embodiments, the first antigen-binding site comprises a single-chain variable fragment (scFv). In certain embodiments, the third antigen-binding site comprises a single domain antibody (sdAb). In certain embodiments, the second antigen-binding site comprises an scFv.

In certain embodiments, the second antigen-binding site binds human CD3ε. In certain embodiments, the second antigen-binding site binds human CD3ε with a $K_D$ in the range of 1-100 nM.

In certain embodiments, the second antigen-binding site comprises a VH comprising complementarity determining regions HCDR1, HCDR2, and HCDR3, and a VL comprising complementarity determining regions LCDR1, LCDR2, and LCDR3, wherein the HCDR1, HCDR2, HCDR3, LCDR1, LCDR2, and LCDR3 comprise the amino acid sequences set forth in SEQ ID NOs: 415, 416, 418, 419, 420, and 421, respectively. In certain embodiments, the VH comprises an amino acid sequence at least 85%, at least 90%, at least 95%, at least 99%, or 100% identical to SEQ ID NO: 412, and the VL comprises an amino acid sequence at least 85%, at least 90%, at least 95%, at least 99%, or 100% identical to SEQ ID NO: 413. In certain embodiments, the antigen-binding site comprises the amino acid sequence of SEQ ID NO: 422 or 423.

In certain embodiments, the second antigen-binding site comprises a VH comprising complementarity determining regions HCDR1, HCDR2, and HCDR3, and a VL comprising complementarity determining regions LCDR1, LCDR2, and LCDR3, wherein the HCDR1, HCDR2, HCDR3, LCDR1, LCDR2, and LCDR3 comprise the amino acid sequences set forth in SEQ ID NOs: 415, 416, 426, 419, 420, and 421, respectively. In certain embodiments, the VH comprises an amino acid sequence at least 85%, at least 90%, at least 95%, at least 99%, or 100% identical to SEQ ID NO: 424, and the VL comprises an amino acid sequence at least 85%, at least 90%, at least 95%, at least 99%, or 100% identical to SEQ ID NO: 413. In certain embodiments, the antigen-binding site comprises the amino acid sequence of SEQ ID NO: 427 or 428.

In certain embodiments, the second antigen-binding site comprises a VH comprising complementarity determining regions HCDR1, HCDR2, and HCDR3, and a VL comprising complementarity determining regions LCDR1, LCDR2, and LCDR3, wherein the HCDR1, HCDR2, HCDR3, LCDR1, LCDR2, and LCDR3 comprise the amino acid sequences set forth in SEQ ID NOs: 415, 431, 418, 419, 420, and 432, respectively. In certain embodiments, the VH comprises an amino acid sequence at least 85%, at least 90%, at least 95%, at least 99%, or 100% identical to SEQ ID NO: 429, and the VL comprises an amino acid sequence at least 85%, at least 90%, at least 95%, at least 99%, or 100% identical to SEQ ID NO: 430. In certain embodiments, the antigen-binding site comprises the amino acid sequence of SEQ ID NO: 433 or 434.

In certain embodiments, at least two adjacent antigen-binding sites are connected by a peptide linker. In certain embodiments, each of the adjacent antigen-binding sites are connected by a peptide linker. In certain embodiments, the peptide linker comprises the amino acid sequence of SEQ ID NO: 298, 299, or 302. In certain embodiments, the peptide linker consists of the amino acid sequence of SEQ ID NO: 298, 299, or 302.

In certain embodiments, the multi-specific binding protein comprises an amino acid sequence selected from the group consisting of SEQ ID NOs: 694-710.

In certain embodiments, the multi-specific binding protein does not comprise an antibody Fc region. In certain embodiments, the molecular weight of the multi-specific binding protein is at least 65 kD. In certain embodiments, the serum half-life of the multi-specific binding protein is at least 24, 36, 48, or 60 hours.

In another aspect, the instant disclosure provides a pharmaceutical composition comprising: (a) a multi-specific binding protein or an antibody disclosed herein; and (b) a pharmaceutically acceptable carrier.

The instant disclosure also provides an isolated polynucleotide encoding a multi-specific binding protein or an antibody disclosed herein. In addition, the instant disclosure provides a vector comprising the polynucleotide disclosed herein, and a recombinant host cell comprising the polynucleotide or vector disclosed herein.

The instant disclosure also provides a method of producing a multi-specific binding protein or an antibody, the method comprising culturing a host cell disclosed herein under suitable conditions that allow expression of the multi-specific binding protein or the antibody. In certain embodiments, the method further comprises isolating the multi-specific binding protein or the antibody. In certain embodiments, the method further comprises formulating the isolated multi-specific binding protein or antibody with a pharmaceutically acceptable carrier.

In addition, the instant disclosure provides a method of stimulating an immune response against a cell expressing CD19, the method comprising exposing the cell and a T lymphocyte to a multi-specific binding protein, an antibody, or a pharmaceutical composition disclosed herein.

The instant disclosure also provides a method of treating a hematologic cancer in a subject in need thereof, the method comprising administering to the subject an effective amount of a multi-specific binding protein, an antibody, or a pharmaceutical composition disclosed herein. In certain embodiments, the hematologic cancer is a B-cell hematologic malignancy.

In addition, the instant disclosure provides a complex comprising a T cell expressing CD3, a B cell expressing CD19, and a multi-specific binding protein disclosed herein, wherein the multi-specific binding protein simultaneously bind both the T cell and the B cell. In certain embodiments, the complex further comprises serum albumin.

DETAILED DESCRIPTION

Figure 1:
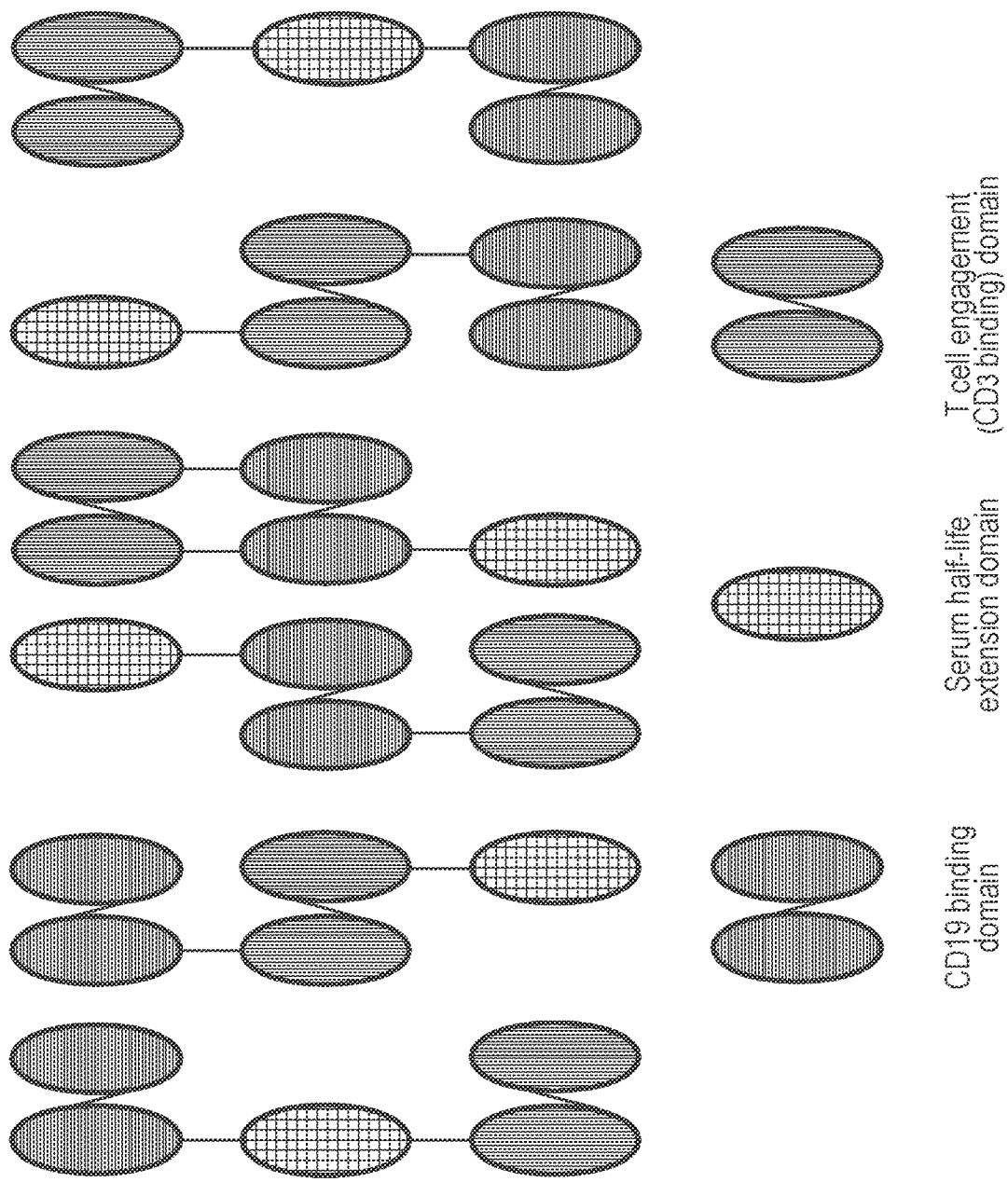
FIG. 1 is a schematic representation of six domain arrangements of single-chain multi-specific binding proteins. The CD19 binding domain in the form of an scFv, the CD3 binding domain in the form of an scFv, and the HSA binding domain in the form of an sdAb are linked in different orientations. The top of each construct represents the N-terminus and the bottom of each construct represents the C-terminus of a given polypeptide chain.

The present invention is based, in part, upon the development of new antibodies that bind CD19. Also provided are multi-specific binding proteins comprising a first domain that binds CD19 (e.g., human CD19), a second domain that binds CD3 (e.g., human CD3), and optionally a half-life extension domain, which can be a third domain that binds serum albumin (e.g., human serum albumin), wherein the first domain is derived from these new antibodies. These domains are linked in certain manners for favorable therapeutic efficacy and in vivo half-life. The anti-CD19 antibodies and multi-specific binding proteins are useful for treating diseases and disorders associated with aberrant cells expressing CD19, such as certain B-cell hematologic malignancies.

To facilitate an understanding of the present invention, a number of terms and phrases are defined below.

The term "multi-specific binding protein" refers to a protein or protein conjugate capable of binding two or more different targets (e.g., two or more different antigens or two or more different epitopes of the same antigen). For example, the multi-specific binding protein can bind two or more different targets through two or more different binding domains. The structure and/or function of the multi-specific binding protein can be based on the structure and/or function of an antibody, e.g., a full-length or whole immunoglobulin molecule, an antibody heavy chain variable domain (VH) and/or light chain variable domain (VL), and/or a single chain antibody. In one example, each one of the binding domains of a multi-specific binding protein according to the invention comprises the minimum structural requirements of an antibody which allow for the target binding. This minimum requirement may be, e.g., defined by the presence of at least the three heavy chain CDRs (i.e. CDR1, CDR2 and CDR3 of the VH domain) and/or the three light chain CDRs (i.e. CDR1, CDR2 and CDR3 of the VL domain). An alternative approach to defining the minimal structural requirements of an antibody is defining the epitope of a specific target to which the antibody binds, or by referring to a known antibody with which the antibody competes to bind to the same epitope that the known antibody binds. The antibodies on which the constructs according to the invention are based include for example monoclonal, recombinant, chimeric, deimmunized, humanized and human antibodies.

Any one of the binding domains of a multi-specific binding protein according to the invention may comprise the above referred groups of CDRs. Those CDRs may be comprised in the framework of a VH and/or VL. Fd fragments, for example, have two VH domains and often retain some antigen-binding function of the intact antigen-binding domain. Additional examples for formats of antibody fragments, antibody variants or binding domains include: (1) a Fab fragment, a monovalent fragment having the VL, VH, CL and CH1 domains; (2) a F(ab')$_2$ fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody; (5) a dAb fragment (Ward et al., (1989) Nature 341:544-546), which has a VH domain; (6) an isolated complementarity determining region (CDR); and (7) a single chain Fv (scFv), which may be derived, for example, from an scFv-library. Exemplary formats of multi-specific binding proteins according to the invention are described in, e.g., WO2000006605A2, WO2005040220A1, WO2008119567A2, WO2010037838A2, WO2013026837A1, WO2013026833A1, US20140308285A1, US20140302037A1, WO2014144722A2, WO2014151910A1, and WO2015048272A1.

Multi-specific binding proteins according to the invention may also comprise modified fragments of antibodies, also called antibody variants, such as di-scFv or bi(s)-scFv, scFv-Fc, scFv-zipper, scFab, Fab$_2$, Fab$_3$, diabodies, single chain diabodies, tandem diabodies (Tandab's), tandem di-scFv, tandem tri-scFv, "multibodies" such as triabodies or tetrabodies, or single-domain antibodies such as nanobodies or single variable domain antibodies comprising a single variable domain, which might be VH (also called VHH in the context of an sdAb) or VL, that specifically bind an antigen or epitope independently of other V regions or domains.

As used herein, the terms "single-chain Fv," "single-chain antibody," and "scFv" refer to a single-polypeptide-chain antibody fragment that comprise the variable regions from both the heavy and light chains, but lack the constant regions. Generally, a single-chain antibody further comprises a peptide linker connecting the VH and VL domains which enables it to form the desired structure to bind to antigen. Single chain antibodies are discussed in detail by Pluckthun in The Pharmacology of Monoclonal Antibodies, vol. 113, Rosenburg and Moore eds. Springer-Verlag, New York, pp. 269-315 (1994). Various methods of generating single chain antibodies are known, including those described in U.S. Pat. Nos. 4,694,778 and 5,260,203; International Patent Application Publication No. WO 88/01649; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041. In specific embodiments, single-chain antibodies can also be bispecific, multispecific, human, humanized and/or synthetic.

Furthermore, the "multi-specific binding protein" described herein can be a monovalent, bivalent or polyvalent/multivalent construct. Moreover, the "multi-specific binding protein" described herein can include a molecule consisting of only one polypeptide chain, or a molecules consisting of more than one polypeptide chain, wherein the chains can be either identical (homodimers, homotrimers or homo oligomers) or different (heterodimer, heterotrimer or heterooligomer). Examples for the above identified antibodies and the variants or derivatives thereof are described, for example, in Harlow and Lane, Antibodies a laboratory manual, CSHL Press (1988); Using Antibodies: a laboratory manual, CSHL Press (1999); Kontermann and Dibel, Antibody Engineering, Springer, 2nd ed. 2010; and Little, Recombinant Antibodies for Immunotherapy, Cambridge University Press 2009.

The domains of the multi-specific binding protein of the present invention may be connected through one or more peptide bonds and/or peptide linkers. The term "peptide linker" comprises in accordance with the present invention an amino acid sequence linking two domains. The peptide linkers can also be used to fuse the third domain to the other domains of the multi-specific binding protein of the invention. An essential technical feature of such peptide linker is that it does not comprise any polymerization activity. Among the suitable peptide linkers are those described in U.S. Pat. Nos. 4,751,180 and 4,935,233 or WO198809344A1.

The multi-specific binding proteins of the present invention may be in vitro generated multi-specific binding proteins. The term "in vitro generated multi-specific binding protein" refers to a multi-specific binding protein according to the above definition where all or part of the variable region (e.g., at least one CDR) is generated by non-immune cell selection, e.g., an in vitro phage display, protein chip or any other method in which candidate sequences can be tested for their ability to bind to an antigen. The multi-specific binding proteins of the present invention may also be generated by genomic rearrangement in an immune cell in an animal. A "recombinant antibody" is an antibody made through the use of recombinant DNA technology or genetic engineering.

The multi-specific binding protein of the invention may be monoclonal. The term "monoclonal," as used herein, means that the proteins obtained from a population are substantially homogeneous, i.e., the individual proteins in the population are identical except for naturally occurring mutations and/or post-translation modifications (e.g., isomerizations, amidations) that may be present. In the context of antibodies, monoclonal antibodies are highly specific, being directed against a single antigenic side or determinant on the antigen, in contrast to conventional (polyclonal) antibody preparations which typically include different antibodies directed against different determinants (or epitopes). The modifier "monoclonal" indicates the character of the antibody as being obtained from a substantially homogeneous population of antibodies, and is not to be construed as requiring production of the antibody by any particular method.

The multi-specific binding protein of the invention or one or more antigen-binding site thereof may be affinity matured. In immunology, affinity maturation is the process by which B cells produce antibodies with increased affinity for antigen during the course of an immune response. With repeated exposures to the same antigen, a host will produce antibodies of successively greater affinities. Like the natural prototype, the in vitro affinity maturation is based on the principles of mutation and selection. Two or three rounds of mutation and selection using display methods such as phage display can result in antibody fragments with affinities in the low nanomolar range.

An amino acid substitution variation can be introduced into the multi-specific binding proteins by substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sides (e.g., 6-7 sides) are mutated to generate all possible amino acid substitutions at each side. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sides for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the binding domains. Such contact residues and neighboring residues are candidates for substitution according to the techniques elaborated herein. Once such variants are generated, the panel of variants is subjected to screening as described herein and antibodies with superior properties in one or more relevant assays may be selected for further development.

The multi-specific binding proteins of the present invention specifically can comprise "chimeric" antibodies (immunoglobulins) or fragments thereof in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, so long as they exhibit the desired biological activity (U.S. Pat. No. 4,816,567; Morrison et al. (1984) Proc. Natl. Acad. Sci. U.S.A., 81: 6851-55). Chimeric antibodies of interest herein include "primatized" antibodies comprising variable domain antigen-binding sequences derived from a non-human primate (e.g., Old World Monkey, Ape etc.) or human constant region sequences. A variety of approaches for making chimeric antibodies have been described. See e.g., Morrison et al. (1985) Proc. Natl. Acad. Sci. U.S.A., 81:6851; Takeda et al. (1985) Nature, 314: 452; U.S. Pat. Nos. 4,816,567; 4,816, 397; European Patent No. EP0171496; European Patent Application Publication No. EP0173494; and U.K. Patent No. GB2177096.

The term "binding domain" or "domain that binds (an antigen)" characterizes in connection with the present invention a domain which (specifically) binds to or interacts with a given target epitope or a given target side on the target molecules (antigens), e.g. CD19, serum albumin, and CD3, respectively. The structure and function of the first binding domain, the second binding domain, and/or the third binding domain can be based on the structure and/or function of an antibody, e.g. of a full-length or whole immunoglobulin molecule. A binding domain can be drawn from the VH and/or VL or VHH domain of an antibody or fragment thereof. For example, a binding domain can include three light chain CDRs (i.e., CDR1, CDR2 and CDR3 of the VL domain) and/or three heavy chain CDRs (i.e., CDR1, CDR2 and CDR3 of the VH domain). A binding domain can also include VHH CDRs (i.e., CDR1, CDR2 and CDR3 of the VHH region).

The terms "variable domain" and "variable region" are used interchangeably and refer to the portions of the antibody or immunoglobulin domains that exhibit variability in their sequence and that are involved in determining the specificity and binding affinity of a particular antibody. Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FRM or FR) and provide a scaffold for the six CDRs in three dimensional space to form an antigen-binding surface.

In the present invention, any one of the binding domains of the multi-specific binding protein may comprise a single domain antibody (sdAb). A single domain antibody comprises a single, monomeric antibody variable domain which is able to bind selectively to a specific antigen, independently of other variable regions or domains. The first single domain antibodies were engineered from heavy chain antibodies found in camelids, and these are called VHH fragments. Cartilaginous fishes also have heavy chain antibodies (IgNAR) from which single domain antibodies called $V_{NAR}$ fragments can be obtained. An alternative approach is to split the dimeric variable domains from common immunoglobulins e.g., from humans or rodents into monomers, hence obtaining VH or VL as a single domain antibody. Although most research into single domain antibodies is currently based on heavy chain variable domains, nanobodies derived from light chains have also been shown to bind specifically to target epitopes. Examples of single domain antibodies include nanobodies and single variable domain antibodies.

As used herein, the term "antigen-binding site" refers to the part of an immunoglobulin molecule or a derivative or variant thereof that participates in antigen binding. In human antibodies, the antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FR." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide.

As used herein, the term "antibody" refers to a protein or a protein conjugate that comprises an antigen-binding site. An antibody can be monospecific or multi-specific (e.g., bispecific).

The terms "a" and "an" as used herein mean "one or more" and include the plural unless the context is inappropriate.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA (1975).

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the van able controls.

C. Anti-CD19 Antibodies

In one aspect, the present disclosure provides an antigen-binding site that binds CD19 (e.g., human CD19) derived from the antibodies listed in Table 116. The present disclosure also provides an antibody comprising the antigen-binding site. The CDR sequences are identified under the Kabat numbering scheme unless indicated by an asterisk (*).

TABLE 1

Sequences of Exemplary Antibodies That Bind CD19

| Antibody | VH and HCDRs | VL and LCDRs |
|---|---|---|
| CNG-CD19-101 | QVQLVQSGAEVKKPGASVKVSCKASG YDFTDYIMHWVRQAPGQGLEWMGYIN PYNDGSKYTDKFQERVTMTSDTSISTA YMELSRLRSDDTAVYYCARGTYYYGP ELFDYWGQGTTVTVSS (SEQ ID NO: 1)<br><br>HCDR1*: YDFTDYIMH (SEQ ID NO: 3)<br>HCDR1: DYIMH (SEQ ID NO: 4)<br>HCDR2: YINPYNDGSKYTDKFQE (SEQ ID NO: 5)<br>HCDR3*: ARGTYYYGPELFDY (SEQ ID NO: 6)<br>HCDR3: GTYYYGPELFDY (SEQ ID NO: 7)<br><br>scFv with Cys substitutions:<br>DIVMTQTPLSLSVTPGQPASISCKSSQSLETTTGTTYLNWYLQKPGQSPQLLIY RASKRFSGVPDRFSGSGSGTDFTLKISRVEAEDVGVYYCLQLLEDPYTFG<u>C</u>GT KLEIK<u>GGGGSGGGGSGGGGS</u>QVQLVQSGAEVKKPGASVKVSCKASGYDFTD YIMHWVRQAPGQ<u>C</u>LEWMGYINPYNDGSKYTDKFQERVTMTSDTSISTAYME LSRLRSDDTAVYYCARGTYYYGPELFDYWGQGTTVTVSS (SEQ ID NO: 11) | DIVMTQTPLSLSVTPGQPASISCK SSQSLETTTGTTYLNWYLQKPGQ SPQLLIYRASKRFSGVPDRFSGSG SGTDFTLKISRVEAEDVGVYYCL QLLEDPYTFGQGTKLEIK (SEQ ID NO: 2)<br><br>LCDR1: KSSQSLETTTGTTYLN (SEQ ID NO: 8)<br>LCDR2: RASKRFS (SEQ ID NO: 9)<br>LCDR3: LQLLEDPYT (SEQ ID NO: 10) |
| CNG-CD19-102 | QVQLVQSGAEVKKPGASVKVSCKASG YEFTDYIMHWVRQAPGQGLEWMGYIN PYNDGSKYTEKFQPRVTMTSDTSISTAY MELSRLRSDDTAVYYCARGTYYYGPQ LFDYWGQGTTVTVSS (SEQ ID NO: 12)<br><br>HCDR1*: YEFTDYIMH (SEQ ID NO: 14)<br>HCDR1: DYIMH (SEQ ID NO: 4)<br>HCDR2: YINPYNDGSKYTEKFQP (SEQ ID NO: 15)<br>HCDR3*: ARGTYYYGPQLFDY (SEQ ID NO: 16)<br>HCDR3: GTYYYGPQLFDY (SEQ ID NO: 17) | DIVMTQTPLSLSVTPGQPASISCK SSQSLETSTGTTYLNWYLQKPGQ SPQLLIYRVSKRFSGVPDRFSGSG SGTDFTLKISRVEAEDVGVYYCL QLLEDPYTFGQGTKLEIK (SEQ ID NO: 13)<br><br>LCDR1: KSSQSLETSTGTTYLN (SEQ ID NO: 18)<br>LCDR2: RVSKRFS (SEQ ID NO: 19)<br>LCDR3: LQLLEDPYT (SEQ ID NO: 10) |
| CNG-CD19-103 | QVQLVQSGAEVKKPGASVKVSCKASG YTFTDYIMHWVRQAPGQGLEWMGYIN PYNDGSKYTEKFQGRVTMTSDTSISTA YMELSRLRSDDTAVYYCARGTYYYGP QLFDYWGQGTTVTVSS (SEQ ID NO: 20)<br><br>HCDR1*: YTFTDYIMH (SEQ ID NO: 22)<br>HCDR1: DYIMH (SEQ ID NO: 4)<br>HCDR2: YINPYNDGSKYTEKFQG (SEQ ID NO: 23)<br>HCDR3*: ARGTYYYGPQLFDY (SEQ ID NO: 16)<br>HCDR3: GTYYYGPQLFDY (SEQ ID NO: 17) | DIVMTQTPLSLSVTPGQPASISCK SSQSLETATGTTYLNWYLQKPGQ SPQLLIYRVSRRFSGVPDRFSGSG SGTDFTLKISRVEAEDVGVYYCL QLLEDPYSFGQGTKLEIK (SEQ ID NO: 21)<br><br>LCDR1: KSSQSLETATGTTYLN (SEQ ID NO: 24)<br>LCDR2: RVSRRFS (SEQ ID NO: 25)<br>LCDR3: LQLLEDPYS (SEQ ID NO: 26) |
| CNG-CD19-104 | QVQLVQSGAEVKKPGASVKVSCKASG YDFTDYIVHWVRQAPGQGLEWMGYIN PYNDGSKYTEKFQGRVTMTSDTSISTA | DIVMTQTPLSLSVTPGQPASISCK SGQSLETSTGTTYLNWYLQKPGQ SPQLLIYRVSRRFSGVPDRFSGSG |

TABLE 1-continued

Sequences of Exemplary Antibodies That Bind CD19

| Antibody | VH and HCDRs | VL and LCDRs |
|---|---|---|
| | YMELSRLRSDDTAVYYCARGTYYYGP ELFDYWGQGTTVTVSS (SEQ ID NO: 27) | SGTDFTLKISRVEAEDVGVYYCL QLLEDPYTFGQGTKLEIK (SEQ ID NO: 28) |
| | HCDR1*: YDFTDYIVH (SEQ ID NO: 29) | LCDR1: KSGQSLETSTGTTYLN (SEQ ID NO: 31) |
| | HCDR1: DYIVH (SEQ ID NO: 30) | LCDR2: RVSRRFS (SEQ ID NO: 25) |
| | HCDR2: YINPYNDGSKYTEKFQG (SEQ ID NO: 23) | LCDR3: LQLLEDPYT (SEQ ID NO: 10) |
| | HCDR3*: ARGTYYYGPELFDY (SEQ ID NO: 6) | |
| | HCDR3: GTYYYGPELFDY (SEQ ID NO: 7) | |
| CNG-CD19-105 | QVQLVQSGAEVKKPGASVKVSCKASG YEFTDYIMHWVRQAPGQGLEWMGYIN PYNDGSKYTEKFEGRVTMTSDTSISTAY MELSRLRSDDTAVYYCARGTYYYGPEL FDYWGQGTTVTVSS (SEQ ID NO: 32) | DIVMTQTPLSLSVTPGQPASISCK SSQRLETSTGTTYLNWYLQKPGQ SPQLLIYRVSRRFSGVPDRFSGSG SGTDFTLKISRVEAEDVGVYYCL QLLEDPPTFGQGTKLEIK (SEQ ID NO: 33) |
| | HCDR1*: YEFTDYIMH (SEQ ID NO: 14) | LCDR1: KSSQRLETSTGTTYLN (SEQ ID NO: 35) |
| | HCDR1: DYIMH (SEQ ID NO: 4) | LCDR2: RVSRRFS (SEQ ID NO: 25) |
| | HCDR2: YINPYNDGSKYTEKFEG (SEQ ID NO: 34) | LCDR3: LQLLEDPPT (SEQ ID NO: 36) |
| | HCDR3*: ARGTYYYGPELFDY (SEQ ID NO: 6) | |
| | HCDR3: GTYYYGPELFDY (SEQ ID NO: 7) | |
| CNG-CD19-106 | QVQLVQSGAEVKKPGASVKVSCKASG YDFTDYIMHWVRQAPGQGLEWMGYIN PYNDGSEYTEKFQGRVTMTSDTSISTAY MELSRLRSDDTAVYYCARGTYYYGPQ LFDYWGQGTTVTVSS (SEQ ID NO: 37) | DIVMTQTPLSLSVTPGQPASISCK SSQSLETATGTTYLNWYLQKPGQ SPQLLIYRVSRRFSGVPDRFSGSG SGTDFTLKISRVEAEDVGVYYCL QLLEDPYTFGQGTKLEIK (SEQ ID NO: 38) |
| | HCDR1*: YDFTDYIMH (SEQ ID NO: 3) | LCDR1: KSSQSLETATGTTYLN (SEQ ID NO: 24) |
| | HCDR1: DYIMH (SEQ ID NO: 4) | LCDR2: RVSRRFS (SEQ ID NO: 25) |
| | HCDR2: YINPYNDGSEYTEKFQG (SEQ ID NO: 39) | LCDR3: LQLLEDPYT (SEQ ID NO: 10) |
| | HCDR3*: ARGTYYYGPQLFDY (SEQ ID NO: 16) | |
| | HCDR3: GTYYYGPQLFDY (SEQ ID NO: 17) | |
| CNG-CD19-107 | QVQLVQSGAEVKKPGASVKVSCKASG YDFTDYIMHWVRQAPGQGLEWMGYIN PYNDGSKYTEKFQHRVTMTSDTSISTA YMELSRLRSDDTAVYYCARGTYYYGP QLFDYWGQGTTVTVSS (SEQ ID NO: 40) | DIVMTQTPLSLSVTPGQPASISCK SSQSLETSTGTTYLNWYLQKPGQ SPQLLIYRVSRRFSGVPDRFSGSG SGTDFTLKISRVEAEDVGVYYCL QLLEDPYTFGQGTKLEIK (SEQ ID NO: 41) |
| | HCDR1*: YDFTDYIMH (SEQ ID NO: 3) | LCDR1: KSSQSLETSTGTTYLN (SEQ ID NO: 18) |
| | HCDR1: DYIMH (SEQ ID NO: 4) | LCDR2: RVSRRFS (SEQ ID NO: 25) |
| | HCDR2: YINPYNDGSKYTEKFQH (SEQ ID NO: 42) | LCDR3: LQLLEDPYT (SEQ ID NO: 10) |
| | HCDR3*: ARGTYYYGPQLFDY (SEQ ID NO: 16) | |
| | HCDR3: GTYYYGPQLFDY (SEQ ID NO: 17) | |

TABLE 1-continued

Sequences of Exemplary Antibodies That Bind CD19

| Antibody | VH and HCDRs | VL and LCDRs |
| --- | --- | --- |
| CNG-CD19-108 | QVQLVQSGAEVKKPGASVKVSCKASG YDFTDYIVHWVRQAPGQGLEWMGYIN PYNDGSKYTEKFQGRVTMTSDTSISTA YMELSRLRSDDTAVYYCARGTYYYGP QLFDYWGQGTTVTSS (SEQ ID NO: 43) HCDR1*: YDFTDYIVH (SEQ ID NO: 29) HCDR1: DYIVH (SEQ ID NO: 30) HCDR2: YINPYNDGSKYTEKFQG (SEQ ID NO: 23) HCDR3*: ARGTYYYGPQLFDY (SEQ ID NO: 16) HCDR3: GTYYYGPQLFDY (SEQ ID NO: 17) | DIVMTQTPLSLSVTPGQPASISCK SSQSLETVTGTTYLNWYLQKPGQ SPQLLIYRVSKRFSGVPDRFSGSG SGTDFTLKISRVEAEDVGVYYCL QLLEDPPTFGQGTKLEIK (SEQ ID NO: 44) LCDR1: KSSQSLETVTGTTYLN (SEQ ID NO: 45) LCDR2: RVSKRFS (SEQ ID NO: 19) LCDR3: LQLLEDPPT (SEQ ID NO: 36) |
| CNG-CD19-109 | QVQLVQSGAEVKKPGASVKVSCKASG YDFTDYIVHWVRQAPGQGLEWMGYIN PYNDGSLYTEKFQGRVTMTSDTSISTAY MELSRLRSDDTAVYYCARGTYYYGPQ LFDYWGQGTTVTSS (SEQ ID NO: 46) HCDR1*: YDFTDYIVH (SEQ ID NO: 29) HCDR1: DYIVH (SEQ ID NO: 30) HCDR2: YINPYNDGSLYTEKFQG (SEQ ID NO: 48) HCDR3*: ARGTYYYGPQLFDY (SEQ ID NO: 16) HCDR3: GTYYYGPQLFDY (SEQ ID NO: 17) | DIVMTQTPLSLSVTPGQPASISCK SSQQLETSTGTTYLNWYLQKPGQ SPQLLIYRASKRFSGVPDRFSGSG SGTDFTLKISRVEAEDVGVYYCL QLLEDPYSFGQGTKLEIK (SEQ ID NO: 47) LCDR1: KSSQQLETSTGTTYLN (SEQ ID NO: 49) LCDR2: RASKRFS (SEQ ID NO: 9) LCDR3: LQLLEDPYS (SEQ ID NO: 26) |
| CNG-CD19-110 | QVQLVQSGAEVKKPGASVKVSCKASG YTFTDYIMHWVRQAPGQGLEWMGYIN PYNDGSKYTEKFQGRVTMTSDTSISTA YMELSRLRSDDTAVYYCARGTYYYGP QLFDYWGQGTTVTSS (SEQ ID NO: 20) HCDR1*: YTFTDYIMH (SEQ ID NO: 22) HCDR1: DYIMH (SEQ ID NO: 4) HCDR2: YINPYNDGSKYTEKFQG (SEQ ID NO: 23) HCDR3*: ARGTYYYGPQLFDY (SEQ ID NO: 16) HCDR3: GTYYYGPQLFDY (SEQ ID NO: 17) | DIVMTQTPLSLSVTPGQPASISCK SSQSLETSTGTTYLNWYLQKPGQ SPQLLIYRSSKRFSGVPDRFSGSGS GTDFTLKISRVEAEDVGVYYCLQ LLEDPPTFGQGTKLEIK (SEQ ID NO: 50) LCDR1: KSSQSLETSTGTTYLN (SEQ ID NO: 18) LCDR2: RSSKRFS (SEQ ID NO: 51) LCDR3: LQLLEDPPT (SEQ ID NO: 36) |
| Consensus-1 (CNG-CD19-101 to -110) | HCDR1*: YX$_1$FTDYIX$_2$H, wherein X$_1$ is T, D, or E; and X$_2$ is M or V (SEQ ID NO: 52) HCDR1: DYIXH, wherein X is M or V (SEQ ID NO: 53) HCDR2: YINPYNDGSX$_1$YTX$_2$KFX$_3$X$_4$, wherein X$_1$ is K, L, or E; X$_2$ is E or D; X$_3$ is Q or E; and X$_4$ is G, H, E, or P (SEQ ID NO: 54) HCDR3*: ARGTYYYGPXLFDY, wherein X is Q or E (SEQ ID NO: 55) HCDR3: GTYYYGPXLFDY, wherein X is Q or E (SEQ ID NO: 56) | LCDR1: KSX$_1$QX$_2$LX$_3$TX$_4$TGTTYLN, wherein X$_1$ is S or G; X$_2$ is S, R, or Q; X$_3$ is E or F; and X$_4$ is S, A, T, or V (SEQ ID NO: 57) LCDR2: RX$_1$SX$_2$RFS, wherein X$_1$ is V, A, or S; and X$_2$ is K or R (SEQ ID NO: 58) LCDR3: LQLLEDPX$_1$X$_2$, wherein X$_1$ is Y or P; and X$_2$ is T or S (SEQ ID NO: 59) |

TABLE 1-continued

Sequences of Exemplary Antibodies That Bind CD19

| Antibody | VH and HCDRs | VL and LCDRs |
|---|---|---|
| Consensus-2 (CNG-CD19-101 to -109) | HCDR1*: YX$_1$FTDYIX$_2$H, wherein X$_1$ is T, D, or E; and X$_2$ is M or V (SEQ ID NO: 52)<br>HCDR1: DYIXH, wherein X is M or V (SEQ ID NO: 53)<br>HCDR2: YINPYNDGSXiYTX$_2$KFX$_3$X$_4$, wherein X$_1$ is K, L, or E; X$_2$ is E or D; X$_3$ is Q or E; and X$_4$ is G, H, E, or P (SEQ ID NO: 54)<br>HCDR3*: ARGTYYYGPXLFDY, wherein X is Q or E (SEQ ID NO: 55)<br>HCDR3: GTYYYGPXLFDY, wherein X is Q or E (SEQ ID NO: 56) | LCDR1: KSX$_1$QX$_2$LX$_3$TX$_4$TGTTYLN, wherein X$_1$ is S or G; X$_2$ is S, R, or Q; X$_3$ is E or F; and X$_4$ is S, A, T, or V (SEQ ID NO: 57)<br>LCDR2: RX$_1$SX$_2$RFS, wherein X$_1$ is V or A; and X$_2$ is K or R (SEQ ID NO: 60)<br>LCDR3: LQLLEDPX$_1$X$_2$, wherein X$_1$ is Y or P; and X$_2$ is T or S (SEQ ID NO: 59) |
| Consensus-3 (CNG-CD19-101, -103 to -105, and -107 to -109) | HCDR1*: YX$_1$FTDYIX$_2$H, wherein X$_1$ is T, D, or E; and X$_2$ is M or V (SEQ ID NO: 52)<br>HCDR1: DYIXH, wherein X is M or V (SEQ ID NO: 53)<br>HCDR2: YINPYNDGSX$_1$YTX$_2$KFX$_3$X$_4$, wherein X$_1$ is K or L; X$_2$ is E or D; X$_3$ is Q or E; and X$_4$ is G, H, or E (SEQ ID NO: 61)<br>HCDR3*: ARGTYYYGPXLFDY, wherein X is Q or E (SEQ ID NO: 55)<br>HCDR3: GTYYYGPXLFDY, wherein X is Q or E (SEQ ID NO: 56) | LCDR1: KSX$_1$QX$_2$LX$_3$TX$_4$TGTTYLN, wherein X$_1$ is S or G; X$_2$ is S, R, or Q; X$_3$ is E or F; and X$_4$ is S, A, T, or V (SEQ ID NO: 57)<br>LCDR2: RX$_1$SX$_2$RFS, wherein X$_1$ is V or A; and X$_2$ is K or R (SEQ ID NO: 60)<br>LCDR3: LQLLEDPX$_1$X$_2$, wherein X$_1$ is Y or P; and X$_2$ is T or S (SEQ ID NO: 59) |

In certain embodiments, the antigen-binding site that binds CD19 of the present invention comprises an antibody heavy chain variable domain (VH) that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VH of an antibody disclosed in Table 1, and an antibody light chain variable domain (VL) that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VL of the same antibody disclosed in Table 1. In certain embodiments, the antigen-binding site comprises the HCDR1, HCDR2, HCDR3, LCDR1, LCDR2, and LCDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J Mol Biol 196: 901-917), MacCallum (see MacCallum R M et al., (1996) J Mol Biol 262: 732-745), IMGT (see Lefranc, (1999) The Immunologist, 7, 132-136), or any other CDR determination method known in the art, of the VH and VL sequences of an antibody disclosed in Table 1. In certain embodiments, the antigen-binding site comprises the HCDR1, HCDR2, HCDR3, LCDR1, LCDR2, and LCDR3 sequences of an antibody disclosed in Table 1. In certain embodiments, the antigen-binding site comprises the VH and VL sequences of an antibody disclosed in Table 1.

Series 1 Constructs

In certain embodiments, the antigen-binding site that binds CD19 comprises a VH comprising HCDR1, HCDR2, and HCDR3 sequences set forth in SEQ ID NOs: 52, 54, and 55, respectively, and a VL comprising LCDR1, LCDR2, and LCDR3 sequences set forth in SEQ ID NOs: 57, 58, and 59, respectively, wherein the antigen-binding site does not comprise HCDR1, HCDR2, HCDR3, LCDR1, LCDR2, and LCDR3 sequences set forth in SEQ ID NOs: 22, 23, 16, 18, 19, and 10, respectively. In certain embodiments, the HCDR1 sequence is selected from the group consisting of SEQ ID NOs: 3, 14, 22, and 29; the HCDR2 sequence is selected from the group consisting of SEQ ID NOs: 5, 15, 23, 34, 39, 42, and 48; the HCDR3 sequence is selected from the group consisting of SEQ ID NOs: 6 and 16; the LCDR1 sequence is selected from the group consisting of SEQ ID NOs: 8, 18, 24, 31, 35, 45, and 49; the LCDR2 sequence is selected from the group consisting of SEQ ID NOs: 9, 19, 25, and 51; and/or the LCDR3 sequence is selected from the group consisting of SEQ ID NOs: 10, 26, and 36.

In certain embodiments, the antigen-binding site comprises a VH comprising HCDR1, HCDR2, and HCDR3 sequences set forth in SEQ ID NOs: 53, 54, and 56, respectively, and a VL comprising LCDR1, LCDR2, and LCDR3 sequences set forth in SEQ ID NOs: 57, 58, and 59, respectively, wherein the antigen-binding site does not comprise HCDR1, HCDR2, HCDR3, LCDR1, LCDR2, and LCDR3 sequences set forth in SEQ ID NOs: 4, 23, 17, 18, 19, and 10, respectively. In certain embodiments, the HCDR1 sequence is selected from the group consisting of SEQ ID NOs: 4 and 30; the HCDR2 sequence is selected from the group consisting of SEQ ID NOs: 5, 15, 23, 34, 39, 42, and 48; the HCDR3 sequence is selected from the group consisting of SEQ ID NOs: 7 and 17; the LCDR1 sequence is selected from the group consisting of SEQ ID NOs: 8, 18, 24, 31, 35, 45, and 49; the LCDR2 sequence is selected from the group consisting of SEQ ID NOs: 9, 19, 25, and 51; and/or the LCDR3 sequence is selected from the group consisting of SEQ ID NOs: 10, 26, and 36.

In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 1, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 2.

In certain embodiments, the antigen-binding site has a higher binding affinity to human and/or cynomolgus CD19 relative to an antigen-binding site having VH and VL sequences set forth in SEQ ID NOs: 20 and 13, respectively.
Series 2 Constructs In certain embodiments, the antigen-binding site that binds CD19 comprises a VH comprising HCDR1, HCDR2, and HCDR3 sequences set forth in SEQ ID NOs: 52, 54, and 55, respectively, and a VL comprising LCDR1, LCDR2, and LCDR3 sequences set forth in SEQ ID NOs: 57, 60, and 59, respectively, wherein the antigen-binding site does not comprise HCDR1, HCDR2, HCDR3, LCDR1, LCDR2, and LCDR3 sequences set forth in SEQ ID NOs: 22, 23, 16, 18, 19, and 10, respectively. In certain embodiments, the HCDR1 sequence is selected from the group consisting of SEQ ID NOs: 3, 14, 22, and 29; the HCDR2 sequence is selected from the group consisting of SEQ ID NOs: 5, 15, 23, 34, 39, 42, and 48; the HCDR3 sequence is selected from the group consisting of SEQ ID NOs: 6 and 16; the LCDR1 sequence is selected from the group consisting of SEQ ID NOs: 8, 18, 24, 31, 35, 45, and 49; the LCDR2 sequence is selected from the group consisting of SEQ ID NOs: 9, 19, and 25; and/or the LCDR3 sequence is selected from the group consisting of SEQ ID NOs: 10, 26, and 36.

In certain embodiments, the antigen-binding site comprises a VH comprising HCDR1, HCDR2, and HCDR3 sequences set forth in SEQ ID NOs: 53, 54, and 56, respectively, and a VL comprising LCDR1, LCDR2, and LCDR3 sequences set forth in SEQ ID NOs: 57, 60, and 59, respectively, wherein the antigen-binding site does not comprise HCDR1, HCDR2, HCDR3, LCDR1, LCDR2, and LCDR3 sequences set forth in SEQ ID NOs: 4, 23, 17, 18, 19, and 10, respectively. In certain embodiments, the HCDR1 sequence is selected from the group consisting of SEQ ID NOs: 4 and 30; the HCDR2 sequence is selected from the group consisting of SEQ ID NOs: 5, 15, 23, 34, 39, 42, and 48; the HCDR3 sequence is selected from the group consisting of SEQ ID NOs: 7 and 17; the LCDR1 sequence is selected from the group consisting of SEQ ID NOs: 8, 18, 24, 31, 35, 45, and 49; the LCDR2 sequence is selected from the group consisting of SEQ ID NOs: 9, 19, and 25; and/or the LCDR3 sequence is selected from the group consisting of SEQ ID NOs: 10, 26, and 36.

In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 1, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 2.

In certain embodiments, the antigen-binding site has a higher binding affinity to human CD19 relative to an antigen-binding site having VH and VL sequences set forth in SEQ ID NOs: 20 and 13, respectively. In certain embodiments, the antigen-binding site binds human CD19 or an extracellular fragment thereof with a $K_D$ lower than or equal to 0.3 nM, as measured by surface plasmon resonance (SPR) when the antigen-binding site is present as a monomer. In certain embodiments, the antigen-binding site binds human CD19 or an extracellular fragment thereof with a $K_D$ in the range of 0.05-0.3 nM or in the range of 0.1-0.3 nM, as measured by SPR when the antigen-binding site is present as a monomer.

Series 3 Constructs

In certain embodiments, the antigen-binding site that binds CD19 comprises a VH comprising HCDR1, HCDR2, and HCDR3 sequences set forth in SEQ ID NOs: 52, 61, and 55, respectively, and a VL comprising LCDR1, LCDR2, and LCDR3 sequences set forth in SEQ ID NOs: 57, 60, and 59, respectively, wherein the antigen-binding site does not comprise HCDR1, HCDR2, HCDR3, LCDR1, LCDR2, and LCDR3 sequences set forth in SEQ ID NOs: 22, 23, 16, 18, 19, and 10, respectively. In certain embodiments, the HCDR1 sequence is selected from the group consisting of SEQ ID NOs: 3, 14, 22, and 29; the HCDR2 sequence is selected from the group consisting of SEQ ID NOs: 5, 23, 34, 42, and 48; the HCDR3 sequence is selected from the group consisting of SEQ ID NOs: 6 and 16; the LCDR1 sequence is selected from the group consisting of SEQ ID NOs: 8, 18, 24, 31, 35, 45, and 49; the LCDR2 sequence is selected from the group consisting of SEQ ID NOs: 9, 19, and 25; and/or the LCDR3 sequence is selected from the group consisting of SEQ ID NOs: 10, 26, and 36.

In certain embodiments, the antigen-binding site comprises a VH comprising HCDR1, HCDR2, and HCDR3 sequences set forth in SEQ ID NOs: 53, 61, and 56, respectively, and a VL comprising LCDR1, LCDR2, and LCDR3 sequences set forth in SEQ ID NOs: 57, 60, and 59, respectively, wherein the antigen-binding site does not comprise HCDR1, HCDR2, HCDR3, LCDR1, LCDR2, and LCDR3 sequences set forth in SEQ ID NOs: 4, 23, 17, 18, 19, and 10, respectively. In certain embodiments, the HCDR1 sequence is selected from the group consisting of SEQ ID NOs: 4 and 30; the HCDR2 sequence is selected from the group consisting of SEQ ID NOs: 5, 23, 34, 42, and 48; the HCDR3 sequence is selected from the group consisting of SEQ ID NOs: 7 and 17; the LCDR1 sequence is selected from the group consisting of SEQ ID NOs: 8, 18, 24, 31, 35, 45, and 49; the LCDR2 sequence is selected from the group consisting of SEQ ID NOs: 9, 19, and 25; and/or the LCDR3 sequence is selected from the group consisting of SEQ ID NOs: 10, 26, and 36.

In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 1, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 2.

In certain embodiments, the antigen-binding site has a higher binding affinity to human CD19 relative to an antigen-binding site having VH and VL sequences set forth in SEQ ID NOs: 20 and 13, respectively. In certain embodiments, the antigen-binding site binds human CD19 or an extracellular fragment thereof with a $K_D$ lower than or equal to 0.2 nM, as measured by SPR when the antigen-binding site is present as a monomer. In certain embodiments, the antigen-binding site binds human CD19 or an extracellular fragment thereof with a $K_D$ in the range of 0.05-0.2 nM or in the range of 0.1-0.2 nM, as measured by SPR when the antigen-binding site is present as a monomer.

Individual Constructs

In certain embodiments, the antigen-binding site that binds CD19 is derived from CNG-CD19-101. In certain embodiments, the antigen-binding site comprises a VH comprising HCDR1, HCDR2, and HCDR3 sequences set forth in SEQ ID NOs: 3, 5, and 6, respectively, and a VL comprising LCDR1, LCDR2, and LCDR3 sequences set forth in SEQ ID NOs: 8, 9, and 10, respectively. In certain embodiments, the antigen-binding site comprises a VH comprising HCDR1, HCDR2, and HCDR3 sequences set forth in SEQ ID NOs: 4, 5, and 7, respectively, and a VL comprising LCDR1, LCDR2, and LCDR3 sequences set forth in SEQ ID NOs: 8, 9, and 10, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 1, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 2. In certain embodiments, the VH and the VL comprise the amino acid sequences of SEQ ID NOs: 1 and 2, respectively.

In certain embodiments, the antigen-binding site that binds CD19 is derived from CNG-CD19-102. In certain embodiments, the antigen-binding site comprises a VH comprising HCDR1, HCDR2, and HCDR3 sequences set forth in SEQ ID NOs: 14, 15, and 16, respectively, and a VL comprising LCDR1, LCDR2, and LCDR3 sequences set forth in SEQ ID NOs: 18, 19, and 10, respectively. In certain embodiments, the antigen-binding site comprises a VH comprising HCDR1, HCDR2, and HCDR3 sequences set forth in SEQ ID NOs: 4, 15, and 17, respectively, and a VL comprising LCDR1, LCDR2, and LCDR3 sequences set forth in SEQ ID NOs: 18, 19, and 10, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 12, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 13. In certain embodiments, the VH and the VL comprise the amino acid sequences of SEQ ID NOs: 12 and 13, respectively.

In certain embodiments, the antigen-binding site that binds CD19 is derived from CNG-CD19-103. In certain embodiments, the antigen-binding site comprises a VH comprising HCDR1, HCDR2, and HCDR3 sequences set forth in SEQ ID NOs: 22, 23, and 16, respectively, and a VL comprising LCDR1, LCDR2, and LCDR3 sequences set forth in SEQ ID NOs: 24, 25, and 26, respectively. In certain embodiments, the antigen-binding site comprises a VH comprising HCDR1, HCDR2, and HCDR3 sequences set forth in SEQ ID NOs: 4, 23, and 17, respectively, and a VL comprising LCDR1, LCDR2, and LCDR3 sequences set forth in SEQ ID NOs: 24, 25, and 26, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 20, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 21. In certain embodiments, the VH and the VL comprise the amino acid sequences of SEQ ID NOs: 20 and 21, respectively.

In certain embodiments, the antigen-binding site that binds CD19 is derived from CNG-CD19-104. In certain embodiments, the antigen-binding site comprises a VH comprising HCDR1, HCDR2, and HCDR3 sequences set forth in SEQ ID NOs: 29, 23, and 6, respectively, and a VL comprising LCDR1, LCDR2, and LCDR3 sequences set forth in SEQ ID NOs: 31, 25, and 10, respectively. In certain embodiments, the antigen-binding site comprises a VH comprising HCDR1, HCDR2, and HCDR3 sequences set forth in SEQ ID NOs: 30, 23, and 7, respectively, and a VL comprising LCDR1, LCDR2, and LCDR3 sequences set forth in SEQ ID NOs: 31, 25, and 10, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 27, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 28. In certain embodiments, the VH and the VL comprise the amino acid sequences of SEQ ID NOs: 27 and 28, respectively.

In certain embodiments, the antigen-binding site that binds CD19 is derived from CNG-CD19-105. In certain embodiments, the antigen-binding site comprises a VH comprising HCDR1, HCDR2, and HCDR3 sequences set forth in SEQ ID NOs: 14, 34, and 6, respectively, and a VL comprising LCDR1, LCDR2, and LCDR3 sequences set forth in SEQ ID NOs: 35, 25, and 36, respectively. In certain embodiments, the antigen-binding site comprises a VH comprising HCDR1, HCDR2, and HCDR3 sequences set forth in SEQ ID NOs: 4, 34, and 7, respectively, and a VL comprising LCDR1, LCDR2, and LCDR3 sequences set forth in SEQ ID NOs: 35, 25, and 36, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 32, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 33. In certain embodiments, the VH and the VL comprise the amino acid sequences of SEQ ID NOs: 32 and 33, respectively.

In certain embodiments, the antigen-binding site that binds CD19 is derived from CNG-CD19-106. In certain embodiments, the antigen-binding site comprises a VH comprising HCDR1, HCDR2, and HCDR3 sequences set forth in SEQ ID NOs: 3, 39, and 16, respectively, and a VL comprising LCDR1, LCDR2, and LCDR3 sequences set forth in SEQ ID NOs: 24, 25, and 10, respectively. In certain embodiments, the antigen-binding site comprises a VH comprising HCDR1, HCDR2, and HCDR3 sequences set forth in SEQ ID NOs: 4, 39, and 17, respectively, and a VL comprising LCDR1, LCDR2, and LCDR3 sequences set forth in SEQ ID NOs: 24, 25, and 10, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 37, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 38. In certain embodiments, the VH and the VL comprise the amino acid sequences of SEQ ID NOs: 37 and 38, respectively.

In certain embodiments, the antigen-binding site that binds CD19 is derived from CNG-CD19-107. In certain embodiments, the antigen-binding site comprises a VH comprising HCDR1, HCDR2, and HCDR3 sequences set forth in SEQ ID NOs: 3, 42, and 16, respectively, and a VL comprising LCDR1, LCDR2, and LCDR3 sequences set forth in SEQ ID NOs: 18, 25, and 10, respectively. In certain embodiments, the antigen-binding site comprises a VH comprising HCDR1, HCDR2, and HCDR3 sequences set forth in SEQ ID NOs: 4, 42, and 17, respectively, and a VL comprising LCDR1, LCDR2, and LCDR3 sequences set forth in SEQ ID NOs: 18, 25, and 10, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 40, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 41. In certain embodiments, the VH and the VL comprise the amino acid sequences of SEQ ID NOs: 40 and 41, respectively.

In certain embodiments, the antigen-binding site that binds CD19 is derived from CNG-CD19-108. In certain embodiments, the antigen-binding site comprises a VH comprising HCDR1, HCDR2, and HCDR3 sequences set forth in SEQ ID NOs: 29, 23, and 16, respectively, and a VL comprising LCDR1, LCDR2, and LCDR3 sequences set forth in SEQ ID NOs: 45, 19, and 36, respectively. In certain embodiments, the antigen-binding site comprises a VH comprising HCDR1, HCDR2, and HCDR3 sequences set forth in SEQ ID NOs: 30, 23, and 17, respectively, and a VL comprising LCDR1, LCDR2, and LCDR3 sequences set forth in SEQ ID NOs: 45, 19, and 36, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 43, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 44. In certain embodiments, the VH and the VL comprise the amino acid sequences of SEQ ID NOs: 43 and 44, respectively.

In certain embodiments, the antigen-binding site that binds CD19 is derived from CNG-CD19-109. In certain embodiments, the antigen-binding site comprises a VH comprising HCDR1, HCDR2, and HCDR3 sequences set forth in SEQ ID NOs: 29, 48, and 16, respectively, and a VL comprising LCDR1, LCDR2, and LCDR3 sequences set forth in SEQ ID NOs: 49, 9, and 26, respectively. In certain embodiments, the antigen-binding site comprises a VH comprising HCDR1, HCDR2, and HCDR3 sequences set forth in SEQ ID NOs: 30, 48, and 17, respectively, and a VL comprising LCDR1, LCDR2, and LCDR3 sequences set forth in SEQ ID NOs: 49, 9, and 26, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 46, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 47. In certain embodiments, the VH and the VL comprise the amino acid sequences of SEQ ID NOs: 46 and 47, respectively.

In certain embodiments, the antigen-binding site that binds CD19 is derived from CNG-CD19-110. In certain embodiments, the antigen-binding site comprises a VH comprising HCDR1, HCDR2, and HCDR3 sequences set forth in SEQ ID NOs: 22, 23, and 16, respectively, and a VL comprising LCDR1, LCDR2, and LCDR3 sequences set forth in SEQ ID NOs: 18, 51, and 36, respectively. In certain embodiments, the antigen-binding site comprises a VH comprising HCDR1, HCDR2, and HCDR3 sequences set forth in SEQ ID NOs: 4, 23, and 17, respectively, and a VL comprising LCDR1, LCDR2, and LCDR3 sequences set forth in SEQ ID NOs: 18, 51, and 36, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 20, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 50. In certain embodiments, the VH and the VL comprise the amino acid sequences of SEQ ID NOs: 20 and 50, respectively.

In certain embodiments, the antigen-binding site derived from CNG-CD19-101, CNG-CD19-102, CNG-CD19-103, CNG-CD19-110, CNG-CD19-104, CNG-CD19-105, CNG-CD19-106, CNG-CD19-107, CNG-CD19-108, or CNG-CD19-109 has a higher binding affinity to human and/or cynomolgus CD19 relative to an antigen-binding site having VH and VL sequences set forth in SEQ ID NOs: 20 and 13, respectively.

In certain embodiments, the antigen-binding site derived from CNG-CD19-101, CNG-CD19-102, CNG-CD19-103, CNG-CD19-104, CNG-CD19-105, CNG-CD19-106, CNG-CD19-107, CNG-CD19-108, or CNG-CD19-109 binds human CD19 or an extracellular fragment thereof with a $K_D$ lower than or equal to 0.3 nM, as measured by SPR when the antigen-binding site is present as a monomer. In certain embodiments, the antigen-binding site derived from CNG-CD19-101, CNG-CD19-102, CNG-CD19-103, CNG-CD19-104, CNG-CD19-105, CNG-CD19-106, CNG-CD19-107, CNG-CD19-108, or CNG-CD19-109 binds human CD19 or an extracellular fragment thereof with a $K_D$ in the range of 0.05-0.3 nM or in the range of 0.1-0.3 nM, as measured by SPR when the antigen-binding site is present as a monomer.

In certain embodiments, the antigen-binding site derived from CNG-CD19-101, CNG-CD19-103, CNG-CD19-104, CNG-CD19-105, CNG-CD19-107, CNG-CD19-108, or CNG-CD19-109 binds human CD19 or an extracellular fragment thereof with a $K_D$ lower than or equal to 0.2 nM, as measured by SPR when the antigen-binding site is present as a monomer. In certain embodiments, the antigen-binding site derived from CNG-CD19-101, CNG-CD19-103, CNG-CD19-104, CNG-CD19-105, CNG-CD19-107, CNG-CD19-108, or CNG-CD19-109 binds human CD19 or an extracellular fragment thereof with a $K_D$ in the range of 0.05-0.2 nM or in the range of 0.1-0.2 nM, as measured by SPR when the antigen-binding site is present as a monomer.

In certain embodiments, the antigen-binding site derived from CNG-CD19-103, CNG-CD19-110, CNG-CD19-104, CNG-CD19-105, CNG-CD19-106, CNG-CD19-107, CNG-CD19-108, or CNG-CD19-109 binds cynomolgus CD19 with a $K_D$ lower than or equal to 9 nM, 8 nM, 7 nM, 6 nM, 5 nM, 4 nM, or 3 nM, as measured by SPR when the antigen-binding site is present as a monomer. In certain embodiments, the antigen-binding site derived from CNG-CD19-103, CNG-CD19-110, CNG-CD19-104, CNG-CD19-105, CNG-CD19-106, CNG-CD19-107, CNG-CD19-108, or CNG-CD19-109 binds cynomolgus CD19 with a $K_D$ in the range of 1-9 nM, 1-8 nM, 1-7 nM, 1-6 nM, 1-5 nM, 1-4 nM, or 1-3 nM, as measured by SPR when the antigen-binding site is present as a monomer.

The present disclosure also provides an antigen-binding site that competes for binding CD19 (e.g., human CD19) with an antibody or antigen-binding site comprising the VH, VL and/or scFv sequences provided in Table 1.

In certain embodiments, the antigen-binding site that binds CD19 is in the form of an scFv. In certain embodiments, the VH is positioned C-terminal to the VL. In certain embodiments, the VH is positioned N-terminal to the VL. In certain embodiments, the VH and the VL are linked by a peptide linker, for example, a linker disclosed in subsection E below titled "Linkers." To stabilize the scFv, the amino acid residues at position 44 of the VH and at position 100 of the VL (under Kabat numbering) can be substituted by Cys, thereby facilitating the formation of a disulfide bond between the VH and the VL. Accordingly, in certain embodiments, the VH and VL comprise Cys at positions 100 and 44, respectively. In certain embodiments, the scFv comprises the amino acid sequence of SEQ ID NO: 11.

In another aspect, the present disclosure provides an antigen-binding site that binds CD19 (e.g., human CD19) derived from the antibodies listed in Table 2. The present disclosure also provides an antibody comprising the antigen-binding site. The CDR sequences are identified under the Kabat numbering scheme unless indicated by an asterisk (*).

TABLE 2

Sequences of Exemplary Antibodies That Bind CD19

| Antibody | VH and HCDRs | VL and LCDRs |
| --- | --- | --- |
| CNG-CD19-701 | QVQLQESGPGLVKPSQTLSLTCTVSGGS ISTSTMGVGWIRQHPGKGLEWIGFIWW DDDKRYNPNLKSRVTMSVDTSKNQFSL KLSSVTAADTAVYYCARMELWSYYFD YWGQGTLVTVSS (SEQ ID NO: 62)<br><br>HCDR1*: GSISTSTMGVG (SEQ ID NO: 64)<br><br>HCDR1: TSTMGVG (SEQ ID NO: 65)<br><br>HCDR2: FIWWDDDKRYNPNLKS (SEQ ID NO: 66)<br><br>HCDR3*: ARMELWSYYFDY (SEQ ID NO: 67)<br><br>HCDR3: MELWSYYFDY (SEQ ID NO: 68)<br><br>scFv:<br>EIVLTQSPATLSLSPGERATLSCSASSSVGYMHWYQQKPGQAPRLLIYDTSKL ASGIPARFSGSGSGTDFTLTISSLEPEDFAVYYCFQGSVYPFTFGQGTKLEIK GGGGSGGGGSGGGGSQVQLQESGPGLVKPSQTLSLTCTVSGGSISTSTMGVGW IRQHPGKGLEWIGFIWWDDDKRYNPNLKSRVTMSVDTSKNQFSLKLSSVTAAD TAVYYCARMELWSYYFD YWGQGTLVTVSS (SEQ ID NO: 72) | EIVLTQSPATLSLSPGERATLSCSA SSSVGYMHWYQQKPGQAPRLLIY DTSKLASGIPARFSGSGSGTDFTL TISSLEPEDFAVYYCFQGSVYPFT FGQGTKLEIK (SEQ ID NO: 63)<br><br>LCDR1: SASSSVGYMH (SEQ ID NO: 69)<br><br>LCDR2: DTSKLAS (SEQ ID NO: 70)<br><br>LCDR3: FQGSVYPFT (SEQ ID NO: 71) |
| CNG-CD19-702 | QVQLQESGPGLVKPSQTLSLTCTVSGGS TSTSGMGVSWIRQHPGKGLEWIGHIWW DDDKRYNPVLKSRVTISVDTSKNQFSL KLSSVTAADTAVYYCARMELWSYYFD PWGQGTLVTVSS (SEQ ID NO: 73)<br><br>HCDR1*: GSTSTSGMGVS (SEQ ID NO: 75)<br><br>HCDR1: TSGMGVS (SEQ ID NO: 76) | EIVLTQSPATLSLSPGERATLSCSA SSSVSYMHWYQQKPGQAPRLLIY DTSKLASGIPARFSGSGSGTDFTL TISSLEPEDFAVYYCFQGSVYPFT FGQGTKLEIK (SEQ ID NO: 74)<br><br>LCDR1: SASSSVSYMH (SEQ ID NO: 80)<br><br>LCDR2: DTSKLAS (SEQ ID NO: 70) |

TABLE 2-continued

Sequences of Exemplary Antibodies That Bind CD19

| Antibody | VH and HCDRs | VL and LCDRs |
|---|---|---|
| | HCDR2: HIWWDDDKRYNPVLKS (SEQ ID NO: 77)<br><br>HCDR3*: ARMELWSYYFDP (SEQ ID NO: 78)<br><br>HCDR3: MELWSYYFDP (SEQ ID NO: 79) | LCDR3: FQGSVYPFT (SEQ ID NO: 71) |
| CNG-CD19-703 | QVQLQESGPGLVKPSQTLSLTCTVSGGS ISTSTMGVGWIRQHPGKGLEWIGFIWW DDDKRYNPNLKSRVTMSVDTSKNQFSL KLSSVTAADTAVYYCARMELWSYYFE YWGQGTLVTVSS (SEQ ID NO: 81)<br><br>HCDR1*: GSISTSTMGVG (SEQ ID NO: 64)<br><br>HCDR1: TSTMGVG (SEQ ID NO: 65)<br><br>HCDR2: FIWWDDDKRYNPNLKS (SEQ ID NO: 66)<br><br>HCDR3*: ARMELWSYYFEY (SEQ ID NO: 82)<br><br>HCDR3: MELWSYYFEY (SEQ ID NO: 83) | EIVLTQSPATLSLSPGERATLSCSA SSSSVSYMHWYQQKPGQAPRLLIY DTSKLASGIPARFSGSGSGTDFTL TISSLEPEDFAVYYCFQGSVYPFT FGQGTKLEIK (SEQ ID NO: 74)<br><br>LCDR1: SASSSVSYMH (SEQ ID NO: 80)<br><br>LCDR2: DTSKLAS (SEQ ID NO: 70)<br><br>LCDR3: FQGSVYPFT (SEQ ID NO: 71) |
| CNG-CD19-704 | QVQLQESGPGLVKPSQTLSLTCTVSGGS IASGMGVGWIRQHPGKGLEWIGHIWW DDDKRYNPALKSRVTISVDTSKNQFSL KLSSVTAADTAVYYCARMELWSYYFD GWGQGTLVTVSS (SEQ ID NO: 84)<br><br>HCDR1*: GSIASGMGVG (SEQ ID NO: 85)<br><br>HCDR1: SGMGVG (SEQ ID NO: 86)<br><br>HCDR2: HIWWDDDKRYNPALKS (SEQ ID NO: 87)<br><br>HCDR3*: ARMELWSYYFDG (SEQ ID NO: 88)<br><br>HCDR3: MELWSYYFDG (SEQ ID NO: 89) | EIVLTQSPATLSLSPGERATLSCSA SSSSVSYMHWYQQKPGQAPRLLIY DTSKLASGIPARFSGSGSGTDFTL TISSLEPEDFAVYYCFQGSVYPFT FGQGTKLEIK (SEQ ID NO: 74)<br><br>LCDR1: SASSSVSYMH (SEQ ID NO: 80)<br><br>LCDR2: DTSKLAS (SEQ ID NO: 70)<br><br>LCDR3: FQGSVYPFT (SEQ ID NO: 71) |
| CNG-CD19-705 | QVQLQESGPGLVKPSQTLSLTCTVSGGS ISTSGMGVGWIRQHPGKGLEWIGHIWW DDDKRYNPALKSRVTISVDTSKNQFSL KLSSVTAADTAVYYCARMELWSYYFD YWGQGTLVTVSS (SEQ ID NO: 90)<br><br>HCDR1*: GSISTSGMGVG (SEQ ID NO: 92)<br><br>HCDR1: TSGMGVG (SEQ ID NO: 93)<br><br>HCDR2: HIWWDDDKRYNPALKS (SEQ ID NO: 87)<br><br>HCDR3*: ARMELWSYYFDY (SEQ ID NO: 67)<br><br>HCDR3: MELWSYYFDY (SEQ ID NO: 68) | EIVLTQSPATLSLSPGERATLSCSA SSSSVGYMHWYQQKPGQAPRLLIY DTSSLASGIPARFSGSGSGTDFTLT ISSLEPEDFAVYYCFQGSVYPFTF GQGTKLEIK (SEQ ID NO: 91)<br><br>LCDR1: SASSSVGYMH (SEQ ID NO: 69)<br><br>LCDR2: DTSSLAS (SEQ ID NO: 94)<br><br>LCDR3: FQGSVYPFT (SEQ ID NO: 71) |
| CNG-CD19-706 | QVQLQESGPGLVKPSQTLSLTCTVSGGS IASGMGVSWIRQHPGKGLEWIGHIWWD DDKRYNPALKSRVTISVDTSKNQFSLKL SSVTAADTAVYYCARMELWSYYFDPW GQGTLVTVSS (SEQ ID NO: 95)<br><br>HCDR1*: GSIASGMGVS (SEQ ID NO: 96)<br><br>HCDR1: SGMGVS (SEQ ID NO: 97) | EIVLTQSPATLSLSPGERATLSCSA SSSSVGYMHWYQQKPGQAPRLLIY DTSKLASGIPARFSGSGSGTDFTL TISSLEPEDFAVYYCFQGSVYPFT FGQGTKLEIK (SEQ ID NO: 63)<br><br>LCDR1: SASSSVGYMH (SEQ ID NO: 69) |

TABLE 2-continued

Sequences of Exemplary Antibodies That Bind CD19

| Antibody | VH and HCDRs | VL and LCDRs |
|---|---|---|
| | HCDR2: HIWWDDDKRYNPALKS (SEQ ID NO: 87) | LCDR2: DTSKLAS (SEQ ID NO: 70) |
| | HCDR3*: ARMELWSYYFDP (SEQ ID NO: 78) | LCDR3: FQGSVYPFT (SEQ ID NO: 71) |
| | HCDR3: MELWSYYFDP (SEQ ID NO: 79) | |
| CNG-CD19-707 | QVQLQESGPGLVKPSQTLSLTCTVSGGSISTSTMGVGWIRQHPGKGLEWIGFIWWDDDKRYNPNLKSRVTMSVDTSKNQFSLKLSSVTAADTAVYYCARMELWSYYFDPWGQGTLVTVSS (SEQ ID NO: 98) | EIVLTQSPATLSLSPGERATLSCSASSSVGYMHWYQQKPGQAPRLLIYDTSKLASGIPARFSGSGSGTDFTLTISSLEPEDFAVYYCFQGSVYPFTFGQGTKLEIK (SEQ ID NO: 63) |
| | HCDR1*: GSISTSTMGVG (SEQ ID NO: 64) | LCDR1: SASSSVGYMH (SEQ ID NO: 69) |
| | HCDR1: TSTMGVG (SEQ ID NO: 65) | LCDR2: DTSKLAS (SEQ ID NO: 70) |
| | HCDR2: FIWWDDDKRYNPNLKS (SEQ ID NO: 66) | LCDR3: FQGSVYPFT (SEQ ID NO: 71) |
| | HCDR3*: ARMELWSYYFDP (SEQ ID NO: 78) | |
| | HCDR3: MELWSYYFDP (SEQ ID NO: 79) | |
| CNG-CD19-708 | QVQLQESGPGLVKPSQTLSLTCTVSGGSISTSTMGVGWIRQHPGKGLEWIGFIWWDDDKRYNPNLKSRVTMSVDTSKNQFSLKLSSVTAADTAVYYCARMELWSYYFDPWGQGTLVTVSS (SEQ ID NO: 98) | EIVLTQSPATLSLSPGERATLSCSASSSVGYMHWYQQKPGQAPRLLIYDTSKLSSGIPARFSGSGSGTDFTLTISSLEPEDFAVYYCFQGSVYPFTFGQGTKLEIK (SEQ ID NO: 99) |
| | HCDR1*: GSISTSTMGVG (SEQ ID NO: 64) | LCDR1: SASSSVGYMH (SEQ ID NO: 69) |
| | HCDR1: TSTMGVG (SEQ ID NO: 65) | LCDR2: DTSKLSS (SEQ ID NO: 100) |
| | HCDR2: FIWWDDDKRYNPNLKS (SEQ ID NO: 66) | LCDR3: FQGSVYPFT (SEQ ID NO: 71) |
| | HCDR3*: ARMELWSYYFDP (SEQ ID NO: 78) | |
| | HCDR3: MELWSYYFDP (SEQ ID NO: 79) | |
| CNG-CD19-709 | QVQLQESGPGLVKPSQTLSLTCTVSGGSISTSTMGVGWIRQHPGKGLEWIGFIWWDDDKRYNPNLKSRVTMSVDTSKNQFSLKLSSVTAADTAVYYCARMELWSYYFDPWGQGTLVTVSS (SEQ ID NO: 98) | EIVLTQSPATLSLSPGERATLSCSASSSVGYMHWYQQKPGQAPRLLIYDTSKLAFGIPARFSGSGSGTDFTLTISSLEPEDFAVYYCFQGSVYPFTFGQGTKLEIK (SEQ ID NO: 101) |
| | HCDR1*: GSISTSTMGVG (SEQ ID NO: 64) | LCDR1: SASSSVGYMH (SEQ ID NO: 69) |
| | HCDR1: TSTMGVG (SEQ ID NO: 65) | LCDR2: DTSKLAF (SEQ ID NO: 102) |
| | HCDR2: FIWWDDDKRYNPNLKS (SEQ ID NO: 66) | LCDR3: FQGSVYPFT (SEQ ID NO: 71) |
| | HCDR3*: ARMELWSYYFDP (SEQ ID NO: 78) | |
| | HCDR3: MELWSYYFDP (SEQ ID NO: 79) | |
| CNG-CD19-710 | QVQLQESGPGLVKPSQTLSLTCTVSGVSISTSSMGVGWIRQHPGKGLEWIGHAWWDDDKRYNPALKSRVTISVDTSKNQFSLKLSSVTAADTAVYYCARMELWSYYFDPWGQGTLVTVSS (SEQ ID NO: 103) | EIVLTQSPATLSLSPGERATLSCSASSSFSYMHWYQQKPGQAPRLLIYDTSKLASGIPARFSGSGSGTDFTLTISSLEPEDFAVYYCFQGSVYPFTFGQGTKLEIK (SEQ ID NO: 104) |
| | HCDR1*: VSISTSSMGVG (SEQ ID NO: 105) | LCDR1: SASSSFSYMH (SEQ ID NO: 108) |
| | HCDR1: TSSMGVG (SEQ ID NO: 106) | LCDR2: DTSKLAS (SEQ ID NO: 70) |

TABLE 2-continued

Sequences of Exemplary Antibodies That Bind CD19

| Antibody | VH and HCDRs | VL and LCDRs |
|---|---|---|
| | HCDR2: HAWWDDDKRYNPALKS (SEQ ID NO: 107) | LCDR3: FQGSVYPFT (SEQ ID NO: 71) |
| | HCDR3*: ARMELWSYYFDP (SEQ ID NO: 78) | |
| | HCDR3: MELWSYYFDP (SEQ ID NO: 79) | |
| Consensus-1 (CNG-CD19-701 to -710) | HCDR1*: $X_1SX_2X_3X_4SX_5MGVX_6$, wherein $X_1$ is G or V; $X_2$ is I or T; $X_3$ is S or A; $X_4$ is T or no amino acid residue; $X_5$ is G or T; and $X_6$ is G or S (SEQ ID NO: 109) | LCDR1: SASSSXXYMH, wherein $X_1$ is V or F; and $X_2$ is S or G (SEQ ID NO: 114) |
| | HCDR1: $X_1SX_2MGVX_3$, wherein $X_1$ is T or no amino acid residue; $X_2$ is G or T; and $X_3$ is G or S (SEQ ID NO: 110) | LCDR2: $DTSX_1LX_2X_3$, wherein $X_1$ is K or S; $X_2$ is A or S; and $X_3$ is S or F (SEQ ID NO: 115) |
| | HCDR2: $X_1X_2WWDDDKRYNPX_3LKS$, wherein $X_1$ is H or F; $X_2$ is I or A; and $X_3$ is A, N, or V (SEQ ID NO: 111) | LCDR3: FQGSVYPFT (SEQ ID NO: 71) |
| | HCDR3*: $ARMELWSYYFX_1X_2$, wherein $X_1$ is D or E; and $X_2$ is Y, P, or G (SEQ ID NO: 112) | |
| | HCDR3: $MELWSYYFX_1X_2$, wherein $X_1$ is D or E; and $X_2$ is Y, P, or G (SEQ ID NO: 113) | |
| Consensus-2 (CNG-CD19-701 and -706 to -710) | HCDR1*: $X_1SIX_2X_3SX_4MGVX_5$, wherein $X_1$ is G or V; $X_2$ is S or A; $X_3$ is T or no amino acid residue; $X_4$ is G or T; and $X_5$ is G or S (SEQ ID NO: 116) | LCDR1: SASSSXXYMH, wherein $X_1$ is V or F; and $X_2$ is S or G (SEQ ID NO: 114) |
| | HCDR1: $X_1SX_2MGVX_3$, wherein $X_1$ is T or no amino acid residue; $X_2$ is G or T; and $X_3$ is G or S (SEQ ID NO: 110) | LCDR2: $DTSKLX_1X_2$, wherein $X_1$ is A or S; and $X_2$ is S or F (SEQ ID NO: 120) |
| | HCDR2: $X_1X_2WWDDDKRYNPX_3LKS$, wherein $X_1$ is H or F; $X_2$ is I or A; and $X_3$ is A or N (SEQ ID NO: 117) | LCDR3: FQGSVYPFT (SEQ ID NO: 71) |
| | HCDR3*: ARMELWSYYFDX, wherein X is Y or P (SEQ ID NO: 118) | |
| | HCDR3: MELWSYYFDX, wherein X is Y or P (SEQ ID NO: 119) | |

In certain embodiments, the antigen-binding site that binds CD19 of the present invention comprises a VH that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VH of an antibody disclosed in Table 2, and a VL that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VL of the same antibody disclosed in Table 2. In certain embodiments, the antigen-binding site comprises the HCDR1, HCDR2, HCDR3, LCDR1, LCDR2, and LCDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J Mol Biol 196: 901-917), MacCallum (see MacCallum R M et al., (1996) J Mol Biol 262: 732-745), IMGT (see Lefranc, (1999) The Immunologist, 7, 132-136), or any other CDR determination method known in the art, of the VH and VL sequences of an antibody disclosed in Table 2. In certain embodiments, the antigen-binding site comprises the HCDR1, HCDR2, HCDR3, LCDR1, LCDR2, and LCDR3 sequences of an antibody disclosed in Table 2. In certain embodiments, the antigen-binding site comprises the VH and VL sequences of an antibody disclosed in Table 2.

Series 1 Constructs

In certain embodiments, the antigen-binding site that binds CD19 comprises a VH comprising HCDR1, HCDR2, and HCDR3 sequences set forth in SEQ ID NOs: 109, 111, and 112, respectively, and a VL comprising LCDR1, LCDR2, and LCDR3 sequences set forth in SEQ ID NOs: 114, 115, and 71, respectively, wherein the antigen-binding site does not comprise HCDR1, HCDR2, HCDR3, LCDR1, LCDR2, and LCDR3 sequences set forth in SEQ ID NOs: 92, 87, 67, 80, 70, and 71, respectively. In certain embodiments, the HCDR1 sequence is selected from the group consisting of SEQ ID NOs: 64, 75, 85, 92, 96, and 105; the HCDR2 sequence is selected from the group consisting of SEQ ID NOs: 66, 77, 87, and 107; the HCDR3 sequence is selected from the group consisting of SEQ ID NOs: 67, 78, 82, and 88; the LCDR1 sequence is selected from the group consisting of SEQ ID NOs: 69, 80, and 108; the LCDR2 sequence is selected from the group consisting of SEQ ID NOs: 70, 94, 100, and 102; and/or the LCDR3 sequence is SEQ ID NO: 71.

In certain embodiments, the antigen-binding site comprises a VH comprising HCDR1, HCDR2, and HCDR3 sequences set forth in SEQ ID NOs: 110, 111, and 113, respectively, and a VL comprising LCDR1, LCDR2, and LCDR3 sequences set forth in SEQ ID NOs: 114, 115, and 71, respectively, wherein the antigen-binding site does not comprise HCDR1, HCDR2, HCDR3, LCDR1, LCDR2, and LCDR3 sequences set forth in SEQ ID NOs: 93, 87, 68, 80, 70, and 71, respectively. In certain embodiments, the HCDR1 sequence is selected from the group consisting of SEQ ID NOs: 65, 76, 86, 93, 97, and 106; the HCDR2 sequence is selected from the group consisting of SEQ ID NOs: 66, 77, 87, and 107; the HCDR3 sequence is selected from the group consisting of SEQ ID NOs: 68, 79, 83, and 89; the LCDR1 sequence is selected from the group consisting of SEQ ID NOs: 69, 80, and 108; the LCDR2 sequence is selected from the group consisting of SEQ ID NOs: 70, 94, 100, and 102; and/or the LCDR3 sequence is SEQ ID NO: 71.

In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 62, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 63.

In certain embodiments, the antigen-binding site has a higher binding affinity to human CD19 relative to an antigen-binding site having VH and VL sequences set forth in SEQ ID NOs: 90 and 74, respectively. In certain embodiments, the antigen-binding site binds human CD19 or an extracellular fragment thereof with a $K_D$ lower than or equal to 2 nM, 1 nM, or 0.5 nM, as measured by surface plasmon resonance (SPR) when the antigen-binding site is present as a monomer. In certain embodiments, the antigen-binding site binds human CD19 or an extracellular fragment thereof with a $K_D$ in the range of 0.05-2 nM, in the range of 0.05-1 nM, or in the range of 0.05-0.5 nM, as measured by SPR when the antigen-binding site is present as a monomer.

Series 2 Constructs

In certain embodiments, the antigen-binding site that binds CD19 comprises a VH comprising HCDR1, HCDR2, and HCDR3 sequences set forth in SEQ ID NOs: 116, 117, and 118, respectively, and a VL comprising LCDR1, LCDR2, and LCDR3 sequences set forth in SEQ ID NOs: 114, 120, and 71, respectively, wherein the antigen-binding site does not comprise HCDR1, HCDR2, HCDR3, LCDR1, LCDR2, and LCDR3 sequences set forth in SEQ ID NOs: 92, 87, 67, 80, 70, and 71, respectively. In certain embodiments, the HCDR1 sequence is selected from the group consisting of SEQ ID NOs: 64, 96, and 105; the HCDR2 sequence is selected from the group consisting of SEQ ID NOs: 66, 87, and 107; the HCDR3 sequence is selected from the group consisting of SEQ ID NOs: 67 and 78; the LCDR1 sequence is selected from the group consisting of SEQ ID NOs: 69 and 108; the LCDR2 sequence is selected from the group consisting of SEQ ID NOs: 70, 100, and 102; and/or the LCDR3 sequence is SEQ ID NO: 71.

In certain embodiments, the antigen-binding site comprises a VH comprising HCDR1, HCDR2, and HCDR3 sequences set forth in SEQ ID NOs: 110, 117, and 119, respectively, and a VL comprising LCDR1, LCDR2, and LCDR3 sequences set forth in SEQ ID NOs: 114, 120, and 71, respectively, wherein the antigen-binding site does not comprise HCDR1, HCDR2, HCDR3, LCDR1, LCDR2, and LCDR3 sequences set forth in SEQ ID NOs: 93, 87, 68, 80, 70, and 71, respectively. In certain embodiments, the HCDR1 sequence is selected from the group consisting of SEQ ID NOs: 65, 97, and 106; the HCDR2 sequence is selected from the group consisting of SEQ ID NOs: 66, 87, and 107; the HCDR3 sequence is selected from the group consisting of SEQ ID NOs: 68 and 79; the LCDR1 sequence is selected from the group consisting of SEQ ID NOs: 69 and 108; the LCDR2 sequence is selected from the group consisting of SEQ ID NOs: 70, 100, and 102; and/or the LCDR3 sequence is SEQ ID NO: 71.

In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 62, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 63.

In certain embodiments, the antigen-binding site has a higher binding affinity to human CD19 relative to an antigen-binding site having VH and VL sequences set forth in SEQ ID NOs: 90 and 74, respectively. In certain embodiments, the antigen-binding site binds human CD19 or an extracellular fragment thereof with a $K_D$ lower than or equal to 0.4 nM, 0.3 nM, 0.2 nM, or 0.1 nM, as measured by SPR when the antigen-binding site is present as a monomer. In certain embodiments, the antigen-binding site binds human CD19 or an extracellular fragment thereof with a $K_D$ in the range of 0.05-0.4 nM, 0.05-0.3 nM, 0.05-0.2 nM, or 0.05-0.1 nM, as measured by SPR when the antigen-binding site is present as a monomer.

Individual Constructs

In certain embodiments, the antigen-binding site that binds CD19 is derived from CNG-CD19-701. In certain embodiments, the antigen-binding site comprises a VH comprising HCDR1, HCDR2, and HCDR3 sequences set forth in SEQ ID NOs: 64, 66, and 67, respectively, and a VL comprising LCDR1, LCDR2, and LCDR3 sequences set forth in SEQ ID NOs: 69, 70, and 71, respectively. In certain embodiments, the antigen-binding site comprises a VH comprising HCDR1, HCDR2, and HCDR3 sequences set forth in SEQ ID NOs: 65, 66, and 68, respectively, and a VL comprising LCDR1, LCDR2, and LCDR3 sequences set forth in SEQ ID NOs: 69, 70, and 71, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 62, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 63. In certain embodiments, the VH and the VL comprise the amino acid sequences of SEQ ID NOs: 62 and 63, respectively.

In certain embodiments, the antigen-binding site that binds CD19 is derived from CNG-CD19-702. In certain embodiments, the antigen-binding site comprises a VH comprising HCDR1, HCDR2, and HCDR3 sequences set forth in SEQ ID NOs: 75, 77, and 78, respectively, and a VL comprising LCDR1, LCDR2, and LCDR3 sequences set forth in SEQ ID NOs: 80, 70, and 71, respectively. In certain embodiments, the antigen-binding site comprises a VH comprising HCDR1, HCDR2, and HCDR3 sequences set forth in SEQ ID NOs: 76, 77, and 79, respectively, and a VL comprising LCDR1, LCDR2, and LCDR3 sequences set forth in SEQ ID NOs: 80, 70, and 71, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 73, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 74. In certain embodiments, the VH and the VL comprise the amino acid sequences of SEQ ID NOs: 73 and 74, respectively.

In certain embodiments, the antigen-binding site that binds CD19 is derived from CNG-CD19-703. In certain embodiments, the antigen-binding site comprises a VH comprising HCDR1, HCDR2, and HCDR3 sequences set forth in SEQ ID NOs: 64, 66, and 82, respectively, and a VL comprising LCDR1, LCDR2, and LCDR3 sequences set forth in SEQ ID NOs: 80, 70, and 71, respectively. In certain embodiments, the antigen-binding site comprises a VH comprising HCDR1, HCDR2, and HCDR3 sequences set forth in SEQ ID NOs: 65, 66, and 83, respectively, and a VL comprising LCDR1, LCDR2, and LCDR3 sequences set forth in SEQ ID NOs: 80, 70, and 71, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 81, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 74. In certain embodiments, the VH and the VL comprise the amino acid sequences of SEQ ID NOs: 81 and 74, respectively.

In certain embodiments, the antigen-binding site that binds CD19 is derived from CNG-CD19-704. In certain embodiments, the antigen-binding site comprises a VH comprising HCDR1, HCDR2, and HCDR3 sequences set forth in SEQ ID NOs: 85, 87, and 88, respectively, and a VL comprising LCDR1, LCDR2, and LCDR3 sequences set forth in SEQ ID NOs: 80, 70, and 71, respectively. In certain embodiments, the antigen-binding site comprises a VH comprising HCDR1, HCDR2, and HCDR3 sequences set forth in SEQ ID NOs: 86, 87, and 89, respectively, and a VL comprising LCDR1, LCDR2, and LCDR3 sequences set forth in SEQ ID NOs: 80, 70, and 71, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 84, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 74. In certain embodiments, the VH and the VL comprise the amino acid sequences of SEQ ID NOs: 84 and 74, respectively.

In certain embodiments, the antigen-binding site that binds CD19 is derived from CNG-CD19-705. In certain embodiments, the antigen-binding site comprises a VH comprising HCDR1, HCDR2, and HCDR3 sequences set forth in SEQ ID NOs: 92, 87, and 67, respectively, and a VL comprising LCDR1, LCDR2, and LCDR3 sequences set forth in SEQ ID NOs: 69, 94, and 71, respectively. In certain embodiments, the antigen-binding site comprises a VH comprising HCDR1, HCDR2, and HCDR3 sequences set forth in SEQ ID NOs: 93, 87, and 68, respectively, and a VL comprising LCDR1, LCDR2, and LCDR3 sequences set forth in SEQ ID NOs: 69, 94, and 71, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 90, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 91. In certain embodiments, the VH and the VL comprise the amino acid sequences of SEQ ID NOs: 90 and 91, respectively.

In certain embodiments, the antigen-binding site that binds CD19 is derived from CNG-CD19-706. In certain embodiments, the antigen-binding site comprises a VH comprising HCDR1, HCDR2, and HCDR3 sequences set forth in SEQ ID NOs: 96, 87, and 78, respectively, and a VL comprising LCDR1, LCDR2, and LCDR3 sequences set forth in SEQ ID NOs: 69, 70, and 71, respectively. In certain embodiments, the antigen-binding site comprises a VH comprising HCDR1, HCDR2, and HCDR3 sequences set forth in SEQ ID NOs: 97, 87, and 79, respectively, and a VL comprising LCDR1, LCDR2, and LCDR3 sequences set forth in SEQ ID NOs: 69, 70, and 71, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 95, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 63. In certain embodiments, the VH and the VL comprise the amino acid sequences of SEQ ID NOs: 95 and 63, respectively.

In certain embodiments, the antigen-binding site that binds CD19 is derived from CNG-CD19-707. In certain embodiments, the antigen-binding site comprises a VH comprising HCDR1, HCDR2, and HCDR3 sequences set forth in SEQ ID NOs: 64, 66, and 78, respectively, and a VL comprising LCDR1, LCDR2, and LCDR3 sequences set forth in SEQ ID NOs: 69, 70, and 71, respectively. In certain embodiments, the antigen-binding site comprises a VH comprising HCDR1, HCDR2, and HCDR3 sequences set forth in SEQ ID NOs: 65, 66, and 79, respectively, and a VL comprising LCDR1, LCDR2, and LCDR3 sequences set forth in SEQ ID NOs: 69, 70, and 71, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 98, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 63. In certain embodiments, the VH and the VL comprise the amino acid sequences of SEQ ID NOs: 98 and 63, respectively.

In certain embodiments, the antigen-binding site that binds CD19 is derived from CNG-CD19-708. In certain embodiments, the antigen-binding site comprises a VH comprising HCDR1, HCDR2, and HCDR3 sequences set forth in SEQ ID NOs: 64, 66, and 78, respectively, and a VL comprising LCDR1, LCDR2, and LCDR3 sequences set forth in SEQ ID NOs: 69, 100, and 71, respectively. In certain embodiments, the antigen-binding site comprises a VH comprising HCDR1, HCDR2, and HCDR3 sequences set forth in SEQ ID NOs: 65, 66, and 79, respectively, and a VL comprising LCDR1, LCDR2, and LCDR3 sequences set forth in SEQ ID NOs: 69, 100, and 71, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 98, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 99. In certain embodiments, the VH and the VL comprise the amino acid sequences of SEQ ID NOs: 98 and 99, respectively.

In certain embodiments, the antigen-binding site that binds CD19 is derived from CNG-CD19-709. In certain embodiments, the antigen-binding site comprises a VH comprising HCDR1, HCDR2, and HCDR3 sequences set forth in SEQ ID NOs: 64, 66, and 78, respectively, and a VL comprising LCDR1, LCDR2, and LCDR3 sequences set forth in SEQ ID NOs: 69, 102, and 71, respectively. In certain embodiments, the antigen-binding site comprises a VH comprising HCDR1, HCDR2, and HCDR3 sequences set forth in SEQ ID NOs: 65, 66, and 79, respectively, and a VL comprising LCDR1, LCDR2, and LCDR3 sequences set forth in SEQ ID NOs: 69, 102, and 71, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 98, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 101. In certain embodiments, the VH and the VL comprise the amino acid sequences of SEQ ID NOs: 98 and 101, respectively.

In certain embodiments, the antigen-binding site that binds CD19 is derived from CNG-CD19-710. In certain embodiments, the antigen-binding site comprises a VH comprising HCDR1, HCDR2, and HCDR3 sequences set forth in SEQ ID NOs: 105, 107, and 78, respectively, and a VL comprising LCDR1, LCDR2, and LCDR3 sequences set forth in SEQ ID NOs: 108, 70, and 71, respectively. In certain embodiments, the antigen-binding site comprises a VH comprising HCDR1, HCDR2, and HCDR3 sequences set forth in SEQ ID NOs: 106, 107, and 79, respectively, and a VL comprising LCDR1, LCDR2, and LCDR3 sequences set forth in SEQ ID NOs: 108, 70, and 71, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 103, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 104. In certain embodiments, the VH and the VL comprise the amino acid sequences of SEQ ID NOs: 103 and 104, respectively.

In certain embodiments, the antigen-binding site derived from CNG-CD19-701, CNG-CD19-702, CNG-CD19-703, CNG-CD19-704, CNG-CD19-705, CNG-CD19-706, CNG-CD19-707, CNG-CD19-708, CNG-CD19-709, or CNG-CD19-710 has a higher binding affinity to human CD19 relative to an antigen-binding site having VH and VL sequences set forth in SEQ ID NOs: 90 and 74, respectively.

In certain embodiments, the antigen-binding site derived from CNG-CD19-701, CNG-CD19-702, CNG-CD19-703, CNG-CD19-704, CNG-CD19-705, CNG-CD19-706, CNG-CD19-707, CNG-CD19-708, CNG-CD19-709, or CNG-CD19-710 binds human CD19 or an extracellular fragment thereof with a $K_D$ lower than or equal to 2 nM, 1 nM, or 0.5 nM, as measured by surface plasmon resonance (SPR) when the antigen-binding site is present as a monomer. In certain embodiments, the antigen-binding site derived from CNG-CD19-701, CNG-CD19-702, CNG-CD19-703, CNG-CD19-704, CNG-CD19-705, CNG-CD19-706, CNG-CD19-707, CNG-CD19-708, CNG-CD19-709, or CNG-CD19-710 binds human CD19 or an extracellular fragment thereof with a $K_D$ in the range of 0.05-2 nM, in the range of 0.05-1 nM, or in the range of 0.05-0.5 nM, as measured by SPR when the antigen-binding site is present as a monomer.

In certain embodiments, the antigen-binding site derived from CNG-CD19-701, CNG-CD19-706, CNG-CD19-707, CNG-CD19-708, CNG-CD19-709, or CNG-CD19-710 binds human CD19 or an extracellular fragment thereof with a $K_D$ lower than or equal to 0.4 nM, 0.3 nM, 0.2 nM, or 0.1 nM, as measured by SPR when the antigen-binding site is present as a monomer. In certain embodiments, the antigen-binding site derived from CNG-CD19-701, CNG-CD19-706, CNG-CD19-707, CNG-CD19-708, CNG-CD19-709, or CNG-CD19-710 binds human CD19 or an extracellular fragment thereof with a $K_D$ in the range of 0.05-0.4 nM, 0.05-0.3 nM, 0.05-0.2 nM, or 0.05-0.1 nM, as measured by SPR when the antigen-binding site is present as a monomer.

In certain embodiments, the antigen-binding site derived from CNG-CD19-701, CNG-CD19-702, CNG-CD19-703, CNG-CD19-704, CNG-CD19-705, CNG-CD19-706, CNG- CD19-707, CNG-CD19-708, CNG-CD19-709, or CNG-CD19-710 binds cynomolgus CD19 with a $K_D$ lower than or equal to 8 nM, 7 nM, 6 nM, 5 nM, 4 nM, or 3 nM, as measured by SPR when the antigen-binding site is present as a monomer. In certain embodiments, the antigen-binding site derived from CNG-CD19-701, CNG-CD19-702, CNG-CD19-703, CNG-CD19-704, CNG-CD19-705, CNG-CD19-706, CNG-CD19-707, CNG-CD19-708, CNG-CD19-709, or CNG-CD19-710 binds cynomolgus CD19 with a $K_D$ in the range of 1-8 nM, 1-7 nM, 1-6 nM, 1-5 nM, 1-4 nM, or 1-3 nM, as measured by SPR when the antigen-binding site is present as a monomer.

The present disclosure also provides an antigen-binding site that competes for binding CD19 (e.g., human CD19) with an antibody or antigen-binding site comprising the VH, VL and/or scFv sequences provided in Table 2.

In certain embodiments, the antigen-binding site that binds CD19 is in the form of an scFv. In certain embodiments, the VH is positioned C-terminal to the VL. In certain embodiments, the VH is positioned N-terminal to the VL. In certain embodiments, the VH and the VL are linked by a peptide linker, for example, a linker disclosed in subsection E below titled "Linkers." To stabilize the scFv, the amino acid residues at position 44 of the VH and at position 100 of the VL (under Kabat numbering) can be substituted by Cys, thereby facilitating the formation of a disulfide bond between the VH and the VL. Accordingly, in certain embodiments, the VH and VL comprise Cys at positions 100 and 44, respectively.

It is understood, however, that CNG-CD19-701 to CNG-CD19-710 exhibit high stability, having a melting temperature in the range of 80-85° C. when present in the form of an Fab. As a result, it is contemplated that antigen-binding sites derived from these antibodies are stable in the absence of such Cys substitutions. It is further contemplated that the absence of Cys substitution is advantageous in the context of a multi-specific binding protein, given that a multi-specific binding protein may comprise another antigen-binding site stabilized by a disulfide bridge formed between two Cys residues introduced. Without wishing to be bound by theory, it is possible that the presence of two pairs of Cys residues may increase the risk of misfolding as a result of formation of undesired disulfide bridge. Therefore, use of an antigen-binding site that is stable in the absence of intramolecular disulfide bridge may confer flexibility to selecting another antigen-binding site when constructing a multi-specific binding protein. Accordingly, in certain embodiments, the VH and VL do not comprise Cys at positions 100 and 44, respectively. In certain embodiments, the scFv comprises the amino acid sequence of SEQ ID NO: 72.

II. Multi-Specific Binding Proteins

In one aspect, the present disclosure provides a multi-specific binding protein that comprises a first domain (e.g., a first antigen-binding site) that binds CD19 (e.g., human CD19); a second domain (e.g., a second antigen-binding site) that binds CD3 (e.g., human and/or Macaca CD3), such as CD3ε (epsilon), CD3δ (delta), and/or CD3γ (gamma); and optionally a half-life extension domain. The multi-specific binding protein is configured to bring CD19-expressing cells, such as B cells, into spacial proximity with CD3-expressing cells, such as T cells, to enhance cytotoxicity of the CD3-expressing cells against the CD19-expressing cells. This target-specific cytotoxicity is desirable for treating diseases associated with CD19-expressing cells. The activation of the CD3-expressing cells can also result in cytokine production. Such cytokine production, when in the appropriate amount can be beneficial for T cell activation and proliferation, leading to optimal and sustained T cell re-direct target killing. However, when cytokine production is excessive it can lead to undesirable systemic toxicities such as cytokine release syndrome. To achieve target-specific cytotoxicity without eliciting excessive cytokine production, multi-specific binding proteins have been designed with high affinity to CD19 (with a $K_D$ greater than 5 pM and smaller than 1 nM as measured by SPR) and varying affinity to CD3 (with a $K_D$ ranging from lower than 10 nM to greater than 50 nM as measured by SPR). The results described in Example 9 infra, comparing multi-specific binding proteins having different binding affinities to CD3, demonstrate the benefit of using a CD3-binding domain with a $K_D$ lower than 10 nM where the multi-specific binding protein has a very high affinity to CD19 (e.g., with a $K_D$ lower than 1 nM, 0.1 nM, 50 pM, or 20 pM as measured by SPR). Specifically, a CD3-binding domain that binds CD3 with a $K_D$ in the range of 0.5 nM to 10 nM as measured by SPR, relative to a CD3-binding domain that binds CD3 with a $K_D$ greater than 10 nM as measured by SPR, confers an improvement in the multi-specific binding protein's cytotoxic activity at least as robustly as an increase in its ability to induce cytokine production. It is contemplated, therefore, that a multi-specific binding protein having an affinity to CD19 with a $K_D$ in the range of 5 pM to 1 nM, as measured by SPR, and an affinity to CD3 with a $K_D$ in the range of 0.5 nM to 10 nM, as measured by SPR, can be used, for example, at low doses, to achieve a therapeutic effect while minimizing potential safety issues. Accordingly, in certain embodiments of the multi-specific binding protein disclosed herein, the first domain binds CD19 (e.g., human CD19) with a $K_D$ within the range of 5 pM to 1 nM, and the second domain binds CD3 (e.g., human CD3) with a $K_D$ within the range of 0.5 nM to 10 nM, each $K_D$ measured by SPR.

In certain embodiments, each $K_D$ is measured by surface plasmon resonance (SPR). In certain embodiments, the first antigen-binding site binds CD19 (e.g., human CD19) with a $K_D$, as measured by SPR, within the range of 5 pM to 1 nM, 5 pM to 0.5 nM, 5 pM to 0.2 nM, 5 pM to 0.1 nM, 5 pM to 50 pM, 5 pM to 20 pM, 5 pM to 10 pM, 10 pM to 1 nM, 10 pM to 0.5 nM, 10 pM to 0.2 nM, 10 pM to 0.1 nM, 10 pM to 50 pM, or 10 pM to 20 pM. In certain embodiments, the second antigen-binding site binds CD3 (e.g., human CD3) with a $K_D$, as measured by SPR, within the range of 0.5 nM to 10 nM, 0.5 nM to 5 nM, 0.5 nM to 2 nM, 0.5 nM to 1 nM, 1 nM to 10 nM, 1 nM to 5 nM, or 1 nM to 2 nM. In certain embodiments, the first antigen-binding site binds CD19 (e.g., human CD19) with a $K_D$, as measured by SPR, within the range of 5 pM to 0.1 nM, 5 pM to 50 pM, 5 pM to 20 pM, 10 pM to 1 nM, 10 pM to 0.1 nM, 10 pM to 50 pM, or 10 pM to 20 pM, and the second antigen-binding site binds CD3 (e.g., human CD3) with a $K_D$, as measured by SPR, within the range of 0.5 nM to 10 nM. In certain embodiments, the first antigen-binding site binds CD19 (e.g., human CD19) with a $K_D$, as measured by SPR, within the range of 5 pM to 0.1 nM, 5 pM to 50 pM, 5 pM to 20 pM, 10 pM to 1 nM, 10 pM to 0.1 nM, 10 pM to 50 pM, or 10 pM to 20 pM, and the second antigen-binding site binds CD3 (e.g., human CD3) with a $K_D$, as measured by SPR, within the range of 1 nM to 10 nM.

In certain embodiments, each $K_D$ is measured by bio-layer interferometry (BLI). In certain embodiments, the first antigen-binding site binds CD19 (e.g., human CD19) with a $K_D$, as measured by BLI, within the range of 50 pM to 1 nM, 50 pM to 0.5 nM, 50 pM to 0.2 nM, 50 pM to 0.1 nM, 0.1 nM to 1 nM, 0.1 nM to 0.5 nM, or 0.1 nM to 0.2 nM. In certain embodiments, the second antigen-binding site binds CD3

(e.g., human CD3) with a $K_D$, as measured by BLI, within the range of 5 nM to 100 nM, 5 nM to 50 nM, 5 nM to 20 nM, 5 nM to 10 nM, 10 nM to 100 nM, 10 nM to 50 nM, or 10 nM to 20 nM. In certain embodiments, the first antigen-binding site binds CD19 (e.g., human CD19) with a $K_D$, as measured by BLI, within the range of 50 pM to 1 nM, 50 pM to 0.5 nM, 50 pM to 0.2 nM, 0.1 nM to 10 nM, 0.1 nM to 0.5 nM, or 0.1 nM to 0.2 nM, and the second antigen-binding site binds CD3 (e.g., human CD3) with a $K_D$, as measured by BLI, within the range of 5 nM to 100 nM. In certain embodiments, the first antigen-binding site binds CD19 (e.g., human CD19) with a $K_D$, as measured by BLI, within the range of 50 pM to 1 nM, 50 pM to 0.5 nM, 50 pM to 0.2 nM, 0.1 nM to 10 nM, 0.1 nM to 0.5 nM, or 0.1 nM to 0.2 nM, and the second antigen-binding site binds CD3 (e.g., human CD3) with a $K_D$, as measured by BLI, within the range of 10 nM to 100 nM.

In certain embodiments, the ratio of the $K_D$ with which the second antigen-binding site binds CD3 (e.g., human CD3) to the $K_D$ with which the first antigen-binding site binds CD19 (e.g., human CD19) is within the range of 10:1 to 1,000:1, 10:1 to 500:1, 10:1 to 200:1, 10:1 to 150:1, 20:1 to 1,000:1, 20:1 to 500:1, 20:1 to 200:1, 20:1 to 150:1, 50:1 to 1,000:1, 50:1 to 500:1, 50:1 to 200:1, 50:1 to 150:1, 100:1 to 1,000:1, 100:1 to 500:1, 100:1 to 200:1, or 100:1 to 150:1. In certain embodiments, the $K_D$ with which the first antigen-binding site binds CD19 and the $K_D$ with which the second antigen-binding site binds CD3 are measured by the same method (e.g., both by SPR or both by BLI).

The optional half-life extension domain can be a third domain (e.g., a third antigen-binding site) that binds serum albumin (e.g., HSA). In certain embodiments of the multi-specific binding protein disclosed herein, the first domain comprises an antigen-binding site disclosed in section I above titled "Anti-CD19 Antibodies." In certain embodiments, the first, second, and third domains comprise a first antigen-binding site, a second antigen-binding site, and a third antigen-binding site, respectively. In certain embodiments, the first antigen-binding site of the multi-specific binding protein is an antigen-binding site that binds CD19 disclosed in section I above titled "Anti-CD19 Antibodies."

Each of the antigen-binding sites of the multi-specific binding protein can take various forms, such as single-chain variable fragment (scFv), Fab fragment, or single domain antibody (sdAb). In certain embodiments, the first antigen-binding site comprises an scFv. In certain embodiments, the second antigen-binding site comprises an scFv. In certain embodiments, the third antigen-binding site comprises an sdAb.

Alternatively, it is also contemplated that one or more of the binding domains may not comprise an antigen-binding site. For example, U.S. Patent Application Publication No. US20130316952A1 discloses a polypeptide that binds serum albumin having the amino acid sequence of LKEAKEKAIEELKKAGITSDYYFDLINKAKTVEG-VNALKDEILKA (SEQ ID NO: 282). Additional exemplary polypeptides that bind HSA are described in Dennis et al. (2002) J. Biol. Chem., 277: 35035-43; Jacobs et al. (2015) Protein Eng. Des. Sel., 28: 385-93; and Zorzi et al. (2017) Nat. Commun., 8: 16092.

In certain embodiments, the multi-specific binding protein further comprises an antibody Fc region. The presence of an Fc region may increase the serum half-life of the multi-specific binding protein. Depending on the specific Fc subtype and variant used, the Fc region may also alter the activity (e.g., cytotoxic activity) of the multi-specific binding protein.

In other embodiments, the multi-specific binding protein does not comprise an antibody Fc region. The absence of Fc contributes to a smaller size of the multi-specific binding protein, which can exhibit improved tissue penetration and pharmacokinetic properties. In certain embodiments, the multi-specific binding proteins consists of or consists essentially of the first, second, and third antigen-binding sites and the linkers between them. In certain embodiments, the multi-specific binding proteins consists essentially of the first, second, and third antigen-binding sites.

In certain embodiments, the multi-specific binding protein binds CD19, CD3, and/or serum albumin monovalently. The exclusion of additional binding domains reduces the risk of non-specific immune cell activation and decreases the size of the multi-specific binding protein.

A. Antigen-Binding Site that Binds CD19

The first antigen-binding site of the multi-specific binding protein binds CD19 (e.g., human CD19). In certain embodiments, the first antigen-binding site is an antigen-binding site that binds CD19 disclosed in section I above titled "Anti-CD19 Antibodies."

Alternatively, the first antigen-binding site that binds CD19 can be derived from, for example, MT-103 (a single-chain bispecific CD19/CD3 antibody; see, Hoffman et al. (2005) Int. J. Cancer, 115: 98-104; Schlereth et al. (2006) Cancer Immunol. Immunother. 55: 503-14), a CD19/CD16 diabody (see, Schlenzka et al. (2004) Anti-cancer Drugs 15: 915-19; Kipriyanov et al. (2002) J. Immunol. 169: 137-44), BU12-saporin (see, Flavell et al. (1995) Br. J. Cancer 72: 1373-79), and anti-CD19-idarubicin (see, Rowland et al. (1993) Cancer Immunol. Immunother. 55: 503-14). Additional exemplary antigen-binding sites that bind CD19, from which the instant first antigen-binding site may be derived, are disclosed in U.S. Patent Application Publication Nos. US20170174786A1, US20090042291A1, US20160046730A1, US20070154473A1, US20090142349A1, US20180142018A1, US20090136526A1, US20060257398A1, and US20180230225A1, and PCT Publication No. WO2019057100A1. For example, in certain embodiments, the first antigen-binding site that binds CD19 is derived from an antibody listed in Table 3.

TABLE 3

Sequences of Exemplary Antibodies That Bind CD19

| Antibody | VH and HCDRs | VL and LCDRs |
|---|---|---|
| CNG-CD19-1 | QVQLVQSGAEVKKPGASVKVSCKASG YTFTDYIMHWVRQAPGQGLEWMGYIN PYNDGSKYTEKFQGRVTMTSDTSISTA YMELSRLRSDDTAVYYCARGTYYYGP QLFDYWGQGTTVTVSS (SEQ ID NO: 20) | DIVMTQTPLSLSVTPGQPASISCKSS QSLETSTGTTYLNWYLQKPGQSPQ LLIYRVSKRFSGVPDRFSGSGSGTD FTLKISRVEAEDVGVYYCLQLLEDP YTFGQGTKLEIK (SEQ ID NO: 13) |

TABLE 3-continued

Sequences of Exemplary Antibodies That Bind CD19

| Antibody | VH and HCDRs | VL and LCDRs |
|---|---|---|
| | HCDR1*: YTFTDYIMH (SEQ ID NO: 22) | LCDR1: KSSQSLETSTGTTYLN (SEQ ID NO: 18) |
| | HCDR1: DYIMH (SEQ ID NO: 4) | LCDR2: RVSKRFS (SEQ ID NO: 19) |
| | HCDR2: YINPYNDGSKYTEKFQG (SEQ ID NO: 23) | LCDR3: LQLLEDPYT (SEQ ID NO: 10) |
| | HCDR3*: ARGTYYYGPQLFDY (SEQ ID NO: 16) | |
| | HCDR3: GTYYYGPQLFDY (SEQ ID NO: 17) | |
| CNG-CD19-7 | QVQLQESGPGLVKPSQTLSLTCTVSGGS ISTSGMGVGWIRQHPGKGLEWIGHIWW DDDKRYNPALKSRVTISVDTSKNQFSL KLSSVTAADTAVYYCARMELWSYYFD YWGQGTLVTVSS (SEQ ID NO: 90) | EIVLTQSPATLSLSPGERATLSCSAS SSVSYMHWYQQKPGQAPRLLIYDT SKLASGIPARFSGSGSGTDFTLTISSL EPEDFAVYYCFQGSVYPFTFGQGT KLEIK (SEQ ID NO: 74) |
| | HCDR1*: GSISTSGMGVG (SEQ ID NO: 92) | LCDR1: SASSSVSYMH (SEQ ID NO: 80) |
| | HCDR1: TSGMGVG (SEQ ID NO: 93) | LCDR2: DTSKLAS (SEQ ID NO: 70) |
| | HCDR2: HIWWDDDKRYNPALKS (SEQ ID NO: 87) | LCDR3: FQGSVYPFT (SEQ ID NO: 71) |
| | HCDR3*: ARMELWSYYFDY (SEQ ID NO: 67) | |
| | HCDR3: MELWSYYFDY (SEQ ID NO: 68) | |
| Xencor mAb | EVQLVESGGGLVKPGGSLKLSCAASGY TFTSYVMHWVRQAPGKGLEWIGYINP YNDGTKYNEKFQGRVTISSDKSISTAY MELSSLRSEDTAMYYCARGTYYYGTR VFDYWGQGTLVTVSS (SEQ ID NO: 197) | DIVMTQSPATLSLSPGERATLSCRSS KSLQNVNGNTYLYWFQQKPGQSP QLLIYRMSNLNSGVPDRFSGSGSGT EFTLTISSLEPEDFAVYYCMQHLEY PITFGAGTKLEIK (SEQ ID NO: 198) |
| | HCDR1: SYVMH (SEQ ID NO: 199) | LCDR1: RSSKSLQNVNGNTYLY (SEQ ID NO: 202) |
| | HCDR2: WIGYINPYNDGTKY (SEQ ID NO: 200) | LCDR2: RMSNLNS (SEQ ID NO: 203) |
| | HCDR3: GTYYYGTRVFDY (SEQ ID NO: 201) | LCDR3: MQHLEYPIT (SEQ ID NO: 204) |
| Abbvie mAb | QVQLQQSGAELVRPGSSVKISCKASGY AFSSYWMNWVKQRPGQGLEWIGQIWP GDGDTNYNGKFKGKATLTADESSSTA YMQLSSLASEDSAVYFCARRETTTVGR YYYAMDYWGQGTSVTVSS (SEQ ID NO: 205) | DILLTQTPASLAVSLGQRATISCKAS QSVDYDGDSYLNWYQQIPGQPPKL LIYDASNLVSGIPPRFSGSGSGTDFT LNIHPVEKVDAATYHCQQSTEDPW TFGGGTKLEIK (SEQ ID NO: 206) |
| | HCDR1: SYWMN (SEQ ID NO: 207) | LCDR1: KASQSVDYDGDSYLN (SEQ ID NO: 210) |
| | HCDR2: QIWPGDGDTNYNGKFKG (SEQ ID NO: 208) | LCDR2: DASNLVS (SEQ ID NO: 211) |
| | HCDR3: RETTTVGRYYYAMDY (SEQ ID NO: 209) | LCDR3: QQSTEDPWT (SEQ ID NO: 212) |
| Immuno-medics mAb | QVQLQQSGAEVKKPGSSVKVSCKASG YAFSSYWMNWVRQRPGQGLEWIGQIW PGDGDTNYNGKFKGRATITADESTNTA YMELSSLRSEDTAFYSCARRETTTVGR YYYAMDYWGQGTTVTVSS (SEQ ID NO: 213) | DIQLTQSPSSLSASVGDRVTITCKAS QSVDYDGDSYLNWYQQIPGKAPKL LIYDASNLVSGIPPRFSGSGSGTDYT FTISSLQPEDIATYHCQQSTEDPWTF GGGTKLQIKR (SEQ ID NO: 214) |
| | HCDR1: SYWMN (SEQ ID NO: 29) | LCDR1: KASQSVDYDGDSYLN (SEQ ID NO: 217) |

TABLE 3-continued

Sequences of Exemplary Antibodies That Bind CD19

| Antibody | VH and HCDRs | VL and LCDRs |
|---|---|---|
| | HCDR2: QIWPGDGDTNYNGKFKG (SEQ ID NO: 215) | LCDR2: DASNLVS (SEQ ID NO: 218) |
| | HCDR3: RETTTVGRYYYAMDY (SEQ ID NO: 216) | LCDR3: QQSTEDPWT (SEQ ID NO: 219) |
| Merck mAb | QVQLEQPGAEVVKPGASVKVSCKTSG YTFTSNWMHWVKQTPGKGLEWIGEID PSDSYTNYNQKFDGKAKLTVDKSSSTA YMEVSDLTAEDSATYYCARGSNPYYY AMDYWGQGTSVTVSS (SEQ ID NO: 220) | QIVLTQSPATLSASPGEKATMTCSA SSGVNYMHWYQQKPGTSPKRWIY DTDKTASGVPARFSGSGSGTSYSLT ISSMEAEDAATYYCHQRGSYTFGG GTKLEIK (SEQ ID NO: 221) |
| | HCDR1: SNWMH (SEQ ID NO: 222) | LCDR1: SASSGVNYMH (SEQ ID NO: 225) |
| | HCDR2: EIDPSDSYTN (SEQ ID NO: 223) | LCDR2: DTDKTAS (SEQ ID NO: 226) |
| | HCDR3: GSNPYYYAMDY (SEQ ID NO: 224) | LCDR3: HQRGSYT (SEQ ID NO: 227) |
| Medarex mAb 21D4a | EVQLVQSGAEVKKPGESLKISCKGSY SFSSSWIGWVRQMPGKGLEWMGIIYPD DSDTRYSPSFQGQVTISADKSIRTAYLQ WSSLKASDTAMYYCARHVTMIWGVII DFWGQGTLVTVSS (SEQ ID NO: 228) | AIQLTQSPSSLSASVGDRVTITCRAS QGISSALAWYQQKPGKAPKLLIYD ASSLESGVPSRFSGSGSGTDFTLTIS SLQPEDFATYYCQQFNSYPFTFGPG TKVDIK (SEQ ID NO: 229) |
| | HCDR1: SSWIG (SEQ ID NO: 230) | LCDR1: RASQGISSALA (SEQ ID NO: 233) |
| | HCDR2: IIYPDDSDTRYSPSFQG (SEQ ID NO: 231) | LCDR2: DASSLES (SEQ ID NO: 234) |
| | HCDR3: HVTMIWGVIIDF (SEQ ID NO: 232) | LCDR3: QQFNSYPFT (SEQ ID NO: 235) |
| Medarex mAb 21D4 | EVQLVQSGAEVKKPGESLKISCKGSY SFSSSWIGWVRQMPGKGLEWMGIIYPD DSDTRYSPSFQGQVTISADKSIRTAYLQ WSSLKASDTAMYYCARHVTMIWGVII DFWGQGTLVTVSS (SEQ ID NO: 236) | AIQLTQSPSSLSASVGDRVTITCRAS QGISSALAWYQQKPGKAPKLLIYD ASSLESGVPSRFSGSGSGTDFTLTIS SLQPEDFATYYCQQFNSYPYTFGQ GTKLEIK (SEQ ID NO: 237) |
| | HCDR1: SSWIG (SEQ ID NO: 238) | LCDR1: RASQGISSALA (SEQ ID NO: 241) |
| | HCDR2: IIYPDDSDTRYSPSFQG (SEQ ID NO: 239) | LCDR2: DASSLES (SEQ ID NO: 242) |
| | HCDR3: HVTMIWGVIIDF (SEQ ID NO: 240) | LCDR3: QQFNSYPYT (SEQ ID NO: 243) |
| Medarex mAb 47G4 | QVQLVQSGAEVKKPGSSVKVSCKDSG GTFSSYAISWVRQAPGQGLEWMGGIIPI FGTTNYAQQFQGRVTITADESTSTAYM ELSSLRSEDTAVYYCAREAVAADWLDP WGQGTLVTVSS (SEQ ID NO: 244) | EIVLTQSPGTLSLSPGERATLSCRAS QSVSSSYLAWYQQKPGQAPRLLIY GASSRATGIPDRFSGSGSGTDFTLTI SRLEPEDFAVYYCQQYGSSRFTFGP GTKVDIK (SEQ ID NO: 245) |
| | HCDR1: SYAIS (SEQ ID NO: 246) | LCDR1: RASQSVSSSYLA (SEQ ID NO: 249) |
| | HCDR2: GIIPIFGTTNYAQQFQG (SEQ ID NO: 247) | LCDR2: GASSRAT (SEQ ID NO: 250) |
| | HCDR3: EAVAADWLDP (SEQ ID NO: 248) | LCDR3: QQYGSSRFT (SEQ ID NO: 251) |
| Medarex mAb 27F3 | EVQLVQSGAEVKKPGESLKISCKGSY SFTSYWIAWVRQMPGKGLEWMGIIYPG DSDTRYSPSFQGQVTISADKSISTAYLQ WSSLKASDTAMYYCARQGYSSGWDSY YGMGVWGQGTTVTVSS (SEQ ID NO: 252) | AIQLTQSPSSLSASVGDRVTITCRAS QGISSALAWYQQKPGKAPKLLIYD ASSLESGVPSRFSGSGSGTDFTLTIS SLQPEDFATYYCQQFNSYPYTFGQ GTKLEIK (SEQ ID NO: 253) |
| | HCDR1: SYWIA (SEQ ID NO: 254) | LCDR1: RASQGISSALA (SEQ ID NO: 257) |

TABLE 3-continued

Sequences of Exemplary Antibodies That Bind CD19

| Antibody | VH and HCDRs | VL and LCDRs |
|---|---|---|
| | HCDR2: IIYPGDSDTRYSPSFQG (SEQ ID NO: 255) | LCDR2: DASSLES (SEQ ID NO: 258) |
| | HCDR3: QGYSSGWDSYYGMGV (SEQ ID NO: 256) | LCDR3: QQFNSYPYT (SEQ ID NO: 259) |
| Medarex mAb 3C10 | QVQLVQSGAEVKKPGSSVKVSCKASG GTFSSYTINWVRQAPGQGLEWMGGIIPI FGIPNYAQKFQGRVTITADESTNTAYM ELSSLRAEDTAVYYCARASGGSADYSY GMDVWGQGTAVTVSS (SEQ ID NO: 260) | DIQMTQSPSSLSASVGDRVTITCRA SQGISSWLAWYQQKPEKAPKSLIY AASSLQSGVPSRFSGSGSGTDFTLTI SSLQPEDFATYYCQQYKRYPYTFG QGIKLEIK (SEQ ID NO: 261) |
| | HCDR1: SYTIN (SEQ ID NO: 262) | LCDR1: RASQGISSWLA (SEQ ID NO: 265) |
| | HCDR2: GIIPIFGIPNYAQKFQG (SEQ ID NO: 263) | LCDR2: AASSLQS (SEQ ID NO: 266) |
| | HCDR3: ASGGSADYSYGMDV (SEQ ID NO: 264) | LCDR3: QQYKRYPYT (SEQ ID NO: 267) |
| Medarex mAb 5G7 | EVQLVQSGAEVKKPGESLNISCKGSGY SFTSYWIGWVRQMPGKGLEWMGIIYPG DSDTRYSPSFQGQVTISADKSINTAYLQ WSSLKASDTAMYYCARGVSMIWGVIM DVWGQGTTVTVSS (SEQ ID NO: 268) | AIQLTQSPSSLSASVGDRVTITCRAS QGISSALAWYQQKPGKAPKLLIYD ASSSLESGVPSRFSGSGSGTDFTLTIS SLQPEDFATYYCQQFNSYPWTFGQ GTKVEIK (SEQ ID NO: 269) |
| | HCDR1: SYWIG (SEQ ID NO: 270) | LCDR1: RASQGISSALA (SEQ ID NO: 273) |
| | HCDR2: IIYPGDSDTRYSPSFQG (SEQ ID NO: 271) | LCDR2: DASSLES (SEQ ID NO: 274) |
| | HCDR3: GVSMIWGVIMDV (SEQ ID NO: 272) | LCDR3: QQFNSYPWT (SEQ ID NO: 275) |
| Medarex mAb 13F1 | EVQLVQSGAEVKKPGESLQISCKGSGY TFTNYWIAWVRQMPGKGLEWMGIIYP GDSDTRYSPSFQGQVTISADKSISTAYL QWSGLKASDTAMYYCARQGYSSGWR SYYGMGVWGQGTTVTVSS (SEQ ID NO: 276) | AIQLTQSPSSLSASVGDRVTITCRAS QGISSALAWYQQKPGKAPKLLIYD ASSLESGVPSRFSGSGSGTDFTLTIS SLQPEDFATYYCQQFNSYPHTFGQ GTKLEIK (SEQ ID NO: 277) |
| | HCDR1: NYWIA (SEQ ID NO: 278) | LCDR1: RASQGISSALA (SEQ ID NO: 281) |
| | HCDR2: IIYPGDSDTRYSPSFQG (SEQ ID NO: 279) | LCDR2: DASSLES (SEQ ID NO: 282) |
| | HCDR3: QGYSSGWRSYYGMGV (SEQ ID NO: 280) | LCDR3: QQFNSYPHT (SEQ ID NO: 283) |
| Medarex mAb 46E8 | EVQLVQSGAEVKKPGESLQISCKGSGY TFTNYWIAWVRQMPGKGLEWMGIIYP GDSDTRYSPSFQGQVTISADKSISTAYL QWSGLKASDTAMYYCARQGYSSGWR SYYGMGVWGQGTTVTVSS (SEQ ID NO: 284) | AIQLTQSPSSLSASVGDRVTITCRAS QGISSALAWYQQKPGKAPKLLIYD ASSLESGVPSRFSGSGSGTDFTLTIS SLQPEDFATYYCQQFNSYPHTFGQ GTKLEIK (SEQ ID NO: 285) |
| | HCDR1: NYWIA (SEQ ID NO: 286) | LCDR1: RASQGISSALA (SEQ ID NO: 289) |
| | HCDR2: IIYPGDSDTRYSPSFQG (SEQ ID NO: 287) | LCDR2: DASSLES (SEQ ID NO: 290) |
| | HCDR3: QGYSSGWRSYYGMGV (SEQ ID NO: 288) | LCDR3: QQFNSYPHT (SEQ ID NO: 291) |
| Novimmune mAb | EVQLVQSGAEVKKPGESLKISCKGSGY SFTSYWIGWVRQMPGKGLEWMGIIYPG DSDTRYSPSFQGQVTISADKSISTAYLQ WSSLKASDTAMYYCARGVSGIYNLHG FDIWGQGTLVTVSS (SEQ ID NO: 315) | DIQMTQSPSSLSASVGDRVTITCRA SQSISSYLNWYQQKPGKAPKLLIYA ASSLQSGVPSRFSGSGSGTDFTLTIS SLQPEDFATYYCQQGRFGSPFTFGQ GTKVEIK (SEQ ID NO: 316) |

TABLE 3-continued

Sequences of Exemplary Antibodies That Bind CD19

| Antibody | VH and HCDRs | VL and LCDRs |
|---|---|---|
| | HCDR1: GYSFTSYW (SEQ ID NO: 317) | LCDR1: QSISSY (SEQ ID NO: 320) |
| | HCDR2: IYPGDSDT (SEQ ID NO: 318) | LCDR2: AAS (SEQ ID NO: 321) |
| | HCDR3: ARGVSGIYNLHGFDI (SEQ ID NO: 319) | LCDR3: QQGRFGSPFT (SEQ ID NO: 322) |
| Eureka mAb-1 | QVQLVETGGGLVQPGGSLRLSCAASGF TFSSYAMSWVRQAPGKGLEWVSAISGS GGSTYYADSVKGRFTISRDNSKNTLYL QMNSLRAEDTAVYYCARYYYSRLDY WGQGTLVTVSS (SEQ ID NO: 323) | QTVVTQEPSVSAAPGQKVTISCSGS SSNIGNNYVSWYQQLPGTAPKLLIY DNNKRPSGIPDRFSGSKSGTSATLGI TGLQTGDEADYYCGTWDSSLSAGV FGTGTKLTVLGSR (SEQ ID NO: 324) |
| Eureka mAb-2 | QVQLVESGGGLVQPGGSLRLSCAASGF TFSSYAMSWVRQAPGKGLEWVSGISAS GGSTYYADSVKGRFTISRDNSKNTLYL QMNSLRAEDTAVYYCARYYLSQIDSW GQGTLVTVSS (SEQ ID NO: 325) | QSVLTQPPSVSAAPGQKVTISCSGSS SNIGNNYVSWYRQLPGTAPKLLIYE NNKRPSGIPDRFSGSKSGTSATLGIT GLQTGDEADYYCGTWDSSLRAGV FGTGTKVTVL (SEQ ID NO: 326) |
| Eureka mAb-3 | EVQLVQSGAEVKKPGATVKISCKVSGY TFTDYYMHWVQQAPGKGLEWMGLVD PEDGETIYAEKFQGRVTITADTSTDTAY MELSSLRSEDTAVYYCATGIYSRPLGY WGQGTLVTVSS (SEQ ID NO: 327) | QSVLTQPPSASGTPGQRVTISCSGSS SNIGSNTVNWYQQLPGTAPKLLIYS NNQRPSGVPDRFSGSKSGTSASLAI SGLQSEDEADYYCAAWDDSLNGH VVFGGGTKLTVL (SEQ ID NO: 328) |
| Eureka mAb-4 | EVQLVETGGGLVQPGGSLRLSCAASGF TFSSYAMSWVRQAPGKGLEWVSAISGS GGSTYYADSVKGRFTISRDNSKNTLYL QMNSLRAEDTAVYYCARSDGKHFWQ QYDAWGQGTLVTVSS (SEQ ID NO: 329) | SYVLTQPPSASGTPGQRVTISCSGSS SNIGSHTVNWYQQLPGTAPKLLIYS NNQRPSGVPDRFSGSKSGTSASLAI SGLQSEDEADYYCAAWDDSLNGY VFGTGTKVTVL (SEQ ID NO: 330) |
| Eureka mAb-5 | EVQLVESGGGLVQPGGSLRLSCAASGF TVSSNYMSWVRQAPGKGLEWVSAISG SGGSTYYADSVKGRFTISRDNSKNTLY LQMNSLRAEDTAVYYCARMNIDYWG QGTLVTVSS (SEQ ID NO: 331) | DIQLTQSPSSLSAYVGDRVTITCRAS QGITNSLAWYQQKPGKAPKLLLHA ASRLESGVPSRFSGSGFGTDFTLTIS SLQPEDFAVYYCQHYLGTPYSFGQ GTKVEIK (SEQ ID NO: 332) |
| Eureka mAb-6 | EVQLVQSGAEVKRPGESLTISCKGSEYS FASYWITWVRQMPGKGLEWMGRIDPS DSYTNYSPSFQGHVTISADKSISTAYLQ WSSLKASDTAIYYCARPFQYDYGGYSD AFDIWGQGTMVTVSS (SEQ ID NO: 333) | EIVLTQSPSSLSASVGDRVTISCRAS QSVSRFLNWYQQKPGKAPKLLIYG VSTLERGVPSRFSGSGSGTDFTLTIS SLQPEDFATYYCQESYIIPLTFGGGT KLEIK (SEQ ID NO: 334) |
| Eureka mAb-7 | QMQLVQSGAEVKKAGSSVKVSCETSG GTFSSSSVNWVRQAPGQGLEWMGGIIPI VGTPNYAQKFQDRVTITAVESTFTAYM ELSGLRSEDTAVYYCARGGYRDYMDV WGRGTTVTVSS (SEQ ID NO: 335) | EIVMTQSPLSLSVTPGEPASISCRSS QSLLDSNGFNSLDWYLQKPGQSPQ LLIHLGSDRASGVPDRFSGSGSGTD FTLKISRVEAEDVGIYYCMQSLQIPT FGQGTKVEIK (SEQ ID NO: 336) |
| Eureka mAb-8 | EVQLVESGGGLIQPGGSLRLSCAASGFT VSSNYMSWVRQAPGKGLEWVSVIYSG GSTYYADSVKGRFTISRDNSKNTLYLQ MNSLRAEDTAVYYCARGGFGAEFDYW GQGTLVTVSS (SEQ ID NO: 337) | SYELTQPPSASGTPGQRVTISCSGSS SNIGSNYVYWYQQLPGTAPKLLIYR NNQRPSGVPDRFSGSKSGTSASLAI SGLRSEDEADYYCAAWDDSLSGYV FGTGTKVTVL (SEQ ID NO: 338) |
| Eureka mAb-9 | EVQLVESGGGLIQPGGSLRLSCAASGFT VSSNYMSWVRQAPGKGLEWVSVIYSG GSTYYADSVKGRFTISRDNSKNTLYLQ MNSLRAEDTAVYYCARGGISDDYYGS GSYDNWGQGTLVTVSS (SEQ ID NO: 339) | SYVLTQPPSVSVSPGQTASITCSGD KLGDKYASWYQQKPGQSPVLVIYQ DNKRPSGIPERFSGSNSGNTATLTIS GTQAMDEADYYCQAWDSSTEDVF GPGTKVTVL (SEQ ID NO: 340) |
| Eureka mAb-10 | EVQLVESGGGLVQPGGSLRLSCAASGF TVSSNYMSWVRQAPGKGLEWVSVIYS GGSTYYADSVKGRFTISRDNSKNTLYL QMNSLRAEDTAVYYCARERGMGYAFD IWGQGTMVTVSS (SEQ ID NO: 341) | DIQLTQSPSSLSASVGDRVTITCRAS QSISSYLNWYQQKPGKAPKLLIYAA SSLQSGVPSRFSGSGSGTDFTLTISS LQPEDFATYYCQQSYSTPFTFGGGT KVEIK (SEQ ID NO: 342) |
| Eureka mAb-11 | QLQLQESGPGLVKPSETLSLTCSVSGVS MSENYWSWIRQPPGKRLEWIGCAHYT GDTHYNPSLKGRVTISLDTSMNQFSLRL NSVTAADTAVYYCASYHPFNYWGQGT LVTVSS (SEQ ID NO: 343) | DIQMTQSPSSLSASVGDRVTITCRA SQGIGSYLAWYQQKPGKAPKLLIYP ASTLQSGVPSRFSGSGSGTEFTLTIS SLQPEDFATYYCQQLNSLFGQGTRL EIK (SEQ ID NO: 344) |

TABLE 3-continued

Sequences of Exemplary Antibodies That Bind CD19

| Antibody | VH and HCDRs | VL and LCDRs |
|---|---|---|
| Eureka mAb-12 | EVQLVQSGAEVRRPGATVKISCKVSGY TFNDFYLHWVRQAPGKGLEWMGRIDP EDGKTRYAEKFQGRLTITADTSTDTLY MQLGGLTSDDTAVYYCTTDWGYSSSL REEDIWYDCWGQGTLVTVSS (SEQ ID NO: 345) | QAVLTQPPSASGTPGQRVTISCSGSS SNIGTKTVNWYQVLPGTAPKLLIYS NYRRPSGVPDRFSGSKSGTSASLAIS GLQSDDEADYYCALWDDSLDGYV FGTGTKVTVL (SEQ ID NO: 346) |
| Eureka mAb-13 | EVQLVQSGAEVKKPGSSVKVSCKASGG TFSSYAISWVRQAPGQGLEWMGGIIPIF GTANYAQKFQGRVTITADESTSTAYME LSSLRSEDTAVYYCARDYGYGDYGDA FDIWGQGTMVTVSS (SEQ ID NO: 347) | SYELTQPPSVSVAPGKTARITCGGN NIGSKSVHWYQQKPGQAPVLVIYY DSDRPSGIPERFSGSNSGNTATLTIS RVEAGDEADYYCQVWDSSSDHYV FGTGTKVTVL (SEQ ID NO: 348) |
| Eureka mAb-14 | EVQLVQSGAEVKKPGESLKISCKGSGY SFTSYWIGWVRQMPGKGLEWMGIIYPG DSDTRYSPSFQGQVTISADKSISTAYLQ WSSLKASDTAMYYCARVVGTIYSMQY DVWGQGTLVTVSS (SEQ ID NO: 349) | SYVLTQPPSVSVAPGKTARITCGGN NIGSKSVHWYQQRPGQAPVLVVYD DSDRPSGIPERFSGSNSGNTATLTIS RVEAGDEADYSCQVWDSSSDHYV FGPGTKVTVL (SEQ ID NO: 350) |
| Eureka mAb-15 | EVQLVQSGAEVKKPGESLKISCKGSGY SFTSYWIGWVRQMPGKGLEWMGIIYPG DSDTRYSPSFQGQVTISADKSISTAYLQ WSSLKASDTAMYYCARQVWGWQGG MYPRSNWWYNMDSWGQGTLVTVSS (SEQ ID NO: 351) | LPVLTQPPSVSVAPGKTARITCGGN NIGSKSVHWYQQKPGQAPVLVVY DDSDRPSGIPERFSGSNSGNTATLTI SRVEAGDEADYYCQVWDSSSDYV VFGGGTKLTVL (SEQ ID NO: 352) |
| Eureka mAb-16 | EVQLVQSGAEVKKPGESLKISCKGSGY SFTSYWIGWVRQMPGKGLEWMGIIYPG DSDTRYSPSFQGQVTISADKSISTAYLQ WSSLKASDTAMYYCARWSSTWD SMY MDYWGQGTLVTVSS (SEQ ID NO: 353) | QAVLTQPPSVSEAPRQRVTISCSGSS SNVGNNAVNWYQQVPGKAPKLLI YYDDLLSSGVSDRFSGSKSGTSASL AISGLQSEDEADYYCGAAWDDSLNG PVFGGGTKLTVL (SEQ ID NO: 354) |
| Eureka mAb-17 | EVQLVQSGAEVKKPGESLRISCKGSGY SFTSYWIGWVRQMPGKGLEWMGIIYPG DSDTRYSPSFQGQVTISADKSISTAYLQ WSSLKASDTAMYYCARVTYSMDSYYF DSWGQGTLVTVSS (SEQ ID NO: 355) | QPVLTQPPSVSVAPGKTARITCGGN NIGSESVHWYQQKPGQAPMVVIYY DSNRPSGIPERFSGSNSGNTATLTVS RVEAEDEADYYCQVWNSSSDHRG VFGGGTKLTV (SEQ ID NO: 356) |
| WuXi WBP7011 -4.34.11 | EVQLQQSGPELVKPGASVKMSCKASG YTFTNYVIHWVKQKPGQGLEWIGYFNP YNDGTEYNEKFKAKATLTSDKSSSTAY MELSSLTSEDSAVYYCAKGPYYYGSSP FDYWGQGTTLTVSS (SEQ ID NO: 357)<br><br>HCDR1: GYTFTNYVIH (SEQ ID NO: 359)<br><br>HCDR2: YFNPYNDGTEYNEKFKA (SEQ ID NO: 360)<br><br>HCDR3: GPYYYGSSPFDY (SEQ ID NO: 361) | DAVMTQTPLSLPVSLGDQASISCRS SQSLENSNGNTYLNWYLQKPGQSP QLLIYRVSNRFSGVLDRFSGSGSGT DFTLKISRVEAEDLGVYFCLQVTHV PYTFGGGTKLEIK (SEQ ID NO: 358)<br><br>LCDR1: RSSQSLENSNGNTYLN (SEQ ID NO: 362)<br><br>LCDR2: RVSNRFS (SEQ ID NO: 363)<br><br>LCDR3: RVSNRFS (SEQ ID NO: 364) |
| WuXi WBP7011 -4.87.6 | QVQLQQSGAELVRPGSSVKISCKASGY AFSTYWMNWVKQRPGQGLEWIGQIYP GDDDTKYNGKFKGKASLTADKSSSTA YMQLISLTSEDSAVYFCARRYFRYDYW YSDVWGAGTTVTVTS (SEQ ID NO: 365)<br><br>HCDR1: GYAFSTYWMN (SEQ ID NO: 367)<br><br>HCDR2: QIYPGDDDTKYNGKFKG (SEQ ID NO: 368)<br><br>HCDR3: RYFRYDYWYSDV (SEQ ID NO: 369) | DIQMTQTTSSLSASLGDRVTISCRAS QDISNYLNWYQQKPDGTVKLLIYY TSRLHSGVPARFSGSGSGTDYSLTIS NLEQEDIATYFCHQGNTLPLTFGAG TKLELK (SEQ ID NO: 366)<br><br>LCDR1: RASQDISNYLN (SEQ ID NO: 370)<br><br>LCDR2: YTSRLHS (SEQ ID NO: 371)<br><br>LCDR3: HQGNTLPLT (SEQ ID NO: 372) |
| WuXi WBP7011 4.155.8 | EIQLQQSGPELVKPGASVKVSCKASGY AFTSYNMYWVKQSHGKSLEWIGYIDP YNGDTTYNQKFKGKATLTVDKSSSTA YMHLNSLTSEDSAVYYCLTTAYAMDY WGQGTSVTVSS (SEQ ID NO: 373) | QIVLTQSPAIMSASLGEEITLTCSAS STVNYMHWYQQKSGTSPKLLIYST SNLASGVPSRFSGSGSGTFYSLTIRS VEAEDAADYYCHQWSSYPYTFGG GTKLEIK (SEQ ID NO: 374) |

TABLE 3-continued

Sequences of Exemplary Antibodies That Bind CD19

| Antibody | VH and HCDRs | VL and LCDRs |
|---|---|---|
| | HCDR1: GYAFTSYNMY (SEQ ID NO: 375) | LCDR1: SASSTVNYMH (SEQ ID NO: 378) |
| | HCDR2: YIDPYNGDTTYNQKFKG (SEQ ID NO: 376) | LCDR2: STSNLAS (SEQ ID NO: 379) |
| | HCDR3: TAYAMDY (SEQ ID NO: 377) | LCDR3: HQWSSYPYT (SEQ ID NO: 380) |
| WuXi WBP7011-4.34.11-z1-m5 | QVQLVQSGAEVKKPGSSVKVSCKASG YTFTDYVIHWVRQAPGQGLEWMGYFN PYNDGTEYNEKFKARVTITADKSTSTA YMELSSLRSEDTAVYYCARGPYYYGSS PFDYWGQGTTVTVSS (SEQ ID NO: 381) | DIVMTQTPLSLPVTPGEPASISCRSS QSLENSNHNTYINWYLQKPGQSPQ LLIYRVSKRFSGVPDRFSGSGSGTD FTLKISRVEAEDVGVYYCHQVTHV PYTFGQGTKLEIK (SEQ ID NO: 382) |
| | HCDR1: GYTFTNYVIH (SEQ ID NO: 383) | LCDR1: RSSQSLENSNHNTYIN (SEQ ID NO: 386) |
| | HCDR2: YFNPYNDGTEYNEKFKA (SEQ ID NO: 384) | LCDR2: RVSKRFS (SEQ ID NO: 19) |
| | HCDR3: GPYYYGSSPFDY (SEQ ID NO: 385) | LCDR3: HQVTHVPYT (SEQ ID NO: 387) |
| WuXi WBP7011 -4.87.6-z1(N-S) | QVQLVQSGAEVKKPGASVKVSCKASG YAFSTYWMNWVRQAPGQGLEWMGQI YPGDDDTKYSGKFKGRVTITADKSTST AYMELSSLRSEDTAVYYCARRYFRYD YWYSDVWGQGTTVTVSS (SEQ ID NO: 388) | DIQMTQSPSSLSASVGDRVTITCRA SQDISNYLNWYQQKPGKVPKLLIY YTSRLHSGVPSRFSGSGSGTDFTLTI SSLQPEDVATYYCHQGNTLPLTFG QGTKLEIK (SEQ ID NO: 389) |
| | HCDR1: GYAFSTYWMN (SEQ ID NO: 390) | LCDR1: RASQDISNYLN (SEQ ID NO: 393) |
| | HCDR2: QIYPGDDDTKYSGKFKG (SEQ ID NO: 391) | LCDR2: YTSRLHS (SEQ ID NO: 394) |
| | HCDR3: RYFRYDYWYSDV (SEQ ID NO: 392) | LCDR3: HQGNTLPLT (SEQ ID NO: 395) |
| WuXi WBP7011 4.155.8-z1-P15 | QMQLVQSGPEVKKPGTSVKVSCKASG YAFTSYNMYWVRQARGQRLEWIGYID PYNADTTYNQKFKGRVTITRDMSTSTA YMELSSLRSEDTAVYYCLTTAYAMD Y WGQGTLVTVSS (SEQ ID NO: 396) | DIQLTQSPSFLSASVGDRVTITCSAS STVNYMHWYQQKPGKAPKLLIYST SNLASGVPSRFSGSGSGTEFTLTISS LQPEDFATYYCHQWSSYPYTFGQG TKLEIK (SEQ ID NO: 397) |
| | HCDR1: GYAFTSYNMY (SEQ ID NO: 398) | LCDR1: SASSTVNYMH (SEQ ID NO: 401) |
| | HCDR2: YIDPYNADTTYNQKFKG (SEQ ID NO: 399) | LCDR2: STSNLAS (SEQ ID NO: 402) |
| | HCDR3: TAYAMDY (SEQ ID NO: 400) | LCDR3: HQWSSYPYT (SEQ ID NO: 403) |
| Legend mAb | QVKLEESGGGELVQPGGPLRLSCAASGNI FSINRMGWYRQAPGKQRAFVASITVRG ITNYADSVKGRFTISVDKSKNTIYLQMN ALKPEDTAVYYCNAVSSNRDPDYWGQ GTQVTVSS (SEQ ID NO: 404) | N/A |
| | HCDR1: INRMG (SEQ ID NO: 405) | |
| | HCDR2: SITVRGITNYADSVKG (SEQ ID NO: 406) | |
| | HCDR3: VSSNRDPDY (SEQ ID NO: 407) | |

Where the VL and LCDR sequences are noted as "N/A," the antigen-binding site is an sdAb having a VH (e.g., VHH) only.

In certain embodiments, the first antigen-binding site comprises a VH that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VH of an antibody disclosed in Table 3, and a VL that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VL of the same antibody disclosed in Table 3. In certain embodiments, the antigen-binding site comprises the HCDR1, HCDR2, HCDR3, LCDR1, LCDR2, and LCDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J Mol Biol 196: 901-917), MacCallum (see MacCallum R M et al., (1996) J Mol Biol 262: 732-745), IMGT (see Lefranc, (1999) The Immunologist, 7, 132-136), or any other CDR determination method known in the art, of the VH and/or VL sequences of an antibody disclosed in Table 3. In certain embodiments, the antigen-binding site comprises the HCDR1, HCDR2, HCDR3, LCDR1, LCDR2, and LCDR3 sequences of an antibody disclosed in Table 3. In certain embodiments, the antigen-binding site comprises the VH and VL sequences of an antibody disclosed in Table 3.

Such antigen-binding site may take the form of scFv. In certain embodiments, the VH is positioned C-terminal to the VL. In certain embodiments, the VH is positioned N-terminal to the VL. In certain embodiments, the VH and the VL are linked by a peptide linker, for example, a linker disclosed in subsection E below titled "Linkers." To stabilize the scFv, the amino acid residues at position 44 of the VH and at position 100 of the VL (under Kabat numbering) can be substituted by Cys, thereby facilitating the formation of a disulfide bond between the VH and the VL. Accordingly, in certain embodiments, the VH and VL comprise Cys at positions 100 and 44, respectively.

In other embodiments, the first antigen-binding site comprises an sdAb comprising a VH comprising complementarity determining regions HCDR1, HCDR2, and HCDR3. In certain embodiments, the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VH of an sdAb antibody provided in Table 3. In certain embodiments, the VH comprises the HCDR1, HCDR2, and HCDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J Mol Biol 196: 901-917), MacCallum (see MacCallum R M et al., (1996) J Mol Biol 262: 732-745), IMGT (see Lefranc, (1999) The Immunologist, 7, 132-136), or any other CDR determination method known in the art, of the VH sequence of an antibody disclosed in Table 3. In certain embodiments, the VH comprises the HCDR1, HCDR2, and HCDR3 sequences of the antibody provided in Table 3. In certain embodiments, the VH comprises the amino acid sequence of the VH of an sdAb provided in Table 3.

In certain embodiments, the first antigen-binding site binds CD19 with a $K_D$ lower than or equal to 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 90 pM, 80 pM, 70 pM, 60 pM, 50 pM, 40 pM, 30 pM, 20 pM, or 10 pM. For example, in certain embodiments, the first antigen-binding site binds CD19 with a $K_D$ about 5 pM-about 1 nM, about 5 pM-about 0.9 nM, about 5 pM-about 0.8 nM, about 5 pM-about 0.7 nM, about 5 pM-about 0.6 nM, about 5 pM nM-about 0.5 nM, about 5 pM-about 0.4 nM, about 5 pM-about 0.3 nM, about 5 pM-about 0.2 nM, about 5 pM-about 0.1 nM, about 5 pM-about 50 pM, about 5 pM-about 20 pM, about 5 pM-to about 10 pM, about 10 pM-about 1 nM, about 10 pM-about 0.9 nM, about 10 pM-about 0.8 nM, about 10 pM-about 0.7 nM, about 10 pM-about 0.6 nM, about 10 pM-about 0.5 nM, about 10 pM-about 0.4 nM, about 10 pM-about 0.3 nM, about 10 pM-about 0.2 nM, about 10 pM-about 0.1 nM, about 10 pM-about 50 pM, about 10 pM-about 20 pM, about 50 pM-about 1 nM, about 50 pM-about 0.9 nM, about 50 pM-about 0.8 nM, about 50 pM-about 0.7 nM, about 50 pM-about 0.6 nM, about 50 pM nM-about 0.5 nM, about 50 pM-about 0.4 nM, about 50 pM-about 0.3 nM, about 50 pM-about 0.2 nM, about 50 pM-about 0.1 nM, about 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 0.5 nM-about 10 nM, about 1 nM-about 10 nM, about 2 nM-about 10 nM, about 3 nM-about 10 nM, about 4 nM-about 10 nM, about 5 nM-about 10 nM, about 6 nM-about 10 nM, about 7 nM-about 10 nM, about 8 nM-about 10 nM, or about 9 nM-about 10 nM. In certain embodiments, the $K_D$ value is measured by surface plasmon resonance (SPR). In certain embodiments, the $K_D$ value is measured by bio-layer interferometry (BLI).

It is understood that the binding affinity to CD19 of the first antigen-binding site alone may be different from the binding affinity of the same antigen-binding site in the context of the multi-specific binding protein disclosed herein, possibly due to the conformational restraint from the other domains. The context-dependent binding affinity is described in subsection G below titled "Binding Affinity."

In certain embodiments, the first antigen-binding site, when present in the form of an Fab, has a melting temperature of at least 60° C., at least 65° C., at least 70° C., at least 75° C., or at least 80° C. In certain embodiments, the first antigen-binding site, when present in the form of an Fab, has a melting temperature in the range of 60-85° C., 60-80° C., 60-75° C., 60-70° C., 60-65° C., 65-85° C., 65-80° C., 65-75° C., 65-70° C., 70-85° C., 70-80° C., 70-75° C., 75-85° C., 75-80° C., or 80-85° C.

B. Antigen-Binding Site that Binds CD3

The second antigen-binding site of the multi-specific binding protein binds CD3 (e.g., human CD3 and/or Macaca CD3). In certain embodiments, the second antigen-binding site binds CD3ε (epsilon). In certain embodiments, the second antigen-binding site binds CD3δ (delta). In certain embodiments, the second antigen-binding site binds CD3γ (gamma).

Earlier BiTE® constructs bind conformational epitopes of CD3 and typically are species-specific (see, PCT Publication No. WO2008119567A2). Improved BiTE® constructs, such as blinatumomab (also called AMG 103; see, PCT Publication No. WO1999054440A1) and solitomab (also called AMG 110; see, PCT Publication No. WO2005040220A1), bind context-independent epitopes at the N-terminus of CD3ε chain (e.g., amino acid residues 1-27 of human CD3ε extracellular domain) and show cross-species specificity for human, *Callithrix jacchus*, *Saguinus Oedipus*, and *Saimiri sciureus* CD3ε chain (see id.). These constructs do not nonspecifically activate T cells to the same degree as observed with the earlier BiTE® constructs, and are therefore believed to bear a lower risk of side effects (see, Brischwein et al. (2007) J. Immunother., 30(8): 798-807).

In certain embodiments, the second antigen-binding site of the multi-specific binding protein binds an epitope at the N-terminus of CD3ε chain. In certain embodiments, the second antigen-binding site binds an epitope localized in amino acid residues 1-27 of human CD3ε extracellular domain. This epitope or a homologous variant thereof is also present in certain non-human primates. Accordingly, in certain embodiments, the second antigen-binding site binds CD3 in different primates, for example, human, new world primates (such as *Callithrix jacchus, Saguinus Oedipus*, or *Saimiri sciureus*), old world primates (such as baboons and macaques), gibbons, and non-human homininae. *Callithrix jacchus* and *Saguinus oedipus* are new world primates belonging to the family of Callitrichidae, while *Saimiri sciureus* is a new world primate belonging to the family of Cebidae. In certain embodiments, the second antigen-binding site binds human CD3ε and/or Macaca CD3ε. In certain embodiments, the second antigen-binding site further binds *Callithrix jacchus, Saguinus Oedipus*, and/or *Saimiri sciureus* CD3ε.

The second antigen-binding site that binds an extracellular epitope of human and/or Macaca CD3 can be derived from, for example, muromonab-CD3 (OKT3) as described in WO2008101154; otelixizumab (TRX4) as described in WO2007145941; teplizumab (MGA031) as described in WO2013040164; visilizumab (Nuvion) as described in WO2004052397; SP34 as described in WO2015181098; X35, VIT3, or BMA03 (BW264/56) as described in WO2015006749; CLB-T3/3, CRIS7, CLB-T3.4.2, WT32, 11D8, XIII-141, XIII-46, XIII-87, 12F6, T3/RW2-8C8, T3/RW2-4B6, OKT3D, M-T301, SMC2, or F101.01 as described in WO2004106381, YTH12.5 or SPv-T3b as described in WO2004106383, F1 11-409 as described in WO2012084895, TR-66 as described in WO2013158856; UCHT-1 as described in WO2000041474; WT-31 as depicted in WO2016085889, or an antibody described in WO2008119567. For example, in certain embodiments, the second antigen-binding site that binds CD3 is derived from an antibody listed in Table 4.

TABLE 4

Sequences of Exemplary Antibodies That Bind CD3

| Antibody | VH and HCDRs | VL and LCDRs |
|---|---|---|
| CNG-CD3-1 | QVQLVQSGAEVKKPGASVKVSCKASG FNIKDYYMHWVRQAPGQRLEWMGWI DLENANTIYDAKFQGRVTITRDTSAST AYMELSSLRSEDTAVYYCARDAYGRY FYDVWGQGTLVTVSS (SEQ ID NO: 412) | DIVMTQSPDSLAVSLGERATINCKS SQSLLNARTGKNYLAWYQQKPGQP PKLLIYWASTRESGVPDRFSGSGSG TDFTLTISSLQAEDVAVYYCKQSYS RRTFGGGTKVEIK (SEQ ID NO: 413) |
| | HCDR1*: FNIKDYYMH (SEQ ID NO: 414) | LCDR1: KSSQSLLNARTGKNYLA (SEQ ID NO: 419) |
| | HCDR1: DYYMH (SEQ ID NO: 415) | LCDR2: WASTRES (SEQ ID NO: 420) |
| | HCDR2: WIDLENANTIYDAKFQG (SEQ ID NO: 416) | LCDR3: KQSYSRRT (SEQ ID NO: 421) |
| | HCDR3*: ARDAYGRYFYDV (SEQ ID NO: 417) | |
| | HCDR3: DAYGRYFYDV (SEQ ID NO: 418) | |
| | scFv: DIVMTQSPDSLAVSLGERATINCKSSQSLLNARTGKNYLAWYQQKPGQPPKLLI YWASTRESGVPDRFSGSGSGTDFTLTISSLQAEDVAVYYCKQSYSRRTFGGGT KVEIKGGGGSGGGGSGGGGSGGGGSQVQLVQSGAEVKKPGASVKVSCKASGF NIKDYYMHWVRQAPGQRLEWMGWIDLENANTIYDAKFQGRVTITRDTSASTAY MELSSLRSEDTAVYYCARDAYGRYFYDVWGQGTLVTVSS (SEQ ID NO: 422) | |
| | scFv with Cys substitutions: DIVMTQSPDSLAVSLGERATINCKSSQSLLNARTGKNYLAWYQQKPGQPPKLLI YWASTRESGVPDRFSGSGSGTDFTLTISSLQAEDVAVYYCKQSYSRRTFGCGT KVEIKGGGGSGGGGSGGGGSGGGGSQVQLVQSGAEVKKPGASVKVSCKASGF NIKDYYMHWVRQAPGQCLEWMGWIDLENANTIYDAKFQGRVTITRDTSASTA YMELSSLRSEDTAVYYCARDAYGRYFYDVWGQGTLVTVSS (SEQ ID NO: 423) | |
| CNG-CD3-2 | QVQLVQSGAEVKKPGASVKVSCKASG FNIKDYYMHWVRQAPGQRLEWMGWI DLENANTIYDAKFQGRVTITRDTSAST AYMELSSLRSEDTAVYYCARDQYGRY FYDVWGQGTLVTVSS (SEQ ID NO: 424) | DIVMTQSPDSLAVSLGERATINCKS SQSLLNARTGKNYLAWYQQKPGQP PKLLIYWASTRESGVPDRFSGSGSG TDFTLTISSLQAEDVAVYYCKQSYS RRTFGGGTKVEIK (SEQ ID NO: 413) |
| | HCDR1*: FNIKDYYMH (SEQ ID NO: 414) | LCDR1: KSSQSLLNARTGKNYLA (SEQ ID NO: 419) |
| | HCDR1: DYYMH (SEQ ID NO: 415) | LCDR2: WASTRES (SEQ ID NO: 420) |
| | HCDR2: WIDLENANTIYDAKFQG (SEQ ID NO: 416) | LCDR3: KQSYSRRT (SEQ ID NO: 421) |
| | HCDR3*: ARDQYGRYFYDV (SEQ ID NO: 425) | |
| | HCDR3: DQYGRYFYDV (SEQ ID NO: 426) | |

TABLE 4-continued

Sequences of Exemplary Antibodies That Bind CD3

| Antibody | VH and HCDRs | VL and LCDRs |
|---|---|---|
| | scFv:<br>DIVMTQSPDSLAVSLGERATINCKSSQSLLNARTGKNYLAWYQQKPGQPPKLLI<br>YWASTRESGVPDRFSGSGSGTDFTLTISSLQAEDVAVYYCKQSYSRRTFGGGT<br>KVEIKGGGGSGGGGSGGGGSGGGGSQVQLVQSGAEVKKPGASVKVSCKASGF<br>NIKDYYMHWVRQAPGQRLEWMGWIDLENANTIYDAKFQGRVTITRDTSASTA<br>YMELSSLRSEDTAVYYCARDQYGRYFYDVWGQGTLVTVSS (SEQ ID NO: 427)<br><br>scFv with Cys substitutions:<br>DIVMTQSPDSLAVSLGERATINCKSSQSLLNARTGKNYLAWYQQKPGQPPKLLI<br>YWASTRESGVPDRFSGSGSGTDFTLTISSLQAEDVAVYYCKQSYSRRTFG<u>C</u>GT<br>KVEIKGGGGSGGGGSGGGGSGGGGSQVQLVQSGAEVKKPGASVKVSCKASGF<br>NIKDYYMHWVRQAPGQ<u>C</u>LEWMGWIDLENANTIYDAKFQGRVTITRDTSASTA<br>YMELSSLRSEDTAVYYCARDQYGRYFYDVWGQGTLVTVSS (SEQ ID NO: 428) | |
| CNG-CD3-3 | QVQLVQSGAEVKKPGASVKVSCKASG<br>FNIKDYYMHWVRQAPGQRLEWMGWI<br>DLEEGNTIYDAKFQGRVTITRDTSAST<br>AYMELSSLRSEDTAVYYCARDAYGRY<br>FYDVWGQGTLVTVSS (SEQ ID NO: 429) | DIVMTQSPDSLAVSLGERATINCKS<br>SQSLLNARTGKNYLAWYQQKPGQP<br>PKLLIYWASTRESGVPDRFSGSGSG<br>TDFTLTISSLQAEDVAVYYCKQSYS<br>LRTFGGGTKVEIK (SEQ ID NO: 430) |
| | HCDR1*: FNIKDYYMH (SEQ ID NO: 414) | LCDR1: KSSQSLLNARTGKNYLA (SEQ ID NO: 419) |
| | HCDR1: DYYMH (SEQ ID NO: 415) | LCDR2: WASTRES (SEQ ID NO: 420) |
| | HCDR2: WIDLEEGNTIYDAKFQG (SEQ ID NO: 431) | LCDR3: KQSYSLRT (SEQ ID NO: 432) |
| | HCDR3*: ARDAYGRYFYDV (SEQ ID NO: 417) | |
| | HCDR3: DAYGRYFYDV (SEQ ID NO: 418) | |
| | scFv:<br>DIVMTQSPDSLAVSLGERATINCKSSQSLLNARTGKNYLAWYQQKPGQPPKLLI<br>YWASTRESGVPDRFSGSGSGTDFTLTISSLQAEDVAVYYCKQSYSLRTFGGGT<br>KVEIKGGGGSGGGGSGGGGSGGGGSQVQLVQSGAEVKKPGASVKVSCKASGF<br>NIKDYYMHWVRQAPGQRLEWMGWIDLEEGNTIYDAKFQGRVTITRDTSASTA<br>YMELSSLRSEDTAVYYCARDAYGRYFYDVWGQGTLVTVSS (SEQ ID NO: 433)<br><br>scFv with Cys substitutions:<br>DIVMTQSPDSLAVSLGERATINCKSSQSLLNARTGKNYLAWYQQKPGQPPKLLI<br>YWASTRESGVPDRFSGSGSGTDFTLTISSLQAEDVAVYYCKQSYSLRTFG<u>C</u>GT<br>KVEIKGGGGSGGGGSGGGGSGGGGSQVQLVQSGAEVKKPGASVKVSCKASGF<br>NIKDYYMHWVRQAPGQ<u>C</u>LEWMGWIDLEEGNTIYDAKFQGRVTITRDTSASTA<br>YMELSSLRSEDTAVYYCARDAYGRYFYDVWGQGTLVTVSS (SEQ ID NO: 434) | |
| Adimab mAb333 | QVQLVQSGAEVKKPGASVKVSCKASG<br>FNIKDYYMHWVRQAPGQRLEWMGWI<br>DLENANTIYDAKFQGRVTITRDTSAST<br>AYMELSSLRSEDTAVYYCARDVYGRY<br>FYDLWGQGTLVTVSS (SEQ ID NO: 435) | DIVMTQSPDSLAVSLGERATINCKS<br>SQSLLESRTGKNYLAWYQQKPGQP<br>PKLLIYWASTRESGVPDRFSGSGSG<br>TDFTLTISSLQAEDVAVYYCKQSYS<br>RRTFGGGTKVEIK (SEQ ID NO: 436) |
| | HCDR1: FNIKDYYMH (SEQ ID NO: 437) | LCDR1: KSSQSLLNARTGKNYLA (SEQ ID NO: 440) |
| | HCDR2: WIDLENANTIYDAKFQG (SEQ ID NO: 438) | LCDR2: WASTRES (SEQ ID NO: 441) |
| | HCDR3: ARDVYGRYFYDL (SEQ ID NO: 439) | LCDR3: KQSYSRRT (SEQ ID NO: 442) |
| Adimab mAb334 | QVQLVQSGAEVKKPGASVKVSCKASG<br>FNIKDYYMHWVRQAPGQRLEWMGWI<br>DLENANTIYDAKFQGRVTITRDTSAST<br>AYMELSSLRSEDTAVYYCARDAYGGY<br>FYDVWGQGTLVTVSS (SEQ ID NO: 443) | DIVMTQSPDSLAVSLGERATINCKS<br>SQSLLNSRTGKNYLAWYQQKPGQP<br>PKLLIYWASTRESGVPDRFSGSGSG<br>TDFTLTISSLQAEDVAVYYCKQSYS<br>RRTFG<u>C</u>GTKVEIK (SEQ ID NO: 444) |
| | HCDR1: FNIKDYYMH (SEQ ID NO: 445) | LCDR1: KSSQSLLNARTGKNYLA (SEQ ID NO: 448) |

TABLE 4-continued

Sequences of Exemplary Antibodies That Bind CD3

| Antibody | VH and HCDRs | VL and LCDRs |
|---|---|---|
| | HCDR2: WIDLENANTIYDAKFQG (SEQ ID NO: 446) | LCDR2: WASTRES (SEQ ID NO: 449) |
| | HCDR3: ARDAYGGYFYDV (SEQ ID NO: 447) | LCDR3: KQSYSRRT (SEQ ID NO: 450) |
| Adimab mAb404 | EVQLLESGGGLVQPGGSLRLSCAASGF TFDTYAMNWVRQAPGKGLEWVARIR SKYNNYATYYADSVKDRFTISRDDSKS TLYLQMESLRAEDTAVYYCVRHGNFG NYAVSWFAHWGQGTLVTVSS (SEQ ID NO: 451) | QTVVTQEPSLSVSPGGTVTLTCGSS TGAVTTSNYANWVQQTPGQAPRG LIGGTDKRAPGVPDRFSGSLLGDKA ALTITGAQAEDEADYYCALWYSNH WVFGGGTKLTVL (SEQ ID NO: 452) |
| | HCDR1: FTFDTYAMN (SEQ ID NO: 453) | LCDR1: GSSTGAVTTSNYAN (SEQ ID NO: 456) |
| | HCDR2: RIRSKYNNYATYYADSVKD (SEQ ID NO: 454) | LCDR2: GTDKRAP (SEQ ID NO: 457) |
| | HCDR3: VRHGNFGNYAVSWFAH (SEQ ID NO: 455) | LCDR3: ALWYSNHWV (SEQ ID NO: 458) |
| Adimab mAb405 | EVQLLESGGGLVQPGGSLRLSCAASGF TFDTYAMNWVRQAPGKGLEWVARIR SKYNNYATYYADSVKDRFTISRDDSKS TLYLQMESLRAEDTAVYYCVRHGSFG NHIVSWFAHWGQGTLVTVSS (SEQ ID NO: 459) | QTVVTQEPSLSVSPGGTVTLTCGSS TGAVTTSNYANWVQQTPGQAPRG LIGGTDKRAPGVPDRFSGSLLGDKA ALTITGAQAEDEADYYCALWYSNH WVFGGGTKLTVL (SEQ ID NO: 460) |
| | HCDR1: FTFDTYAMN (SEQ ID NO: 461) | LCDR1: GSSTGAVTTSNYAN (SEQ ID NO: 464) |
| | HCDR2: RIRSKYNNYATYYADSVKD (SEQ ID NO: 462) | LCDR2: GTDKRAP (SEQ ID NO: 465) |
| | HCDR3: VRHGSFGNHIVSWFAH (SEQ ID NO: 463) | LCDR3: ALWYSNHWV (SEQ ID NO: 466) |
| Adimab mAb-1 | QVQLVQSGAEVKKPGASVKVSCKASG FNIKDYYMHWVRQAPGQRLEWMGWI DLENGNTIYDAKFQGRVTITRDTSAST AYMELSSLRSEDTAVYYCARDGYGRY FYDVWGQGTLVTVSS (SEQ ID NO: 467) | DIVMTQSPDSLAVSLGERATINCKS SQSLLNSRTRKNYLAWYQQKPGQP PKLLIYWASTRESGVPDRFSGSGSG TDFTLTISSLQAEDVAVYYCKQSYS RRTFGGGTKVEIK (SEQ ID NO: 468) |
| Adimab mAb-2 | QVQLVQSGAEVKKPGASVKVSCKASG FNIKDYYMHWVRQAPGQRLEWMGWI DLENANTIYDAKFQGRVTITRDTSAST AYMELSSLRSEDTAVYYCARDVYGRY LYDVWGQGTLVTVSS (SEQ ID NO: 469) | DIVMTQSPDSLAVSLGERATINCKS SQSLLNNRTRKNYLAWYQQKPGQP PKLLIYWASTRESGVPDRFSGSGSG TDFTLTISSLQAEDVAVYYCKQSYS RRTFGGGTKVEIK (SEQ ID NO: 470) |
| Adimab mAb-3 | QVQLVQSGAEVKKPGASVKVSCKASG FNIKDYYMHWVRQAPGQRLEWMGWI DLENGNTIYDPKFQGRVTITRDTSAST AYMELSSLRSEDTAVYYCARDAYGRY FYDVWGQGTLVTVSS (SEQ ID NO: 471) | DIVMTQSPDSLAVSLGERATINCRS SQSLLNSRTRKNYLAWYQQKPGQP PKLLIYWASTRESGVPDRFSGSGSG TDFTLTISSLQAEDVAVYYCKQSYS RRTFGGGTKVEIK (SEQ ID NO: 472) |
| Adimab mAb-4 | QVQLVQSGAEVKKPGASVKVSCKASG FNIKDYYMHWVRQAPGQRLEWMGWI DLEEGNTIYDAKFQGRVTITRDTSAST AYMELSSLRSEDTAVYYCARDAYGRY FYDVWGQGTLVTVSS (SEQ ID NO: 429) | DIVMTQSPDSLAVSLGERATINCKS SQSLLNGRTRKNYLAWYQQKPGQP PKLLIYWASTRESGVPDRFSGSGTG TDFTLTISSLQAEDVAVYYCKQSYS RRTFGGGTKVEIK (SEQ ID NO: 473) |
| Adimab mAb-5 | QVQLVQSGAEVKKPGASVKVSCKASG FNIKDYYMHWVRQAPGQRLEWMGWI DLENANTIYDAKFQGRVTITRDTSAST AYMELSSLRSEDTAVYYCARDNYGGY FYDVWGQGTLVTVSS (SEQ ID NO: 474) | DIVMTQSPDSLAVPLGERATINCKS SQSLLNSRTRKNYLAWYQQKPGQP PKLLIYWASTRESGVPDRFSGSGSG TDFTLTISSLQAEDVAVYYCKQSYS RRTFGGGTKVEIK (SEQ ID NO: 475) |

TABLE 4-continued

Sequences of Exemplary Antibodies That Bind CD3

| Antibody | VH and HCDRs | VL and LCDRs |
|---|---|---|
| Adimab mAb-6 | QVQLVQSGAEVKKPGASVKVSCKASG FNIKDYYMHWVRQAPGQRLEWMGWI DLENGNTIYDPKFQGRVTITRDTSAST AYMELSSLRSEDTAVYYCARDGYGRY FYDVWGQGTLVTVSS (SEQ ID NO: 476) | DIVMTQSPDSLAVSLGERATINCKS SQSLLNSRTRKNYLAWYQQKPGQP PKLLIYWASTRESGVPDRFSGSGSG TDFTLTISSLQAEDVAVYYCKQSYS LRTFGGGTKVEIK (SEQ ID NO: 477) |
| Adimab mAb-7 | QVQLVQSGAEVKKPGASVKVSCKASG FNIKDYYMHWVRQAPGQRLEWMGWI DLENGNTIYDPKFQGRVTITRDTSAST AYMELSSLRSEDTAVYYCARDGYGRY FFDVWGQGTLVTVSS (SEQ ID NO: 478) | DIVMTQSPDSLAVSLGERATINCKS SQSLLNSRTRKNYLAWYQQKPGQP PKLLIYWASTRESGVPDRFSGSGSG TDFTLTISSLQAEDVAVYYCKQSYN LRTFGGGTKVEIK (SEQ ID NO: 479) |
| Adimab mAb-8 | QVQLVQSGAEVKKPGASVKVSCKASG FNIKDYYMHWVRQAPGQRLEWMGWI DLENGNTIYDPKFQGRVTITRDTSAST AYMELSSLRSEDTAVYYCAREGYGRY FYDVWGQGTLVTVSS (SEQ ID NO: 480) | DIVMTQSPDSLAVSLGERATINCKS SQSLLNSRTRKNYLAWYQQKPGQP PKLLIYWASTRESGVPDRFSGSGSG TDFTLTISSLQAEDVAVYYCKQSYF RRAFGGGTKVEIK (SEQ ID NO: 481) |
| Adimab mAb-9 | QVQLVQSGAEVKKPGASVKVSCKASG FNIKDYYMHWVRQAPGQRLEWMGWI DLENGNTIYDPKFQGRVTITRDTSAST AYMELSSLRSEDTAVYYCARDGYGRY YYDVWGQGTLVTVSS (SEQ ID NO: 482) | DIVMTQSPDSLAVSLGERATINCKS SQSLLNSRTRKNYLAWYQQKPGQP PKLLIYWASTRESGVPDRFSGSGSG TDFTLTISSLQAEDVAVYYCKQSYN LRTFGGGTKLEIK (SEQ ID NO: 483) |
| Adimab mAb-10 | QVQLVQSGAEVKKPGASVKVSCKASG FNIKDYYMHWVRQAPGQRLEWMGWI DLENGNTIYQPKFQGRVTITRDTSAST AYMELSSLRSEDTAVYYCARDGYGRY FYDVWGQGTLVTVSS (SEQ ID NO: 484) | DIVMTQSPDSLAVSLGERATINCKS SQSLLNSRTRKNYLAWYQQKPGQS PKLLIYWASTRESGVPDRFTGSGSG TDFTLTISSLQAEDVAVYYCKQSYS LRTFGGGTKVEIK (SEQ ID NO: 485) |
| Adimab mAb-11 | QVQLVQSGAEVKKPGASVKVSCKASG FNIKDYYMHWVRQAPGQRLEWMGWI DLENGNTIYDPKFQGRVTITRDTSAST AYMELSSLRSEDTAVYYCARDGYGRY FYDYWGQGTLVTVSS (SEQ ID NO: 486) | DIVMTQSPDSLAVSLGERATINCKS SQSLLESRTGKNYLAWYQQKPGQP PKLLIYWASTRESGVPDRFSGSGSG TDFTLTISSLQAEDVAVYYCKQSYS LRTFGGGTKVEIK (SEQ ID NO: 487) |
| CD3 domain in blinatumomab binding | DIKLQQSGAELARPGASVKMSCKTSG YTFTRYTMHWVKQRPGQGLEWIGYIN PSRGYTNYNQKFKDKATLTTDKSSSTA YMQLSSLTSEDSAVYYCARYYDDHYC LDYWGQGTTLTVSSVE (SEQ ID NO: 488)<br><br>scFv: DIKLQQSGAELARPGASVKMSCKTSGYTFTRYTMHWVKQRPGQGLEWIGYIN PSRGYTNYNQKFKDKATLTTDKSSSTAYMQLSSLTSEDSAVYYCARYYDDHY CLDYWGQGTTLTVSSVEGGSGGSGGSGGSGGVDDIQLTQSPAIMSASPGEKVT MTCRASSSVSYMNWYQQKSGTSPKRWIYDTSKVASGVPYRFSGSGSGTSYSLT ISSMEAEDAATYYCQQWSSNPLTFGAGTKLELK (SEQ ID NO: 490) | VDDIQLTQSPAIMSASPGEKVTMTC RASSSVSYMNWYQQKSGTSPKRWI YDTSKVASGVPYRFSGSGSGTSYSL TISSMEAEDAATYYCQQWSSNPLTF GAGTKLELK (SEQ ID NO: 489) |
| Novimmune 28F11 | QVQLVESGGGVVQPGRSLRLSCAASG FKFSGYGMHWVRQAPGKGLEWVAVI WYDGSKKYYVD S VKGRFTISRDNSKN TLYLQMNSLRAEDTAVYYCARQMGY WHFDLWGRGTLVTVSS (SEQ ID NO: 491)<br><br>HCDR1: GYGMH (SEQ ID NO: 493)<br><br>HCDR2: VIWYDGSKKYYVDSVKG (SEQ ID NO: 494)<br><br>HCDR3: QMGYWHFDL (SEQ ID NO: 495) | EIVLTQSPATLSLSPGERATLSCRAS QSVSSYLAWYQQKPGQAPRLLIYD ASNRATGIPARFSGSGSGTDFTLTIS SLEPEDFAVYYCQQRSNWPPLTFG GGTKVEIK (SEQ ID NO: 492)<br><br>LCDR1: RASQSVSSYLA (SEQ ID NO: 496)<br><br>LCDR2: DASNRAT (SEQ ID NO: 497)<br><br>LCDR3: QQRSNWPPLT (SEQ ID NO: 498) |
| Novimmune 27H5 | EVQLLESGGGLVQPGGSLRLSCAASGF TFSSFPMAWVRQAPGKGLEWVSTISTS GGRTYYRDSVKGRFTISRDNSKNTLYL QMNSLRAEDTAVYYCAKFRQYSGGFD YWGQGTLVTVSS (SEQ ID NO: 499) | DFMLTQPHSVSESPGKTVIISCWYQ QRPGRAPTTVIFGVPDRFSGSIDRSS NSASLTISGLQTEDEADYYCFGGGT KLTVLGQPKAAPSVTLFPPSSEELQ (SEQ ID NO: 500) |

TABLE 4-continued

Sequences of Exemplary Antibodies That Bind CD3

| Antibody | VH and HCDRs | VL and LCDRs |
|---|---|---|
| Glaxo mAb | EVQLLESGGGLVQPGGSLRLSCAASGF TFSSFPMAWVRQAPGKGLEWVSTISTS GGRTYYRDSVKGRFTISRDNSKNTLYL QMNSLRAEDTAVYYCAKFRQYSGGFD YWGQGTLVTVSS (SEQ ID NO: 501) | DIQLTQPNSVSTSLGSTVKLSCTLSS GNIENNYVHWYQLYEGRSPTTMIY DDDKRPDGVPDRFSGSIDRSSNSAF LTIHNVAIEDEAIYFCHSYVSSFNVF GGGTKLTVLR (SEQ ID NO: 502) |
| Eureka mAb | DVQLVQSGAEVKKPGASVKVSCKASG YTFTRYTMHWVRQAPGQGLEWIGYIN PSRGYTNYADSVKGRFTITTDKSTSTA YMELSSLRSEDTATYYCARYYDDHYC LDYWGQGTTVTVSS (SEQ ID NO: 503) | DIVLTQSPATLSLSPGERATLSCRAS QSVSYMNWYQQKPGKAPKRWIYD TSKVASGVPARFSGSGSGTDYSLTI NSLEAEDAATYYCQQWSSNPLTFG GGTKVEIK (SEQ ID NO: 504) |
|  | scFv:<br>DVQLVQSGAEVKKPGASVKVSCKASGYTFTRYTMHWVRQAPGQGLEWIGYI NPSRGYTNYADSVKGRFTITTDKSTSTAYMELSSLRSEDTATYYCARYYDDHY CLDYWGQGTTVTVSSGEGTSTGSGGSGGSGADDIVLTQSPATLSLSPGERAT LSCRASQSVSYMNWYQQKPGKAPKRWIYDTSKVASGVPARFSGSGSGTDYSL TINSLEAEDAATYYCQQWSSNPLTFGGGTKVEIK (SEQ ID NO: 505) | |
| Muromonab | QVQLVQSGGGVVQPGRSLRLSCKASG YTFTRYTMHWVRQAPGKGLEWIGYIN PSRGYTNYNQKVKDRFTISRDNSKNTA FLQMDSLRPEDTGVYFCARYYDDHYC LDYWGQGTPVTVSS (SEQ ID NO: 506) | DDIQMTQSPSSLSASVGDRVTITCS ASSSVSYMNWYQQTPGKAPKRWIY DTSKLASGVPSRFSGSGSGTDYTFTI SSLQPEDIATYYCQQWSSNPFTFGQ GTKLQIT (SEQ ID NO: 507) |
| MacroGenics mAb humanized OKT3 | QVQLVQSGGGVVQPGRSLRLSCKASG YTFTRYTMHWVRQAPGKGLEWIGYIN PSRGYTNYNQKFKDRFTISTDKSKSTA FLQMDSLRPEDTAVYYCARYYDDHYC LDYWGQGTPVTVSS (SEQ ID NO: 508) | DIQMTQSPSSLSASVGDRVTITCSAS SSVSYMNWYQQTPGKAPKRWIYD TSKLASGVPSRFSGSGSGTDYTFTIS SLQPEDIATYYCQQWSSNPFTFGQG TKLQITR (SEQ ID NO: 509) |
| Roche CH2527 | EVQLLESGGGLVQPGGSLRLSCAASGF TFSTYAMNWVRQAPGKGLEWVSRIRS KYNNYATYYADSVKGRFTISRDDSKN TLYLQMNSLRAEDTAVYYCVRHGNFG NSYVSWFAYWGQGTLVTVSS (SEQ ID NO: 600) | QAVVTQEPSLTVSPGGTVTLTCGSS TGAVTTSNYANWVQEKPGQAFRG LIGGTNKRAPGTPARFSGSLLGGKA ALTLSGAQPEDEAEYYCALWYSNL WVFGGGTKLTVL (SEQ ID NO: 601) |
| Regeneron mAb (anti-CD3/anti-CD20) | EVQLVESGGGLVQPGRSLRLSCAASGF TFDDYTMHWVRQAPGKGLEWVSGIS WNSGSIGYADSVKGRFTISRDNAKKSL YLQMNSLRAEDTALYYCAKDNSGYG HYYYGMDVWGQGTTVTVAS (SEQ ID NO: 602) | AEIVMTQSPATLSVSPGERATLSCR ASQSVSSNLAWYQQKPGQAPRLLI YGASTRATGIPARFSGSGSGTEFTLT ISSLQSEDFAVYYCQHYINWPLTFG GGTKVEIK (SEQ ID NO: 603) |
| WuXi WBP3311_ 2.166.48-z1 | QVQLVQSGAEVKKPGSSVKVSCKASG YSFTTYYIHWVRQAPGQGLEWMGWIF PGNDNIKYSEKFKGRVTITADKSTSTA YMELSSLRSEDTAVYYCAIDSVSIYYF DYWGQGTLVTVSS (SEQ ID NO: 604) | DIVMTQSPDSLAVSLGERATINCKS SQSLLNSRTKNYLAWYQQKPGQP PKLLIYWASTRKSGVPDRFSGSGSG TDFTLTISSLQAEDVAVYYCTQSFIL RTFGGGTKVEIK (SEQ ID NO: 605) |
|  | HCDR1: GYSFTTYYIH (SEQ ID NO: 606) | LCDR1: KSSQSLLNSRTKNYLA (SEQ ID NO: 609) |
|  | HCDR2: WIFPGNDNIKYSEKFKG (SEQ ID NO: 607) | LCDR2: WASTRKS (SEQ ID NO: 610) |
|  | HCDR3: DSVSIYYFDY (SEQ ID NO: 608) | LCDR3: TQSFILRT (SEQ ID NO: 611) |
| WuXi WBP3311_ 2.306.4-z1 | QVQLVQSGAEVKKPGSSVKVSCKASG FAFTDYYIHWVRQAPGQGLEWMGWIS PGNVNTKYNENFKGRVTITADKSTSTA YMELSSLRSEDTAVYYCARDGYSLYY FDYWGQGTLVTVSS (SEQ ID NO: 612) | DIVMTQSPDSLAVSLGERATINCKS SQSLLNSRTKNYLAWYQQKPGQP PKLLIYWASTRQSGVPDRFSGSGSG TDFTLTISSLQAEDVAVYYCTQSHT LRTFGGGTKVEIK (SEQ ID NO: 613) |
|  | HCDR1: GFAFTDYYIH (SEQ ID NO: 614) | LCDR1: KSSQSLLNSRTKNYLA (SEQ ID NO: 617) |
|  | HCDR2: WISPGNVNTKYNENFKG (SEQ ID NO: 615) | LCDR2: WASTRQS (SEQ ID NO: 618) |
|  | HCDR3: DGYSLYYFDY (SEQ ID NO: 616) | LCDR3: TQSHTLRT (SEQ ID NO: 619) |

TABLE 4-continued

Sequences of Exemplary Antibodies That Bind CD3

| Antibody | VH and HCDRs | VL and LCDRs |
|---|---|---|
| ADLQ mAb-1 | MAESGGGSVQTGGSLRLSCAYTASSV CMAWFRQAPGKEREGVAVTREGLTKT GYADSVKGRFAISQDYAKKTLYLQMS SLKPEDTARYYCAARPTSPCTVDGELL ASTYNYWGQGTQVTV (SEQ ID NO: 620) | N/A |
| ADLQ mAb-2 | MAESGGGSVQTGGSLRLSCAYTASSV CMAWFRQAPGKEREGVAVTREGLTKT GYADSVKGRFAISQDYAKKTLYLQMS SLKPEDTARYYCAARPTSPCTVDGELL ASTYDYWGQGTQVTV (SEQ ID NO: 621) | N/A |
| ADLQ mAb-3 | MAESGGGSVQTGGSLRLSCAYTASSV CMAWFRQAPGKEREGVAVTREGLTQT GYADSVKGRFAISQDYAKKTLYLQMS SLKPEDTARYYCAARPTSPCTVDGELL ASTYNYWGQGTQVTV (SEQ ID NO: 622) | N/A |
| ADLQ mAb-4 | MAESGGGSVQTGGSLRLSCAYTASSV CMAWFRQAPGKEREGVAVTREGLTQT GYADSVKGRFAISQDYAKKTLYLQMS SLKPEDTARYYCAARPTSPCTVDGELL ASTYDYWGQGTQVTV (SEQ ID NO: 623) | N/A |

Where the VL and LCDR sequences are noted as "N/A," the antigen-binding site is an sdAb having a VH (e.g., VHH) only.

In certain embodiments, the second antigen-binding site comprises a VH that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VH of an antibody disclosed in Table 4, and a VL that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VL of the same antibody disclosed in Table 4. In certain embodiments, the antigen-binding site comprises the HCDR1, HCDR2, HCDR3, LCDR1, LCDR2, and LCDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J Mol Biol 196: 901-917), MacCallum (see MacCallum R M et al., (1996) J Mol Biol 262: 732-745), IMGT (see Lefranc, (1999) The Immunologist, 7, 132-136), or any other CDR determination method known in the art, of the VH and/or VL sequences of an antibody disclosed in Table 4. In certain embodiments, the antigen-binding site comprises the HCDR1, HCDR2, HCDR3, LCDR1, LCDR2, and LCDR3 sequences of an antibody disclosed in Table 4. In certain embodiments, the antigen-binding site comprises the VH and VL sequences of an antibody disclosed in Table 4.

In certain embodiments, the second antigen-binding site that binds CD3 is derived from CNG-CD3-1. In certain embodiments, the second antigen-binding site comprises a VH comprising HCDR1, HCDR2, and HCDR3 sequences set forth in SEQ ID NOs: 414, 416, and 417, respectively, and a VL comprising LCDR1, LCDR2, and LCDR3 sequences set forth in SEQ ID NOs: 419, 420, and 421, respectively. In certain embodiments, the second antigen-binding site comprises a VH comprising HCDR1, HCDR2, and HCDR3 sequences set forth in SEQ ID NOs: 415, 416, and 418, respectively, and a VL comprising LCDR1, LCDR2, and LCDR3 sequences set forth in SEQ ID NOs: 419, 420, and 421, respectively. In certain embodiments, the second antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 412, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 413. In certain embodiments, the VH and the VL of the second antigen-binding site comprise the amino acid sequences of SEQ ID NOs: 412 and 413, respectively.

In certain embodiments, the second antigen-binding site that binds CD3 is derived from CNG-CD3-2. In certain embodiments, the second antigen-binding site comprises a VH comprising HCDR1, HCDR2, and HCDR3 sequences set forth in SEQ ID NOs: 414, 416, and 425, respectively, and a VL comprising LCDR1, LCDR2, and LCDR3 sequences set forth in SEQ ID NOs: 419, 420, and 421, respectively. In certain embodiments, the second antigen-binding site comprises a VH comprising HCDR1, HCDR2, and HCDR3 sequences set forth in SEQ ID NOs: 415, 416, and 426, respectively, and a VL comprising LCDR1, LCDR2, and LCDR3 sequences set forth in SEQ ID NOs: 419, 420, and 421, respectively. In certain embodiments, the second antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 424, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 413. In certain embodiments, the VH and the VL of the second antigen-binding site comprise the amino acid sequences of SEQ ID NOs: 424 and 413, respectively.

In certain embodiments, the second antigen-binding site that binds CD3 is derived from CNG-CD3-3. In certain embodiments, the second antigen-binding site comprises a VH comprising HCDR1, HCDR2, and HCDR3 sequences set forth in SEQ ID NOs: 414, 431, and 417, respectively, and a VL comprising LCDR1, LCDR2, and LCDR3 sequences set forth in SEQ ID NOs: 419, 420, and 432, respectively. In certain embodiments, the second antigen-binding site comprises a VH comprising HCDR1, HCDR2, and HCDR3 sequences set forth in SEQ ID NOs: 415, 431, and 418, respectively, and a VL comprising LCDR1, LCDR2, and LCDR3 sequences set forth in SEQ ID NOs: 419, 420, and 432, respectively. In certain embodiments, the second antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 429, and a VL that comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 430. In certain embodiments, the VH and the VL of the second antigen-binding site comprise the amino acid sequences of SEQ ID NOs: 429 and 430, respectively.

Such antigen-binding site may take the form of scFv. In certain embodiments, the VH is positioned C-terminal to the VL. In certain embodiments, the VH is positioned N-terminal to the VL. In certain embodiments, the VH and the VL are linked by a peptide linker, for example, a linker disclosed in subsection E below titled "Linkers." In certain embodiments, the second antigen-binding site comprises the amino acid sequence of SEQ ID NO: 422, 427, or 433. To stabilize the scFv, the amino acid residues at position 44 of the VH and at position 100 of the VL (under Kabat numbering) can be substituted by Cys, thereby facilitating the formation of a disulfide bond between the VH and the VL. Accordingly, in certain embodiments, the VH and VL comprise Cys at positions 100 and 44, respectively. In certain embodiments, the second antigen-binding site comprises the amino acid sequence of SEQ ID NO: 423, 428, or 434.

In other embodiments, the second antigen-binding site comprises an sdAb comprising a VH comprising complementarity determining regions HCDR1, HCDR2, and HCDR3. In certain embodiments, the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VH of an sdAb antibody provided in Table 4. In certain embodiments, the VH comprises the HCDR1, HCDR2, and HCDR3 sequences of the antibody provided in Table 4. In certain embodiments, the VH comprises the amino acid sequence of the VH of an sdAb provided in Table 4.

In certain embodiments, the second antigen-binding site competes for binding CD3 (e.g., human CD3 and/or Macaca CD3) with an antibody or antigen-binding fragment thereof comprising the VH, VL and/or scFv sequences provided in Table 4.

In certain embodiments, the second antigen-binding site of the multi-specific binding protein binds CD3 (e.g., human CD3 and/or Macaca CD3) with a dissociation constant ($K_D$) of about 0.1 nM-about 1 pM. The $K_D$ can be measured by a method known in the art. In certain embodiments, the $K_D$ is measured by SPR to CD3 or an extracellular fragment thereof immobilized on a chip. In certain embodiments, the $K_D$ is measured by flow cytometry to CD3 expressed on the surface of cells, for example, following the method described in Example 7 below.

In certain embodiments, the second antigen-binding site binds CD3 with a $K_D$, as measured by SPR, lower than or equal to 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 90 pM, 80 pM, 70 pM, 60 pM, 50 pM, 40 pM, 30 pM, 20 pM, or 10 pM. For example, in certain embodiments, the first antigen-binding site binds CD3 with a $K_D$, as measured by SPR, within the range of about 10 pM-about 1 nM, about 10 pM-about 0.9 nM, about 10 pM-about 0.8 nM, about 10 pM-about 0.7 nM, about 10 pM-about 0.6 nM, about 10 pM-about 0.5 nM, about 10 pM-about 0.4 nM, about 10 pM-about 0.3 nM, about 10 pM-about 0.2 nM, about 10 pM-about 0.1 nM, about 10 pM-about 50 pM, 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 0.5 nM-about 10 nM, about 0.5 nM-about 9 nM, about 0.5 nM-about 8 nM, about 0.5 nM-about 7 nM, about 0.5 nM-about 6 nM, about 0.5 nM-about 5 nM, about 0.5 nM-about 4 nM, about 0.5 nM-about 3 nM, about 0.5 nM-about 2 nM, about 0.5 nM-about 1 nM, about 1 nM-about 10 nM, about 1 nM-about 9 nM, about 1 nM-about 8 nM, about 1 nM-about 7 nM, about 1 nM-about 6 nM, about 1 nM-about 5 nM, about 1 nM-about 4 nM, about 1 nM-about 3 nM, about 1 nM-about 2 nM, about 2 nM-about 10 nM, about 3 nM-about 10 nM, about 4 nM-about 10 nM, about 5 nM-about 10 nM, about 6 nM-about 10 nM, about 7 nM-about 10 nM, about 8 nM-about 10 nM, or about 9 nM-about 10 nM.

In certain embodiments, the second antigen-binding site binds CD3 with a $K_D$, as measured by BLI, lower than or equal to 50 nM, 40 nM, 30 nM, 20 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. For example, in certain embodiments, the first antigen-binding site binds CD3 with a $K_D$, as measured by BLI, within the range of about 0.1 nM-about 20 nM, about 0.1 nM-about 19 nM, about 0.1 nM-about 18 nM, about 0.1 nM-about 17 nM, about 0.1 nM-about 16 nM, about 0.1 nM-about 15 nM, about 0.1 nM-about 14 nM, about 0.1 nM-about 13 nM, about 0.1 nM-about 12 nM, about 0.1 nM-about 11 nM, 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 1 nM-about 50 nM, about 1 nM-about 40 nM, about 1 nM-about 30 nM, about 1 nM-about 20 nM, about 1 nM-about 19 nM, about 1 nM-about 18 nM, about 1 nM-about 17 nM, about 1 nM-about 16 nM, about 1 nM-about 15 nM, about 1 nM-about 14 nM, about 1 nM-about 13 nM, about 1 nM-about 12 nM, about 1 nM-about 11 nM, about 1 nM-about 10 nM, or about 1 nM-about 5 nM.

In certain embodiments, the second antigen-binding site binds CD3 (e.g., human CD3, e.g., human CD3ε) with a $K_D$, as measured by SPR, greater than or equal to 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, or 100 nM. In certain embodiments, the second antigen-binding site binds CD3 with a $K_D$, as measured by SPR, within the range of about 1 nM-about 100 nM, about 1 nM-about 90 nM, about 1 nM-about 80 nM, about 1 nM-about 70 nM, about 1 nM-about 60 nM, about 1 nM-about 50 nM, about 1 nM-about 40 nM, about 1 nM-about 30 nM, about 1 nM-about 20 nM, about 1 nM-about 10 nM, about 10 nM-about 100 nM, about 10 nM-about 90 nM, about 10 nM-about 80 nM, about 10 nM-about 70 nM, about 10 nM-about 60 nM, about 10 nM-about 50 nM, about 10 nM-about 40 nM, about 10 nM-about 30 nM, or about 10 nM-about 20 nM. In certain embodiments, the second antigen-binding site binds CD3 (e.g., human CD3, e.g., human CD3ε) with a $K_D$, as measured by BLI, greater than or equal to 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, or 1 pM. In certain embodiments, the second antigen-binding site binds CD3 with a $K_D$, as measured by BLI, within the range of about 10 nM-about 1 pM, about 10 nM-about 900 nM, about 10 nM-about 800 nM, about 10 nM-about 700 nM, about 10 nM-about 600 nM, about 10 nM-about 500 nM, about 10 nM-about 400 nM, about 10 nM-about 300 nM, about 10 nM-about 200 nM, about 10 nM-about 100 nM, about 100 nM-about 1 pM, about 100 nM-about 900 nM, about 100 nM-about 800 nM, about 100 nM-about 700 nM, about 100 nM-about 600 nM, about 100 nM-about 500 nM, about 100 nM-about 400 nM, about 100 nM-about 300 nM, or about 100 nM-about 200 nM.

It is understood that the binding affinity to CD3 of the second antigen-binding site alone may be different from the binding affinity of the same antigen-binding site in the context of the multi-specific binding protein disclosed herein, possibly due to the conformational restraint from the other domains. The context-dependent binding affinity is described in the subsection G below titled "Binding Affinity."

In certain embodiments, the second antigen-binding site, when present in the form of an Fab, has a melting temperature of at least 60° C., at least 65° C., at least 70° C., at least 75° C., or at least 80° C. In certain embodiments, the second antigen-binding site, when present in the form of an Fab, has a melting temperature in the range of 60-85° C., 60-80° C., 60-75° C., 60-70° C., 60-65° C., 65-85° C., 65-80° C., 65-75° C., 65-70° C., 70-85° C., 70-80° C., 70-75° C., 75-85° C., 75-80° C., or 80-85° C.

C. Half-Life Extension Domain

In certain embodiments, the multi-specific binding protein comprises a half-life extension domain. As used herein, the term "half-life extension domain" refers to a protein domain that prolongs the half-life of a protein to which it is fused, within a subject (e.g., the blood of the subject). Exemplary half-life extension domains include Fc domains, serum albumin domains, and protein domains that bind serum albumin. In certain embodiments, the half-life extension domain in the multi-specific binding protein comprises a third antigen-binding site that binds serum albumin (e.g., HSA). It is contemplated that a serum albumin binding domain may facilitate recycling of the multi-specific binding protein through binding to neonatal Fc receptor (FcRn), thereby extending the serum half-life of the multi-specific binding protein. Accordingly, in certain embodiments, the third antigen-binding site does not bind the D-III domain of HSA (the domain that mediates the interaction between HSA and FcRn). In certain embodiments, the third antigen-binding site extends the serum half-life of the multi-specific binding protein.

In certain embodiments, the third antigen-binding site is an antigen-binding site that binds serum albumin (e.g., human serum albumin (HSA)) derived from the single domain antibodies listed in Table 5. The CDR sequences are identified under the Kabat numbering scheme unless indicated by an asterisk (*).

TABLE 5

Sequences of Exemplary Antibodies That Bind Serum Albumin

| Antibody | VH and HCDRs |
|---|---|
| CNG-HSA-101 | KVQLVESGGGLVQPGGSLRLSCAASGFTFSSFGMTWVRQAPGKGLEWVSSISG SGSDTLYADSVRGRFTISRDNSKNTLYLQMNSLRAEDTAVYYCTIGGSLSPSSQ GTLVTVSS (SEQ ID NO: 121) |
| | HCDR1*: FTFSSFGMT (SEQ ID NO: 122) |
| | HCDR1: SFGMT (SEQ ID NO: 123) |
| | HCDR2: SISGSGSDTLYADSVRG (SEQ ID NO: 124) |
| | HCDR3*: TIGGSLSP (SEQ ID NO: 125) |
| | HCDR3: GGSLSP (SEQ ID NO: 126) |
| CNG-HSA-102 | KVQLLESGGGLVQPGGSLRLSCAASGFTFSSFGMSWVRQAPGKGLEWVSSISG SGSDTLYADSVRGRFTISRDNSKNTLYLQMNSLRPEDTAVYYCTIGGSLSPSSQ GTLVTVSS (SEQ ID NO: 127) |
| | HCDR1*: FTFSSFGMS (SEQ ID NO: 128) |
| | HCDR1: SFGMS (SEQ ID NO: 129) |

TABLE 5-continued

Sequences of Exemplary Antibodies That Bind Serum Albumin

| Antibody | VH and HCDRs |
|---|---|
| | HCDR2: SISGSGSDTLYADSVRG (SEQ ID NO: 124) |
| | HCDR3*: TIGGSLSP (SEQ ID NO: 125) |
| | HCDR3: GGSLSP (SEQ ID NO: 126) |
| CNG-HSA-103 | KVQLVESGGGLVQPGGSLRLSCAASGFTFSSFGMTWVRQAPGKGLEWVSSISGSGSDTLYADSVRGRFTISRDNSKNTLYLQMNSLRPEDTAVYYCTIGGSLSPSSQGTLVTVSS (SEQ ID NO: 130) |
| | HCDR1*: FTFSSFGMT (SEQ ID NO: 122) |
| | HCDR1: SFGMT (SEQ ID NO: 123) |
| | HCDR2: SISGSGSDTLYADSVRG (SEQ ID NO: 124) |
| | HCDR3*: TIGGSLSP (SEQ ID NO: 125) |
| | HCDR3: GGSLSP (SEQ ID NO: 126) |
| CNG-HSA-104 | KVQLLESGGGLVQPGGSLRLSCAASGFTFHSFGMSWVRQAPGKGLEWVSSISGSGSDTLYADSVKGRFTISRDNSKNTLYLQMNSLRPEDTAVYYCTIGGSLSRSSQGTLVTVSS (SEQ ID NO: 131) |
| | HCDR1*: FTFHSFGMS (SEQ ID NO: 132) |
| | HCDR1: SFGMS (SEQ ID NO: 129) |
| | HCDR2: SISGSGSDTLYADSVKG (SEQ ID NO: 133) |
| | HCDR3*: TIGGSLSR (SEQ ID NO: 134) |
| | HCDR3: GGSLSR (SEQ ID NO: 135) |
| CNG-HSA-105 | EVQLLESGGGLVQPGGSLRLSCAASGFVFSSFGMSWVRQAPGKGLEWVSSISGSGSDTLYADSVKGRFTISRDNSKNTLYLQMNSLRPEDTAVYYCTIGGSLSRSSQGTLVTVSS (SEQ ID NO: 136) |
| | HCDR1*: FVFSSFGMS (SEQ ID NO: 137) |
| | HCDR1: SFGMS (SEQ ID NO: 129) |
| | HCDR2: SISGSGSDTLYADSVKG (SEQ ID NO: 133) |
| | HCDR3*: TIGGSLSR (SEQ ID NO: 134) |
| | HCDR3: GGSLSR (SEQ ID NO: 135) |
| CNG-HSA-106 | KVQLLESGGGLVQPGGSLRLSCAASGFTFSSFGMSWVRQAPGKGLEWVSSISGSGSDTLYADSVRGRFTISRDNSKNTLYLQMDSLRAEDTAVYYCTIGGSRSISSQGTLVTVSS (SEQ ID NO: 138) |
| | HCDR1*: FTFSSFGMS (SEQ ID NO: 128) |
| | HCDR1: SFGMS (SEQ ID NO: 129) |
| | HCDR2: SISGSGSDTLYADSVRG (SEQ ID NO: 124) |
| | HCDR3*: TIGGSRSI (SEQ ID NO: 139) |
| | HCDR3: GGSRSI (SEQ ID NO: 140) |
| CNG-HSA-107 | KVQLLESGGGLVQPGGSLRLSCAASGFTFSSFGMSWVRQAPGKGLEWVSSISGSGSDTLYADSVRGRFTISRDNSKNTLYLQMNSLRAEDTAVYYCSIGGSLIRSSQGTLVTVSS (SEQ ID NO: 141) |
| | HCDR1*: FTFSSFGMS (SEQ ID NO: 128) |
| | HCDR1: SFGMS (SEQ ID NO: 129) |
| | HCDR2: SISGSGSDTLYADSVRG (SEQ ID NO: 124) |
| | HCDR3*: SIGGSLIR (SEQ ID NO: 142) |
| | HCDR3: GGSLIR (SEQ ID NO: 143) |

TABLE 5-continued

Sequences of Exemplary Antibodies That Bind Serum Albumin

| Antibody | VH and HCDRs |
| --- | --- |

CNG-HSA-108
KVQLVESGGGLVQPGGSLRLSCAASGFTFGSFGMSWVRQAPGKGLEWVSSISG
SGADTLYADSVKGRFTISRDNSKNTLYLQMNSLRAEDTAVYYCTIGGSLRASS
QGTLVTVSS (SEQ ID NO: 144)

HCDR1*: FTFGSFGMS (SEQ ID NO: 145)

HCDR1: SFGMS (SEQ ID NO: 129)

HCDR2: SISGSGADTLYADSVKG (SEQ ID NO: 146)

HCDR3*: TIGGSLRA (SEQ ID NO: 147)

HCDR3: GGSLRA (SEQ ID NO: 148)

CNG-HSA-109
KVQLVESGGGLVQPGNSLRLSCAASGFTFGSFGMSWVRQAPGKGPEWVSSISG
SGSDTLYADSVKGRFTISRDNSKNTLYLQMNSLRPEDTAVYYCTIGGSLSRSSQ
GTLVTVSS (SEQ ID NO: 149)

HCDR1*: FTFGSFGMS (SEQ ID NO: 145)

HCDR1: SFGMS (SEQ ID NO: 129)

HCDR2: SISGSGSDTLYADSVRG (SEQ ID NO: 133)

HCDR3*: TIGGSLSR (SEQ ID NO: 134)

HCDR3: GGSLSR (SEQ ID NO: 135)

CNG-HSA-110
KVQLVESGGGLVQPGNSLRLSCAASGFTFSSFGMSWVRQAPGKGLEWVSSISG
SGGDTLYADSAKGRFTISRDNSKNTLYLQMNSLRPEDTAVYYCTIGGSLSRSSQ
GTLVTVSS (SEQ ID NO: 150)

HCDR1*: FTFSSFGMS (SEQ ID NO: 128)

HCDR1: SFGMS (SEQ ID NO: 129)

HCDR2: SISGSGGDTLYADSAKG (SEQ ID NO: 151)

HCDR3*: TIGGSLSR (SEQ ID NO: 134)

HCDR3: GGSLSR (SEQ ID NO: 135)

CNG-HSA-111
KVQLVESGGGLVQPGGSLRLSCAASGFTFSSFGMSWVRQAPGKGLEWVSSISG
SGSDTLYADSVEGRFTISRDNSKNTLYLQMNSLRAEDTAVYYCTIGGSLKQSSQ
GTLVTVSS (SEQ ID NO: 152)

HCDR1*: FTFSSFGMS (SEQ ID NO: 128)

HCDR1: SFGMS (SEQ ID NO: 129)

HCDR2: SISGSGSDTLYADSVEG (SEQ ID NO: 153)

HCDR3*: TIGGSLKQ (SEQ ID NO: 154)

HCDR3: GGSLKQ (SEQ ID NO: 155)

CNG-HSA-112
KVQLLESGGGLVQPGGSLRLSCAASGFTFPSFGMSWVRQAPGKGLEWVSSISG
SGSDTLYADSVKGRFTISRDNAKTTLYLQMNSLRPEDTAVYYCTIGGSVSKSSR
GTLVTVSS (SEQ ID NO: 156)

HCDR1*: FTFPSFGMS (SEQ ID NO: 157)

HCDR1: SFGMS (SEQ ID NO: 129)

HCDR2: SISGSGSDTLYADSVKG (SEQ ID NO: 133)

HCDR3*: TIGGSVSK (SEQ ID NO: 158)

HCDR3: GGSVSK (SEQ ID NO: 159)

CNG-HSA-113
GVQLLESGGGLVQPGGSLRLSCAASGFTFSSFGMSWVRQAPGKGLEWVSSISG
TGSDTLYADSVKGRFTISRDNSKNTLYLQMNSLRPEDTAVYYCTIGGSLRYSSQ
GTLVTVSS (SEQ ID NO: 160)

TABLE 5-continued

Sequences of Exemplary Antibodies That Bind Serum Albumin

| Antibody | VH and HCDRs |
|---|---|
| | HCDR1*: FTFSSFGMS (SEQ ID NO: 128) |
| | HCDR1: SFGMS (SEQ ID NO: 129) |
| | HCDR2: SISGTGSDTLYADSVKG (SEQ ID NO: 161) |
| | HCDR3*: TIGGSLRY (SEQ ID NO: 162) |
| | HCDR3: GGSLRY (SEQ ID NO: 163) |
| CNG-HSA-114 | KVQLVESGGGLVQPGNSLRLSCAASGFTFSSFGMSWVRQAPGKGLEWVSSISGSGSDTLTADSVKGRFTISRDNSKNTLYLQMNSLRAEDTAVYYCTIGGSLVRSSQGTLVTVSS (SEQ ID NO: 164) |
| | HCDR1*: FTFSSFGMS (SEQ ID NO: 128) |
| | HCDR1: SFGMS (SEQ ID NO: 129) |
| | HCDR2: SISGSGSDTLTADSVKG (SEQ ID NO: 165) |
| | HCDR3*: TIGGSLVR (SEQ ID NO: 166) |
| | HCDR3: GGSLVR (SEQ ID NO: 167) |
| CNG-HSA-115 | KVQLVESGGGLVQPGNSLRLSCAASGFTFSSFGMGWVRQAPGKGLEWVSSISGSGSDTLYAPSVKGRFTISRDNSKNTLYLQMNSLRPEDTAVYYCTFAGSLSRSSQGTLVTVSS (SEQ ID NO: 168) |
| | HCDR1*: FTFSSFGMG (SEQ ID NO: 169) |
| | HCDR1: SFGMG (SEQ ID NO: 170) |
| | HCDR2: SISGSGSDTLYAPSVKG (SEQ ID NO: 171) |
| | HCDR3*: TFAGSLSR (SEQ ID NO: 172) |
| | HCDR3: AGSLSR (SEQ ID NO: 173) |
| CNG-HSA-116 | KVQLVESGGGLVQPGGSLRLSCAASGFTFSSFGMSWVRQAPGKGPEWVSSISGSGSDTLYADSVKGRFTISRDNSKNTLYLQMNSLRAEDTAVYYCTIGGSLRASSQGTLVTVSS (SEQ ID NO: 174) |
| | HCDR1*: FTFSSFGMS (SEQ ID NO: 128) |
| | HCDR1: SFGMS (SEQ ID NO: 129) |
| | HCDR2: SISGSGSDTLYADSVKG (SEQ ID NO: 133) |
| | HCDR3*: TIGGSLRA (SEQ ID NO: 147) |
| | HCDR3: GGSLRA (SEQ ID NO: 148) |
| CNG-HSA-117 | KVQLVESGGGLVQPGNSLRLSCAASGFTFSSFGMSWVRQAPGKGLEWVSSISGSGSDTLYADSVKGRFTISRDNSKNTLYLQMNSLRAEDTAVYYCTIGGSLTRSSQGTLVTVSS (SEQ ID NO: 175) |
| | HCDR1*: FTFSSFGMS (SEQ ID NO: 128) |
| | HCDR1: SFGMS (SEQ ID NO: 129) |
| | HCDR2: SISGSGSDTLYADSVKG (SEQ ID NO: 133) |
| | HCDR3*: TIGGSLTR (SEQ ID NO: 176) |
| | HCDR3: GGSLTR (SEQ ID NO: 177) |
| CNG-HSA-118 | KVQLVESGGGLVQPGNSLRLSCAASGFTFSSFGMSWVRQAPGKGLEWVSSISGGGSDTLYADSVRGRFTISRDNSKNTLYLQMNSLRAEDTAVYYCTIGGSLRASSQGTLVTVSS (SEQ ID NO: 178) |
| | HCDR1*: FTFSSFGMS (SEQ ID NO: 128) |
| | HCDR1: SFGMS (SEQ ID NO: 129) |
| | HCDR2: SISGGGSDTLYADSVRG (SEQ ID NO: 179) |

TABLE 5-continued

Sequences of Exemplary Antibodies That Bind Serum Albumin

| Antibody | VH and HCDRs |
|---|---|

HCDR3*: TIGGSLRA (SEQ ID NO: 147)

HCDR3: GGSLRA (SEQ ID NO: 148)

CNG-HSA-119    KVQLVESGGGLVQPGNSLRLSCAASGFTFSSFGMSWVRQAPGKGLEWVSSISG
SGSDALYADSAKGRFTISRDNAKTTLYLQMNSLRAEDTAVYYCTIGGSLSPSSQ
GTLVTVSS (SEQ ID NO: 180)

HCDR1*: FTFSSFGMS (SEQ ID NO: 128)

HCDR1: SFGMS (SEQ ID NO: 129)

HCDR2: SISGSGSDALYADSAKG (SEQ ID NO: 181)

HCDR3*: TIGGSLSP (SEQ ID NO: 125)

HCDR3: GGSLSP (SEQ ID NO: 126)

CNG-HSA-120    KVQLVESGGGLVQPGGSLRLSCAASGFTFSSFGMSWVRQAPGKGPEWVSSISG
SGSDTLYADSVKGRFTISRDNSKNTLYLQMNSLRPEDTAVYYCTIGGSLKQSSQ
GTLVTVSS (SEQ ID NO: 182)

HCDR1*: FTFSSFGMS (SEQ ID NO: 128)

HCDR1: SFGMS (SEQ ID NO: 129)

HCDR2: SISGSGSDTLYADSVKG (SEQ ID NO: 133)

HCDR3*: TIGGSLKQ (SEQ ID NO: 154)

HCDR3: GGSLKQ (SEQ ID NO: 155)

Consensus-1 (CNG-HSA-101 to -120)    HCDR1*: FX$_1$FX$_2$SFGMX$_3$, wherein X$_1$ is T or V; X$_2$ is S, H, G, or P; and X is S, T, or G (SEQ ID NO: 408)

HCDR1: SFGMX, wherein X is S, T, or G (SEQ ID NO: 184)

HCDR2: SISGX$_1$GX$_2$DX$_3$LX$_4$AX$_5$SX$_6$X$_7$G, wherein X$_1$ is S, T, or G; X is S, A, or G; X$_3$ is T or A; X$_4$ is Y or T; X$_5$ is D or P; X is V or A; and X$_7$ is K, R, or E (SEQ ID NO: 409)

HCDR3*: X$_1$X$_2$X$_3$GSX$_4$X$_5$X$_6$, wherein X$_1$ is T or S; X$_2$ is I or F; X$_3$ is G or A; X$_4$ is L, R, or V; X$_5$ is S, I, R, K, V, or T; and X is R, P, I, A, Q, K, or Y (SEQ ID NO: 410)

HCDR3: X$_1$GSX$_2$X$_3$X$_4$, wherein X$_1$ is G or A; X$_2$ is L, R, or V; X$_3$ is S, 1, R, K, V, or T; and X$_4$ is R, P, I, A, Q, K, or Y (SEQ ID NO: 411)

Consensus-2 (CNG-HSA-101 to -104, -108 to-112, and -115 to -120)    HCDR1*: FTFX$_1$SFGMX$_2$, wherein X$_1$ is S, H, G, or P; and X$_2$ is S, T, or G (SEQ ID NO: 183)

HCDR1: SFGMX, wherein X is S, T, or G (SEQ ID NO: 184)

HCDR2: SISGX$_1$GX$_2$DX$_3$LYAX$_4$SX$_5$XG, wherein X$_1$ is S or G; X$_2$ is S, A, or G; X$_3$ is T or A; X$_4$ is D or P; X$_5$ is V or A; and X$_6$ is K, R, or E (SEQ ID NO: 185)

HCDR3*: TX1X2GSX$_3$X$_4$X$_5$, wherein X$_1$ is I or F; X$_2$ is G or A; X$_3$ is L or V; X$_4$ is S, R, K, or T; and X$_5$ is R, P, A, Q, or K (SEQ ID NO: 186)

HCDR3: X$_1$GSX$_2$X$_3$X$_4$, wherein X$_1$ is G or A; X$_2$ is L or V; X$_3$ is S, R, K, or T; and X$_4$ is R, P, A, Q, or K (SEQ ID NO: 187)

TABLE 5-continued

Sequences of Exemplary Antibodies That Bind Serum Albumin

| Antibody | VH and HCDRs |
|---|---|
| Consensus-3 (CNG-HSA-101, -102, -104, -109, -113, -116, and -117) | HCDR1*: FTFX₁SFGMX₂, wherein X₁ is S, H, or G; and X₂ is S or T (SEQ ID NO: 188)<br><br>HCDR1: SFGMX, wherein X is S or T (SEQ ID NO: 189)<br><br>HCDR2: SISGX₁GSDTLYADSVX₂G, wherein X₁ is S or T; and X₂ is K or R (SEQ ID NO: 190)<br><br>HCDR3*: TIGGSLX₁X₂, wherein X₁ is S, R, or T; and X₂ is R, P, Y, or A (SEQ ID NO: 191)<br><br>HCDR3: GGSLX₁X₂, wherein X₁ is S, R, or T; and X₂ is R, P, Y, or A (SEQ ID NO: 192) |
| Consensus-4 (CNG-HSA-101, -102, -104, -109, -116, and -117) | HCDR1*: FTFX₁SFGMX₂, wherein X₁ is S, H, or G; and X₂ is S or T (SEQ ID NO: 188)<br><br>HCDR1: SFGMX, wherein X is S or T (SEQ ID NO: 189)<br><br>HCDR2: SISGSGSDTLYADSVXG, wherein X is K or R (SEQ ID NO: 193)<br><br>HCDR3*: TIGGSLX₁X₂, wherein X₁ is S, R, or T; and X₂ is R, P, or A (SEQ ID NO: 194)<br><br>HCDR3: GGSLX₁X₂, wherein X₁ is S, R, or T; and X₂ is R, P, or A (SEQ ID NO: 195) |

In certain embodiments, the antigen-binding site that binds serum albumin comprises a VH that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VH of an antibody disclosed in Table 5. In certain embodiments, the antigen-binding site comprises the HCDR1, HCDR2, and HCDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J Mol Biol 196: 901-917), MacCallum (see MacCallum R M et al., (1996) J Mol Biol 262: 732-745), IMGT (see Lefranc, (1999) The Immunologist, 7, 132-136), or any other CDR determination method known in the art, of the VH sequence of an antibody disclosed in Table 5. In certain embodiments, the antigen-binding site comprises the HCDR1, HCDR2, and HCDR3 sequences of an antibody disclosed in Table 5. In certain embodiments, the antigen-binding site comprises the VH sequence of an antibody disclosed in Table 5.

Series 1 Constructs

In certain embodiments, the antigen-binding site that binds HSA comprises a VH comprising HCDR1, HCDR2, and HCDR3 sequences set forth in SEQ ID NOs: 408, 409, and 410, respectively, wherein the antigen-binding site does not comprise HCDR1, HCDR2, and HCDR3, sequences set forth in SEQ ID NOs: 128, 133, and 134, respectively. In certain embodiments, the HCDR1 sequence is selected from the group consisting of SEQ ID NOs: 122, 128, 132, 137, 145, 157, and 169; the HCDR2 sequence is selected from the group consisting of SEQ ID NOs: 124, 133, 146, 151, 153, 161, 165, 171, 179, and 181; and/or the HCDR3 sequence is selected from the group consisting of SEQ ID NOs: 125, 134, 142, 147, 154, 158, 162, 166, 172, and 176.

In certain embodiments, the antigen-binding site comprises a VH comprising HCDR1, HCDR2, and HCDR3 sequences set forth in SEQ ID NOs: 184, 409, and 411, respectively, wherein the antigen-binding site does not comprise HCDR1, HCDR2, and HCDR3 sequences set forth in SEQ ID NOs: 129, 133, and 135, respectively. In certain embodiments, the HCDR1 sequence is selected from the group consisting of SEQ ID NOs: 123, 129, and 170; the HCDR2 sequence is selected from the group consisting of SEQ ID NOs: 124, 133, 146, 151, 153, 161, 165, 171, 179, and 181; and/or the HCDR3 sequence is selected from the group consisting of SEQ ID NOs: 126, 135, 143, 148, 155, 159, 163, 167, 173, and 177.

In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 121.

In certain embodiments, the antigen-binding site has a higher binding affinity to human serum albumin, cynomolgus serum albumin, mouse serum albumin, and/or protein A relative to an antigen-binding site having VH sequence set forth in SEQ ID NO: 196.

Series 2 Constructs

In certain embodiments, the antigen-binding site that binds HSA comprises a VH comprising HCDR1, HCDR2, and HCDR3 sequences set forth in SEQ ID NOs: 183, 185, and 186, respectively, wherein the antigen-binding site does not comprise HCDR1, HCDR2, and HCDR3, sequences set forth in SEQ ID NOs: 128, 133, and 134, respectively. In certain embodiments, the HCDR1 sequence is selected from the group consisting of SEQ ID NOs: 122, 128, 132, 145, 157, and 169; the HCDR2 sequence is selected from the group consisting of SEQ ID NOs: 124, 133, 146, 151, 153, 171, 179, and 181; and/or the HCDR3 sequence is selected from the group consisting of SEQ ID NOs: 125, 134, 147, 154, 158, 172, and 176.

In certain embodiments, the antigen-binding site comprises a VH comprising HCDR1, HCDR2, and HCDR3 sequences set forth in SEQ ID NOs: 184, 185, and 187, respectively, wherein the antigen-binding site does not comprise HCDR1, HCDR2, and HCDR3 sequences set forth in SEQ ID NOs: 129, 133, and 135, respectively. In certain embodiments, the HCDR1 sequence is selected from the group consisting of SEQ ID NOs: 123, 129, and 170; the HCDR2 sequence is selected from the group consisting of SEQ ID NOs: 124, 133, 146, 151, 153, 171, 179, and 181; and/or the HCDR3 sequence is selected from the group consisting of SEQ ID NOs: 126, 135, 148, 155, 159, 173, and 177.

In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 121.

In certain embodiments, the antigen-binding site has a higher binding affinity to human serum albumin relative to an antigen-binding site having VH sequence set forth in SEQ ID NO: 196. In certain embodiments, the antigen-binding site binds human serum albumin with a $K_D$ lower than or equal to 10 nM, 9 nM, 8 nM, 7 nM, 6 nM, 5 nM, 4 nM, or 3 nM, as measured by SPR when the antigen-binding site is present as a monomer. In certain embodiments, the antigen-binding site binds human serum albumin with a $K_D$ in the range of 1-10 nM, 1-9 nM, 1-8 nM, 1-7 nM, 1-6 nM, 1-5 nM, 1-4 nM, or 1-3 nM, as measured by SPR when the antigen-binding site is present as a monomer.

Series 3 Constructs

In certain embodiments, the antigen-binding site that binds HSA comprises a VH comprising HCDR1, HCDR2, and HCDR3 sequences set forth in SEQ ID NOs: 188, 190, and 191, respectively, wherein the antigen-binding site does not comprise HCDR1, HCDR2, and HCDR3, sequences set forth in SEQ ID NOs: 128, 133, and 134, respectively. In certain embodiments, the HCDR1 sequence is selected from the group consisting of SEQ ID NOs: 122, 128, 132, and 145; the HCDR2 sequence is selected from the group consisting of SEQ ID NOs: 124, 133, and 161; and/or the HCDR3 sequence is selected from the group consisting of SEQ ID NOs: 125, 134, 162, 147, and 176.

In certain embodiments, the antigen-binding site comprises a VH comprising HCDR1, HCDR2, and HCDR3 sequences set forth in SEQ ID NOs: 189, 190, and 192, respectively, wherein the antigen-binding site does not comprise HCDR1, HCDR2, and HCDR3 sequences set forth in SEQ ID NOs: 129, 133, and 135, respectively. In certain embodiments, the HCDR1 sequence is selected from the group consisting of SEQ ID NOs: 123 and 129; the HCDR2 sequence is selected from the group consisting of SEQ ID NOs: 124, 133, and 161; and/or the HCDR3 sequence is selected from the group consisting of SEQ ID NOs: 126, 135, 163, 148, and 177.

In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 121.

In certain embodiments, the antigen-binding site has a higher binding affinity to protein A relative to an antigen-binding site having VH sequence set forth in SEQ ID NO: 196. In certain embodiments, the antigen-binding site binds protein A with a $K_D$ lower than or equal to 2.5 nM or 2 nM, as measured by SPR when the antigen-binding site is present as a monomer. In certain embodiments, the antigen-binding site binds protein A with a $K_D$ in the range of 1-2.5 nM or 1-2 nM, as measured by SPR when the antigen-binding site is present as a monomer.

Series 4 Constructs

In certain embodiments, the antigen-binding site that binds HSA comprises a VH comprising HCDR1, HCDR2, and HCDR3 sequences set forth in SEQ ID NOs: 188, 193, and 194, respectively, wherein the antigen-binding site does not comprise HCDR1, HCDR2, and HCDR3, sequences set forth in SEQ ID NOs: 128, 133, and 134, respectively. In certain embodiments, the HCDR1 sequence is selected from the group consisting of SEQ ID NOs: 122, 128, 132, and 145; the HCDR2 sequence is selected from the group consisting of SEQ ID NOs: 124 and 133; and/or the HCDR3 sequence is selected from the group consisting of SEQ ID NOs: 125, 134, 147, and 176.

In certain embodiments, the antigen-binding site comprises a VH comprising HCDR1, HCDR2, and HCDR3 sequences set forth in SEQ ID NOs: 189, 193, and 195, respectively, wherein the antigen-binding site does not comprise HCDR1, HCDR2, and HCDR3 sequences set forth in SEQ ID NOs: 129, 133, and 135, respectively. In certain embodiments, the HCDR1 sequence is selected from the group consisting of SEQ ID NOs: 123 and 129; the HCDR2 sequence is selected from the group consisting of SEQ ID NOs: 124 and 133; and/or the HCDR3 sequence is selected from the group consisting of SEQ ID NOs: 126, 135, 148, and 177.

In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 121.

In certain embodiments, the antigen-binding site has a higher binding affinity to human serum albumin and a higher affinity to protein A relative to an antigen-binding site having VH sequence set forth in SEQ ID NO: 196. In certain embodiments, the antigen-binding site binds human serum albumin with a $K_D$ lower than or equal to 10 nM, 9 nM, 8 nM, 7 nM, 6 nM, 5 nM, 4 nM, or 3 nM and binds protein A with a $K_D$ lower than or equal to 2.5 nM or 2 nM, as measured by SPR when the antigen-binding site is present as a monomer. In certain embodiments, the antigen-binding site binds human serum albumin with a $K_D$ in the range of 1-10 nM, 1-9 nM, 1-8 nM, 1-7 nM, 1-6 nM, 1-5 nM, 1-4 nM, or 1-3 nM and binds protein A with a $K_D$ in the range of 1-2.5 nM or 1-2 nM, as measured by SPR when the antigen-binding site is present as a monomer.

Individual Constructs

In certain embodiments, the antigen-binding site that binds serum albumin is derived from CNG-HSA-101. In certain embodiments, the antigen-binding site comprises a VH comprising HCDR1, HCDR2, and HCDR3 sequences set forth in SEQ ID NOs: 122, 124, and 125, respectively. In certain embodiments, the antigen-binding site comprises a VH comprising HCDR1, HCDR2, and HCDR3 sequences set forth in SEQ ID NOs: 123, 124, and 126, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 121. In certain embodiments, the VH comprises the amino acid sequence of SEQ ID NO: 121.

In certain embodiments, the antigen-binding site that binds serum albumin is derived from CNG-HSA-102. In certain embodiments, the antigen-binding site comprises a VH comprising HCDR1, HCDR2, and HCDR3 sequences set forth in SEQ ID NOs: 128, 124, and 125, respectively. In certain embodiments, the antigen-binding site comprises a VH comprising HCDR1, HCDR2, and HCDR3 sequences set forth in SEQ ID NOs: 129, 124, and 126, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 127. In certain embodiments, the VH comprises the amino acid sequence of SEQ ID NO: 127.

In certain embodiments, the antigen-binding site that binds serum albumin is derived from CNG-HSA-103. In certain embodiments, the antigen-binding site comprises a VH comprising HCDR1, HCDR2, and HCDR3 sequences set forth in SEQ ID NOs: 122, 124, and 125, respectively. In certain embodiments, the antigen-binding site comprises a VH comprising HCDR1, HCDR2, and HCDR3 sequences set forth in SEQ ID NOs: 123, 124, and 126, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 130. In certain embodiments, the VH comprises the amino acid sequence of SEQ ID NO: 130.

In certain embodiments, the antigen-binding site that binds serum albumin is derived from CNG-HSA-104. In certain embodiments, the antigen-binding site comprises a VH comprising HCDR1, HCDR2, and HCDR3 sequences set forth in SEQ ID NOs: 132, 133, and 134, respectively. In certain embodiments, the antigen-binding site comprises a VH comprising HCDR1, HCDR2, and HCDR3 sequences set forth in SEQ ID NOs: 129, 133, and 135, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 131. In certain embodiments, the VH comprises the amino acid sequence of SEQ ID NO: 131.

In certain embodiments, the antigen-binding site that binds serum albumin is derived from CNG-HSA-105. In certain embodiments, the antigen-binding site comprises a VH comprising HCDR1, HCDR2, and HCDR3 sequences set forth in SEQ ID NOs: 137, 133, and 134, respectively. In certain embodiments, the antigen-binding site comprises a VH comprising HCDR1, HCDR2, and HCDR3 sequences set forth in SEQ ID NOs: 129, 133, and 135, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 136. In certain embodiments, the VH comprises the amino acid sequence of SEQ ID NO: 136.

In certain embodiments, the antigen-binding site that binds serum albumin is derived from CNG-HSA-106. In certain embodiments, the antigen-binding site comprises a VH comprising HCDR1, HCDR2, and HCDR3 sequences set forth in SEQ ID NOs: 128, 124, and 139, respectively. In certain embodiments, the antigen-binding site comprises a VH comprising HCDR1, HCDR2, and HCDR3 sequences set forth in SEQ ID NOs: 129, 124, and 140, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 138. In certain embodiments, the VH comprises the amino acid sequence of SEQ ID NO: 138.

In certain embodiments, the antigen-binding site that binds serum albumin is derived from CNG-HSA-107. In certain embodiments, the antigen-binding site comprises a VH comprising HCDR1, HCDR2, and HCDR3 sequences set forth in SEQ ID NOs: 128, 124, and 142, respectively. In certain embodiments, the antigen-binding site comprises a VH comprising HCDR1, HCDR2, and HCDR3 sequences set forth in SEQ ID NOs: 129, 124, and 143, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 141. In certain embodiments, the VH comprises the amino acid sequence of SEQ ID NO: 141.

In certain embodiments, the antigen-binding site that binds serum albumin is derived from CNG-HSA-108. In certain embodiments, the antigen-binding site comprises a VH comprising HCDR1, HCDR2, and HCDR3 sequences set forth in SEQ ID NOs: 145, 146, and 147, respectively. In certain embodiments, the antigen-binding site comprises a VH comprising HCDR1, HCDR2, and HCDR3 sequences set forth in SEQ ID NOs: 129, 146, and 148, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 144. In certain embodiments, the VH comprises the amino acid sequence of SEQ ID NO: 144.

In certain embodiments, the antigen-binding site that binds serum albumin is derived from CNG-HSA-109. In certain embodiments, the antigen-binding site comprises a VH comprising HCDR1, HCDR2, and HCDR3 sequences set forth in SEQ ID NOs: 145, 133, and 134, respectively. In certain embodiments, the antigen-binding site comprises a VH comprising HCDR1, HCDR2, and HCDR3 sequences set forth in SEQ ID NOs: 129, 133, and 135, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, In certain embodiments, the antigen-binding site that binds serum albumin is derived from CNG-HSA-110. In certain embodiments, the antigen-binding site comprises a VH comprising HCDR1, HCDR2, and HCDR3 sequences set forth in SEQ ID NOs: 128, 151, and 134, respectively. In certain embodiments, the antigen-binding site comprises a VH comprising HCDR1, HCDR2, and HCDR3 sequences set forth in SEQ ID NOs: 129, 151, and 135, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 150. In certain embodiments, the VH comprises the amino acid sequence of SEQ ID NO: 150.

In certain embodiments, the antigen-binding site that binds serum albumin is derived from CNG-HSA-111. In certain embodiments, the antigen-binding site comprises a VH comprising HCDR1, HCDR2, and HCDR3 sequences set forth in SEQ ID NOs: 128, 153, and 154, respectively. In certain embodiments, the antigen-binding site comprises a VH comprising HCDR1, HCDR2, and HCDR3 sequences set forth in SEQ ID NOs: 129, 153, and 155, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 152. In certain embodiments, the VH comprises the amino acid sequence of SEQ ID NO: 152.

In certain embodiments, the antigen-binding site that binds serum albumin is derived from CNG-HSA-112. In certain embodiments, the antigen-binding site comprises a VH comprising HCDR1, HCDR2, and HCDR3 sequences set forth in SEQ ID NOs: 157, 133, and 158, respectively. In certain embodiments, the antigen-binding site comprises a VH comprising HCDR1, HCDR2, and HCDR3 sequences set forth in SEQ ID NOs: 129, 133, and 159, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 156. In certain embodiments, the VH comprises the amino acid sequence of SEQ ID NO: 156.

In certain embodiments, the antigen-binding site that binds serum albumin is derived from CNG-HSA-113. In certain embodiments, the antigen-binding site comprises a VH comprising HCDR1, HCDR2, and HCDR3 sequences set forth in SEQ ID NOs: 128, 161, and 162, respectively. In certain embodiments, the antigen-binding site comprises a VH comprising HCDR1, HCDR2, and HCDR3 sequences set forth in SEQ ID NOs: 129, 161, and 163, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 160. In certain embodiments, the VH comprises the amino acid sequence of SEQ ID NO: 160.

In certain embodiments, the antigen-binding site that binds serum albumin is derived from CNG-HSA-114. In certain embodiments, the antigen-binding site comprises a VH comprising HCDR1, HCDR2, and HCDR3 sequences set forth in SEQ ID NOs: 128, 165, and 166, respectively. In certain embodiments, the antigen-binding site comprises a VH comprising HCDR1, HCDR2, and HCDR3 sequences set forth in SEQ ID NOs: 129, 165, and 167, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 164. In certain embodiments, the VH comprises the amino acid sequence of SEQ ID NO: 164.

In certain embodiments, the antigen-binding site that binds serum albumin is derived from CNG-HSA-115. In certain embodiments, the antigen-binding site comprises a VH comprising HCDR1, HCDR2, and HCDR3 sequences set forth in SEQ ID NOs: 169, 171, and 172, respectively. In certain embodiments, the antigen-binding site comprises a VH comprising HCDR1, HCDR2, and HCDR3 sequences set forth in SEQ ID NOs: 170, 171, and 173, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 168. In certain embodiments, the VH comprises the amino acid sequence of SEQ ID NO: 168.

In certain embodiments, the antigen-binding site that binds serum albumin is derived from CNG-HSA-116. In certain embodiments, the antigen-binding site comprises a VH comprising HCDR1, HCDR2, and HCDR3 sequences set forth in SEQ ID NOs: 128, 133, and 147, respectively. In certain embodiments, the antigen-binding site comprises a VH comprising HCDR1, HCDR2, and HCDR3 sequences set forth in SEQ ID NOs: 129, 133, and 148, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 174. In certain embodiments, the VH comprises the amino acid sequence of SEQ ID NO: 174.

In certain embodiments, the antigen-binding site that binds serum albumin is derived from CNG-HSA-117. In certain embodiments, the antigen-binding site comprises a VH comprising HCDR1, HCDR2, and HCDR3 sequences set forth in SEQ ID NOs: 128, 133, and 176, respectively. In certain embodiments, the antigen-binding site comprises a VH comprising HCDR1, HCDR2, and HCDR3 sequences set forth in SEQ ID NOs: 129, 133, and 177, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 175. In certain embodiments, the VH comprises the amino acid sequence of SEQ ID NO: 175.

In certain embodiments, the antigen-binding site that binds serum albumin is derived from CNG-HSA-118. In certain embodiments, the antigen-binding site comprises a VH comprising HCDR1, HCDR2, and HCDR3 sequences set forth in SEQ ID NOs: 128, 179, and 147, respectively. In certain embodiments, the antigen-binding site comprises a VH comprising HCDR1, HCDR2, and HCDR3 sequences set forth in SEQ ID NOs: 129, 179, and 148, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 178. In certain embodiments, the VH comprises the amino acid sequence of SEQ ID NO: 178.

In certain embodiments, the antigen-binding site that binds serum albumin is derived from CNG-HSA-119. In certain embodiments, the antigen-binding site comprises a VH comprising HCDR1, HCDR2, and HCDR3 sequences set forth in SEQ ID NOs: 128, 181, and 125, respectively. In certain embodiments, the antigen-binding site comprises a VH comprising HCDR1, HCDR2, and HCDR3 sequences set forth in SEQ ID NOs: 129, 181, and 126, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 180. In certain embodiments, the VH comprises the amino acid sequence of SEQ ID NO: 180.

In certain embodiments, the antigen-binding site that binds serum albumin is derived from CNG-HSA-120. In certain embodiments, the antigen-binding site comprises a VH comprising HCDR1, HCDR2, and HCDR3 sequences set forth in SEQ ID NOs: 128, 133, and 154, respectively. In certain embodiments, the antigen-binding site comprises a VH comprising HCDR1, HCDR2, and HCDR3 sequences set forth in SEQ ID NOs: 129, 133, and 155, respectively. In certain embodiments, the antigen-binding site comprises a VH comprising an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 180. In certain embodiments, the VH comprises the amino acid sequence of SEQ ID NO: 180.

In certain embodiments, the antigen-binding site derived from CNG-HSA-101, CNG-HSA-102, CNG-HSA-103, CNG-HSA-104, CNG-HSA-108, CNG-HSA-109, CNG-HSA-110, CNG-HSA-111, CNG-HSA-112, CNG-HSA-115, CNG-HSA-116, CNG-HSA-117, CNG-HSA-118, CNG-HSA-119, or CNG-HSA-120 has a higher binding affinity to human, cynomolgus, and/or mouse serum albumin relative to an antigen-binding site having VH sequence set forth in SEQ ID NO: 196.

In certain embodiments, the antigen-binding site derived from CNG-HSA-101, CNG-HSA-102, CNG-HSA-103, CNG-HSA-104, CNG-HSA-108, CNG-HSA-109, CNG-HSA-110, CNG-HSA-111, CNG-HSA-112, CNG-HSA-115, CNG-HSA-116, CNG-HSA-117, CNG-HSA-118, CNG-HSA-119, or CNG-HSA-120 binds human serum albumin with a $K_D$ lower than or equal to 10 nM, 9 nM, 8 nM, 7 nM, 6 nM, 5 nM, 4 nM, or 3 nM, as measured by SPR when the antigen-binding site is present as a monomer. In certain embodiments, the antigen-binding site derived from CNG-HSA-101, CNG-HSA-102, CNG-HSA-103, CNG-HSA-104, CNG-HSA-108, CNG-HSA-109, CNG-HSA-110, CNG-HSA-111, CNG-HSA-112, CNG-HSA-115, CNG-HSA-116, CNG-HSA-117, CNG-HSA-118, CNG-HSA-119, or CNG-HSA-120 binds human serum albumin with a $K_D$ in the range of 1-10 nM, 1-9 nM, 1-8 nM, 1-7 nM, 1-6 nM, 1-5 nM, 1-4 nM, or 1-3 nM, as measured by SPR when the antigen-binding site is present as a monomer.

In certain embodiments, the antigen-binding site derived from CNG-HSA-101, CNG-HSA-102, CNG-HSA-103, CNG-HSA-104, CNG-HSA-108, CNG-HSA-109, CNG-HSA-110, CNG-HSA-111, CNG-HSA-112, CNG-HSA-115, CNG-HSA-116, CNG-HSA-117, CNG-HSA-118, CNG-HSA-119, or CNG-HSA-120 binds cynomolgus serum albumin with a $K_D$ lower than or equal to 9 nM, 8 nM, 7 nM, 6 nM, 5 nM, 4 nM, or 3 nM, as measured by SPR when the antigen-binding site is present as a monomer. In certain embodiments, the antigen-binding site derived from CNG-HSA-101, CNG-HSA-102, CNG-HSA-103, CNG-HSA-104, CNG-HSA-108, CNG-HSA-109, CNG-HSA-110, CNG-HSA-111, CNG-HSA-112, CNG-HSA-115, CNG-HSA-116, CNG-HSA-117, CNG-HSA-118, CNG-HSA-119, or CNG-HSA-120 binds cynomolgus serum albumin with a $K_D$ in the range of 1-9 nM, 1-8 nM, 1-7 nM, 1-6 nM, 1-5 nM, 1-4 nM, or 1-3 nM, as measured by SPR when the antigen-binding site is present as a monomer.

In certain embodiments, the antigen-binding site derived from CNG-HSA-101, CNG-HSA-102, CNG-HSA-103, CNG-HSA-104, CNG-HSA-108, CNG-HSA-109, CNG-HSA-110, CNG-HSA-111, CNG-HSA-112, CNG-HSA-115, CNG-HSA-116, CNG-HSA-117, CNG-HSA-118, CNG-HSA-119, or CNG-HSA-120 binds mouse serum albumin with a $K_D$ lower than or equal to 100 nM, 90 nM, 80 nM, 70 nM, 60 nM, 50 nM, 40 nM, 30 nM, 20 nM, or 10 nM, as measured by SPR when the antigen-binding site is present as a monomer. In certain embodiments, the antigen-binding site derived from CNG-HSA-101, CNG-HSA-102, CNG-HSA-103, CNG-HSA-104, CNG-HSA-108, CNG-HSA-109, CNG-HSA-110, CNG-HSA-111, CNG-HSA-112, CNG-HSA-115, CNG-HSA-116, CNG-HSA-117, CNG-HSA-118, CNG-HSA-119, or CNG-HSA-120 binds mouse serum albumin with a $K_D$ in the range of 1-100 nM, 1-90 nM, 1-80 nM, 1-70 nM, 1-60 nM, 1-50 nM, 1-40 nM, 1-30 nM, 1-20 nM, or 1-10 nM, as measured by SPR when the antigen-binding site is present as a monomer.

In certain embodiments, the antigen-binding site derived from CNG-HSA-101, CNG-HSA-103, CNG-HSA-106, CNG-HSA-107, CNG-HSA-108, CNG-HSA-109, CNG-HSA-111, CNG-HSA-113, CNG-HSA-114, CNG-HSA-115, CNG-HSA-116, CNG-HSA-118, or CNG-HSA-120 binds human serum albumin with a first $K_D$ and binds mouse serum albumin with a second $K_D$, wherein the ratio of the second $K_D$ to the first $K_D$ is in the range of 0.5-10, 0.5-9, 0.5-8, 0.5-7, 0.5-6, 0.5-5, 0.5-4, 0.5-3, 0.5-2, 0.9-10, 0.9-9, 0.9-8, 0.9-7, 0.9-6, 0.9-5, 0.9-4, 0.9-3, 0.9-2, 1-10, 1-9, 1-8, 1-7, 1-6, 1-5, 1-4, 1-3, or 1-2. It is understood that an antigen-binding site having a ratio closer to 1 has more similar affinity to mouse serum albumin relative to affinity to human serum albumin, which allows assessment of the pharmacokinetics of the antigen-binding site or a protein comprising the same using a mouse model at higher accuracy.

In certain embodiments, the antigen-binding site derived from CNG-HSA-101, CNG-HSA-102, CNG-HSA-104, CNG-HSA-109, CNG-HSA-113, CNG-HSA-116, or CNG-HSA-117 has a higher binding affinity to protein A relative to an antigen-binding site having VH sequence set forth in SEQ ID NO: 196. It is understood that increased affinity to protein A allows purification of the antigen-binding site, or a protein that comprises the antigen-binding site but not an antibody Fc region, by protein A chromatography. In certain embodiments, the antigen-binding site derived from CNG-HSA-101, CNG-HSA-102, CNG-HSA-104, CNG-HSA-109, CNG-HSA-113, CNG-HSA-116, or CNG-HSA-117 binds human serum albumin with a $K_D$ lower than or equal to 10 nM, 9 nM, 8 nM, 7 nM, 6 nM, 5 nM, 4 nM, or 3 nM and binds protein A with a $K_D$ lower than or equal to 2.5 nM or 2 nM, as measured by SPR when the antigen-binding site is present as a monomer. In certain embodiments, the antigen-binding site derived from CNG-HSA-101, CNG-HSA-102, CNG-HSA-104, CNG-HSA-109, CNG-HSA-113, CNG-HSA-116, or CNG-HSA-117 binds human serum albumin with a $K_D$ in the range of 1-10 nM, 1-9 nM, 1-8 nM, 1-7 nM, 1-6 nM, 1-5 nM, 1-4 nM, or 1-3 nM and binds protein A with a $K_D$ in the range of 1-2.5 nM or 1-2 nM, as measured by SPR when the antigen-binding site is present as a monomer.

In certain embodiments, the antigen-binding site derived from CNG-HSA-101, CNG-HSA-102, CNG-HSA-104, CNG-HSA-109, CNG-HSA-116, or CNG-HSA-117 has a higher binding affinity to human serum albumin and a higher affinity to protein A relative to an antigen-binding site having VH sequence set forth in SEQ ID NO: 196. In certain embodiments, the antigen-binding site derived from CNG-HSA-101, CNG-HSA-102, CNG-HSA-104, CNG-HSA-109, CNG-HSA-116, or CNG-HSA-117 binds protein A with a $K_D$ lower than or equal to 2.5 nM or 2 nM, as measured by SPR when the antigen-binding site is present as a monomer. In certain embodiments, the antigen-binding site derived from CNG-HSA-101, CNG-HSA-102, CNG-HSA-104, CNG-HSA-109, CNG-HSA-116, or CNG-HSA-117 binds protein A with a $K_D$ in the range of 1-2.5 nM or 1-2 nM, as measured by SPR when the antigen-binding site is present as a monomer.

Melting temperature represents the thermostability of the antigen-binding site and can be measured by differential scanning fluorimetry, for example, as described in Durowoju et al. (2017) J. Vis. Exp. (121): 55262. The thermostability of an antibody or fragment thereof may be enhanced by grafting CDRs onto stable frameworks, introducing non-canonical disulfide bonds, and other mutagenesis, as described in McConnell et al. (2014) MAbs, 6(5): 1274-82; and Goldman et al. (2017) Front. Immunol., 8: 865. In certain embodiments, the antigen-binding site derived from CNG-HSA-101, CNG-HSA-102, CNG-HSA-103, CNG-HSA-104, CNG-HSA-105, CNG-HSA-106, CNG-HSA-108, CNG-HSA-109, CNG-HSA-113, CNG-HSA-116, CNG-HSA-117, or CNG-HSA-120 has a melting temperature greater than or equal to 60° C., as measured by differential scanning fluorimetry. In certain embodiments, the antigen-binding site derived from CNG-HSA-101, CNG-HSA-102, CNG-HSA-103, CNG-HSA-106, or CNG-HSA-120 has a melting temperature greater than or equal to 65° C., as measured by differential scanning fluorimetry.

In certain embodiments, the third antigen-binding site competes for binding serum (e.g., human serum albumin) and/or competes for binding protein A with an antibody or antigen-binding site comprising the VH sequence provided in Table 5.

Alternatively, the third antigen-binding site that binds serum albumin can be derived from, for example, the antigen-binding sites disclosed in U.S. Pat. No. 8,188,223, and PCT Publication Nos. WO2017085172, and WO2018050833. For example, in certain embodiments, the third antigen-binding site that binds serum albumin is derived from an antibody listed in Table 6.

TABLE 6

Sequences of Exemplary Antigen-Binding Sites That Bind Serum Albumin

| Antigen-Binding Site | VH and HCDRs | VL and LCDRs |
| --- | --- | --- |
| CNG-HSA-1 | EVQLVESGGGLVQPGNSLRLSCAASGFT FSSFGMSWVRQAPGKGLEWVSSISGSGS DTLYADSVKGRFTISRDNAKTTLYLQMN SLRPEDTAVYYCTIGGSLSRSSQGTLVTV SS (SEQ ID NO: 196)<br><br>HCDR1*: FTFSSFGMS (SEQ ID NO: 128)<br><br>HCDR1: SFGMS (SEQ ID NO: 129)<br><br>HCDR2: SISGSGSDTLYADSVKG (SEQ ID NO: 133)<br><br>HCDR3*: TIGGSLSR (SEQ ID NO: 134)<br><br>HCDR3: GGSLSR (SEQ ID NO: 135) | N/A |
| Ablynx ALB3 | EVQLVESGGGLVQPGGSLRLSCAASGFT FRSFGMSWVRQAPGKEPEWVSSISGSGS DTLYADSVKGRFTISRDNAKTTLYLQMN SLKPEDTAVYYCTIGGSLSRSSQGTQVT VSS (SEQ ID NO: 624)<br><br>HCDR1*: FTFRSFGMS (SEQ ID NO: 625)<br><br>HCDR1: SFGMS (SEQ ID NO: 129) | N/A |

TABLE 6-continued

Sequences of Exemplary Antigen-Binding Sites That Bind Serum Albumin

| Antigen-Binding Site | VH and HCDRs | VL and LCDRs |
|---|---|---|
| | HCDR2: SISGSGSDTLYADSVKG (SEQ ID NO: 133) | |
| | HCDR3: GGSLSR (SEQ ID NO: 135) | |
| Ablynx ALB4 | EVQLVESGGGLVQPGGSLRLSCAASGFTFSSFGMSWVRQAPGKEPEWVSSISGSGSDTLYADSVKGRFTISRDNAKTTLYLQMNSLKPEDTAVYYCTIGGSLSRSSQGTQVTVSS (SEQ ID NO: 626) | N/A |
| | HCDR1*: FTFSSFGMS (SEQ ID NO: 128) | |
| | HCDR1: SFGMS (SEQ ID NO: 129) | |
| | HCDR2: SISGSGSDTLYADSVKG (SEQ ID NO: 133) | |
| | HCDR3: GGSLSR (SEQ ID NO: 135) | |
| Ablynx ALB5 | EVQLVESGGGLVQPGGSLRLSCAASGFTFRSFGMSWVRQAPGKGLEWVSSISGSGSDTLYADSVKGRFTISRDNAKTTLYLQMNSLKPEDTAVYYCTIGGSLSRSSQGTQVTVSS (SEQ ID NO: 627) | N/A |
| | HCDR1*: FTFRSFGMS (SEQ ID NO: 628) | |
| | HCDR1: SFGMS (SEQ ID NO: 129) | |
| | HCDR2: SISGSGSDTLYADSVKG (SEQ ID NO: 133) | |
| | HCDR3: GGSLSR (SEQ ID NO: 135) | |
| Ablynx ALB6 | EVQLVESGGGLVQPGNSLRLSCAASGFTFRSFGMSWVRQAPGKGLEWVSSISGSGSDTLYADSVKGRFTISRDNAKTTLYLQMNSLKPEDTAVYYCTIGGSLSRSSQGTLVTVSS (SEQ ID NO: 629) | N/A |
| | HCDR1*: FTFRSFGMS (SEQ ID NO: 630) | |
| | HCDR1: SFGMS (SEQ ID NO: 129) | |
| | HCDR2: SISGSGSDTLYADSVKG (SEQ ID NO: 133) | |
| | HCDR3: GGSLSR (SEQ ID NO: 135) | |
| Ablynx ALB7 | EVQLVESGGGLVQPGNSLRLSCAASGFTFRSFGMSWVRQAPGKGLEWVSSISGSGSDTLYADSVKGRFTISRDNAKTTLYLQMNSLRPEDTAVYYCTIGGSLSRSSQGTLVTVSS (SEQ ID NO: 631) | N/A |
| | HCDR1*: FTFRSFGMS (SEQ ID NO: 632) | |
| | HCDR1: SFGMS (SEQ ID NO: 129) | |
| | HCDR2: SISGSGSDTLYADSVKG (SEQ ID NO: 133) | |
| | HCDR3: GGSLSR (SEQ ID NO: 135) | |
| Ablynx ALB9 | EVQLVESGGGLVQPGNSLRLSCAASGFTFSSFGMSWVRQAPGKGLEWVSSISGSGSDTLYADSVKGRFTISRDNAKNTLYLQMNSLRPEDTAVYYCTIGGSLSRSSQGTLVTVSS (SEQ ID NO: 633) | N/A |

TABLE 6-continued

Sequences of Exemplary Antigen-Binding Sites That Bind Serum Albumin

| Antigen-Binding Site | VH and HCDRs | VL and LCDRs |
|---|---|---|
| | HCDR1*: FTFSSFGMS (SEQ ID NO: 128) <br><br> HCDR1: SFGMS (SEQ ID NO: 129) <br><br> HCDR2: SISGSGSDTLYADSVKG (SEQ ID NO: 133) <br><br> HCDR3: GGSLSR (SEQ ID NO: 135) | |
| Ablynx ALB 10 | EVQLVESGGGLVQPGNSLRLSCAASGFTFSSFGMSWVRQAPGKGLEWVSSISGSGSDTLYADSVKGRFTISRDNAKNTLYLQMNSLRPEDTAVYYCTIGGSLSRSGQGTLVTVSS (SEQ ID NO: 634) <br><br> HCDR1*: FTFSSFGMS (SEQ ID NO: 128) <br><br> HCDR1: SFGMS (SEQ ID NO: 129) <br><br> HCDR2: SISGSGSDTLYADSVKG (SEQ ID NO: 133) <br><br> HCDR3: GGSLSR (SEQ ID NO: 135) | N/A |
| Ablynx ALB23 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS (SEQ ID NO: 635) <br><br> HCDR1*: FTFRSFGMS (SEQ ID NO: 636) <br><br> HCDR1: SFGMS (SEQ ID NO: 129) <br><br> HCDR2: SISGSGSDTLYADSVKG (SEQ ID NO: 133) <br><br> HCDR3: GGSLSR (SEQ ID NO: 135) | N/A |
| Ablynx mAb-1 | EVQLVESGGGVVQPGNSLRLSCAASGFTFSSFGMSWVRQAPGKGLEWVSSISGSGSDTLYADSVKGRFTISRDNAKTTLYLQMNSLRPEDTATYYCTIGGSLSRS SQGTL VTVSSA (SEQ ID NO: 637) <br><br> HCDR1*: FTFSSFGMS (SEQ ID NO: 128) <br><br> HCDR1: SFGMS (SEQ ID NO: 129) <br><br> HCDR2: SISGSGSDTLYADSVKG (SEQ ID NO: 133) <br><br> HCDR3: GGSLSR (SEQ ID NO: 135) | N/A |
| Ablynx mAb-2 | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRS SQGTLVTVSSA (SEQ ID NO: 638) <br><br> HCDR1*: FTFRSFGMS (SEQ ID NO: 639) <br><br> HCDR1: SFGMS (SEQ ID NO: 129) or <br><br> HCDR2: SISGSGSDTLYADSVKG (SEQ ID NO: 133) <br><br> HCDR3: GGSLSR (SEQ ID NO: 135) | N/A |

TABLE 6-continued

Sequences of Exemplary Antigen-Binding Sites That Bind Serum Albumin

| Antigen-Binding Site | VH and HCDRs | VL and LCDRs |
|---|---|---|
| Ablynx mAb-3 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVKVSSA (SEQ ID NO: 640)<br><br>HCDR1*: FTFSSFGMS (SEQ ID NO: 128)<br><br>HCDR1: SFGMS (SEQ ID NO: 129) or<br><br>HCDR2: SISGSGSDTLYADSVKG (SEQ ID NO: 133)<br><br>HCDR3: GGSLSR (SEQ ID NO: 135) | N/A |
| Ablynx mAb-4 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRS SQGTLVTVSS (SEQ ID NO: 641)<br><br>HCDR1*: FTFSSFGMS (SEQ ID NO: 128)<br><br>HCDR1: SFGMS (SEQ ID NO: 129)<br><br>HCDR2: SISGSGSDTLYADSVKG (SEQ ID NO: 133)<br><br>HCDR3: GGSLSR (SEQ ID NO: 135) | N/A |
| Ablynx mAb-5 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRS SQGTLVTVSSA (SEQ ID NO: 642)<br><br>HCDR1*: FTFSSFGMS (SEQ ID NO: 128)<br><br>HCDR1: SFGMS (SEQ ID NO: 129)<br><br>HCDR2: SISGSGSDTLYADSVKG (SEQ ID NO: 133)<br><br>HCDR3: GGSLSR (SEQ ID NO: 135) | N/A |
| Ablynx mAb-6 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRS SQGTLVTVSSAA (SEQ ID NO: 643)<br><br>HCDR1*: FTFSSFGMS (SEQ ID NO: 128)<br><br>HCDR1: SFGMS (SEQ ID NO: 129)<br><br>HCDR2: SISGSGSDTLYADSVKG (SEQ ID NO: 133)<br><br>HCDR3: GGSLSR (SEQ ID NO: 135) | N/A |
| Ablynx mAb-7 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRS SQGTLVTVSSAAA (SEQ ID NO: 644)<br><br>HCDR1*: FTFSSFGMS (SEQ ID NO: 128)<br><br>HCDR1: SFGMS (SEQ ID NO: 129)<br><br>HCDR2: SISGSGSDTLYADSVKG (SEQ ID NO: 133)<br><br>HCDR3: GGSLSR (SEQ ID NO: 135) | N/A |

TABLE 6-continued

Sequences of Exemplary Antigen-Binding Sites That Bind Serum Albumin

| Antigen-Binding Site | VH and HCDRs | VL and LCDRs |
|---|---|---|
| Ablynx mAb-8 | EVQLVESGGGVVQPGNSLRLSCAASGFT FSSFGMSWVRQAPGKGLEWVSSISGSGS DTLYADSVKGRFTISRDNAKTTLYLQMN SLRPEDTALYYCTIGGSLSRS SQGTLVTV SSG (SEQ ID NO: 645)<br><br>HCDR1*: FTFSSFGMS (SEQ ID NO: 128)<br><br>HCDR1: SFGMS (SEQ ID NO: 129)<br><br>HCDR2: SISGSGSDTLYADSVKG (SEQ ID NO: 133)<br><br>HCDR3: GGSLSR (SEQ ID NO: 135) | N/A |
| Ablynx mAb-9 | EVQLVESGGGVVQPGNSLRLSCAASGFT FSSFGMSWVRQAPGKGLEWVSSISGSGS DTLYADSVKGRFTISRDNAKTTLYLQMN SLRPEDTALYYCTIGGSLSRS SQGTLVTV SSGG (SEQ ID NO: 646)<br><br>HCDR1*: GFTFSSFGMS (SEQ ID NO:)<br><br>HCDR1: SFGMS (SEQ ID NO: 129)<br><br>HCDR2: SISGSGSDTLYADSVKG (SEQ ID NO: 133)<br><br>HCDR3: GGSLSR (SEQ ID NO: 135) | N/A |
| Ablynx mAb-10 | EVQLVESGGGVVQPGNSLRLSCAASGFT FSSFGMSWVRQAPGKGLEWVSSISGSGS DTLYADSVKGRFTISRDNAKTTLYLQMN SLRPEDTALYYCTIGGSLSRS SQGTLVTV SSGGG (SEQ ID NO: 647)<br><br>HCDR1*: FTFSSFGMS (SEQ ID NO: 128)<br><br>HCDR1: SFGMS (SEQ ID NO: 129)<br><br>HCDR2: SISGSGSDTLYADSVKG (SEQ ID NO: 133)<br><br>HCDR3: GGSLSR (SEQ ID NO: 135) | N/A |
| Ablynx PMP6A6 | AVQLVESGGGLVQPGNSLRLSCAASGFT FRSFGMSWVRQAPGKEPEWVSSISGSGS DTLYADSVKGRFTISRDNAKTTLYLQMN SLKPEDTAVYYCTIGGSLSRSSQGTQVT VSS (SEQ ID NO: 648)<br><br>HCDR1*: FTFRSFGMS (SEQ ID NO: 649)<br><br>HCDR1: SFGMS (SEQ ID NO: 129)<br><br>HCDR2: SISGSGSDTLYADSVKG (SEQ ID NO: 133)<br><br>HCDR3: GGSLSR (SEQ ID NO: 135) | N/A |
| Ablynx PMP6C1 | AVQLVDSGGGLVQPGGSLRLSCAASGFS FGSFGMSWVRQYPGKEPEWVSSINGRG DDTRYADSVKGRFSISRDNAKNTLYLQ MNSLKPEDTAEYYCTIGRSVSRSRTQGT QVTVSS (SEQ ID NO: 650)<br><br>HCDR1*: FSFGSFGMS (SEQ ID NO: 651)<br><br>HCDR1: SFGMS (SEQ ID NO: 129) | N/A |

TABLE 6-continued

Sequences of Exemplary Antigen-Binding Sites That Bind Serum Albumin

| Antigen-Binding Site | VH and HCDRs | VL and LCDRs |
|---|---|---|
| | HCDR2: SINGRGDDTRYADSVKG (SEQ ID NO: 652) | |
| | HCDR3: GRSVSRS (SEQ ID NO: 653) | |
| Ablynx PMP6G8 | AVQLVESGGGLVQPGGSLRLTCTASGFT FRSFGMSWVRQAPGKDQEWVSAISADS STKNYADSVKGRFTISRDNAKKMLYLE MNSLKPEDTAVYYCVIGRGSPSSPGTQV TVSS (SEQ ID NO: 654) | N/A |
| | HCDR1*: FTFRSFGMS (SEQ ID NO: 655) | |
| | HCDR1: SFGMS (SEQ ID NO: 129) | |
| | HCDR2: AISADSSTKNYADSVKG (SEQ ID NO: 656) | |
| | HCDR3: GRGSP (SEQ ID NO: 657) | |
| Ablynx PMP6A5 | QVQLAESGGGLVQPGGSLRLTCTASGFT FGSFGMSWVRQAPGEGLEWVSAISADSS DKRYADSVKGRFTISRDNAKKMLYLEM NSLKSEDTAVYYCVIGRGSPASQGTQVT VSS (SEQ ID NO: 658) | N/A |
| | HCDR1*: FTFGSFGMS (SEQ ID NO: 145) | |
| | HCDR1: SFGMS (SEQ ID NO: 129) | |
| | HCDR2: AISADSSDKRYADSVKG (SEQ ID NO: 659) | |
| | HCDR3: GRGSP (SEQ ID NO: 660) | |
| Ablynx PMP6G7 | QVQLVESGGGLVQPGGSLRLSCAASGFT FSNYWMYWVRVAPGKGLERISRDISTG GGYSYYADSVKGRFTISRDNAKNTLYLQ MNSLKPEDTALYYCAKDREAQVDTLDF DYRGQGTQVTVSS (SEQ ID NO: 661) | N/A |
| | HCDR1*: FTFSNYWMY (SEQ ID NO: 662) | |
| | HCDR1: NYWMY (SEQ ID NO: 663) | |
| | HCDR2: RDISTGGGYSYYADSVKG (SEQ ID NO: 664) | |
| | HCDR3: DREAQVDTLDFDY (SEQ ID NO: 665) | |
| Ablynx PMP6A8 | AVQLVESGGGLVQGGGSLRLACAASERI FDLNLMGWYRQGPGNERELVATCITVG DSTNYADSVKGRFTISMDYTKQTVYLH MNSLRPEDTGLYYCKIRRTWHSELWGQ GTQVTVSS (SEQ ID NO: 666) | N/A |
| | HCDR1*: SERIFDLNLMG (SEQ ID NO: 667) | |
| | HCDR1: LNLMG (SEQ ID NO: 668) | |
| | HCDR2: TCITVGDSTNYADSVKG (SEQ ID NO: 669) | |
| | HCDR3: RRTWHSEL (SEQ ID NO: 670) | |
| Ablynx PMP6C1 | EVQLVESGGGLVQEGGSLRLACAASERI WDINLLGWYRQGPGNERELVATITVGD STSYADSVKGRFTISRDYDKNTLYLQMN SLRPEDTGLYYCKIRRTWHSELWGQGT QVTVSS (SEQ ID NO: 671) | N/A |
| | HCDR1*: SERIWDINLLG (SEQ ID NO: 672) | |

TABLE 6-continued

Sequences of Exemplary Antigen-Binding Sites That Bind Serum Albumin

| Antigen-Binding Site | VH and HCDRs | VL and LCDRs |
|---|---|---|
| | HCDR1: INLLG (SEQ ID NO: 673)<br><br>HCDR2: TITVGDSTSYADSVKG (SEQ ID NO: 674)<br><br>HCDR3: RRTWHSEL (SEQ ID NO: 675) | |
| Harpoon mAb-1 | EVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSS (SEQ ID NO: 676)<br><br>HCDR1: GFTFSKFGMS (SEQ ID NO: 677)<br><br>HCDR2: SISGSGRDTLYAESVK (SEQ ID NO: 678)<br><br>HCDR3: GGSLSV (SEQ ID NO: 679) | N/A |
| Harpoon mAb-2 | EVQLVESGGGLVQPGNSLRLSCAASGFTFSRFGMSWVRQAPGKGLEWVSSISGSGSDTLYAESVKGRFTISRDNAKTTLYLQMNSLRPEDTAVYYCTIGGSLSRSSQGTLVTVSS (SEQ ID NO: 680)<br><br>HCDR1: GFTFSRFGMS (SEQ ID NO: 681)<br><br>HCDR2: SISGSGSDTLYAESVK (SEQ ID NO: 682)<br><br>HCDR3: GGSLSR (SEQ ID NO: 135) | N/A |
| Harpoon mAb-3 | EVQLVESGGGLVQPGNSLRLSCAASGFTFSKFGMSWVRQAPGKGLEWVSSISGSGTDTLYAESVKGRFTISRDNAKTTLYLQMNSLRPEDTAVYYCTIGGSLSRSSQGTLVTVSS (SEQ ID NO: 683)<br><br>HCDR1: GFTFSKFGMS (SEQ ID NO: 677)<br><br>HCDR2: SISGSGTDTLYAESVK (SEQ ID NO: 684)<br><br>HCDR3: GGSLSR (SEQ ID NO: 135) | N/A |
| Domantis DOM7h-22 | EVQLLESGGGLVQPGGSLRLSCAASGFTFSKYWMSWVRQAPGKGLEWVSSIDFMGPHTYYADSVKGRFTISRDNSKNTLYLQMNSLRAEDTAVYYCAKGRTSMLPMKGKFDYWGQGTLVTVSS (SEQ ID NO: 685) | N/A |
| Domantis DOM7h-26 | EVQLLESGGGLVQPGGSLRLSCTASGFTFDEYNMSWVRQAPGKGLEWVSTILPHGDRTYYADSVKGRFTISRDNSKNTLYLQMNSLRAEDTAVYYCAKQDPLYRFDYWGQGTLVTVSS (SEQ ID NO: 686) | |
| Domantis DOM7h-2 | N/A | DIQMTQSPSSLSASVGDRVTITCRASQKIATYLNWYQQKPGKAPKLLIYRSSSLQSAVPSRFSGSGSGTVFTLTISSLQPEDFATYYCQQTYAVPPTFGQGTKVEIKR (SEQ ID NO: 687) |
| Domantis DOM7h-8 | N/A | DIQMTQSPSSLSASVGDRVTITCRASQSISSYLNWYQQKPGKAPKLLIYRNSPLQSGVPSRFSGSGSGTDFTLTISSLQPEDFATYYCQQTYRVPPTFGQGTKVEIKR (SEQ ID NO: 688) |

TABLE 6-continued

Sequences of Exemplary Antigen-Binding Sites That Bind Serum Albumin

| Antigen-Binding Site | VH and HCDRs | VL and LCDRs |
|---|---|---|
| MSA21 | QVQLQESGGGLVQPGGSLRLSCEASGFT FSRFGMTWVRQAPGKGVEWVSGISSLG DSTLYADSVKGRFTISRDNAKNTLYLQM NSLKPEDTAVYYCTIGGSLNPGGQGTQV TVSS (SEQ ID NO: 689) | N/A |
| UCB mAb-1 | EVQLLESGGGLVQPGGSLRLSCAVSGID LSNYAINWVRQAPGKCLEWIGIIWASGT TFYATWAKGRFTISRDNSKNTVYLQMN SLRAEDTAVYYCARTVPGYSTAPYFDL WGQGTLVTVSS (SEQ ID NO: 690) | DIQMTQSPSSVSASVGDRVTITCQSS PSVWSNFLSWYQQKPGKAPKLLIY EASKLTSGVPSRFSGSGSGTDFTLTI SSLQPEDFATYYCGGGYSSISDTTF GCGTKVEIKRT (SEQ ID NO: 691) |
| UCB mAb-2 | EVQLLESGGGLVQPGGSLRLSCAVSGID LSNYAINWVRQAPGKCLEWIGIIWASGT TFYATWAKGRFTISRDNSKNTVYLQMN SLRAEDTAVYYCARTVPGYSTAPYFDL WGQGTLVTVSS (SEQ ID NO: 692) | DIQMTQSPSSVSASVGDRVTITCQSS PSVWSNFLSWYQQKPGKAPKLLIY EASKLTSGVPSRFSGSGSGTDFTLTI SSLQPEDFATYYCGGGYSSISDTTF GGGTKVEIKRT (SEQ ID NO: 693) |

Where the VL and LCDR sequences are noted as "N/A," the antigen-binding site is an sdAb having a VH (e.g., VHH) only. Where the VH and HCDR sequences are noted as "N/A," the antigen-binding site is an sdAb having a VL only.

In certain embodiments, the third antigen-binding site comprises a VH that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VH of an antibody disclosed in Table 6, and a VL that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the VL of the same antibody disclosed in Table 6. In certain embodiments, the antigen-binding site comprises the HCDR1, HCDR2, HCDR3, LCDR1, LCDR2, and LCDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J Mol Biol 196: 901-917), MacCallum (see MacCallum R M et al., (1996) J Mol Biol 262: 732-745), IMGT (see Lefranc, (1999) The Immunologist, 7, 132-136), or any other CDR determination method known in the art, of the VH and/or VL sequences of an antibody disclosed in Table 6. In certain embodiments, the antigen-binding site comprises the HCDR1, HCDR2, HCDR3, LCDR1, LCDR2, and LCDR3 sequences of an antibody disclosed in Table 6. In certain embodiments, the antigen-binding site comprises the VH and VL sequences of an antibody disclosed in Table 6.

In other embodiments, the third antigen-binding site comprises an sdAb comprising a VH comprising complementarity determining regions HCDR1, HCDR2, and HCDR3. In certain embodiments, the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VH of an sdAb antibody provided in Table 6. In certain embodiments, the VH comprises the HCDR1, HCDR2, and HCDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J Mol Biol 196: 901-917), MacCallum (see MacCallum R M et al., (1996) J Mol Biol 262: 732-745), IMGT (see Lefranc, (1999) The Immunologist, 7, 132-136), or any other CDR determination method known in the art, of the VH sequence of an antibody disclosed in Table 6. In certain embodiments, the VH comprises the HCDR1, HCDR2, and HCDR3 sequences of the antibody provided in Table 6. In certain embodiments, the VH comprises the amino acid sequence of the VH of an sdAb provided in Table 6.

In certain embodiments, the third antigen-binding site binds serum albumin (e.g., HSA) with a $K_D$ lower than or equal to 100 nM, 90 nM, 80 nM, 70 nM, 60 nM, 50 nM, 40 nM, 30 nM, 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. For example, in certain embodiments, the third antigen-binding site binds serum albumin with a $K_D$ about 0.1 nM-about 100 nM, about 0.1 nM-about 50 nM, about 0.1 nM-about 10 nM, about 0.1 nM-about 1 nM, about 1 nM-about 100 nM, about 1 nM-about 50 nM, about 1 nM-about 10 nM, about 10 nM-about 100 nM, or about 10 nM-about 50 nM. It is understood that given the high abundance of serum albumin in the blood, a very high affinity of the third antigen-binding site to serum albumin may not be required for effective extension of the serum half-life of the multi-specific binding protein. Accordingly, antigen-binding sites that have lower affinity to serum albumin are also contemplated.

It is understood that the binding affinity to serum albumin of the third antigen-binding site alone may be different from the binding affinity of the same antigen-binding site in the context of the multi-specific binding protein disclosed herein, possibly due to the conformational restraint from the other domains. The context-dependent binding affinity is described in subsection G below titled "Binding Affinity."

In certain embodiments, the third antigen-binding site has a melting temperature of at least 50° C., at least 55° C., at least 56° C., at least 57° C., at least 58° C., at least 59° C., at least 60° C., at least 61° C., at least 62° C., at least 63° C., at least 64° C., at least 65° C., at least 70° C., at least 75° C., or at least 80° C. In certain embodiments, the third antigen-binding site has a melting temperature in the range of 50-80°

C., 50-70° C., 50-65° C., 50-60° C., 50-55° C., 55-70° C., 55-65° C., 55-60° C., 56-65° C., 56-60° C., 57-65° C., 57-60° C., 58-65° C., 58-60° C., 59-65° C., 59-60° C., 60-80° C., 60-75° C., 60-70° C., 60-65° C., 65-80° C., 65-75° C., 65-70° C., 70-80° C., or 70-75° C.

D. Construct Formats

The first, second, and third antigen-binding sites may take various forms. In certain embodiments, the first, second, and/or third antigen-binding sites comprises two antibody variable domains (e.g., a VH and a VL). The VH and the VL can be mutated to introduce a disulfide bond (e.g., between H44 and L100) that stabilizes the antigen-binding site (see, Zhao et al. (2010) Int. J. Mol. Sci., 12(1):1-11). In certain embodiments, the first, second, and/or third antigen-binding sites comprises a single antibody variable domain (e.g., an sdAb).

In an antigen-binding site that contains a VH and a VL, the VH and the VL can be linked to form an scFv. The VH can be positioned N-terminal or C-terminal to the VL. The VH and the VL are typically linked through a linker, such as a peptide linker. Exemplary sequences of peptide linkers are provided in subsection E below titled "Linkers." In certain embodiments, the VH of an antigen-binding domain is connected to the VL of the antigen-binding domain through a peptide linker having an amino acid sequence listed in Table 7. In particular embodiments, the VH of an antigen-binding domain is connected to the VL of the antigen-binding domain through a peptide linker having the amino acid sequence of SEQ ID NO: 298, 299, or 302, wherein the VH is positioned N-terminal to the VL. In other particular embodiments, the VH of an antigen-binding domain is connected to the VL of the antigen-binding domain through a peptide linker having the amino acid sequence of SEQ ID NO: 298, 299, or 302, wherein the VH is positioned C-terminal to the VL.

Alternatively, the VH and the VL may be present on separate polypeptide chains, and the formation of a VH-VL complex may be facilitated by additional domains, such as antibody constant regions CH1 and CL. Accordingly, in certain embodiments, the multi-specific binding protein comprises an Fab comprising a VH and a VL disclosed herein.

In certain embodiments, a multi-specific binding protein of the present invention comprises a first antigen-binding site comprising a single antibody variable domain, a second antigen-binding site comprising a single antibody variable domain, and a third antigen-binding site comprising a single antibody variable domain. In certain embodiments, the multi-specific binding protein comprises a first antigen-binding site in an sdAb format, a second antigen-binding site in an sdAb format, and a third antigen-binding site in an sdAb format.

In certain embodiments, a multi-specific binding protein of the present invention comprises a first antigen-binding site comprising a single antibody variable domain, a second antigen-binding site comprising a single antibody variable domain, and a third antigen-binding site comprising two antibody variable domains. In certain embodiments, the multi-specific binding protein comprises a first antigen-binding site in an sdAb format, a second antigen-binding site in an sdAb format, and a third antigen-binding site in an scFv format.

In certain embodiments, a multi-specific binding protein of the present invention comprises a first antigen-binding site comprising a single antibody variable domain, a second antigen-binding site comprising two antibody variable domains, and a third antigen-binding site comprising a single antibody variable domain. In certain embodiments, the multi-specific binding protein comprises a first antigen-binding site in an sdAb format, a second antigen-binding site in an scFv format, and a third antigen-binding site in an sdAb format.

In certain embodiments, a multi-specific binding protein of the present invention comprises a first antigen-binding site comprising a single antibody variable domain, a second antigen-binding site comprising two antibody variable domains, and a third antigen-binding site comprising two antibody variable domains. In certain embodiments, the multi-specific binding protein comprises a first antigen-binding site in an sdAb format, a second antigen-binding site in an scFv format, and a third antigen-binding site in an scFv format.

In certain embodiments, a multi-specific binding protein of the present invention comprises a first antigen-binding site comprising two antibody variable domains, a second antigen-binding site comprising a single antibody variable domain, and a third antigen-binding site comprising a single antibody variable domain. In certain embodiments, the multi-specific binding protein comprises a first antigen-binding site in an scFv format, a second antigen-binding site in an sdAb format, and a third antigen-binding site in an sdAb format.

In certain embodiments, a multi-specific binding protein of the present invention comprises a first antigen-binding site comprising two antibody variable domains, a second antigen-binding site comprising a single antibody variable domain, and a third antigen-binding site comprising two antibody variable domains. In certain embodiments, the multi-specific binding protein comprises a first antigen-binding site in an scFv format, a second antigen-binding site in an sdAb format, and a third antigen-binding site in an scFv format.

In certain embodiments, a multi-specific binding protein of the present invention comprises a first antigen-binding site comprising two antibody variable domains, a second antigen-binding site comprising two antibody variable domains, and a third antigen-binding site comprising a single antibody variable domain. In certain embodiments, the multi-specific binding protein comprises a first antigen-binding site in an scFv format, a second antigen-binding site in an scFv format, and a third antigen-binding site in an sdAb format.

In certain embodiments, a multi-specific binding protein of the present invention comprises a first antigen-binding site comprising two antibody variable domains, a second antigen-binding site comprising two antibody variable domains, and a third antigen-binding site comprising two antibody variable domains. In certain embodiments, the multi-specific binding protein comprises a first antigen-binding site in an scFv format, a second antigen-binding site in an scFv format, and a third antigen-binding site in an scFv format.

The three antigen-binding sites of the multi-specific binding protein can be linked in any one of the following orientations in an amino-to-carboxyl direction:
  (i) the first antigen-binding site (CD19 binding domain)—the second antigen-binding site (CD3 binding domain)—the third antigen-binding site (serum albumin binding domain);
  (ii) the first antigen-binding site (CD19 binding domain)—the third antigen-binding site (serum albumin binding domain)—the second antigen-binding site (CD3 binding domain);

(iii) the second antigen-binding site (CD3 binding domain)—the first antigen-binding site (CD19 binding domain)—the third antigen-binding site (serum albumin binding domain);

(iv) the second antigen-binding site (CD3 binding domain)—the third antigen-binding site (serum albumin binding domain)—the first antigen-binding site (CD19 binding domain);

(v) the third antigen-binding site (serum albumin binding domain)—the first antigen-binding site (CD19 binding domain)—the second antigen-binding site (CD3 binding domain); and (vi) the third antigen-binding site (serum albumin binding domain)—the second antigen-binding site (CD3 binding domain)—the first antigen-binding site (CD19 binding domain), wherein the dashes above represent a peptide bond and/or a linker (e.g., peptide linker).

In certain embodiments, the third antigen-binding site is not positioned between the first antigen-binding site and the second antigen-binding site. It is contemplated that constructs having such formats have favorable therapeutic efficacy and in vivo half-life. In certain embodiments, the third antigen-binding site is positioned N-terminal to both the first antigen-binding site and the second antigen-binding site or C-terminal to both the first antigen-binding site and the second antigen-binding site. In certain embodiments, the third antigen-binding site is positioned N-terminal to both the first antigen-binding site and the second antigen-binding site. In certain embodiments, the third antigen-binding site is positioned C-terminal to both the first antigen-binding site and the second antigen-binding site.

The position (N-terminal or C-terminal) of one antigen-binding site relative to another is determined under the definitions of "N-terminal" and "C-terminal" as known in the art if a single polypeptide chain comprises both antigen-binding sites. It is understood that if an antigen-binding site comprises two separate polypeptide chains, its position (N-terminal or C-terminal) relative to another antigen-binding site (either having a single polypeptide chain or two polypeptide chains) can be similarly determined if a single polypeptide chain comprises at least one polypeptide chain of the former and at least one polypeptide chain of the latter. It is further understood that if antigen-binding site A is N-terminal to antigen-binding site B and antigen-binding site B is N-terminal to antigen-binding site C, it is deemed that antigen-binding site A is positioned N-terminal to antigen-binding site C even if antigen-binding sites A and C are not present in any single, common polypeptide chain. More complex structures of multi-specific binding proteins are also contemplated, some of which may have orientations difficult to characterize using the terms of "N-terminal" and "C-terminal" as described above due to, for example, different relative positions of two antigen-binding sites on one polypeptide chain versus another polypeptide chain, or the presence of a loop structure.

According to the present invention, the multi-specific binding proteins and its constituent binding domains are in the form of one or more polypeptides. Such polypeptides may include proteinaceous parts and non-proteinaceous parts (e.g., chemical linkers or chemical cross-linking agents such as glutaraldehyde). In certain embodiments, a multi-specific binding protein of the present invention includes a first antigen-binding site, a second antigen-binding site, and a third antigen-binding site, all of which are linked together to form a single polypeptide chain. In certain embodiments, the first, second, and third antigen-binding sites take the forms of scFv and/or sdAb, for example, in a combination as described above, to form a single polypeptide chain.

E. Linkers

As noted above, the antigen-binding sites of the multi-specific binding proteins of the present invention can be linked through a peptide bond or a linker (e.g., peptide linker). In certain embodiments, at least two adjacent antigen-binding sites are connected by a linker (e.g., peptide linker). In certain embodiments, each two adjacent antigen-binding sites are connected by a linker (e.g., peptide linker).

In certain embodiments, the three antigen-binding sites of the multi-specific binding protein can be linked by linkers (e.g., peptide linkers) denoted as $L_1$ and $L_2$ in any one of the following orientations in an amino-to-carboxyl direction:

(i) the first antigen-binding site (CD19 binding domain)—$L_1$—the second antigen-binding site (CD3 binding domain)—$L_2$—the third antigen-binding site (serum albumin binding domain);

(ii) the first antigen-binding site (CD19 binding domain)—$L_1$—the third antigen-binding site (serum albumin binding domain)—$L_2$—the second antigen-binding site (CD3 binding domain);

(iii) the second antigen-binding site (CD3 binding domain)—$L_1$—the first antigen-binding site (CD19 binding domain)—$L_2$—the third antigen-binding site (serum albumin binding domain);

(iv) the second antigen-binding site (CD3 binding domain)—$L_1$—the third antigen-binding site (serum albumin binding domain)—$L_2$—the first antigen-binding site (CD19 binding domain);

(v) the third antigen-binding site (serum albumin binding domain)—$L_1$—the first antigen-binding site (CD19 binding domain)—$L_2$—the second antigen-binding site (CD3 binding domain); and (vi) the third antigen-binding site (serum albumin binding domain)—$L_1$—the second antigen-binding site (CD3 binding domain)—$L_2$—the first antigen-binding site (CD19 binding domain). It is appreciated that in a given construct, $L_1$, $L_2$, or both $L_1$ and $L_2$ may be replaced with a peptide bond.

It is understood that if a single polypeptide chain comprises two adjacent antigen-binding sites, the peptide linker connecting the two antigen-binding sites represents the amino acid sequence between them. If an antigen-binding site comprises two separate polypeptide chains, one of which is present in a single, common polypeptide as an adjacent antigen-binding site or a polypeptide chain thereof, the peptide linker connecting the two antigen-binding sites represents the amino acid sequence between them in the common, single polypeptide.

In certain embodiments, the linkers $L_1$ and $L_2$ are peptide linkers. Suitable lengths of $L_1$ and $L_2$ can be independently selected. For example, in certain embodiments, $L_1$ and/or $L_2$ are about 50 or less amino acid residues in length. In certain embodiments, $L_1$ consists of about 50 or less amino acid residues. In certain embodiments, $L_1$ consists of about 20 or less amino acid residues. In certain embodiments, $L_2$ consists of about 50 or less amino acid residues. In certain embodiments, $L_2$ consists of about 20 or less amino acid residues. In certain embodiments, $L_1$ and $L_2$ independently consist of about 50 or less amino acid residues. In certain embodiments, $L_1$ and $L_2$ independently consist of about 20 or less amino acid residues.

In some embodiments, peptide linkers $L_1$ and $L_2$ have an optimized length and/or amino acid composition. In some embodiments, $L_1$ and $L_2$ are of the same length and have the same amino acid composition. In other embodiments, $L_1$ and $L_2$ are different. In certain embodiments, $L_1$ and/or $L_2$ are "short," i.e., consist of 1, 2, 3, 4, 5, 6, 7, 8, 9, 10, 11 or 12 amino acid residues. Thus, in certain instances, the linkers consist of about 12 or less amino acid residues. In certain embodiments, $L_1$ and/or $L_2$ are "long," e.g., consist of 15, 20 or 25 amino acid residues. In some embodiments, $L_1$ and/or $L_2$ consist of about 3 to about 15, for example 8, 9 or 10 contiguous amino acid residues.

Regarding the amino acid composition of $L_1$ and $L_2$, peptides are selected with properties that confer flexibility to multi-specific binding protein of the present invention, do not interfere with the binding domains as well as resist cleavage from proteases. For example, glycine and serine residues generally provide protease resistance. Examples of the linkers suitable for linking the domains in the multi-specific binding protein include but are not limited to $(GS)_n$, $(GGS)_n$, $(GGGS)_n$, $(GGSG)_n$, $(GGSGG)_n$, and $(GGGGS)_n$, wherein n is 1, 2, 3, 4, 5, 6, 7, 8, 9, 10, 11, 12, 13, 14, 15, 16, 17, 18, 19, or 20. In some embodiments, $L_1$ and/or $L_2$ are independently selected from the peptide sequences listed in Table 7. In some embodiments, $L_1$ and/or $L_2$ are independently selected from SEQ ID NOs: 292, 293, 294, 295, 296, 297, 298, 299, 300, 301, or 302. In some embodiments, $L_1$ and/or $L_2$ are independently selected from SEQ ID NOs: 298, 299, and 302. In some embodiments, $L_1$ and/or $L_2$ comprise the amino acid sequence of SEQ ID NO: 298, 299, or 302. In some embodiments, $L_1$ and/or $L_2$ consist of the amino acid sequence of 298, 299, or 302. In some embodiments, $L_1$ and $L_2$ each comprise the amino acid sequence of SEQ ID NO: 298, 299, or 302. In some embodiments, $L_1$ and $L_2$ each consist of the amino acid sequence of SEQ ID NO: 298, 299, or 302.

TABLE 7

Sequences of Exemplary Peptide Linkers

| Linker | SEQ ID NO | Length | Amino Acid Sequence |
|---|---|---|---|
| $(GS)_{10}$ | 292 | 20 | GSGSGSGSGSGSGSGSGSGS |
| $(GGS)_{10}$ | 293 | 30 | GGSGGSGGSGGSGGSGGSGG SGGSGGSGGS |
| $(GGGS)_{10}$ | 294 | 40 | GGGSGGGSGGGSGGGSGGGS GGGSGGGSGGGSGGGS GGGS |
| $(GGSG)_{10}$ | 295 | 40 | GGSGGGSGGGSGGGSGGGSG GGSGGGSGGGSGGGSG GGSG |
| $(GGSGG)_{10}$ | 296 | 50 | GGSGGGGSGGGGSGGGGSGG GGSGGGGSGGGGSGG GGSGGGGSGGGGSGG |
| $(GGGGS)_{10}$ | 297 | 50 | GGGGSGGGGSGGGGSGGGGS GGGGSGGGGSGGGGS GGGGSGGGGSGGGGS |
| $(GGGGS)_4$ | 298 | 20 | GGGGSGGGGSGGGGSGGGGS |
| $(GGGGS)_3$ | 299 | 15 | GGGGSGGGGSGGGGS |
| $(GGGGS)_{20}$ | 300 | 100 | GGGGSGGGGSGGGGSGGGGS GGGGSGGGGSGGGGS GGGGSGGGGSGGGGSGGGGS GGGGSGGGGSGGGGS GGGGSGGGGSGGGGSGGGGS GGGGSGGGGS |
| $(GGSGG)_{20}$ | 301 | 100 | GGSGGGGSGGGGSGGGGSGG GGSGGGGSGGGGSGG GGSGGGGSGGGGSGGGGSGG GGSGGGGSGGGGSGG GGSGGGGSGGGGSGGGGSGG GGSGGGGSGG |
| Assymetrical linker | 302 | 9 | GGGGSGGGS |

A linker, such as a peptide linker disclosed herein, can also be used to connect the VH and VL of an scFv, as mentioned in subsection D above titled "Construct Formats."

F. Exemplary Multi-Specific Binding Proteins

Listed below in Table 8 are examples of multi-specific binding proteins comprising an scFv that binds CD19, an scFv that binds CD3, and an sdAb that binds serum albumin.

TABLE 8

Exemplary Multi-Specific Binding Proteins

| Construct | Format[1] | CD19 Binder | CD3 Binder[2] | HSA Binder |
|---|---|---|---|---|
| tAb0050 (SEQ ID NO: 694) | HSA:CD19:CD3 | CNG-CD19-701 (SEQ ID NO: 72) | CNG-CD3-1 (SEQ ID NO: 422) | CNG-HSA-101 (SEQ ID NO: 121) |
| tAb0051 (SEQ ID NO: 695) | HSA:CD3:CD19 | CNG-CD19-701 (SEQ ID NO: 72) | CNG-CD3-1 (SEQ ID NO: 422) | CNG-HSA-101 (SEQ ID NO: 121) |
| tAb0052 (SEQ ID NO: 696) | CD19:HSA:CD3 | CNG-CD19-701 (SEQ ID NO: 72) | CNG-CD3-1 (SEQ ID NO: 422) | CNG-HSA-101 (SEQ ID NO: 121) |
| tAb0053 (SEQ ID NO: 697) | CD3:HSA:CD19 | CNG-CD19-701 (SEQ ID NO: 72) | CNG-CD3-1 (SEQ ID NO: 422) | CNG-HSA-101 (SEQ ID NO: 121) |
| tAb0054 (SEQ ID NO: 698) | CD19:CD3:HSA | CNG-CD19-701 (SEQ ID NO: 72) | CNG-CD3-1 (SEQ ID NO: 422) | CNG-HSA-101 (SEQ ID NO: 121) |
| tAb0055 (SEQ ID NO: 699) | CD3:CD19:HSA | CNG-CD19-701 (SEQ ID NO: 72) | CNG-CD3-1 (SEQ ID NO: 422) | CNG-HSA-101 (SEQ ID NO: 121) |
| tAb0056 (SEQ ID NO: 700) | HSA:CD19:CD3 | CNG-CD19-101 (SEQ ID NO: 11) | CNG-CD3-1 (SEQ ID NO: 422) | CNG-HSA-101 (SEQ ID NO: 121) |
| tAb0057 (SEQ ID NO: 701) | HSA:CD3:CD19 | CNG-CD19-101 (SEQ ID NO: 11) | CNG-CD3-1 (SEQ ID NO: 422) | CNG-HSA-101 (SEQ ID NO: 121) |
| tAb0058 (SEQ ID NO: 702) | CD3:HSA:CD19 | CNG-CD19-101 (SEQ ID NO: 11) | CNG-CD3-1 (SEQ ID NO: 422) | CNG-HSA-101 (SEQ ID NO: 121) |

TABLE 8-continued

Exemplary Multi-Specific Binding Proteins

| Construct | Format[1] | CD19 Binder | CD3 Binder[2] | HSA Binder |
|---|---|---|---|---|
| tAb0059 (SEQ ID NO: 703) | CD19:CD3:HSA | CNG-CD19-101 (SEQ ID NO: 11) | CNG-CD3-1 (SEQ ID NO: 422) | CNG-HSA-101 (SEQ ID NO: 121) |
| tAb0060 (SEQ ID NO: 704) | HSA:CD19:CD3 | CNG-CD19-701 (SEQ ID NO: 72) | CNG-CD3-1-DS (SEQ ID NO: 423) | CNG-HSA-101 (SEQ ID NO: 121) |
| tAb0061 (SEQ ID NO: 705) | HSA:CD19:CD3 | CNG-CD19-701 (SEQ ID NO: 72) | CNG-CD3-2 (SEQ ID NO: 427) | CNG-HSA-101 (SEQ ID NO: 121) |
| tAb0062 (SEQ ID NO: 706) | HSA:CD19:CD3 | CNG-CD19-701 (SEQ ID NO: 72) | CNG-CD3-2-DS (SEQ ID NO: 428) | CNG-HSA-101 (SEQ ID NO: 121) |
| tAb0063 (SEQ ID NO: 707) | HSA:CD19:CD3 | CNG-CD19-701 (SEQ ID NO: 72) | CNG-CD3-3 (SEQ ID NO: 433) | CNG-HSA-101 (SEQ ID NO: 121) |
| tAb0064 (SEQ ID NO: 708) | HSA:CD19:CD3 | CNG-CD19-701 (SEQ ID NO: 72) | CNG-CD3-3-DS (SEQ ID NO: 434) | CNG-HSA-101 (SEQ ID NO: 121) |
| tAb0065 (SEQ ID NO: 709) | HSA:CD19:CD3 | CNG-CD19-101 (SEQ ID NO: 11) | CNG-CD3-2 (SEQ ID NO: 427) | CNG-HSA-101 (SEQ ID NO: 121) |
| tAb0066 (SEQ ID NO: 710) | HSA:CD19:CD3 | CNG-CD19-101 (SEQ ID NO: 11) | CNG-CD3-3 (SEQ ID NO: 433) | CNG-HSA-101 (SEQ ID NO: 121) |

[1]The multi-specific binding proteins in this table are present as a single polypeptide. The format shows the order of CD19-binding scFv, the CD3-binding scFv, and the HSA-binding sdAb, from the N-terminus to the C-terminus.
[2]The CD3-binding scFv sequences can contain or lack Cys substitutions at position 44 of VH and position 100 of VL. As a result, two sequences are provided for scFv derived from each of the antibodies CNG-CD3-1, CNG-CD3-2, and CNG-CD3-3 (see also Table 4).

tAb0050
(SEQ ID NO: 694)
KVQLVESGGGLVQPGGSLRLSCAASGFTFSSFGMTWVRQA

PGKGLEWVSSISGSGSDTLYADSVRGRFTISRDNSKNTLY

LQMNSLRAEDTAVYYCTIGGSLSPSSQGTLVTVSSGGGGS

GGGSEIVLTQSPATLSLSPGERATLSCSASSSVGYMHWYQ

QKPGQAPRLLIYDTSKLASGIPARFSGSGSGTDFTLTISS

LEPEDFAVYYCFQGSVYPFTFGQGTKLEIKGGGGSGGGGS

GGGGSQVQLQESGPGLVKPSQTLSLTCTVSGGSISTSTMG

VGWIRQHPGKGLEWIGFIWWDDDKRYNPNLKSRVTMSVDT

SKNQFSLKLSSVTAADTAVYYCARMELWSYYFDYWGQGTL

VTVSSGGGGSGGGGSDIVMTQSPDSLAVSLGERATINCKSS

QSLLNARTGKNYLAWYQQKPGQPPKLLIYWASTRESGVPD

RFSGSGSGTDFTLTISSLQAEDVAVYYCKQSYSRRTFGGG

TKVEIKGGGGSGGGGSGGGGSGGGGSQVQLVQSGAEVKKP

GASVKVSCKASGFNIKDYYMHWVRQAPGQRLEWMGWIDLE

NANTIYDAKFQGRVTITRDTSASTAYMELSSLRSEDTAVY

YCARDAYGRYFYDVWGQGTLVTVSS tAb0051
(SEQ ID NO: 695)
KVQLVESGGGLVQPGGSLRLSCAASGFTFSSFGMTWVRQA

PGKGLEWVSSISGSGSDTLYADSVRGRFTISRDNSKNTLY

LQMNSLRAEDTAVYYCTIGGSLSPSSQGTLVTVSSGGGGS

GGGSDIVMTQSPDSLAVSLGERATINCKSSQSLLNARTGK

NYLAWYQQKPGQPPKLLIYWASTRESGVPDRFSGSGSGTD

FTLTISSLQAEDVAVYYCKQSYSRRTFGGGTKVEIKGGGG

SGGGGSGGGGSGGGGSQVQLVQSGAEVKKPGASVKVSCKA

SGFNIKDYYMHWVRQAPGQRLEWMGWIDLENANTIYDAKF

QGRVTITRDTSASTAYMELSSLRSEDTAVYYCARDAYGRY

FYDVWGQGTLVTVSSGGGGSGGGSEIVLTQSPATLSLSPG

ERATLSCSASSSVGYMHWYQQKPGQAPRLLIYDTSKLASG

IPARFSGSGSGTDFTLTISSLEPEDFAVYYCFQGSVYPFT

FGQGTKLEIKGGGGSGGGGSGGGGSQVQLQESGPGLVKPS

QTLSLTCTVSGGSISTSTMGVGWIRQHPGKGLEWIGFIWW

DDDKRYNPNLKSRVTMSVDTSKNQFSLKLSSVTAADTAVY

YCARMELWSYYFDYWGQGTLVTVSS tAb0052
(SEQ ID NO: 696)
EIVLTQSPATLSLSPGERATLSCSASSSVGYMHWYQQKPG

QAPRLLIYDTSKLASGIPARFSGSGSGTDFTLTISSLEPE

DFAVYYCFQGSVYPFTFGQGTKLEIKGGGGSGGGGSGGGG

SQVQLQESGPGLVKPSQTLSLTCTVSGGSISTSTMGVGWI

RQHPGKGLEWIGFIWWDDDKRYNPNLKSRVTMSVDTSKNQ

FSLKLSSVTAADTAVYYCARMELWSYYFDYWGQGTLVTVS

SGGGGSGGGSKVQLVESGGGLVQPGGSLRLSCAASGFTFS

SFGMTWVRQAPGKGLEWVSSISGSGSDTLYADSVRGRFTI

SRDNSKNTLYLQMNSLRAEDTAVYYCTIGGSLSPSSQGTL

VTVSSGGGGSGGGSDIVMTQSPDSLAVSLGERATINCKSS

QSLLNARTGKNYLAWYQQKPGQPPKLLIYWASTRESGVPD

RFSGSGSGTDFTLTISSLQAEDVAVYYCKQSYSRRTFGGG

TKVEIKGGGGSGGGGSGGGGSGGGGSQVQLVQSGAEVKKP

GASVKVSCKASGFNIKDYYMHWVRQAPGQRLEWMGWIDLE

NANTIYDAKFQGRVTITRDTSASTAYMELSSLRSEDTAVY

YCARDAYGRYFYDVWGQGTLVTVSS tAb0053

-continued (SEQ ID NO: 697)
DIVMTQSPDSLAVSLGERATINCKSSQSLLNARTGKNYLA
WYQQKPGQPPKLLIYWASTRESGVPDRFSGSGSGTDFTLT
ISSLQAEDVAVYYCKQSYSRRTFGGGTKVEIKGGGGSGGG
GSGGGGSGGGGSQVQLVQSGAEVKKPGASVKVSCKASGFN
IKDYYMHWVRQAPGQRLEWMGWIDLENANTIYDAKFQGRV
TITRDTSASTAYMELSSLRSEDTAVYYCARDAYGRYFYDV
WGQGTLVTVSSGGGGSGGGGSKVQLVESGGGLVQPGGSLRL
SCAASGFTFSSFGMTWVRQAPGKGLEWVSSISGSGSDTLY
ADSVRGRFTISRDNSKNTLYLQMNSLRAEDTAVYYCTIGG
SLSPSSQGTLVTVSSGGGGSGGGSEIVLTQSPATLSLSPG
ERATLSCSASSSVGYMHWYQQKPGQAPRLLIYDTSKLASG
IPARFSGSGSGTDFTLTISSLEPEDFAVYYCFQGSVYPFT
FGQGTKLEIKGGGGSGGGGSGGGGSQVQLQESGPGLVKPS
QTLSLTCTVSGGSISTSTMGVGWIRQHPGKGLEWIGFIWW
DDDKRYNPNLKSRVTMSVDTSKNQFSLKLSSVTAADTAVY
YCARMELWSYYFDYWGQGTLVTVSS tAb0054
(SEQ ID NO: 698)
EIVLTQSPATLSLSPGERATLSCSASSSVGYMHWYQQKPG
QAPRLLIYDTSKLASGIPARFSGSGSGTDFTLTISSLEPE
DFAVYYCFQGSVYPFTFGQGTKLEIKGGGGSGGGGSGGGG
SQVQLQESGPGLVKPSQTLSLTCTVSGGSISTSTMGVGWI
RQHPGKGLEWIGFIWWDDDKRYNPNLKSRVTMSVDTSKNQ
FSLKLSSVTAADTAVYYCARMELWSYYFDYWGQGTLVTVS
SGGGGSGGGGSDIVMTQSPDSLAVSLGERATINCKSSQSLL
NARTGKNYLAWYQQKPGQPPKLLIYWASTRESGVPDRFSG
SGSGTDFTLTISSLQAEDVAVYYCKQSYSRRTFGGGTKVE
IKGGGGSGGGGSGGGGSGGGGSQVQLVQSGAEVKKPGASV
KVSCKASGFNIKDYYMHWVRQAPGQRLEWMGWIDLENANT
IYDAKFQGRVTITRDTSASTAYMELSSLRSEDTAVYYCAR
DAYGRYFYDVWGQGTLVTVSSGGGGSGGGSKVQLVESGGG
LVQPGGSLRLSCAASGFTFSSFGMTWVRQAPGKGLEWVSS
ISGSGSDTLYADSVRGRFTISRDNSKNTLYLQMNSLRAED
TAVYYCTIGGSLSPSSQGTLVTVSS tAb0055
(SEQ ID NO: 699)
DIVMTQSPDSLAVSLGERATINCKSSQSLLNARTGKNYLA
WYQQKPGQPPKLLIYWASTRESGVPDRFSGSGSGTDFTLT
ISSLQAEDVAVYYCKQSYSRRTFGGGTKVEIKGGGGSGGG
GSGGGGSGGGGSQVQLVQSGAEVKKPGASVKVSCKASGFN
IKDYYMHWVRQAPGQRLEWMGWIDLENANTIYDAKFQGRV
TITRDTSASTAYMELSSLRSEDTAVYYCARDAYGRYFYDV
WGQGTLVTVSSGGGGSGGGSEIVLTQSPATLSLSPGERAT
LSCSASSSVGYMHWYQQKPGQAPRLLIYDTSKLASGIPAR
FSGSGSGTDFTLTISSLEPEDFAVYYCFQGSVYPFTFGQG
TKLEIKGGGGSGGGGSGGGGSQVQLQESGPGLVKPSQTLS
LTCTVSGGSISTSTMGVGWIRQHPGKGLEWIGFIWWDDDK
RYNPNLKSRVTMSVDTSKNQFSLKLSSVTAADTAVYYCAR
MELWSYYFDYWGQGTLVTVSSGGGGSGGGSKVQLVESGGG
LVQPGGSLRLSCAASGFTFSSFGMTWVRQAPGKGLEWVSS
ISGSGSDTLYADSVRGRFTISRDNSKNTLYLQMNSLRAED
TAVYYCTIGGSLSPSSQGTLVTVSS tAb0056
(SEQ ID NO: 700)
KVQLVESGGGLVQPGGSLRLSCAASGFTFSSFGMTWVRQA
PGKGLEWVSSISGSGSDTLYADSVRGRFTISRDNSKNTLY
LQMNSLRAEDTAVYYCTIGGSLSPSSQGTLVTVSSGGGGS
GGGGSDIVMTQTPLSLSVTPGQPASISCKSSQSLETTTGTT
YLNWYLQKPGQSPQLLIYRASKRFSGVPDRFSGSGSGTDF
TLKISRVEAEDVGVYYCLQLLEDPYTFGCGTKLEIKGGGG
SGGGGSGGGGSQVQLVQSGAEVKKPGASVKVSCKASGYDF
TDYIMHWVRQAPGQCLEWMGYINPYNDGSKYTDKFQERVT
MTSDTSISTAYMELSRLRSDDTAVYYCARGTYYYGPELFD
YWGQGTTVTVSSGGGGSGGGSDIVMTQSPDSLAVSLGERA
TINCKSSQSLLNARTGKNYLAWYQQKPGQPPKLLIYWAST
RESGVPDRFSGSGSGTDFTLTISSLQAEDVAVYYCKQSYS
RRTFGGGTKVEIKGGGGSGGGGSGGGGSGGGGSQVQLVQS
GAEVKKPGASVKVSCKASGFNIKDYYMHWVRQAPGQRLEW
MGWIDLENANTIYDAKFQGRVTITRDTSASTAYMELSSLR
SEDTAVYYCARDAYGRYFYDVWGQGTLVTVSS tAb0057
(SEQ ID NO: 701)
KVQLVESGGGLVQPGGSLRLSCAASGFTFSSFGMTWVRQA
PGKGLEWVSSISGSGSDTLYADSVRGRFTISRDNSKNTLY
LQMNSLRAEDTAVYYCTIGGSLSPSSQGTLVTVSSGGGGS
GGGGSDIVMTQSPDSLAVSLGERATINCKSSQSLLNARTGK
NYLAWYQQKPGQPPKLLIYWASTRESGVPDRFSGSGSGTD
FTLTISSLQAEDVAVYYCKQSYSRRTFGGGTKVEIKGGGG
SGGGGSGGGGSGGGGSQVQLVQSGAEVKKPGASVKVSCKA
SGFNIKDYYMHWVRQAPGQRLEWMGWIDLENANTIYDAKF
QGRVTITRDTSASTAYMELSSLRSEDTAVYYCARDAYGRY
FYDVWGQGTLVTVSSGGGGSGGGSDIVMTQTPLSLSVTPG
QPASISCKSSQSLETTTGTTYLNWYLQKPGQSPQLLIYRA
SKRFSGVPDRFSGSGSGTDFTLKISRVEAEDVGVYYCLQL
LEDPYTFGCGTKLEIKGGGGSGGGGSGGGGSQVQLVQSGA

```
EVKKPGASVKVSCKASGYDFTDYIMHWVRQAPGQCLEWMG
YINPYNDGSKYTDKFQERVTMTSDTSISTAYMELSRLRSD
DTAVYYCARGTYYYGPELFDYWGQGTTVTVSS tAb0058                                (SEQ ID NO: 702)
DIVMTQSPDSLAVSLGERATINCKSSQSLLNARTGKNYLA
WYQQKPGQPPKLLIYWASTRESGVPDRFSGSGSGTDFTLT
ISSLQAEDVAVYYCKQSYSRRTFGGGTKVEIKGGGGSGGG
GSGGGGSGGGGSQVQLVQSGAEVKKPGASVKVSCKASGFN
IKDYYMHWVRQAPGQRLEWMGWIDLENANTIYDAKFQGRV
TITRDTSASTAYMELSSLRSEDTAVYYCARDAYGRYFYDV
WGQGTLVTVSSGGGGSGGGGSKVQLVESGGGLVQPGGSLRL
SCAASGFTFSSFGMTWVRQAPGKGLEWVSSISGSGSDTLY
ADSVRGRFTISRDNSKNTLYLQMNSLRAEDTAVYYCTIGG
SLSPSSQGTLVTVSSGGGGSGGGSDIVMTQTPLSLSVTPG
QPASISCKSSQSLETTTGTTYLNWYLQKPGQSPQLLIYRA
SKRFSGVPDRFSGSGSGTDFTLKISRVEAEDVGVYYCLQL
LEDPYTFGCGTKLEIKGGGGSGGGGSGGGGSQVQLVQSGA
EVKKPGASVKVSCKASGYDFTDYIMHWVRQAPGQCLEWMG
YINPYNDGSKYTDKFQERVTMTSDTSISTAYMELSRLRSD
DTAVYYCARGTYYYGPELFDYWGQGTTVTVSS tAb0059                                (SEQ ID NO: 703)
DIVMTQTPLSLSVTPGQPASISCKSSQSLETTTGTTYLNW
YLQKPGQSPQLLIYRASKRFSGVPDRFSGSGSGTDFTLKI
SRVEAEDVGVYYCLQLLEDPYTFGCGTKLEIKGGGGSGGG
GSGGGGSQVQLVQSGAEVKKPGASVKVSCKASGYDFTDYI
MHWVRQAPGQCLEWMGYINPYNDGSKYTDKFQERVTMTSD
TSISTAYMELSRLRSDDTAVYYCARGTYYYGPELFDYWGQ
GTTVTVSSGGGGSGGGSDIVMTQSPDSLAVSLGERATINC
KSSQSLLNARTGKNYLAWYQQKPGQPPKLLIYWASTRESG
VPDRFSGSGSGTDFTLTISSLQAEDVAVYYCKQSYSRRTF
GGGTKVEIKGGGGSGGGGSGGGGSGGGGSQVQLVQSGAEV
KKPGASVKVSCKASGFNIKDYYMHWVRQAPGQRLEWMGWI
DLENANTIYDAKFQGRVTITRDTSASTAYMELSSLRSEDT
AVYYCARDAYGRYFYDVWGQGTLVTVSSGGGGSGGGSKVQ
LVESGGGLVQPGGSLRLSCAASGFTFSSFGMTWVRQAPGK
GLEWVSSISGSGSDTLYADSVRGRFTISRDNSKNTLYLQM
NSLRAEDTAVYYCTIGGSLSPSSQGTLVTVSS tAb0060                                (SEQ ID NO: 704)
KVQLVESGGGLVQPGGSLRLSCAASGFTFSSFGMTWVRQA
PGKGLEWVSSISGSGSDTLYADSVRGRFTISRDNSKNTLY
LQMNSLRAEDTAVYYCTIGGSLSPSSQGTLVTVSSGGGGS
GGGSEIVLTQSPATLSLSPGERATLSCSASSSVGYMHWYQ
QKPGQAPRLLIYDTSKLASGIPARFSGSGSGTDFTLTISS
LEPEDFAVYYCFQGSVYPFTFGQGTKLEIKGGGGSGGGGS
GGGGSQVQLQESGPGLVKPSQTLSLTCTVSGGSISTSTMG
VGWIRQHPGKGLEWIGFIWWDDDKRYNPNLKSRVTMSVDT
SKNQFSLKLSSVTAADTAVYYCARMELWSYYFDYWGQGTL
VTVSSGGGGSGGGSDIVMTQSPDSLAVSLGERATINCKSS
QSLLNARTGKNYLAWYQQKPGQPPKLLIYWASTRESGVPD
RFSGSGSGTDFTLTISSLQAEDVAVYYCKQSYSRRTFGCG
TKVEIKGGGGSGGGGSGGGGSGGGGSQVQLVQSGAEVKKP
GASVKVSCKASGFNIKDYYMHWVRQAPGQCLEWMGWIDLE
NANTIYDAKFQGRVTITRDTSASTAYMELSSLRSEDTAVY
YCARDAYGRYFYDVWGQGTLVTVSS tAb0061                                (SEQ ID NO: 705)
KVQLVESGGGLVQPGGSLRLSCAASGFTFSSFGMTWVRQA
PGKGLEWVSSISGSGSDTLYADSVRGRFTISRDNSKNTLY
LQMNSLRAEDTAVYYCTIGGSLSPSSQGTLVTVSSGGGGS
GGGSEIVLTQSPATLSLSPGERATLSCSASSSVGYMHWYQ
QKPGQAPRLLIYDTSKLASGIPARFSGSGSGTDFTLTISS
LEPEDFAVYYCFQGSVYPFTFGQGTKLEIKGGGGSGGGGS
GGGGSQVQLQESGPGLVKPSQTLSLTCTVSGGSISTSTMG
VGWIRQHPGKGLEWIGFIWWDDDKRYNPNLKSRVTMSVDT
SKNQFSLKLSSVTAADTAVYYCARMELWSYYFDYWGQGTL
VTVSSGGGGSGGGSDIVMTQSPDSLAVSLGERATINCKSS
QSLLNARTGKNYLAWYQQKPGQPPKLLIYWASTRESGVPD
RFSGSGSGTDFTLTISSLQAEDVAVYYCKQSYSRRTFGGG
TKVEIKGGGGSGGGGSGGGGSGGGGSQVQLVQSGAEVKKP
GASVKVSCKASGFNIKDYYMHWVRQAPGQRLEWMGWIDLE
NANTIYDAKFQGRVTITRDTSASTAYMELSSLRSEDTAVY
YCARDQYGRYFYDVWGQGTLVTVSS tAb0062                                (SEQ ID NO: 706)
KVQLVESGGGLVQPGGSLRLSCAASGFTFSSFGMTWVRQA
PGKGLEWVSSISGSGSDTLYADSVRGRFTISRDNSKNTLY
LQMNSLRAEDTAVYYCTIGGSLSPSSQGTLVTVSSGGGGS
GGGSEIVLTQSPATLSLSPGERATLSCSASSSVGYMHWYQ
QKPGQAPRLLIYDTSKLASGIPARFSGSGSGTDFTLTISS
LEPEDFAVYYCFQGSVYPFTFGQGTKLEIKGGGGSGGGGS
GGGGSQVQLQESGPGLVKPSQTLSLTCTVSGGSISTSTMG
VGWIRQHPGKGLEWIGFIWWDDDKRYNPNLKSRVTMSVDT
SKNQFSLKLSSVTAADTAVYYCARMELWSYYFDYWGQGTL
```

VTVSSGGGGSGGGSDIVMTQSPDSLAVSLGERATINCKSS

QSLLNARTGKNYLAWYQQKPGQPPKLLIYWASTRESGVPD

RFSGSGSGTDFTLTISSLQAEDVAVYYCKQSYSRRTFGCG

TKVEIKGGGGSGGGGSGGGGSGGGGSQVQLVQSGAEVKKP

GASVKVSCKASGFNIKDYYMHWVRQAPGQCLEWMGWIDLE

NANTIYDAKFQGRVTITRDTSASTAYMELSSLRSEDTAVY

YCARDQYGRYFYDVWGQGTLVTVSS tAb0063 (SEQ ID NO: 707)
KVQLVESGGGLVQPGGSLRLSCAASGFTFSSFGMTWVRQA

PGKGLEWVSSISGSGSDTLYADSVRGRFTISRDNSKNTLY

LQMNSLRAEDTAVYYCTIGGSLSPSSQGTLVTVSSGGGGS

GGGSEIVLTQSPATLSLSPGERATLSCSASSSVGYMHWYQ

QKPGQAPRLLIYDTSKLASGIPARFSGSGSGTDFTLTISS

LEPEDFAVYYCFQGSVYPFTFGQGTKLEIKGGGGSGGGGS

GGGGSQVQLQESGPGLVKPSQTLSLTCTVSGGSISTSTMG

VGWIRQHPGKGLEWIGFIWWDDDKRYNPNLKSRVTMSVDT

SKNQFSLKLSSVTAADTAVYYCARMELWSYYFDYWGQGTL

VTVSSGGGGSGGGSDIVMTQSPDSLAVSLGERATINCKSS

QSLLNARTGKNYLAWYQQKPGQPPKLLIYWASTRESGVPD

RFSGSGSGTDFTLTISSLQAEDVAVYYCKQSYSLRTFGGG

TKVEIKGGGGSGGGGSGGGGSGGGGSQVQLVQSGAEVKKP

GASVKVSCKASGFNIKDYYMHWVRQAPGQRLEWMGWIDLE

EGNTIYDAKFQGRVTITRDTSASTAYMELSSLRSEDTAVY

YCARDAYGRYFYDVWGQGTLVTVSS tAb0064 (SEQ ID NO: 708)
KVQLVESGGGLVQPGGSLRLSCAASGFTFSSFGMTWVRQA

PGKGLEWVSSISGSGSDTLYADSVRGRFTISRDNSKNTLY

LQMNSLRAEDTAVYYCTIGGSLSPSSQGTLVTVSSGGGGS

GGGSEIVLTQSPATLSLSPGERATLSCSASSSVGYMHWYQ

QKPGQAPRLLIYDTSKLASGIPARFSGSGSGTDFTLTISS

LEPEDFAVYYCFQGSVYPFTFGQGTKLEIKGGGGSGGGGS

GGGGSQVQLQESGPGLVKPSQTLSLTCTVSGGSISTSTMG

VGWIRQHPGKGLEWIGFIWWDDDKRYNPNLKSRVTMSVDT

SKNQFSLKLSSVTAADTAVYYCARMELWSYYFDYWGQGTL

VTVSSGGGGSGGGSDIVMTQSPDSLAVSLGERATINCKSS

QSLLNARTGKNYLAWYQQKPGQPPKLLIYWASTRESGVPD

RFSGSGSGTDFTLTISSLQAEDVAVYYCKQSYSLRTFGCG

TKVEIKGGGGSGGGGSGGGGSGGGGSQVQLVQSGAEVKKP

GASVKVSCKASGFNIKDYYMHWVRQAPGQCLEWMGWIDLE

EGNTIYDAKFQGRVTITRDTSASTAYMELSSLRSEDTAVY

YCARDAYGRYFYDVWGQGTLVTVSS tAb0065 (SEQ ID NO: 709)
KVQLVESGGGLVQPGGSLRLSCAASGFTFSSFGMTWVRQA

PGKGLEWVSSISGSGSDTLYADSVRGRFTISRDNSKNTLY

LQMNSLRAEDTAVYYCTIGGSLSPSSQGTLVTVSSGGGGS

GGGSDIVMTQTPLSLSVTPGQPASISCKSSQSLETTTGTT

YLNWYLQKPGQSPQLLIYRASKRFSGVPDRFSGSGSGTDF

TLKISRVEAEDVGVYYCLQLLEDPYTFGCGTKLEIKGGGG

SGGGGSGGGGSQVQLVQSGAEVKKPGASVKVSCKASGYDF

TDYIMHWVRQAPGQCLEWMGYINPYNDGSKYTDKFQERVT

MTSDTSISTAYMELSRLRSDDTAVYYCARGTYYYGPELFD

YWGQGTTVTVSSGGGGSGGGSDIVMTQSPDSLAVSLGERA

TINCKSSQSLLNARTGKNYLAWYQQKPGQPPKLLIYWAST

RESGVPDRFSGSGSGTDFTLTISSLQAEDVAVYYCKQSYS

RRTFGGGTKVEIKGGGGSGGGGSGGGGSGGGGSQVQLVQS

GAEVKKPGASVKVSCKASGFNIKDYYMHWVRQAPGQRLEW

MGWIDLENANTIYDAKFQGRVTITRDTSASTAYMELSSLR

SEDTAVYYCARDQYGRYFYDVWGQGTLVTVSS tAb0066 (SEQ ID NO: 710)
KVQLVESGGGLVQPGGSLRLSCAASGFTFSSFGMTWVRQA

PGKGLEWVSSISGSGSDTLYADSVRGRFTISRDNSKNTLY

LQMNSLRAEDTAVYYCTIGGSLSPSSQGTLVTVSSGGGGS

GGGSDIVMTQTPLSLSVTPGQPASISCKSSQSLETTTGTT

YLNWYLQKPGQSPQLLIYRASKRFSGVPDRFSGSGSGTDF

TLKISRVEAEDVGVYYCLQLLEDPYTFGCGTKLEIKGGGG

SGGGGSGGGGSQVQLVQSGAEVKKPGASVKVSCKASGYDF

TDYIMHWVRQAPGQCLEWMGYINPYNDGSKYTDKFQERVT

MTSDTSISTAYMELSRLRSDDTAVYYCARGTYYYGPELFD

YWGQGTTVTVSSGGGGSGGGSDIVMTQSPDSLAVSLGERA

TINCKSSQSLLNARTGKNYLAWYQQKPGQPPKLLIYWAST

RESGVPDRFSGSGSGTDFTLTISSLQAEDVAVYYCKQSYS

LRTFGGGTKVEIKGGGGSGGGGSGGGGSGGGGSQVQLVQS

GAEVKKPGASVKVSCKASGFNIKDYYMHWVRQAPGQRLEW

MGWIDLEEGNTIYDAKFQGRVTITRDTSASTAYMELSSLR

SEDTAVYYCARDAYGRYFYDVWGQGTLVTVSS

The antigen-binding sites listed in a given row of Table 8 can be linked, in the orientation specified in the row, through peptide linkers described in subsection E above. In certain embodiments, at least two adjacent antigen-binding sites are linked by a peptide linker having the amino acid sequence of SEQ ID NO: 302. In certain embodiments, each two adjacent antigen-binding sites are linked by a peptide linker having the amino acid sequence of SEQ ID NO: 302, thereby forming a multi-specific binding protein present in a single polypeptide.

In certain embodiments, the multi-specific binding protein comprises, from N-terminus to C-terminus, SEQ ID NOs: 121, 72, and 422. In certain embodiments, the multi-specific binding protein comprises the amino acid sequence of SEQ ID NO: 694.

In certain embodiments, the multi-specific binding protein comprises, from N-terminus to C-terminus, SEQ ID NOs: 121, 422, and 72. In certain embodiments, the multi-specific binding protein comprises the amino acid sequence of SEQ ID NO: 695.

In certain embodiments, the multi-specific binding protein comprises, from N-terminus to C-terminus, SEQ ID NOs: 72, 121, and 422. In certain embodiments, the multi-specific binding protein comprises the amino acid sequence of SEQ ID NO: 696.

In certain embodiments, the multi-specific binding protein comprises, from N-terminus to C-terminus, SEQ ID NOs: 422, 121, and 72. In certain embodiments, the multi-specific binding protein comprises the amino acid sequence of SEQ ID NO: 697.

In certain embodiments, the multi-specific binding protein comprises, from N-terminus to C-terminus, SEQ ID NOs: 72, 422, and 121. In certain embodiments, the multi-specific binding protein comprises the amino acid sequence of SEQ ID NO: 698.

In certain embodiments, the multi-specific binding protein comprises, from N-terminus to C-terminus, SEQ ID NOs: 422, 72, and 121. In certain embodiments, the multi-specific binding protein comprises the amino acid sequence of SEQ ID NO: 699.

In certain embodiments, the multi-specific binding protein comprises, from N-terminus to C-terminus, SEQ ID NOs: 121, 11, and 422. In certain embodiments, the multi-specific binding protein comprises the amino acid sequence of SEQ ID NO: 700.

In certain embodiments, the multi-specific binding protein comprises, from N-terminus to C-terminus, SEQ ID NOs: 121, 422, and 11. In certain embodiments, the multi-specific binding protein comprises the amino acid sequence of SEQ ID NO: 701.

In certain embodiments, the multi-specific binding protein comprises, from N-terminus to C-terminus, SEQ ID NOs: 422, 121, and 11. In certain embodiments, the multi-specific binding protein comprises the amino acid sequence of SEQ ID NO: 702.

In certain embodiments, the multi-specific binding protein comprises, from N-terminus to C-terminus, SEQ ID NOs: 11, 422, and 121. In certain embodiments, the multi-specific binding protein comprises the amino acid sequence of SEQ ID NO: 703.

In certain embodiments, the multi-specific binding protein comprises, from N-terminus to C-terminus, SEQ ID NOs: 121, 72, and 423. In certain embodiments, the multi-specific binding protein comprises the amino acid sequence of SEQ ID NO: 704.

In certain embodiments, the multi-specific binding protein comprises, from N-terminus to C-terminus, SEQ ID NOs: 121, 72, and 427. In certain embodiments, the multi-specific binding protein comprises the amino acid sequence of SEQ ID NO: 705.

In certain embodiments, the multi-specific binding protein comprises, from N-terminus to C-terminus, SEQ ID NOs: 121, 72, and 428. In certain embodiments, the multi-specific binding protein comprises the amino acid sequence of SEQ ID NO: 706.

In certain embodiments, the multi-specific binding protein comprises, from N-terminus to C-terminus, SEQ ID NOs: 121, 72, and 433. In certain embodiments, the multi-specific binding protein comprises the amino acid sequence of SEQ ID NO: 707.

In certain embodiments, the multi-specific binding protein comprises, from N-terminus to C-terminus, SEQ ID NOs: 121, 72, and 434. In certain embodiments, the multi-specific binding protein comprises the amino acid sequence of SEQ ID NO: 708.

In certain embodiments, the multi-specific binding protein comprises, from N-terminus to C-terminus, SEQ ID NOs: 121, 11, and 427. In certain embodiments, the multi-specific binding protein comprises the amino acid sequence of SEQ ID NO: 709.

In certain embodiments, the multi-specific binding protein comprises, from N-terminus to C-terminus, SEQ ID NOs: 121, 11, and 433. In certain embodiments, the multi-specific binding protein comprises the amino acid sequence of SEQ ID NO: 710.

In certain embodiments, the multi-specific binding protein comprises an antigen-binding site that binds CD19 as disclosed herein, an antigen-binding site that binds CD3, and a half-life extension domain comprising an antibody Fc region. The multi-specific binding protein can take various formats to combine the antigen-binding sites and the Fc region.

In certain embodiments, the multi-specific binding protein comprises an anti-CD19 antibody in an IgG antibody format fused with a CD3-binding scFv at the C-terminus of the IgG Fc region. In certain embodiments, the multi-specific binding protein comprises a first polypeptide chain comprising, from the N-terminus to the C-terminus, the VH of an antigen-binding site that binds CD19, CH1 domain, hinge, CH2 domain, and CH3 domain of an IgG antibody (e.g., human IgG1, IgG2, IgG3, or IgG4), and an scFv that binds CD3; and a second polypeptide chain comprising, from the N-terminus to the C-terminus, the VL of the antigen-binding site that binds CD19 and light chain constant (CL) domain of the IgG antibody. In certain embodiments, the scFv that binds CD3 comprises a VL domain positioned N-terminal to a VH domain. In certain embodiments, the IgG antibody is a human IgG1 antibody. In certain embodiments, the multi-specific binding protein comprises two of the first polypeptide chain and two of the second polypeptide chain, thereby forming a dimeric antibody Fc region.

In certain embodiments, the multi-specific binding protein comprises CNG-CD19-701 as the CD19-binding domain and CNG-CD3-1 as the CD3-binding domain. In certain embodiments, the multi-specific binding protein comprises polypeptide chains having the two amino acid sequences below:

```
CNG-CD19-701-VH_CH1_Fc_CNG-CD3-1-VL_CNG-CD3-1-VH
                                  (SEQ ID NO: 712)
QVQLQESGPGLVKPSQTLSLTCTVSGGSISTSTMG

VGWIRQHPGKGLEWIGFIWWDDDKRYNPNLKSRVT

MSVDTSKNQFSLKLSSVTAADTAVYYCARMELWSY

YFDYWGQGTLVTVSSASTKGPSVFPLAPSSKSTSG

GTAALGCLVKDYFPEPVTVSWNSGALTSGVHTFPA
```

VLQSSGLYSLSSVVTVPSSSLGTQTYICNVNHKPS

NTKVDKKVEPKSCDKTHTCPPCPAPEAAGGPSVFL

FPPKPKDTLMISRTPEVTCVVVDVSHEDPEVKFNW

YVDGVEVHNAKTKPREEQYNSTYRVVSVLTVLHQD

WLNGKEYKCKVSNKALAAPIEKTISKAKGQPREPQ

VYTLPPSRDELTKNQVSLTCLVKGFYPSDIAVEWE

SNGQPENNYKTTPPVLDSDGSFFLYSKLTVDKSRW

QQGNVFSCSVMHEALHNHYTQKSLSLSPGKSGDIV

MTQSPDSLAVSLGERATINCKSSQSLLNARTGKNY

LAWYQQKPGQPPKLLIYWASTRESGVPDRFSGSGS

GTDFTLTISSLQAEDVAVYYCKQSYSRRTFGGGTK

VEIKGGGSGGGGSGGGGSGGGGSQVQLVQSGAEV

KKPGASVKVSCKASGFNIKDYYMHWVRQAPGQRLE

WMGWIDLENANTIYDAKFQGRVTITRDTSASTAYM

ELSSLRSEDTAVYYCARDAYGRYFYDVWGQGTLVT

VSS

CNG-CD19-701-VL_CL
(SEQ ID NO: 713)
EIVLTQSPATLSLSPGERATLSCSASSSVGYMHWY

QQKPGQAPRLLIYDTSKLASGIPARFSGSGSGTDF

TLTISSLEPEDFAVYYCFQGSVYPFTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

In certain embodiments, the multi-specific binding protein comprises CNG-CD19-701 as the CD19-binding domain and CNG-CD3-2 as the CD3-binding domain. In certain embodiments, the multi-specific binding protein comprises polypeptide chains having the two amino acid sequences below:

CNG-CD19-701-VH_CH1_Fc_CNG-CD3-2-VL_CNG-CD3-2-VH
(SEQ ID NO: 714)
QVQLQESGPGLVKPSQTLSLTCTVSGGSISTSTMG

VGWIRQHPGKGLEWIGFIWWDDDKRYNPNLKSRVT

MSVDTSKNQFSLKLSSVTAADTAVYYCARMELWSY

YFDYWGQGTLVTVSSASTKGPSVFPLAPSSKSTSG

GTAALGCLVKDYFPEPVTVSWNSGALTSGVHTFPA

VLQSSGLYSLSSVVTVPSSSLGTQTYICNVNHKPS

NTKVDKKVEPKSCDKTHTCPPCPAPEAAGGPSVFL

FPPKPKDTLMISRTPEVTCVVVDVSHEDPEVKFNW

YVDGVEVHNAKTKPREEQYNSTYRVVSVLTVLHQD

WLNGKEYKCKVSNKALAAPIEKTISKAKGQPREPQ

VYTLPPSRDELTKNQVSLTCLVKGFYPSDIAVEWE

SNGQPENNYKTTPPVLDSDGSFFLYSKLTVDKSRW

QQGNVFSCSVMHEALHNHYTQKSLSLSPGKSGDIV

MTQSPDSLAVSLGERATINCKSSQSLLNARTGKNY

LAWYQQKPGQPPKLLIYWASTRESGVPDRFSGSGS

GTDFTLTISSLQAEDVAVYYCKQSYSRRTFGGGTK

VEIKGGGSGGGGSGGGGSGGGGSQVQLVQSGAEV

KKPGASVKVSCKASGFNIKDYYMHWVRQAPGQRLE

WMGWIDLENANTIYDAKFQGRVTITRDTSASTAYM

ELSSLRSEDTAVYYCARDQYGRYFYDVWGQGTLVT

VSS

CNG-CD19-701-VL_CL
(SEQ ID NO: 713)
EIVLTQSPATLSLSPGERATLSCSASSSVGYMHWY

QQKPGQAPRLLIYDTSKLASGIPARFSGSGSGTDF

TLTISSLEPEDFAVYYCFQGSVYPFTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

In certain embodiments, the multi-specific binding protein comprises CNG-CD19-701 as the CD19-binding domain and CNG-CD3-3 as the CD3-binding domain. In certain embodiments, the multi-specific binding protein comprises polypeptide chains having the two amino acid sequences below:
CNG-CD19-701-VH_CH1_Fc_CNG-CD3-3-VL_CNG-CD3-3-VH
(SEP ID NO: 715)
QVQLQESGPGLVKPSQTLSLTCTVSGGSISTSTMG

VGWIRQHPGKGLEWIGFIWWDDDKRYNPNLKSRVT

MSVDTSKNQFSLKLSSVTAADTAVYYCARMELWSY

YFDYWGQGTLVTVSSASTKGPSVFPLAPSSKSTSG

GTAALGCLVKDYFPEPVTVSWNSGALTSGVHTFPA

VLQSSGLYSLSSVVTVPSSSLGTQTYICNVNHKPS

NTKVDKKVEPKSCDKTHTCPPCPAPEAAGGPSVFL

FPPKPKDTLMISRTPEVTCVVVDVSHEDPEVKFNW

YVDGVEVHNAKTKPREEQYNSTYRVVSVLTVLHQD

WLNGKEYKCKVSNKALAAPIEKTISKAKGQPREPQ

VYTLPPSRDELTKNQVSLTCLVKGFYPSDIAVEWE

SNGQPENNYKTTPPVLDSDGSFFLYSKLTVDKSRW

QQGNVFSCSVMHEALHNHYTQKSLSLSPGKSGDIV

MTQSPDSLAVSLGERATINCKSSQSLLNARTGKNY

LAWYQQKPGQPPKLLIYWASTRESGVPDRFSGSGS

GTDFTLTISSLQAEDVAVYYCKQSYSLRTFGGGTK

VEIKGGGSGGGGSGGGGSGGGGSQVQLVQSGAEV

KKPGASVKVSCKASGFNIKDYYMHWVRQAPGQRLE

WMGWIDLEEGNTIYDAKFQGRVTITRDTSASTAYM

ELSSLRSEDTAVYYCARDAYGRYFYDVWGQGTLVT

VSS

CNG-CD19-701-VL_CL (SEQ ID NO: 713)

EIVLTQSPATLSLSPGERATLSCSASSSVGYMHWY

QQKPGQAPRLLIYDTSKLASGIPARFSGSGSGTDF

TLTISSLEPEDFAVYYCFQGSVYPFTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

In certain embodiments, the multi-specific binding protein comprises an anti-CD19 antibody in an IgG antibody format fused with a CD3-binding scFv at the C-terminus of the IgG light chain constant region. In certain embodiments, the multi-specific binding protein comprises a first polypeptide chain comprising, from the N-terminus to the C-terminus, the VH of an antigen-binding site that binds CD19, CH1 domain, hinge, CH2 domain, and CH3 domain of an IgG antibody (e.g., human IgG1, IgG2, IgG3, or IgG4); and a second polypeptide chain comprising, from the N-terminus to the C-terminus, the VL of the antigen-binding site that binds CD19, light chain constant (CL) domain of the IgG antibody, and an scFv that binds CD3. In certain embodiments, the scFv that binds CD3 comprises a VL domain positioned N-terminal to a VH domain. In certain embodiments, the IgG antibody is a human IgG1 antibody. In certain embodiments, the multi-specific binding protein comprises two of the first polypeptide chain and two of the second polypeptide chain, thereby forming a dimeric antibody Fc region.

In certain embodiments, the multi-specific binding protein comprises CNG-CD19-701 as the CD19-binding domain and CNG-CD3-1 as the CD3-binding domain. In certain embodiments, the multi-specific binding protein comprises polypeptide chains having the two amino acid sequences below:

CNG-CD19-701-VH_CH1_Fc (SEQ ID NO: 716)

QVQLQESGPGLVKPSQTLSLTCTVSGGSISTSTMG

VGWIRQHPGKGLEWIGFIWWDDDKRYNPNLKSRVT

MSVDTSKNQFSLKLSSVTAADTAVYYCARMELWSY

YFDYWGQGTLVTVSSASTKGPSVFPLAPSSKSTSG

GTAALGCLVKDYFPEPVTVSWNSGALTSGVHTFPA

VLQSSGLYSLSSVVTVPSSSLGTQTYICNVNHKPS

NTKVDKKVEPKSCDKTHTCPPCPAPEAAGGPSVFL

FPPKPKDTLMISRTPEVTCVVVDVSHEDPEVKFNW

YVDGVEVHNAKTKPREEQYNSTYRVVSVLTVLHQD

WLNGKEYKCKVSNKALAAPIEKTISKAKGQPREPQ

VYTLPPSRDELTKNQVSLTCLVKGFYPSDIAVEWE

SNGQPENNYKTTPPVLDSDGSFFLYSKLTVDKSRW

QQGNVFSCSVMHEALHNHYTQKSLSLSPGK

CNG-CD19-701-VL_CL_CNG-CD3-1-VL_CNG-CD3-1-VH (SEQ ID NO: 717)

EIVLTQSPATLSLSPGERATLSCSASSSVGYMHWY

QQKPGQAPRLLIYDTSKLASGIPARFSGSGSGTDF

TLTISSLEPEDFAVYYCFQGSVYPFTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GECGGGGSGGGGSGGGGSDIVMTQSPDSLAVSLGE

RATINCKSSQSLLNARTGKNYLAWYQQKPGQPPKL

LIYWASTRESGVPDRFSGSGSGTDFTLTISSLQAE

DVAVYYCKQSYSRRTFGGGTKVEIKGGGGSGGGGS

GGGGSGGGGSQVQLVQSGAEVKKPGASVKVSCKAS

GFNIKDYYMHWVRQAPGQRLEWMGWIDLENANTIY

DAKFQGRVTITRDTSASTAYMELSSLRSEDTAVYY

CARDAYGRYFYDVWGQGTLVTVSS

In certain embodiments, the multi-specific binding protein comprises CNG-CD19-701 as the CD19-binding domain and CNG-CD3-2 as the CD3-binding domain. In certain embodiments, the multi-specific binding protein comprises polypeptide chains having the two amino acid sequences below:

CNG-CD19-701-VH_CH1_Fc (SEQ ID NO: 716)

QVQLQESGPGLVKPSQTLSLTCTVSGGSISTSTMG

VGWIRQHPGKGLEWIGFIWWDDDKRYNPNLKSRVT

MSVDTSKNQFSLKLSSVTAADTAVYYCARMELWSY

YFDYWGQGTLVTVSSASTKGPSVFPLAPSSKSTSG

GTAALGCLVKDYFPEPVTVSWNSGALTSGVHTFPA

VLQSSGLYSLSSVVTVPSSSLGTQTYICNVNHKPS

NTKVDKKVEPKSCDKTHTCPPCPAPEAAGGPSVFL

FPPKPKDTLMISRTPEVTCVVVDVSHEDPEVKFNW

YVDGVEVHNAKTKPREEQYNSTYRVVSVLTVLHQD

WLNGKEYKCKVSNKALAAPIEKTISKAKGQPREPQ

VYTLPPSRDELTKNQVSLTCLVKGFYPSDIAVEWE

SNGQPENNYKTTPPVLDSDGSFFLYSKLTVDKSRW

QQGNVFSCSVMHEALHNHYTQKSLSLSPGK

CNG-CD19-701-VL_CL_CNG-CD3-2-VL_CNG-CD3-2-VH (SEQ ID NO: 718)

EIVLTQSPATLSLSPGERATLSCSASSSVGYMHWY

QQKPGQAPRLLIYDTSKLASGIPARFSGSGSGTDF

```
-continued
TLTISSLEPEDFAVYYCFQGSVYPFTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GECGGGGSGGGGSGGGGSDIVMTQSPDSLAVSLGE

RATINCKSSQSLLNARTGKNYLAWYQQKPGQPPKL

LIYWASTRESGVPDRFSGSGSGTDFTLTISSLQAE

DVAVYYCKQSYSRRTFGGGTKVEIKGGGGSGGGGS

GGGGSGGGGSQVQLVQSGAEVKKPGASVKVSCKAS

GFNIKDYYMHWVRQAPGQRLEWMGWIDLENANTIY

DAKFQGRVTITRDTSASTAYMELSSLRSEDTAVYY

CARDQYGRYFYDVWGQGTLVTVSS
```

In certain embodiments, the multi-specific binding protein comprises CNG-CD19-701 as the CD19-binding domain and CNG-CD3-3 as the CD3-binding domain. In certain embodiments, the multi-specific binding protein comprises polypeptide chains having the two amino acid sequences below:

```
CNG-CD19-701-VH_CH1_Fc
                                        (SEQ ID NO: 716)
QVQLQESGPGLVKPSQTLSLTCTVSGGSISTSTMG

VGWIRQHPGKGLEWIGFIWWDDDKRYNPNLKSRVT

MSVDTSKNQFSLKLSSVTAADTAVYYCARMELWSY

YFDYWGQGTLVTVSSASTKGPSVFPLAPSSKSTSG

GTAALGCLVKDYFPEPVTVSWNSGALTSGVHTFPA

VLQSSGLYSLSSVVTVPSSSLGTQTYICNVNHKPS

NTKVDKKVEPKSCDKTHTCPPCPAPEAAGGPSVFL

FPPKPKDTLMISRTPEVTCVVVDVSHEDPEVKFNW

YVDGVEVHNAKTKPREEQYNSTYRVVSVLTVLHQD

WLNGKEYKCKVSNKALAAPIEKTISKAKGQPREPQ

VYTLPPSRDELTKNQVSLTCLVKGFYPSDIAVEWE

SNGQPENNYKTTPPVLDSDGSFFLYSKLTVDKSRW

QQGNVFSCSVMHEALHNHYTQKSLSLSPGK

CNG-CD19-701-VL_CL_CNG-CD3-3-VL_CNG-CD3-3-VH
                                        (SEQ ID NO: 719)
EIVLTQSPATLSLSPGERATLSCSASSSVGYMHWY

QQKPGQAPRLLIYDTSKLASGIPARFSGSGSGTDF

TLTISSLEPEDFAVYYCFQGSVYPFTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GECGGGGSGGGGSGGGGSDIVMTQSPDSLAVSLGE

RATINCKSSQSLLNARTGKNYLAWYQQKPGQPPKL

LIYWASTRESGVPDRFSGSGSGTDFTLTISSLQAE
```

```
-continued
DVAVYYCKQSYSLRTFGGGTKVEIKGGGGSGGGGS

GGGGSGGGGSQVQLVQSGAEVKKPGASVKVSCKAS

GFNIKDYYMHWVRQAPGQRLEWMGWIDLEEGNTIY

DAKFQGRVTITRDTSASTAYMELSSLRSEDTAVYY

CARDAYGRYFYDVWGQGTLVTVSS
```

In certain embodiments, the multi-specific binding protein disclosed herein further comprises a tag peptide, for example, a Flag tag, a 6×His tag, or 10×His tag (HHHHHHHHHH, SEQ ID NO: 711). Such tag peptides are useful for purifying the multi-specific binding protein. In certain embodiments, the tag peptide (e.g., the 10×His tag) is positioned at the C-terminus of the multi-specific binding protein. In certain embodiments, the tag peptide (e.g., the 10×His tag) is positioned at the N-terminus of the multi-specific binding protein.

G. Binding Affinity

In certain embodiments, the multi-specific binding protein binds CD19 (e.g., human CD19), CD3 (e.g., human CD3 and/or Macaca CD3), and/or serum albumin (e.g., HSA) with a $K_D$ in the range of about 5 pM-about 100 pM. The $K_D$ can be measured by a method known in the art, such as by SPR, BLI, or by flow cytometry as described in Example 1, 2, or 7 below.

In certain embodiments, the multi-specific binding protein binds CD19, CD3, and/or serum albumin with a $K_D$ lower than or equal to (i.e., binding stronger than or equal to) 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 90 pM, 80 pM, 70 pM, 60 pM, 50 pM, 40 pM, 30 pM, 20 pM, or 10 pM. For example, in certain embodiments, the multi-specific binding protein binds CD19, CD3, and/or serum albumin with a $K_D$ in the range of about 10 pM-about 1 nM, about 10 pM-about 0.9 nM, about 10 pM-about 0.8 nM, about 10 pM-about 0.7 nM, about 10 pM-about 0.6 nM, about 10 pM-about 0.5 nM, about 10 pM-about 0.4 nM, about 10 pM-about 0.3 nM, about 10 pM-about 0.2 nM, about 10 pM-about 0.1 nM, about 10 pM-about 50 pM, 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 0.5 nM-about 10 nM, about 1 nM-about 10 nM, about 2 nM-about 10 nM, about 3 nM-about 10 nM, about 4 nM-about 10 nM, about 5 nM-about 10 nM, about 6 nM-about 10 nM, about 7 nM-about 10 nM, about 8 nM-about 10 nM, or about 9 nM-about 10 nM.

In certain embodiments, the multi-specific binding protein binds CD19, CD3, and/or serum albumin with a $K_D$ greater than or equal to (i.e., binding weaker than or equal to) 10 nM, 20 nM, 30 nM, 40 nM, 50 nM, 60 nM, 70 nM, 80 nM, 90 nM, or 100 nM. In certain embodiments, the multi-specific binding protein binds CD19, CD3, and/or serum albumin with a $K_D$ in the range of about 10 nM-about 1000 nM, about 10 nM-about 900 nM, about 10 nM-about 800 nM, about 10 nM-about 700 nM, about 10 nM-about 600 nM, about 10 nM-about 500 nM, about 10 nM-about 400 nM, about 10 nM-about 300 nM, about 10 nM-about 200 nM, about 10 nM-about 100 nM, about 10 nM-about 50 nM, about 50 nM-about 1000 nM, about 100 nM-about 1000 nM, about 200 nM-about 1000 nM, about 300 nM-about 1000 nM, about 400 nM-about 1000 nM, about 500 nM-about 1000 nM, about 600 nM-about 1000 nM, about 700 nM-about 1000 nM, about 800 nM-about 1000 nM, or about 900 nM-about 1000 nM.

In certain embodiments, the $K_D$ of binding to CD19 or CD3 is measured in the absence of serum albumin (e.g., HSA). In certain embodiments, the $K_D$ of binding to CD19 or CD3 is measured in substantial absence of serum albumin (e.g., HSA). In certain embodiments, the $K_D$ of binding to CD19 or CD3 is measured in the presence of serum albumin (e.g., HSA), for example, in the presence of about 10 mg/mL, 15 mg/mL, 20 mg/mL, 25 mg/mL, 30 mg/mL, 35 mg/mL, 40 mg/mL, 45 mg/mL, or 50 mg/mL serum albumin (e.g., HSA).

In certain embodiments, the multi-specific binding protein of the present disclosure binds CD19, CD3, and/or serum albumin with a similar $K_D$ value to that of the respective antigen-binding site alone or a monoclonal antibody having the same antigen-binding site. In certain embodiments, the $K_D$ value of the multi-specific binding protein to CD19, CD3, and/or serum albumin is increased by no more than 1.5 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, or 50 fold compared to that of the respective antigen-binding site alone or a monoclonal antibody having the same antigen-binding site.

In certain embodiments, the multi-specific binding protein of the present disclosure binds CD19 and/or CD3 with a similar $K_D$ value in the presence of serum albumin to that in the absence or substantial absence of serum albumin. In certain embodiments, the $K_D$ value of the multi-specific binding protein for binding CD19 and/or CD3 in the presence of serum albumin is increased by no more than 1.5 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, or 50 fold compared to that in the absence or substantial absence of serum albumin.

H. Therapeutic Activities

The multi-specific binding protein disclosed herein is designed to simultaneously bind B cells and T cells. Recruitment of T cells facilitates lysis of the B cells involving cytolytic synapse formation and delivery of perforin and granzymes. The engaged T cells are capable of serial target cell lysis, and are not affected by immune escape mechanisms interfering with peptide antigen processing and presentation, or clonal T cell differentiation; see, for example, WO2007042261A2. Accordingly, binding of the multi-specific binding proteins to the target B cells destroys the target cells and/or impairs the progression of B cell related diseases.

Cytotoxicity mediated by multi-specific binding proteins of the invention can be measured in various ways in vitro. Effector cells can be e.g., stimulated enriched (human) CD8 positive T cells or unstimulated (human) peripheral blood mononuclear cells (PBMC). If the target cells are of macaque origin or express or are transfected with macaque target cell surface antigen which is bound by the first domain, the effector cells should also be of macaque origin such as a macaque T cell line, e.g., 4119 LnPx. The target cells should express CD19, e.g., human or macaque CD19. The target cells can be a cell line (such as CHO) which is stably or transiently transfected with CD19. Alternatively, the target cells can be a cell line naturally expressing CD19, such as B lymphocytes. The effector to target cell (E:T) ratio is usually about 10:1, but can also vary. Killing of the target cells can be measured in a $^{51}$Cr-release assay (incubation time of about 18 hours) or in a in a FACS-based cytotoxicity assay (incubation time of about 48 hours). Other methods of measuring cell death are well-known to the skilled person, such as MTT or MTS assays, ATP-based assays including bioluminescent assays, the sulforhodamine B (SRB) assay, WST assay, clonogenic assay and the ECIS technology.

In certain embodiments, the cytotoxic activity mediated by the multi-specific binding protein disclosed herein is measured in a cell-based cytotoxicity assay described above. It is represented by the $EC_{50}$ value, which corresponds to the half maximal effective concentration (concentration of the multi-specific binding protein which induces a cytotoxic response halfway between the baseline and maximum). In certain embodiments, the $EC_{50}$ value of the multi-specific binding proteins is ≤5000 pM, for example, ≤4000 pM, ≤3000 pM, ≤2000 pM, ≤1000 pM, ≤500 pM, ≤400 pM, ≤300 pM, ≤200 pM, ≤100 pM, ≤50 pM, ≤20 pM, ≤10 pM, ≤5 pM, ≤4 pM, ≤3 pM, ≤2 pM, or ≤1 pM.

It is understood that an $EC_{50}$ value is generally lower when stimulated/enriched $CD8^+$ T cells are used as effector cells, compared with unstimulated PBMC. It is further understood that the $EC_{50}$ value is generally lower when the target cells express a high level of the target cell surface antigen compared with a low level of the target antigen. For example, when stimulated/enriched human $CD8^+$ T cells are used as effector cells (and either target cell surface antigen transfected cells such as CHO cells or target cell surface antigen positive human cell lines are used as target cells), the $EC_{50}$ value of multi-specific binding protein is ≤1000 pM, for example, ≤500 pM, ≤250 pM, ≤100 pM, ≤50 pM, ≤10 pM, or ≤5 pM. When human PBMCs are used as effector cells, the $EC_{50}$ value of the multi-specific binding protein is ≤5000 pM, for example, ≤4000 pM, ≤2000 pM, ≤1000 pM, ≤500 pM, ≤200 pM, ≤150 pM, ≤100 pM, ≤50 pM, ≤10 pM, or ≤5 pM. When a macaque T cell line such as LnPx4119 is used as effector cells, and a macaque target cell surface antigen transfected cell line such as CHO cells is used as target cell line, the $EC_{50}$ value of the multi-specific binding protein is ≤2000 pM, for example, ≤1500 pM, ≤1000 pM, ≤500 pM, ≤300 pM, ≤250 pM, ≤100 pM, ≤50 pM, ≤10 pM, or ≤5 pM.

Accordingly, in certain embodiments, the $EC_{50}$ value is measured using stimulated/enriched human $CD8^+$ T cells as effector cells. In certain embodiments, the $EC_{50}$ value is measured using human PBMCs as effector cells. In certain embodiments, the $EC_{50}$ value is measured using a macaque T cell line such as LnPx4119 as effector cells and cells (e.g., CHO cells) engineered to express macaque CD19 as target cells.

In certain embodiments, the multi-specific binding protein of the present invention does not induce or mediate lysis of cells that do not express CD19. The term "does not induce lysis" or "does not mediate lysis," or grammatical equivalents thereof, means that the multi-specific binding protein, at a concentration of up to 500 nM, does not induce or mediate lysis of more than 30%, for example, no more than 30%, 25%, 20%, 15%, 10%, 9%, 8%, 7%, 6% or 5% of cells that do not express CD19, whereby lysis of a cell line that expresses CD19 is set to be 100%.

In certain embodiments, a multi-specific binding protein disclosed herein is more effective in killing CD19-expressing cells (e.g., cancer cells) than the corresponding respective anti-CD19 or anti-CD3 monoclonal antibody at the same molar concentration. In certain embodiments, the multi-specific binding protein is more effective in killing CD19-expressing cells (e.g., cancer cells) than a combination of the corresponding respective anti-CD19 and anti-CD3 monoclonal antibodies each at the same molar concentration.

The cytotoxic activity of the multi-specific binding protein can be measured in the presence or absence of serum albumin (e.g., HSA). In certain embodiments, the cytotoxic activity disclosed above is measured in the absence of serum albumin (e.g., HSA). In certain embodiments, the cytotoxic activity disclosed above is measured in substantial absence of serum albumin (e.g., HSA). In certain embodiments, the cytotoxic activity disclosed above is measured in the presence of serum albumin (e.g., HSA), for example, in the presence of about 10 mg/mL, 15 mg/mL, 20 mg/mL, 25 mg/mL, 30 mg/mL, 35 mg/mL, 40 mg/mL, 45 mg/mL, or 50 mg/mL serum albumin (e.g., HSA).

In certain embodiments, the multi-specific binding protein of the present disclosure kills CD19-expressing cells with a similar $EC_{50}$ value in the presence of serum albumin to that in the absence or substantial absence of serum albumin. In certain embodiments, the $EC_{50}$ value of the multi-specific binding protein for killing CD19-expressing cells in the presence of serum albumin is increased by no more than 1.5 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, or 50 fold compared to that in the absence or substantial absence of serum albumin. It is understood that the presence of serum albumin (e.g., about 10 mg/mL, 15 mg/mL, 20 mg/mL, 25 mg/mL, 30 mg/mL, 35 mg/mL, 40 mg/mL, 45 mg/mL, or 50 mg/mL serum albumin) may also alter the $EC_{50}$ value of a multi-specific binding protein nonspecifically. The nonspecific effect can be assessed by comparing the $EC_{50}$ values of a control protein, which does not contain a serum albumin binding domain, in the presence and absence of serum albumin. In certain embodiments, the fold change is offset by the nonspecific effect of serum albumin on a control protein, such as a bispecific protein that binds CD19 and CD3.

I. Construct Size

In certain embodiments, the molecular weight of the multi-specific binding protein is from about 40 kD to about 100 kD. In certain embodiments, the molecular weight of the multi-specific binding protein is at least 60 kD, at least 65 kD, at least 70 kD, at least 75 kD, at least 80 kD, at least 85 kD, at least 90 kD, or at least 95 kD. It is understood that smaller size generally contributes to faster diffusion and tissue penetration, but size reduction may not be as critical for the purpose of treating the indications with substantial presence of target cells (e.g., cancer cells) in the blood.

In certain embodiments, the molecular weight of the multi-specific binding protein is from about 40 kD to about 90 kD, from about 40 kD to about 80 kD, from about 40 kD to about 70 kD, from about 40 kD to about 60 kD, from about 40 kD to about 50 kD, from about 50 kD to about 100 kD, from about 50 kD to about 90 kD, from about 50 kD to about 80 kD, from about 50 kD to about 70 kD, from about 50 kD to about 60 kD, from about 60 kD to about 100 kD, from about 60 kD to about 90 kD, from about 60 kD to about 80 kD, from about 60 kD to about 70 kD, from about 65 kD to about 100 kD, from about 65 kD to about 90 kD, from about 65 kD to about 80 kD, from about 65 kD to about 70 kD, from about 70 kD to about 100 kD, from about 70 kD to about 90 kD, from about 70 kD to about 80 kD, from about 80 kD to about 100 kD, from about 80 kD to about 90 kD, or from about 90 kD to about 100 kD. In certain embodiments, the multi-specific binding protein is lower than 40 kD. In certain embodiments, the multi-specific binding protein is about 50 kD-about 90 kD, about 50 kD-about 80 kD, about 50 kD-about 70 kD, about 50 kD-about 60 kD, about 60 kD-about 90 kD, about 60 kD-about 80 kD, about 60 kD-about 70 kD, about 60 kD-about 65 kD-about 90 kD, about 65 kD-about 80 kD, about 65 kD-about 70 kD, about 70 kD-about 90 kD, or about 70 kD-about 80 kD.

J. Serum Half-Life

Fusion proteins have been developed to increase the in vivo half-life of a small protein, particularly an antibody fragment. For example, fusion with a heterodimeric antibody Fc region, such as an Fc with one or more mutations that extend the in vivo half-life, is described in U.S. Patent Application Publication Nos. US20140302037A1, US20140308285A1, and PCT Publication Nos. WO2014144722A2, WO2014151910A1 and WO2015048272A1. An alternative strategy is fusion with human serum albumin (HSA) or an HSA-binding peptide (see, e.g., PCT Publication Nos. WO2013128027A1 and WO2014140358A1). The neonatal Fc receptor (FcRn) appears to be involved in prolonging the life-span of albumin in circulation (see, Chaudhury et al. (2003) J. Exp. Med., 3: 315-22). Albumin and IgG bind noncooperatively to distinct sites of FcRn and form a ti-molecular (see id.). Binding of human FcRn to HSA and to human IgG is pH dependent, stronger at acidic pH and weaker at neutral or physiological pH (see id.). This observation suggests that proteins and protein complexes containing albumin, similar to those containing IgG (particularly Fc), are protected from degradation through pH-sensitive interaction with FcRn (see id.). Using surface plasmon resonance (SPR) to measure the capacity of individual HSA domains to bind immobilized soluble human FcRn, it has been shown that FcRn and albumin interact via the D-III domain of albumin in a pH-dependent manner, on a site distinct from the IgG binding site (see, Chaudhury et al. (2006) Biochemistry 45:4983-90 and PCT Publication No. WO2008068280A1).

The present disclosure provides multi-specific binding proteins with extended half-life. In certain embodiments, the multi-specific binding protein has a serum half-life of at least 24, 36, 48, 60, 72, 84, or 96 hours. In certain embodiments, the multi-specific binding protein has a serum half-life of at least about 50 hours. In certain embodiments, the multi-specific binding protein has a serum half-life of at least about 100 hours. Methods of measuring serum half-life are known in the art, and exemplary methods are described in Example 6. In certain embodiments, the serum half-life is measured in a non-human primate. In certain embodiments, the serum half-life is measured in human.

In certain embodiments, 50 hours after intravenous administration to a subject, the serum concentration of the multi-specific binding protein is at least 10%, at least 20%, at least 30%, at least 40%, at least 50%, at least 60%, at least 70%, at least 80%, or at least 90% of the serum concentration of the multi-specific binding protein 1 hour after the administration in said subject.

In certain embodiments, the multi-specific binding protein has a serum half-life that is at least 20% longer than a control multi-specific binding protein, wherein the control multi-specific binding protein includes a first domain identical to the first antigen-binding site of the multi-specific binding protein, a second domain identical to the second antigen-binding site of the multi-specific binding protein, but not a third domain identical or substantially identical to the third antigen-binding site of the multi-specific binding protein. In certain embodiments, the control multi-specific binding protein is identical to the multi-specific binding protein but for the absence of the half-life extension domain. In certain embodiments, the serum half-life of the multi-specific binding protein is at least 30%, at least 40%, at least 50%, at least 60%, at least 70%, at least 80%, or at least 90% longer than the serum half-life of the control multi-specific binding protein. In certain embodiments, the serum half-life of the multi-specific binding protein is longer than the serum half-life of the control multi-specific binding protein by at least 2 fold, at least 3 fold, at least 4 fold, at least 5 fold, at least 6 fold, at least 7 fold, at least 8 fold, at least 9 fold, or at least 10 fold.

III. Methods of Preparation

The antibodies and multi-specific binding proteins described above can be made using recombinant DNA technology well known to a skilled person in the art. For example, one or more isolated polynucleotides encoding the antibody or the multi-specific binding protein can be ligated to other appropriate nucleotide sequences, including, for example, constant region coding sequences, and expression control sequences, to produce conventional gene expression constructs (i.e., expression vectors) encoding the desired antibodies or multi-specific binding proteins. Production of defined gene constructs is within routine skill in the art.

Nucleic acids encoding desired antibodies or multi-specific binding proteins can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the antibodies or multi-specific binding proteins.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies then are solubilized, and the protein may be refolded and/or cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. In embodiments involving fusion proteins comprising an antibody or portion thereof, the expression vector optionally contains sequences encoding all or part of a constant region, enabling an entire, or a part of, a heavy or light chain to be expressed. The gene construct can be introduced into eukaryotic host cells using conventional techniques.

The antibodies or multi-specific binding protein disclosed herein may comprise a single polypeptide chain. In this instance, a host cell can be transfected with a single vector expressing the polypeptide (e.g., containing an expression control sequence operably linked to a nucleotide sequence encoding the polypeptide). Alternatively, the antibodies or multi-specific binding proteins disclosed herein may comprise two or more polypeptides. In this instance, a host cell can be co-transfected with more than one expression vector, for example, one expression vector expressing each polypeptide. A host cell can also be transfected with a single expression vector that expresses the two or more polypeptides. For example, the coding sequences of the two or more polypeptides can be operably linked to different expression control sequences (e.g., promoter, enhancer, and/or internal ribosome entry site (IRES)). The coding sequences of the two or more polypeptides can also be separated by a ribosomal skipping sequence or self-cleaving sequence, such as a 2A peptide.

In certain embodiments, in order to express an antibody or multi-specific binding protein, an N-terminal signal sequence is included in the protein construct. Exemplary N-terminal signal sequences include signal sequences from interleukin-2, CD-5, IgG kappa light chain, trypsinogen, serum albumin, and prolactin.

After transfection, single clones can be isolated for cell bank generation using methods known in the art, such as limited dilution, ELISA, FACS, microscopy, or Clonepix. Clones can be cultured under conditions suitable for bioreactor scale-up and maintained expression of the antibodies or multi-specific binding proteins.

The antibodies or multi-specific binding proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

IV. Pharmaceutical Compositions

The present disclosure also features pharmaceutical compositions that contain a therapeutically effective amount of the antibodies or multi-specific binding proteins described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249: 1527-1533, 1990).

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (see, *Remington's Pharmaceutical Sciences,* 18th ed. (Mack Publishing Company, 1990).

In certain embodiments, a pharmaceutical composition may contain nanoparticles, e.g., polymeric nanoparticles, liposomes, or micelles (See Anselmo et al. (2016) BIOENG. TRANSL. MED. 1: 10-29).

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly(2-hydroxyethyl-inethacrylate), ethylene vinyl acetate, or poly-D(−)-3-hydroxybutyric acid. Sustained release compositions may also include liposomes that can be prepared by any of several methods known in the art.

Pharmaceutical compositions containing an antibody or a multi-specific binding protein disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intrathecal and rectal administration. In certain embodiments, a recombinant human sialidase, a recombinant human sialidase fusion protein, or an antibody conjugate disclosed herein is administered by IV infusion. In certain embodiments, a recombinant human sialidase, a recombinant human sialidase fusion protein, or an antibody conjugate disclosed herein is administered by intratumoral injection. Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

An intravenous drug delivery formulation may be contained in a syringe, pen, or bag. In certain embodiments, the bag may be connected to a channel comprising a tube and/or a needle. In certain embodiments, the formulation may be a lyophilized formulation or a liquid formulation. In certain embodiments, the formulation may freeze-dried (lyophilized) and contained in about 12-60 vials. In certain embodiments, the formulation may be freeze-dried and 45 mg of the freeze-dried formulation may be contained in one vial. In certain embodiments, the about 40 mg-about 100 mg of freeze-dried formulation may be contained in one vial. In certain embodiments, freeze dried formulation from 12, 27, or 45 vials are combined to obtained a therapeutic dose of the protein in the intravenous drug formulation. In certain embodiments, the formulation may be a liquid formulation and stored as about 250 mg/vial to about 1,000 mg/vial. In certain embodiments, the formulation may be a liquid formulation and stored as about 600 mg/vial. In certain embodiments, the formulation may be a liquid formulation and stored as about 250 mg/vial.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including the protein of the present disclosure in a pH-buffered solution. The buffer of this invention may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g. sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/ml of citric acid (e.g., 1.305 mg/ml), about 0.3 mg/ml of sodium citrate (e.g., 0.305 mg/ml), about 1.5 mg/ml of disodium phosphate dihydrate (e.g., 1.53 mg/ml), about 0.9 mg/ml of sodium dihydrogen phosphate dihydrate (e.g., 0.86), and about 6.2 mg/ml of sodium chloride (e.g., 6.165 mg/ml). In certain embodiments, the buffer system includes 1-1.5 mg/ml of citric acid, 0.25 to 0.5 mg/ml of sodium citrate, 1.25 to 1.75 mg/ml of disodium phosphate dihydrate, 0.7 to 1.1 mg/ml of sodium dihydrogen phosphate dihydrate, and 6.0 to 6.4 mg/ml of sodium chloride. In certain embodiments, the pH of the formulation is adjusted with sodium hydroxide.

A polyol, which acts as a tonicifier and may stabilize the antibody or multi-specific binding protein, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g., mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/ml. In certain embodiments, the concentration of mannitol may be about 7.5 to 15 mg/ml. In certain embodiments, the concentration of mannitol may be about 10-14 mg/ml. In certain embodiments, the concentration of mannitol may be about 12 mg/ml. In certain embodiments, the polyol sorbitol may be included in the formulation.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In embodiments, the protein product of the present disclosure is formulated as a liquid formulation. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments, the liquid formulation may be diluted with 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

The antibody or multi-specific binding protein may be lyophilized to produce a lyophilized formulation including the proteins and a lyoprotectant. The lyoprotectant may be sugar, e.g., disaccharides. In certain embodiments, the lyoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5. In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide. Before lyophilization, the pH of the solution containing the protein of the present disclosure may be adjusted between 6 to 8. In certain embodiments, the pH range for the lyophilized drug product may be from 7 to 8.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5,000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308: 43-53, 2001; Steimer et al., *Clinica Chimica Acta* 308: 33-41, 2001).

In general, dosages based on body weight are from about 0.01 µg to about 100 mg per kg of body weight, such as about 0.01 µg to about 100 mg/kg of body weight, about 0.01 µg to about 50 mg/kg of body weight, about 0.01 µg to about 10 mg/kg of body weight, about 0.01 µg to about 1 mg/kg of body weight, about 0.01 µg to about 100 µg/kg of body weight, about 0.01 g to about 50 µg/kg of body weight, about 0.01 µg to about 10 µg/kg of body weight, about 0.01 µg to about 1 µg/kg of body weight, about 0.01 µg to about 0.1 µg/kg of body weight, about 0.1 µg to about 100 mg/kg of body weight, about 0.1 µg to about 50 mg/kg of body weight, about 0.1 µg to about 10 mg/kg of body weight, about 0.1 µg to about 1 mg/kg of body weight, about 0.1 µg to about 100 µg/kg of body weight, about 0.1 µg to about 10 µg/kg of body weight, about 0.1 µg to about 1 µg/kg of body weight, about 1 µg to about 100 mg/kg of body weight, about 1 µg to about 50 mg/kg of body weight, about 1 µg to about 10 mg/kg of body weight, about 1 µg to about 1 mg/kg of body weight, about 1 µg to about 100 µg/kg of body weight, about 1 µg to about 50 µg/kg of body weight, about 1 µg to about 10 µg/kg of body weight, about 10 µg to about 100 mg/kg of body weight, about 10 µg to about 50 mg/kg of body weight, about 10 µg to about 10 mg/kg of body weight, about 10 µg to about 1 mg/kg of body weight, about 10 µg to about 100 µg/kg of body weight, about 10 µg to about 50 µg/kg of body weight, about 50 µg to about 100 mg/kg of body weight, about 50 g to about 50 mg/kg of body weight, about 50 µg to about 10 mg/kg of body weight, about 50 µg to about 1 mg/kg of body weight, about 50 µg to about 100 µg/kg of body weight, about 100 µg to about 100 mg/kg of body weight, about 100 µg to about 50 mg/kg of body weight, about 100 µg to about 10 mg/kg of body weight, about 100 µg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

V. Therapeutic Applications

It is contemplated that the antibodies or multi-specific binding proteins can be used either alone or in combination with other therapeutic agents.

A. Indications

The present disclosure provides methods for the treatment or amelioration of a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease in a subject in need thereof, the method comprising administration of a multi-specific binding protein or an antibody that binds CD19 disclosed herein.

In certain embodiments, the cancer to be treated is non-Hodgkin's lymphoma, such as a B-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, chronic lymphocytic leukemia, or primary central nervous system lymphoma. In certain other embodiments, the cancer to be treated is multiple myeloma. In certain other embodiments, the cancer to be treated is acute lymphoblastic leukemia (ALL). In certain embodiments, the ALL is relapsed/refractory adult and pediatric ALL.

B. Combination Therapies

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one aspect, the present disclosure provides a method of treating a subject by the administration of a second therapeutic agent in combination with one or more of the multi-specific binding proteins and/or antibodies that bind CD19 disclosed herein.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, luteinizing hormone releasing factor and variations of the aforementioned agents that may exhibit differential binding to its cognate receptor, and increased or decreased serum half-life.

An additional class of agents that may be used as part of a combination therapy in treating cancer is immune checkpoint inhibitors. The checkpoint inhibitor may, for example, be selected from a PD-1 antagonist, PD-L$_1$ antagonist, CTLA-4 antagonist, adenosine A2A receptor antagonist, B7-H3 antagonist, B7-H4 antagonist, BTLA antagonist, KIR antagonist, LAG3 antagonist, TIM-3 antagonist, VISTA antagonist or TIGIT antagonist.

In certain embodiments, the checkpoint inhibitor is a PD-1 or PD-L$_1$ inhibitor. PD-1 is a receptor present on the surface of T-cells that serves as an immune system checkpoint that inhibits or otherwise modulates T-cell activity at the appropriate time to prevent an overactive immune response. Cancer cells, however, can take advantage of this checkpoint by expressing ligands, for example, PD-L1, that interact with PD-1 on the surface of T-cells to shut down or modulate T-cell activity. Exemplary PD-1/PD-L1 based immune checkpoint inhibitors include antibody based therapeutics. Exemplary treatment methods that employ PD-1/PD-L1 based immune checkpoint inhibition are described in U.S. Pat. Nos. 8,728,474 and 9,073,994, and EP Patent No. 1537878B1, and, for example, include the use of anti-PD-1 antibodies. Exemplary anti-PD-1 antibodies are described, for example, in U.S. Pat. Nos. 8,952,136, 8,779,105, 8,008,449, 8,741,295, 9,205,148, 9,181,342, 9,102,728, 9,102,727, 8,952,136, 8,927,697, 8,900,587, 8,735,553, and 7,488,802. Exemplary anti-PD-1 antibodies include, for example, nivolumab (Opdivo®, Bristol-Myers Squibb Co.), pembrolizumab (Keytruda®, Merck Sharp & Dohme Corp.), PDR001 (Novartis Pharmaceuticals), and pidilizumab (CT-011, Cure Tech). Exemplary anti-PD-L1 antibodies are described, for example, in U.S. Pat. Nos. 9,273,135, 7,943,743, 9,175,082, 8,741,295, 8,552,154, and 8,217,149. Exemplary anti-PD-L$_1$ antibodies include, for example, atezolizumab (Tecentriq®, Genentech), durvalumab (AstraZeneca), MED14736, avelumab, and BMS 936559 (Bristol Myers Squibb Co.).

In certain embodiments, a method or composition described herein is administered in combination with a CTLA-4 inhibitor. In the CTLA-4 pathway, the interaction of CTLA-4 on a T-cell with its ligands (e.g., CD80, also known as B7-1, and CD86) on the surface of an antigen presenting cells (rather than cancer cells) leads to T-cell inhibition. Exemplary CTLA-4 based immune checkpoint inhibition methods are described in U.S. Pat. Nos. 5,811,097, 5,855,887, 6,051,227. Exemplary anti-CTLA-4 antibodies are described in U.S. Pat. Nos. 6,984,720, 6,682,736, 7,311,910; 7,307,064, 7,109,003, 7,132,281, 6,207,156, 7,807,797, 7,824,679, 8,143,379, 8,263,073, 8,318,916, 8,017,114, 8,784,815, and 8,883,984, International (PCT) Publication Nos. WO98/42752, WO00/37504, and WO01/14424, and European Patent No. EP 1212422 B1. Exemplary CTLA-4 antibodies include ipilimumab or tremelimumab.

In certain embodiments, a method or composition described herein is administered in combination with (i) a PD-1 or PD-L1 inhibitor, e.g., a PD-1 or PD-L1 inhibitor disclosed herein, and (ii) CTLA-4 inhibitor, e.g., a CTLA-4 inhibitor disclosed herein.

In certain embodiments, a method or composition described herein is administered in combination with an IDO inhibitor. Exemplary IDO inhibitors include 1-methyl-D-tryptophan (known as indoximod), epacadostat (INCB24360), navoximod (GDC-0919), and BMS-986205.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxy-adenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

It is understood that the antibody or multi-specific binding protein disclosed herein, which is designed to activate T lymphocytes, may cause side effects such as neurotoxicity. Accordingly, in certain embodiments, the second therapeutic agent that can be used in combination with the antibody or multi-specific binding protein comprises an agent that mitigates a side effect of the antibody or multi-specific binding protein, e.g., reduces neurotoxicity. In certain embodiments, the second therapeutic agent inhibits T cell trafficking, for example, reduces or inhibits immune cells from crossing the blood-brain barrier. Non-limiting examples of such therapeutic agents include antagonists (e.g., antagonistic antibodies) of adhesion molecules on immune cells (e.g., α4 integrin), such as natalizumab. In certain embodiments, the second therapeutic agent increases the internalization of a sphingosine-1-phosphate (SIP) receptor (e.g., S1PR1 or S1PR5), such as fingolimod or ozanimod. In certain embodiments, the second therapeutic agent is a nitric oxide synthase (NOS) inhibitor, such as ronopterin, cindunistat, A-84643, ONO-1714, L-NOARG, NCX-456, VAS-2381, GW-273629, NXN-462, CKD-712, K$_D$-7040, or guanidino-ethyldisulfide. In certain embodiments, the second therapeutic agent is an antagonist of CSF1 or CSF1R, such as pexidartinib, emactuzumab, cabiralizumab, LY-3022855, JNJ-40346527, or MCS110. Additional non-limiting examples of the second therapeutic agents include pentosan polysulfate, minocycline, anti-ICAM-1 antibodies, anti-P-selectin antibodies, anti-CD11a antibodies, anti-CD162 antibodies, and anti-IL-6R antibodies (e.g., tocilizumab).

The amount of the antibody or multi-specific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, an antibody or multi-specific binding protein may be administered during a time when the additional therapeutic agent (s) exerts its prophylactic or therapeutic effect, or vice versa.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and is not intended to limit the invention.

Example 1. Characterization of New Anti-CD19 Antibodies

This example describes new anti-CD19 antibodies CNG-CD19-101 to -110 and CNG-CD19-701 to -710. The amino acid sequences of CNG-CD19-101 to -110 are provided in Table 1 above, and the amino acid sequences of CNG-CD19-701 to -710 are provided in Table 2 above.

CNG-CD19-101 to -110 and CNG-CD19-701 to -710 were optimized from parental antibodies CNG-CD19-1 and CNG-CD19-7, respectively, by introducing diversities into the VH and/or VL and shuffling fragments of the VH and VL sequences. The antibody clones were selected for improved binding affinity to biotinylated human CD19 relative to the respective parental antibody. The selected antibodies were then produced from yeast cells and purified using a protein A column.

The binding affinity of the antibodies to isolated CD19 was measured by surface plasmon resonance using a ForteBio Octet HTX system as previously described (see, e.g., Estep et al, High throughput solution-based measurement of antibody-antigen affinity and epitope binning. Mabs 5(2), 270-278 (2013)). Briefly, ForteBio affinity measurements were performed by loading IgGs on-line onto anti-hIgG Fc Capture (AHC) sensors. The sensors were equilibrated off-line in assay buffer for 30 minutes and then monitored on-line for 60 seconds for baseline establishment. The sensors with loaded IgGs were exposed to 100 nM human serum albumin for 3 minutes, and subsequently transferred to assay buffer for 3 minutes for off-rate measurement. All kinetics were analyzed using the 1:1 binding model.

The binding affinity of the antibodies to CD19 expressed on the cell surface was also measured. Briefly, approximately 100,000 Chinese hamster overy (CHO) cells over-expressing the antigen were washed with wash buffer and incubated with 100 μl 100 nM IgG for 15 minutes at room temperature. Cells were then washed twice with wash buffer and incubated with 100 μl of 1:100 Human-PE for 15 minutes on ice. Cells were then washed twice more with wash buffer and analyzed on a FACS Canto II analyzer (BD Biosciences).

TABLE 9

Binding of Anti-CD19 Antibodies to CD19 Proteins and CD19 Expressing Cells

| Construct | Affinity to Human CD19 | | Affinity to Cynomolgus CD19 | | Binding to Cells Expressing Human CD19 (FOB) |
|---|---|---|---|---|---|
| | $K_D$ (M) | $k_{off}$ (1/s) | $K_D$ (M) | $k_{off}$ (1/s) | |
| CNG-CD19-1 | 3.46E−10 | 1.14E−04 | 9.39E−09 | 1.91E−03 | 267 |
| CNG-CD19-101 | 1.44E−10 | 5.72E−05 | 9.91E−09 | 2.33E−03 | 296 |
| CNG-CD19-102 | 2.98E−10 | 9.12E−05 | 1.21E−08 | 2.18E−03 | 258 |
| CNG-CD19-103 | 1.06E−10 | 4.00E−05 | 4.69E−09 | 1.09E−03 | 286 |
| CNG-CD19-104 | 1.44E−10 | 6.00E−05 | 5.83E−09 | 1.48E−03 | 327 |
| CNG-CD19-105 | 1.64E−10 | 8.28E−05 | 2.24E−09 | 6.79E−04 | 351 |

TABLE 9-continued

Binding of Anti-CD19 Antibodies to CD19
Proteins and CD19 Expressing Cells

| Construct | Affinity to Human CD19 | | Affinity to Cynomolgus CD19 | | Binding to Cells Expressing Human CD19 (FOB) |
|---|---|---|---|---|---|
| | $K_D$ (M) | $k_{off}$ (1/s) | $K_D$ (M) | $k_{off}$ (1/s) | |
| CNG-CD19-106 | 1.89E−10 | 1.14E−04 | 3.20E−09 | 1.23E−03 | 354 |
| CNG-CD19-107 | 2.77E−10 | 5.71E−05 | 5.64E−09 | 1.29E−03 | 315 |
| CNG-CD19-108 | 1.64E−10 | 5.26E−05 | 2.25E−09 | 6.50E−04 | 319 |
| CNG-CD19-109 | 1.44E−10 | 4.00E−05 | 4.03E−09 | 1.31E−03 | 334 |
| CNG-CD19-110 | 3.53E−10 | 1.21E−04 | 6.17E−09 | 1.64E−03 | 293 |

As shown in Table 9, CNG-CD19-101 to -110 showed higher binding affinity to human CD19 and/or cynomolgus CD19 than CNG-CD19-1. In particular, CNG-CD19-101 to -109 bound human CD19 with lower $K_D$ values than CNG-CD19-1; CNG-CD19-103 to -110 bound cynomolgus CD19 with lower $K_D$ values than CNG-CD19-1. CNG-CD19-101 and -103 to -110 showed increased binding to CHO cells expressing human CD19 than CNG-CD19-1.

TABLE 10

Binding of Anti-CD19 Antibodies to CD19
Proteins and CD19 Expressing Cells

| Construct | Affinity to Human CD19 | | Affinity to Cynomolgus CD19 | | Binding to Cells Expressing Human CD19 (FOB) |
|---|---|---|---|---|---|
| | $K_D$ (M) | $k_{off}$ (1/s) | $K_D$ (M) | $k_{off}$ (1/s) | |
| CNG-CD19-7 | 2.25E−09 | 3.96E−04 | 8.43E−09 | 8.32E−04 | 71 |
| CNG-CD19-701 | 1.87E−10 | 7.05E−05 | 6.68E−10 | 1.68E−04 | 195 |
| CNG-CD19-702 | 5.00E−10 | 1.75E−04 | 1.30E−09 | 2.95E−04 | 180 |
| CNG-CD19-703 | 2.89E−10 | 8.19E−05 | 2.54E−09 | 3.52E−04 | 135 |
| CNG-CD19-704 | 3.67E−10 | 1.01E−04 | 1.24E−09 | 1.94E−04 | 140 |
| CNG-CD19-705 | 2.48E−10 | 4.70E−05 | 6.02E−09 | 8.37E−04 | 105 |
| CNG-CD19-706 | 8.59E−11 | 4.00E−05 | 3.72E−10 | 1.20E−04 | 241 |
| CNG-CD19-707 | 1.04E−10 | 4.66E−05 | 7.38E−10 | 2.07E−04 | 237 |
| CNG-CD19-708 | 1.56E−10 | 6.69E−05 | 1.02E−09 | 2.23E−04 | 210 |
| CNG-CD19-709 | 1.07E−10 | 4.60E−05 | 6.39E−10 | 1.68E−04 | 234 |
| CNG-CD19-710 | 1.35E−10 | 4.00E−05 | 1.54E−09 | 3.28E−04 | 153 |

As shown in Table 10, CNG-CD19-701 to -710 showed higher binding affinity to human CD19 and cynomolgus CD19 than CNG-CD19-7. In particular, CNG-CD19-701 to -710 bound human CD19 and cynomolgus CD19 with lower $K_D$ values than CNG-CD19-7. CNG-CD19-701 to -710 also showed increased binding to CHO cells expressing human CD19 than CNG-CD19-7.

Additional kinetic analysis of the anti-CD19 VL-VH scFvs, with or without a disulfide bond introduced by Cys substitutions at position 44 of VH and position 100 of VL, was conducted by surface plasmon resonance (SPR). The scFv proteins were serially diluted and assessed at 25° C. in a HBS-EP+ running buffer system (10 mM HEPES pH 7.4, 150 mM NaCl, 3 mM EDTA, 0.05% Surfactant P20) using a Biacore 8K optical biosensor (Global Life Sciences Solutions USA, Marlborough, MA). The sample compartment was maintained at 10° C. for the duration of each experiment.

Each experiment cycle began with an injection (500 s at 2 μL/min) over flow cells 1 and 2 of a 1:20 solution of biotin CAPture reagent (Global Life Sciences Solutions USA) in running buffer. This was followed by an injection (300 s at 4.0 μL/min) of biotinylated CD-19 (40 nM) overflow cell 2. Upon capture of CD19 to the sensor surface, test scFvs (16.2 to 0.067 nM, 3-fold dilution in running buffer) was injected (300 s at 30 uL/min) over flow cells 1 and 2. The dissociation of the scFvs was monitored for a duration of 2564 s. Finally, an injection (90 s at 10 μL/min) of regeneration solution (6 M Guanidine-HCl in 0.25 M NaOH) overflow cells 1 and 2 was used to prepare the sensor surface for another cycle.

The resulting data were processed and fit as follows. Sensorgrams were cropped to include only the scFv association and dissociation steps. The cropped data was subsequently aligned, double reference subtracted, and then nonlinear least squares fit to a 1:1 binding model using Biacore Insight Evaluation software version 3.0.11.15423. (Myszka D. (1999) *J. Mol. Recognit.* 12(5):279-284).

Resultant $K_D$ and $k_{off}$ values for each tested scFv are summarized in Table 11.

TABLE 11

Binding of Anti-CD19 Antibodies to Human CD19 Protein

| Construct | VL-VH scFv | | VL-VH scFv with disulfide bond[1] | |
|---|---|---|---|---|
| | $K_D$ (M) | $k_{off}$ (1/s) | $K_D$ (M) | $k_{off}$ (1/s) |
| CNG-CD19-101 | 6.73E−12 | 2.00E−05 | 1.39E−11 | 4.88E−05 |
| CNG-CD19-103 | 9.91E−12 | 2.41E−05 | 1.78E−11 | 4.85E−05 |
| CNG-CD19-701 | 1.48E−11 | 2.00E−05 | 1.41E−11 | 2.00E−05 |
| CNG-CD19-707 | 1.22E−11 | 2.00E−05 | 1.17E−11 | 2.00E−05 |
| CNG-CD19-710 | 2.18E−11 | 2.00E−05 | 2.13E−11 | 2.54E−05 |

[1]In each scFv construct, a disulfide bond was introduced by Cys substitutions at position 44 of VH and position 100 of VL.

Example 2. Characterization of New Anti-Serum Albumin Antibodies

This example describes new anti-serum albumin antibodies CNG-HSA-101 to -120. The amino acid sequences of these antibodies are provided in Table 5 above.

CNG-HSA-101 to -120 were optimized from parental antibodies CNG-HSA-1, a single domain antibody, by introducing diversities into the heavy chain variable region, generating random mutations by error prone PCR, and shuffling the VH fragments. The antibody clones were selected for improved binding affinity to biotinylated human serum albumin relative to the parental antibody. Additionally, a thermal selection pressure was employed for the VH shuffle optimization cycle. Thermal selection pressures were applied by incubating the libraries at various temperatures and then selecting for antibodies that retained antigen binding following thermal incubation. The selected antibodies were then produced from yeast cells and purified using a protein A column.

The binding affinity of the antibodies to isolated serum albumin was measured by surface plasmon resonance using a ForteBio Octet HTX system as previously described (see, e.g., Estep et al, High throughput solution-based measurement of antibody-antigen affinity and epitope binning. Mabs 5(2), 270-278 (2013)). Briefly, ForteBio affinity measurements were performed by loading the heavy chain antibodies (HCAbs) on-line onto AHC sensors. The sensors were equilibrated off-line in assay buffer for 30 minutes and then monitored on-line for 60 seconds for baseline establishment. The sensors with loaded HCAbs were exposed to 100 nM human serum albumin for 3 minutes, and subsequently transferred to assay buffer for 3 minutes for off-rate measurement. All kinetics were analyzed using the 1:1 binding model.

The melting temperature (Tm) of the VHH fragments were measured by dynamic scanning fluorimetry (DSF). Briefly, 10 µL of 20× Sypro Orange dye is added to 20 µL of 0.2-1 mg/mL HCAb. A BioRad CFX96 RT PCR machine was used to raise the sample plate temperature from 40° to 95° C. at 0.5° C. increments, with 2 minutes equilibration at each temperature. The negative of the first derivative for the raw data was used to extract Tm.

values than CNG-HSA-1. CNG-HSA-101, CNG-HSA-103, CNG-HSA-106, CNG-HSA-107, CNG-HSA-108, CNG-HSA-109, CNG-HSA-111, CNG-HSA-113, CNG-HSA-114, CNG-HSA-115, CNG-HSA-116, CNG-HSA-118, and CNG-HSA-120 bound mouse serum albumin with a $K_D$ value less than 4-fold higher than the $K_D$ with which the same antibody bound human serum albumin. CNG-HSA-101, CNG-HSA-102, CNG-HSA-104, CNG-HSA-109, CNG-HSA-113, CNG-HSA-116, and CNG-HSA-117 bound protein A with lower $K_D$ values than CNG-HSA-1. CNG-HSA-101, CNG-HSA-102, CNG-HSA-103, CNG-HSA-104, CNG-HSA-105, CNG-HSA-106, CNG-HSA-108, CNG-HSA-109, CNG-HSA-113, CNG-HSA-116, CNG-HSA-117, and CNG-HSA-120 showed a melting temperature greater than or equal to 60° C., among which CNG-HSA-101, CNG-HSA-102, CNG-HSA-103, CNG-HSA-106, and CNG-HSA-120 showed a melting temperature greater than or equal to 65° C.

Example 3. Production of Multi-Specific Binding Proteins

This example describes the production and purification of multi-specific binding proteins.

Nucleic acids encoding single-chain multi-specific binding proteins (see Table 13) were constructed and codon

TABLE 12

Binding of Anti-Serum Albumin Antibodies to Serum Albumin and Protein A

| Construct | Affinity to Human Serum Albumin (HSA) | | Affinity to Cynomolgus Serum Albumin | | Affinity to Mouse Serum Albumin (MSA) | | Ratio of MSA-$K_D$ to HSA-$K_D$ | Affinity to Protein A | | Melting Temperature (° C.) |
|---|---|---|---|---|---|---|---|---|---|---|
| | $K_D$ (M) | $k_{off}$ (1/s) | $K_D$ (M) | $k_{off}$ (1/s) | $K_D$ (M) | $k_{off}$ (1/s) | | $K_D$ (M) | $k_{off}$ (1/s) | |
| CNG-HSA-1 | 1.19E-08 | 1.77E-03 | 9.65E-09 | 1.39E-03 | 1.72E-07 | 2.16E-02 | 14.47 | 2.56E-09 | 4.74E-04 | 55.5 |
| CNG-HSA-101 | 5.07E-09 | 7.16E-04 | 3.58E-09 | 5.32E-04 | 1.61E-08 | 3.41E-03 | 3.17 | 1.84E-09 | 2.00E-04 | 65.5 |
| CNG-HSA-102 | 4.89E-09 | 7.48E-04 | 3.65E-09 | 5.68E-04 | 4.14E-08 | 7.38E-03 | 8.46 | 1.70E-09 | 2.00E-04 | 66.5 |
| CNG-HSA-103 | 4.89E-09 | 7.42E-04 | 3.62E-09 | 5.41E-04 | 1.51E-08 | 3.24E-03 | 3.09 | 2.02E-09 | 2.21E-04 | 66.0 |
| CNG-HSA-104 | 7.71E-09 | 1.12E-03 | 6.10E-09 | 8.74E-04 | 5.06E-08 | 1.05E-02 | 6.57 | 1.70E-09 | 2.00E-04 | 63.5 |
| CNG-HSA-105 | 1.52E-08 | 2.00E-03 | 1.27E-08 | 1.63E-03 | 1.54E-07 | 2.06E-02 | 10.12 | 2.76E-09 | 2.97E-04 | 64.0 |
| CNG-HSA-106 | 1.70E-08 | 2.97E-03 | 1.44E-08 | 2.38E-03 | 5.78E-08 | 1.24E-02 | 3.41 | N.B.[1] | | 65.0 |
| CNG-HSA-107 | 1.68E-08 | 2.38E-03 | 1.33E-08 | 1.82E-03 | 4.56E-08 | 8.51E-03 | 2.72 | 3.09E-09 | 3.33E-04 | 59.0 |
| CNG-HSA-108 | 6.19E-09 | 9.58E-04 | 5.27E-09 | 7.94E-04 | 8.06E-09 | 1.85E-03 | 1.30 | 2.94E-09 | 2.94E-04 | 64.0 |
| CNG-HSA-109 | 3.50E-09 | 5.66E-04 | 3.10E-09 | 5.03E-04 | 1.19E-08 | 2.84E-03 | 3.40 | 1.78E-09 | 2.00E-04 | 63.5 |
| CNG-HSA-110 | 5.70E-09 | 8.93E-04 | 5.20E-09 | 7.59E-04 | 3.89E-08 | 8.38E-03 | 6.82 | 3.67E-09 | 3.78E-04 | 57.5 |
| CNG-HSA-111 | 8.35E-09 | 1.17E-03 | 6.13E-09 | 8.84E-04 | 1.02E-08 | 2.31E-03 | 1.23 | 2.84E-09 | 2.00E-04 | 59.0 |
| CNG-HSA-112 | 8.45E-09 | 1.36E-03 | 7.43E-09 | 1.15E-03 | 6.67E-08 | 1.30E-02 | 7.90 | 3.44E-09 | 3.75E-04 | 54.5 |
| CNG-HSA-113 | 1.54E-08 | 2.14E-03 | 1.21E-08 | 1.70E-03 | 5.20E-08 | 1.01E-02 | 3.38 | 1.70E-09 | 2.00E-04 | 62.5 |
| CNG-HSA-114 | 1.47E-08 | 2.21E-03 | 1.20E-08 | 1.73E-03 | 1.75E-08 | 3.80E-03 | 1.20 | N.D.[2] | | 51.0 |
| CNG-HSA-115 | 2.96E-09 | 4.41E-04 | 3.37E-09 | 6.18E-04 | 6.43E-09 | 1.32E-03 | 2.17 | N.D. | | 56.0 |
| CNG-HSA-116 | 4.65E-09 | 6.99E-04 | 3.85E-09 | 5.97E-04 | 4.56E-09 | 1.08E-03 | 0.98 | 1.75E-09 | 2.00E-04 | 64.0 |
| CNG-HSA-117 | 5.56E-09 | 7.93E-04 | 4.05E-09 | 6.08E-04 | 4.48E-08 | 8.77E-03 | 8.07 | 1.78E-09 | 2.00E-04 | 60.5 |
| CNG-HSA-118 | 9.36E-09 | 1.30E-03 | 6.65E-09 | 1.02E-03 | 1.20E-08 | 2.74E-03 | 1.28 | N.D. | | 58.0 |
| CNG-HSA-119 | 7.36E-09 | 1.09E-03 | 5.73E-09 | 8.64E-04 | 4.11E-08 | 8.54E-03 | 5.59 | N.D. | | 53.5 |
| CNG-HSA-120 | 3.15E-09 | 5.07E-04 | 2.60E-09 | 4.22E-04 | 4.32E-09 | 1.07E-03 | 1.37 | N.D. | | 66.0 |

[1]N.B. means no binding was detected under the conditions of this assay.
[2]N.D. means not determined.

As shown in Table 12, CNG-HSA-101 to -120 showed higher binding affinity to human serum albumin, cynomolgus serum albumin, mouse serum albumin, and/or protein A than CNG-HSA-1. In particular, all these antibodies bound mouse serum albumin with lower $K_D$ values than CNG-HSA-1. CNG-HSA-101, CNG-HSA-102, CNG-HSA-103, CNG-HSA-104, CNG-HSA-108, CNG-HSA-109, CNG-HSA-110, CNG-HSA-111, CNG-HSA-112, CNG-HSA-115, CNG-HSA-116, CNG-HSA-117, CNG-HSA-118, CNG-HSA-119, and CNG-HSA-120 bound human serum albumin and cynomolgus serum albumin with lower $K_D$ optimized for expression in human cells and cloned into a mammalian expression vector following standard procedures. Following sequence verification, the expression vectors, in the form of plasmids, were prepared in sufficient quantity for transfection using Plasmid Plus purification kits (Qiagen). Human embryonic kidney 293 (HEK 293) cells were passaged to appropriate density for transient transfection. Cells were transiently transfected with the expression vectors and cultured for six days.

The amino acid sequences of the various multi-specific binding proteins are summarized in Table 13. Constructs tAb0027 to tAb0032 each contained an anti-CD19 scFv having the amino acid sequence set forth in SEQ ID NO: 9, an anti-CD3 scFv having the amino acid sequence set forth in SEQ ID NO: 105, and an anti-HSA sdAb having the amino acid sequence set forth in SEQ ID NO: 121. Constructs tAb0033 to tAb0038 each contained an anti-CD19 scFv having the amino acid sequence set forth in SEQ ID NO: 18, an anti-CD3 scFv having the amino acid sequence set forth in SEQ ID NO: 105, and an anti-HSA sdAb having the amino acid sequence set forth in SEQ ID NO: 121.

TABLE 13

Exemplary Multi-specific Binding Proteins

| Construct | Format | Amino Acid Sequence |
|---|---|---|
| tAb0027 | CD19:CD3:HSA | QVQLVQSGAEVKKPGASVKVSCKASGYTFTDYIMHWVRQAPGQGLEWMGYINPYNDGSKYTEKFQGRVTMTSDTSISTAYMELSRLRSDDTAVYYCARGTYYYGPQLFDYWGQGTTVTVSSGGGGSGGGGSGGGGSDIVMTQTPLSLSVTPGQPASISCKSSQSLETSTGTTYLNWYLQKPGQSPQLLIYRVSKRFSGVPDRFSGSGSGTDFTLKISRVEAEDVGVYYCLQLLEDPYTFGQGTKLEIKGGGGSGGGGSDIVMTQSPDSLAVSLGERATINCKSSQSLLNARTGKNYLAWYQQKPGQPPKLLIYWASTRESGVPDRFSGSGSGTDFTLTISSLQAEDVAVYYCKQSYSRRTFGGGTKVEIKGGGGSGGGGSGGGGSGGGGSQVQLVQSGAEVKKPGASVKVSCKASGFNIKDYYMHWVRQAPGQRLEWMGWIDLENANTIYDAKFQGRVTITRDTSASTAYMELSSLRSEDTAVYYCARDAYGRYFYDVWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSHHHHHHHHHH (SEQ ID NO: 303) |
| tAb0029 | CD3:CD19:HSA | DIVMTQSPDSLAVSLGERATINCKSSQSLLNARTGKNYLAWYQQKPGQPPKLLIYWASTRESGVPDRFSGSGSGTDFTLTISSLQAEDVAVYYCKQSYSRRTFGGGTKVEIKGGGGSGGGGSGGGGSGGGGSQVQLVQSGAEVKKPGASVKVSCKASGFNIKDYYMHWVRQAPGQRLEWMGWIDLENANTIYDAKFQGRVTITRDTSASTAYMELSSLRSEDTAVYYCARDAYGRYFYDVWGQGTLVTVSSGGGGSGGGGSQVQLVQSGAEVKKPGASVKVSCKASGYTFTDYIMHWVRQAPGQGLEWMGYINPYNDGSKYTEKFQGRVTMTSDTSISTAYMELSRLRSDDTAVYYCARGTYYYGPQLFDYWGQGTTVTVSSGGGGSGGGGSGGGGSDIVMTQTPLSLSVTPGQPASISCKSSQSLETSTGTTYLNWYLQKPGQSPQLLIYRVSKRFSGVPDRFSGSGSGTDFTLKISRVEAEDVGVYYCLQLLEDPYTFGQGTKLEIKGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSHHHHHHHHHH (SEQ ID NO: 304) |
| tAb0030 | CD3:HSA:CD19 | DIVMTQSPDSLAVSLGERATINCKSSQSLLNARTGKNYLAWYQQKPGQPPKLLIYWASTRESGVPDRFSGSGSGTDFTLTISSLQAEDVAVYYCKQSYSRRTFGGGTKVEIKGGGGSGGGGSGGGGSGGGGSQVQLVQSGAEVKKPGASVKVSCKASGFNIKDYYMHWVRQAPGQRLEWMGWIDLENANTIYDAKFQGRVTITRDTSASTAYMELSSLRSEDTAVYYCARDAYGRYFYDVWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSQVQLVQSGAEVKKPGASVKVSCKASGYTFTDYIMHWVRQAPGQGLEWMGYINPYNDGSKYTEKFQGRVTMTSDTSISTAYMELSRLRSDDTAVYYCARGTYYYGPQLFDYWGQGTTVTVSSGGGGSGGGGSGGGGSDIVMTQTPLSLSVTPGQPASISCKSSQSLETSTGTTYLNWYLQKPGQSPQLLIYRVSKRFSGVPDRFSGSGSGTDFTLKISRVEAEDVGVYYCLQLLEDPYTFGQGTKLEIKHHHHHHHHHH (SEQ ID NO: 305) |
| tAb0031 | HSA:CD3:CD19 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGGSDIVMTQSPDSLAVSLGERATINCKSSQSLLNARTGKNYLAWYQQKPGQPPKLLIYWASTRESGVPDRFSGSGSGTDFTLTISSLQAEDVAVYYCKQSYSRRTFGGGTKVEIKGGGGSGGGGSGGGGSGGGGSQVQLVQSGAEVKKPGASVKVSCKASGFNIKDYYMHWVRQAPGQRLEWMGWIDLENANTIYDAKFQGRVTITRDTSASTAYMELSSLRSEDTAVYYCARDAYGRYFYDVWGQGTLVTVSSGGGGSGGGSQVQLVQSGAEVKKPGASVKVSCKASGYTFTDYIMHWVRQAPGQGLEWMGYINPYNDGSKYTEKFQGRVTMTSDTSISTAYMELSRLRSDDTAVYYCARGTYYYGPQLFDYWGQGTTVTVSSGGGGSGGGGSGGGGSDIVMTQTPLSLSVTPGQPASISCKSSQSLETSTGTTYLNWYLQKPGQSPQLLIYRVSKRFSGVPDRFSGSGSGTDFTLKISRVEAEDVGVYYCLQLLEDPYTFGQGTKLEIKHHHHHHHHHH (SEQ ID NO: 306) |
| tAb0032 | HSA:CD19:CD3 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSQVQLVQSGAEVKKPGASVKVSCKASGYTFTDYIMHWVRQAPGQGLEWMGYINPYNDGSKYTEKFQGRVTMTSDTSISTAYMELSRLRSDDTAVYYCARGT |

TABLE 13-continued

Exemplary Multi-specific Binding Proteins

| Construct | Format | Amino Acid Sequence |
|---|---|---|
| | | YYYGPQLFDYWGQGTTVTVSSGGGGSGGGGSGGGGSDIVMTQTP<br>LSLSVTPGQPASISCKSSQSLETSTGTTYLNWYLQKPGQSPQLLIYR<br>VSKRFSGVPDRFSGSGSGTDFTLKISRVEAEDVGVYYCLQLLEDPY<br>TFGQGTKLEIKGGGGSGGGGSDIVMTQSPDSLAVSLGERATINCKSS<br>QSLLNARTGKNYLAWYQQKPGQPPKLLIYWASTRESGVPDRFSGS<br>GSGTDFTLTISSLQAEDVAVYYCKQSYSRRTFGGGTKVEIKGGGG<br>SGGGGSGGGGSGGGGSQVQLVQSGAEVKKPGASVKVSCKASGFN<br>IKDYYMHWVRQAPGQRLEWMGWIDLENANTIYDAKFQGRVTITR<br>DTSASTAYMELSSLRSEDTAVYYCARDAYGRYFYDVWGQGTLVT<br>VSSHHHHHHHHHH (SEQ ID NO: 307) |
| tAb0033 | CD19:CD3:<br>HSA | QVQLQESGPGLVKPSQTLSLTCTVSGGSISTSGMGVGWIRQHPGK<br>GLEWIGHIWWDDDKRYNPALKSRVTISVDTSKNQFSLKLSSVTAA<br>DTAVYYCARMELWSYYFDYWGQGTLVTVSSGGGGSGGGGSGGG<br>GSEIVLTQSPATLSLSPGERATLSCSASSSVSYMHWYQQKPGQAPR<br>LLIYDTSKLASGIPARFSGSGSGTDFTLTISSLEPEDFAVYYCFQGSV<br>YPFTFGQGTKLEIKRGGGGSGGGGSDIVMTQSPDSLAVSLGERATIN<br>CKSSQSLLNARTGKNYLAWYQQKPGQPPKLLIYWASTRESGVPD<br>RFSGSGSGTDFTLTISSLQAEDVAVYYCKQSYSRRTFGGGTKVEIK<br>GGGGSGGGGSGGGGSGGGGSQVQLVQSGAEVKKPGASVKVSCK<br>ASGFNIKDYYMHWVRQAPGQRLEWMGWIDLENANTIYDAKFQG<br>RVTITRDTSASTAYMELSSLRSEDTAVYYCARDAYGRYFYDVWG<br>QGTLVTVSSGGGGSGGGSEVQLVESGGGLVQPGNSLRLSCAASGF<br>TFSSFGMSWVRQAPGKGLEWVSSISGSGSDTLYADSVKGRFTISRD<br>NAKTTLYLQMNSLRPEDTAVYYCTIGGSLSRSSQGTLVTVSSHHH<br>HHHHHHH (SEQ ID NO: 308) |
| tAb0034 | CD19:HSA:<br>CD3 | QVQLQESGPGLVKPSQTLSLTCTVSGGSISTSGMGVGWIRQHPGK<br>GLEWIGHIWWDDDKRYNPALKSRVTISVDTSKNQFSLKLSSVTAA<br>DTAVYYCARMELWSYYFDYWGQGTLVTVSSGGGGSGGGGSGGG<br>GSEIVLTQSPATLSLSPGERATLSCSASSSVSYMHWYQQKPGQAPR<br>LLIYDTSKLASGIPARFSGSGSGTDFTLTISSLEPEDFAVYYCFQGSV<br>YPFTFGQGTKLEIKRGGGGSGGGSEVQLVESGGGLVQPGNSLRLS<br>CAASGFTFSSFGMSWVRQAPGKGLEWVSSISGSGSDTLYADSVKG<br>RFTISRDNAKTTLYLQMNSLRPEDTAVYYCTIGGSLSRSSQGTLVT<br>VSSGGGGSGGGGSDIVMTQSPDSLAVSLGERATINCKSSQSLLNART<br>GKNYLAWYQQKPGQPPKLLIYWASTRESGVPDRFSGSGSGTDFTL<br>TISSLQAEDVAVYYCKQSYSRRTFGGGTKVEIKGGGGSGGGGSGG<br>GGSGGGGSQVQLVQSGAEVKKPGASVKVSCKASGFNIKDYYMH<br>WVRQAPGQRLEWMGWIDLENANTIYDAKFQGRVTITRDTSASTA<br>YMELSSLRSEDTAVYYCARDAYGRYFYDVWGQGTLVTVSSHHH<br>HHHHHHH (SEQ ID NO: 309) |
| tAb0035 | CD3:CD19:<br>HSA | DIVMTQSPDSLAVSLGERATINCKSSQSLLNARTGKNYLAWYQQK<br>PGQPPKLLIYWASTRESGVPDRFSGSGSGTDFTLTISSLQAEDVAV<br>YYCKQSYSRRTFGGGTKVEIKGGGGSGGGGSGGGGSGGGGSQVQ<br>LVQSGAEVKKPGASVKVSCKASGFNIKDYYMHWVRQAPGQRLE<br>WMGWIDLENANTIYDAKFQGRVTITRDTSASTAYMELSSLRSEDT<br>AVYYCARDAYGRYFYDVWGQGTLVTVSSGGGGSGGGSQVQLQE<br>SGPGLVKPSQTLSLTCTVSGGSISTSGMGVGWIRQHPGKGLEWIGH<br>IWWDDDKRYNPALKSRVTISVDTSKNQFSLKLSSVTAADTAVYYC<br>ARMELWSYYFDYWGQGTLVTVSSGGGGSGGGGSGGGGSEIVLTQ<br>SPATLSLSPGERATLSCSASSSVSYMHWYQQKPGQAPRLLIYDTSK<br>LASGIPARFSGSGSGTDFTLTISSLEPEDFAVYYCFQGSVYPFTFGQ<br>GTKLEIKRGGGGSGGGSEVQLVESGGGLVQPGNSLRLSCAASGFT<br>FSSFGMSWVRQAPGKGLEWVSSISGSGSDTLYADSVKGRFTISRD<br>NAKTTLYLQMNSLRPEDTAVYYCTIGGSLSRSSQGTLVTVSSHHH<br>HHHHHH (SEQ ID NO: 310) |
| tAb0036 | CD3:HSA:<br>CD19 | DIVMTQSPDSLAVSLGERATINCKSSQSLLNARTGKNYLAWYQQK<br>PGQPPKLLIYWASTRESGVPDRFSGSGSGTDFTLTISSLQAEDVAV<br>YYCKQSYSRRTFGGGTKVEIKGGGGSGGGGSGGGGSGGGGSQVQ<br>LVQSGAEVKKPGASVKVSCKASGFNIKDYYMHWVRQAPGQRLE<br>WMGWIDLENANTIYDAKFQGRVTITRDTSASTAYMELSSLRSEDT<br>AVYYCARDAYGRYFYDVWGQGTLVTVSSGGGGSGGGSEVQLVE<br>SGGGLVQPGNSLRLSCAASGFTFSSFGMSWVRQAPGKGLEWVSSI<br>SGSGSDTLYADSVKGRFTISRDNAKTTLYLQMNSLRPEDTAVYYC<br>TIGGSLSRSSQGTLVTVSSGGGGSGGGSQVQLQESGPGLVKPSQTL<br>SLTCTVSGGSISTSGMGVGWIRQHPGKGLEWIGHIWWDDDKRYN<br>PALKSRVTISVDTSKNQFSLKLSSVTAADTAVYYCARMELWSYYF<br>DYWGQGTLVTVSSGGGGSGGGGSGGGGSEIVLTQSPATLSLSPGE<br>RATLSCSASSSVSYMHWYQQKPGQAPRLLIYDTSKLASGIPARFSG<br>SGSGTDFTLTISSLEPEDFAVYYCFQGSVYPFTFGQGTKLEIKRHHH<br>HHHHHHH (SEQ ID NO: 311) |

TABLE 13-continued

Exemplary Multi-specific Binding Proteins

| Construct | Format | Amino Acid Sequence |
|---|---|---|
| tAb0037 | HSA:CD3:<br>CD19 | EVQLVESGGGLVQPGNSLRLSCAASGFTFSSFGMSWVRQAPGKGL<br>EWVSSISGSGSDTLYADSVKGRFTISRDNAKTTLYLQMNSLRPEDT<br>AVYYCTIGGSLSRSSQGTLVTVSSGGGGSGGGSDIVMTQSPDSLAV<br>SLGERATINCKSSQSLLNARTGKNYLAWYQQKPGQPPKLLIYWAS<br>TRESGVPDRFSGSGSGTDFTLTISSLQAEDVAVYYCKQSYSRRTFG<br>GGTKVEIKGGGGSGGGGSGGGGSGGGGSQVQLVQSGAEVKKPG<br>ASVKVSCKASGFNIKDYYMHWVRQAPGQRLEWMGWIDLENANT<br>IYDAKFQGRVTITRDTSASTAYMELSSLRSEDTAVYYCARDAYGR<br>YFYDVWGQGTLVTVSSGGGGSGGGGSQVQLQESGPGLVKPSQTLS<br>LTCTVSGGSISTSGMGVGWIRQHPGKGLEWIGHIWWDDDKRYNP<br>ALKSRVTISVDTSKNQFSLKLSSVTAADTAVYYCARMELWSYYFD<br>YWGQGTLVTVSSGGGGSGGGGSGGGGSEIVLTQSPATLSLSPGER<br>ATLSCSASSSVSYMHWYQQKPGQAPRLLIYDTSKLASGIPARFSGS<br>GSGTDFTLTISSLEPEDFAVYYCFQGSVYPFTFGQGTKLEIKRHHH<br>HHHHHHH (SEQ ID NO: 312) |
| tAb0038 | HSA:CD19:<br>CD3 | EVQLVESGGGLVQPGNSLRLSCAASGFTFSSFGMSWVRQAPGKGL<br>EWVSSISGSGSDTLYADSVKGRFTISRDNAKTTLYLQMNSLRPEDT<br>AVYYCTIGGSLSRSSQGTLVTVSSGGGGSGGGSQVQLQESGPGLV<br>KPSQTLSLTCTVSGGSISTSGMGVGWIRQHPGKGLEWIGHIWWDD<br>DKRYNPALKSRVTISVDTSKNQFSLKLSSVTAADTAVYYCARMEL<br>WSYYFDYWGQGTLVTVSSGGGGSGGGGSGGGGSEIVLTQSPATL<br>SLSPGERATLSCSASSSVSYMHWYQQKPGQAPRLLIYDTSKLASGI<br>PARFSGSGSGTDFTLTISSLEPEDFAVYYCFQGSVYPFTFGQGTKLE<br>IKRGGGGSGGGSDIVMTQSPDSLAVSLGERATINCKSSQSLLNART<br>GKNYLAWYQQKPGQPPKLLIYWASTRESGVPDRFSGSGSGTDFTL<br>TISSLQAEDVAVYYCKQSYSRRTFGGGTKVEIKGGGGSGGGGSGG<br>GGSGGGGSQVQLVQSGAEVKKPGASVKVSCKASGFNIKDYYMH<br>WVRQAPGQRLEWMGWIDLENANTIYDAKFQGRVTITRDTSASTA<br>YMELSSLRSEDTAVYYCARDAYGRYFYDVWGQGTLVTVSSHHH<br>HHHHHHH (SEQ ID NO: 313) |
| tAb0042 | CD3:HSA:<br>CD19 | EVQLVESGGGLVQPGGSLKLSCAASGFTFNKYAINWVRQAPGKG<br>LEWVARIRSKYNNYATYYADQVKDRFTISRDDSKNTAYLQMNNL<br>KTEDTAVYYCVRHANFGNSYISYWAYWGQGTLVTVSSGGGGSG<br>GGGSGGGGSQTVVTQEPSLTVSPGGTVTLTCASSTGAVTSGNYPN<br>WVQQKPGQAPRGLIGGTKFLVPGTPARFSGSLLGGKAALTLSGVQ<br>PEDEAEYYCTLWYSNRWVFGGGTKLTVLGGGGSGGGSEVQLVES<br>GGGLVQPGNSLRLSCAASGFTFSSFGMSWVRQAPGKGLEWVSSIS<br>GSGSDTLYADSVKGRFTISRDNAKTTLYLQMNSLRPEDTAVYYCT<br>IGGSLSRSSQGTLVTVSSGGGGSGGGSQVQLQESGPGLVKPSQTLS<br>LTCTVSGGSISTSGMGVGWIRQHPGKGLEWIGHIWWDDDKRYNP<br>ALKSRVTISVDTSKNQFSLKLSSVTAADTAVYYCARMELWSYYFD<br>YWGQGTLVTVSSGGGGSGGGGSGGGGSEIVLTQSPATLSLSPGER<br>ATLSCSASSSVSYMHWYQQKPGQAPRLLIYDTSKLASGIPARFSGS<br>GSGTDFTLTISSLEPEDFAVYYCFQGSVYPFTFGQGTKLEIKRHHH<br>HHHHHHH (SEQ ID NO: 314) |

The cultures were harvested by centrifugation at 4000 rpm, and the supernatant filtered through a 0.22 mm filter. The multi-specific binding proteins, which carried a 10×His tag at the C-terminus, were purified in two steps. The first step was Nickel affinity chromatography with elution using PBS containing 400 mM imidazole. The second step was size exclusion chromatography with elution in PBS (phosphate buffered saline) pH7.2. Multi-specific binding protein concentrations were determined by UV spectroscopy, and the protein samples were concentrated when necessary. The purity of the proteins was determined by sodium dodecyl sulphate polyacrylamide gel electrophoresis (SDS-PAGE) and high performance liquid chromatography (HPLC). Specifically, HPLC was performed on an Agilent 1100 series instrument using MabPac size exclusion column run in PBS at 0.2 mL/min. The fractions with an elution time of about 225-240 minutes were collected for further characterization.

As noted above, some of the constructs produced contained an anti-CD19 scFv having the amino acid sequence set forth in SEQ ID NO: 9 or 18. The binding affinity of the two CD19 binding domains to CD19 were measured by SPR using a monomeric CD19 extracellular domain and a dimeric CD19 extracellular domain fused with human IgG1 Fc. Binding kinetic parameters were measured using a ForteBio instrument generally as previously described (see, Estep et al. (2013) MAbs, 5(2): 270-78). When measured with the monomeric CD19 protein, the $K_D$ value of the CD19 binding domain having the sequence of SEQ ID NO: 9 was 7 nM, and the $K_D$ value of the CD19 binding domain having the sequence of SEQ ID NO: 18 was 11 nM. When measured with the dimeric CD19 protein, the $K_D$ value of the CD19 binding domain having the sequence of SEQ ID NO: 9 was 5 nM, and the $K_D$ value of the CD19 binding domain having the sequence of SEQ ID NO: 18 was 15 nM.

Some of the multi-specific binding proteins contained an anti-CD3 scFv derived from CNG-CD3-1, CNG-CD3-2, or CNG-CD3-3, having the amino acid sequences of SEQ ID NOs: 422, 427, or 433 in Table 4, respectively. The binding affinities of these scFv constructs to human CD3 were measured by SPR using the BiaCore method described in International Patent Application Publication No. WO2018208864A1. The CNG-CD3-1 scFv construct bound human CD3 with a $K_D$ value of 1.9 nM; the CNG-CD3-2 scFv construct bound human CD3 with a $K_D$ value of 16 nM;

and the CNG-CD3-3 scFv construct bound human CD3 with a $K_D$ value of 26 nM. The binding affinities of these scFv constructs to human CD3 were measured by BLI using the Octec method described in International Patent Application Publication No. WO2018208864A1. The CNG-CD3-1 scFv construct bound human CD3 with a $K_D$ value of 4.4 nM; the CNG-CD3-2 scFv construct bound human CD3 with a $K_D$ value of 27 nM; and the CNG-CD3-3 scFv construct bound human CD3 with a $K_D$ value of 54 nM.

Example 4. Multi-Specific Binding Proteins Induce T Cell Cytotoxicity Against CD19⁺ Target Cells This example describes the cytotoxic activity of multi-specific binding proteins.

The T cell redirection activity of multi-specific binding proteins and BiTE proteins were evaluated using the KILR Raji Cell Model. Briefly, pan T cells were isolated from primary human PBMCs from a single healthy donor by negative selection using a commercial kit (e.g. Easy Sep Human T Cell Enrichment Kit, StemCell Technologies). T cells were maintained in RPMI 1640 medium supplemented with 10% serum and 300 IU/mL IL-2 to expand T cells. The harvested T cells were washed twice to remove any serum.

KILR Raji cells, which expressed CD19 on the surface, were used as target cells. To opsonize the target cells, each multi-specific binding protein or BiTE (see Table 13) was incubated with the target cells for 30 minutes at 37° C. in RPMI 1640 medium supplemented with 5% heat inactivated low IgG fetal bovine serum and penicillin-streptomycin-glutamine. The proteins were added in serial dilution at 10 different doses, with each dose run in duplicate. Human serum albumin was added to the medium of certain samples at a final concentration of 15 mg/mL. Selective proteins were also evaluated with KILR SKOV3 cells, which were CD19-negative, as negative controls.

After opsonization, the target cells were incubated with the pan T cells at an effector-to-target (E:T) ratio of 10:1 for 6 hours at 37° C. Killing of the KILR Raji cells resulted in release of a labeled housekeeping protein from these cells into the medium, which was quantified by addition of a KILR detection reagent (DiscoverX). The luminescence signals from all wells were read on an Envision plate reader. Spontaneous release and total lysis controls were included on each plate to allow calculation of percent killing.

Percent killing was calculated from the luminescence signal values using the following formula:

% killing=(value from test protein sample−mean value from spontaneous release control)/(mean value from total lysis control−mean value from spontaneous release control)×100.

The EC50 values were calculated from the percent killing by fitting with a dose-response curve using the GraphPad Prism software.

Table 14 lists the EC50 values of T cell-redirected killing in the absence and presence of human serum albumin for exemplary multi-specific binding proteins and comparator anti-CD19 BiTE protein. No substantial killing was observed with the CD19-negative KILR SKOV3 cells.

TABLE 14

Cytotoxic Activity of Multi-specific Binding Proteins

| | | EC50 (pg/mL) | | |
|---|---|---|---|---|
| Construct | Format | −HSA | +HSA | Fold change |
| tAb0027 | CD19:CD3:HSA | 2.33 | 67.9 | 29.1 |
| tAb0029 | CD3:CD19:HSA | 5.48 | 188.1 | 34.3 |
| tAb0030 | CD3:HSA:CD19 | 3.17 | 141.7 | 44.7 |
| tAb0031 | HSA:CD3:CD19 | 6.55 | 189.3 | 28.9 |
| tAb0032 | HSA:CD19:CD3 | 5.71 | 88.4 | 15.5 |
| tAb0033 | CD19:CD3:HSA | 20.4 | 1294 | 63.4 |
| tAb0034 | CD19:HSA:CD3 | 59.3 | 2376 | 40.1 |
| tAb0035 | CD3:CD19:HSA | 51.4 | 2184 | 42.5 |
| tAb0036 | CD3:HSA:CD19 | 103.8 | 4195 | 40.4 |
| tAb0037 | HSA:CD3:CD19 | 175.1 | 2151 | 12.3 |
| tAb0038 | HSA:CD19:CD3 | 52.6 | 288 | 5.5 |
| tAb0042 | CD3:HSA:CD19 | 69.9 | 13290 | 190.1 |
| blinatumomab | CD19:CD3 | 2854 | 10750 | 3.8 |

As shown in Table 14, the multi-specific binding proteins containing the anti-CD19 scFv having the amino acid sequence of SEQ ID NO: 9 showed stronger cytotoxic activity than those containing the anti-CD19 scFv having the amino acid sequence of SEQ ID NO: 18, regardless of the construct format, CD3 binding domain, HSA binding domain, and the presence or absence of HSA in the assay medium. From this data, it is contemplated that constructs containing this anti-CD19 scFv with the higher binding affinity to CD19 will demonstrate stronger therapeutic activity than constructs containing the other anti-CD19 scFv with the lower binding affinity.

Furthermore, all the multi-specific binding proteins tested showed lower $EC_{50}$ value (namely, stronger ability to induce cytotoxicity) in the absence of HSA than in the presence of HSA. Without wishing to be bound by theory, it appears that the presence of HSA causes a change in the protein complex, which was specific to the multi-specific binding proteins containing an HSA binding domain, rather than a nonspecific effect as observed with blinatumomab. The ratio of the $EC_{50}$ value in the presence of HSA to the $EC_{50}$ value in the absence of HSA, also called "fold change" herein, was used to assess the effect of HSA on the potential therapeutic activity of the multi-specific binding protein. As shown in Table 14, the construct formats with the HSA binding domain N-terminal to both the CD19 binding domain and the CD3 binding domain (namely, tAb0031, tAb0032, tAb0037, and tAb0038) showed lower fold changes than the other construct formats, regardless of which CD19 binding domain was used in the construct.

Furthermore, among the constructs having the same CD19 binding domain, CD3 binding domain, and HSA binding domain, the constructs in the CD19:CD3:HSA format (i.e., the CD19 binding domain positioned N-terminal to the CD3 binding domain, and the CD3 binding domain positioned N-terminal to the HSA binding domain), namely, tAb0027 and tAb0033, showed the lowest or second lowest $EC_{50}$ values both in the absence and in the presence of HSA.

Example 5. Cytotoxicity of Multi-Specific Binding Proteins Against CD19⁺ Target Cells This example provides alternative methods for determining the cytotoxic activity of a multi-specific binding protein.

The multi-specific binding proteins disclosed herein can be evaluated in in vitro assays on their mediation of T cell dependent cytotoxicity to B cell antigen positive target cells.

For example, the CD19-binding multi-specific binding protein disclosed herein was evaluated in vitro for mediation of T cell dependent cytotoxicity to CD19+ target cells using the Killing Immune-Lysis Reaction (KILR) assay (euroFins, DiscoverX).

Briefly, multi-specific binding proteins tAb0050 through tAb0064, as described in Table 8, were produced. Raji cells were engineered to express the KILR reporter protein to produce KILR-Raji cells. Cytotoxicity of KILR-Raji cells triggers KILR protein release into medium, which can be quantified by the addition of KILR Detection Reagent. Cryopreserved peripheral blood mononuclear cells (PBMCs) from a single healthy donor were rested for at least 24 h in complete growth medium supplemented with 1× L-glutamine prior to assay. Pan T cells were isolated by negative selection. To evaluate redirected lysis by the multi-specific binding proteins, each multi-specific binding protein was added to KILR-Raji cells at the indicated concentration in duplicate and incubated for 30 min at 37° C. in RPMI-1640+4% heat inactivated very low IgG FBS, 1×PSG, in the presence of 15 mg/ml HSA. Pan T cells were then added at an E:T ratio of 10:1 for 6 h at 37° C. Cytotoxicity was quantified via addition of the KILR Detection Reagent and read on an Envision plate reader. Four-parameter logistic regression was used to calculate the EC50 for each parameter.

Figure 2A:
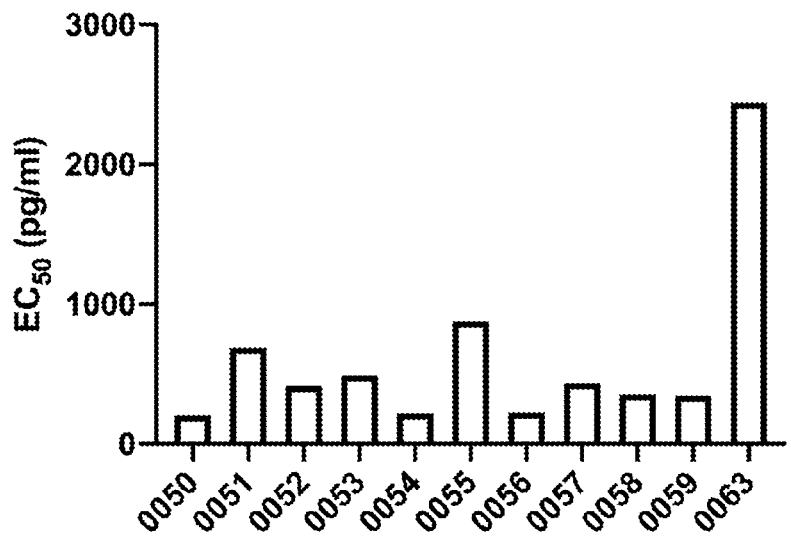
FIGS. 2A-2B are bar graphs showing the $EC_{50}$ values of the indicated multi-specific binding proteins for inducing cytotoxicity of T cells against KILR-Raji cells.
Figure 2B:
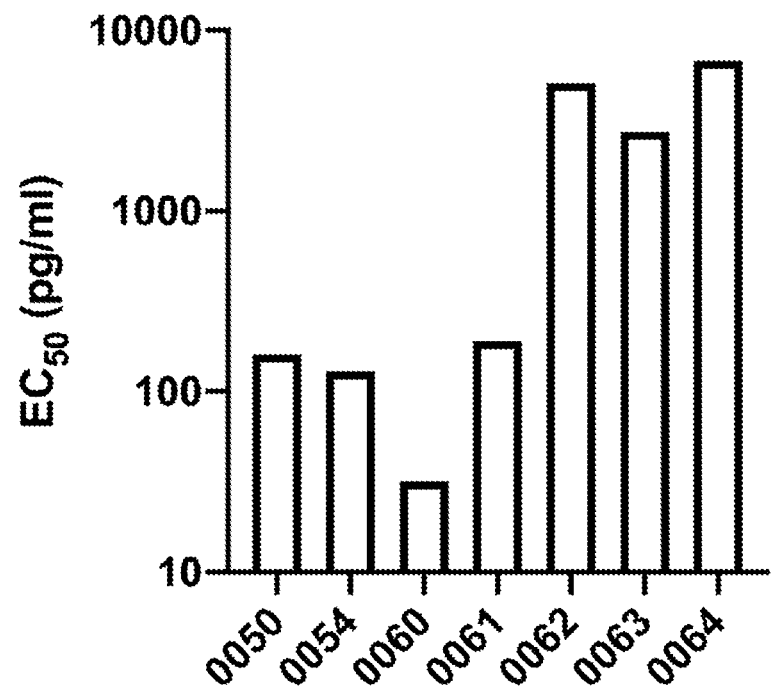

The multi-specific binding proteins in FIG. 2A, except for tAb0063, had a CD3 binder derived from CNG-CD3-1, which bound human CD3 with a $K_D$ of 1.9 nM as measured by SPR. The tAb0063 construct had a CD3 binder derived from CNG-CD3-3, which bound human CD3 with a $K_D$ of 26 nM as measured by SPR. The multi-specific binding proteins containing CNG-CD3-1 scFv showed lower $EC_{50}$ values for mediating T cell cytotoxicity (i.e., stronger activities) than tAb0063. Similarly, in FIG. 2B, tAb0050, tAb0054, and tAb0060 had a CD3 binder derived from CNG-CD3-1, which bound human CD3 with a $K_D$ of 1.9 nM; tAb0061 and tAb0062 had a CD3 binder derived from CNG-CD3-2, which bound human CD3 with a $K_D$ of 16 nM; tAb0063 and tAb0064 had a CD3 binder derived from CNG-CD3-3, which bound human CD3 with a $K_D$ of 26 nM, each measured by SPR. The multi-specific binding proteins containing the relatively higher-affinity CD3 binders showed lower $EC_{50}$ values for mediating T cell cytotoxicity (i.e., stronger activities) than those containing the relatively lower-affinity CD3 binders. The impact of the CD3 binding affinity of the CD3 binder on the target cell killing activity of the multi-specific binding protein was observed irrespective of the relative positioning between the CD19 binder, the CD3 binder, and the HSA binder.

FIG. 2A further shows that between the constructs that had the same CD19 binder, CD3 binder, and HSA binder, lower $EC_{50}$ values for effecting T cell cytotoxicity were observed in the multi-specific binding proteins having, from the N-terminus to the C-terminus, the HSA binder, the CD19 binder, and the CD3 binder (tAb0050 and tAb0056) or, from the N-terminus to the C-terminus, the CD19 binder, the CD3 binder, and the HSA binder (tAb0054, tAb0059).

Alternatively, the CD19-binding multi-specific binding protein disclosed herein can be evaluated in in vitro assays on its mediation of T cell dependent cytotoxicity to CD19+ target cells. Fluorescence labeled CD19+ MEC-1 cells (a CD19+ human chronic B cell leukemia cell line) are incubated with isolated PBMC of random donors or CB15 T-cells (standardized T-cell line) as effector cells in the presence of the CD19-binding multi-specific binding protein. After incubation for 4 hours at 37° C. in a humidified incubator, the release of the fluorescent dye from the target cells into the supernatant is determined in a spectrofluorimeter. Target cells incubated without the CD19-binding multi-specific binding protein and target cells totally lysed by the addition of saponin at the end of the incubation serve as negative and positive controls, respectively. Based on the measured remaining living target cells, the percentage of specific cell lysis can be calculated according to the following formula: $[1-($number of living targets$_{(sample)}$/number of living targets$_{(spontaneous)})]\times 100\%$. Sigmoidal dose response curves and $EC_{50}$ values are calculated by non-linear regression/4-parameter logistic fit using the GraphPad Software. The lysis values obtained for a given multi-specific binding protein concentration are used to calculate sigmoidal dose-response curves by 4 parameter logistic fit analysis using the Prism software. It is expected that the target cell lysis rate induced by CD19-binding multi-specific binding protein is higher than the target cell lysis rate induced by similar constructs lacking either a CD19-binding domain or a CD3-binding domain.

Alternatively, a human T-cell dependent cellular cytotoxicity (TDCC) assay is used to measure the ability of the multi-specific binding protein to direct T cells to kill tumor cells (Nazarian et al. 2015, *J. Biomol. Screen,* 20:519-27). In this assay, T cells and target cancer cell line cells are mixed together at a 10:1 ratio in a 384 wells plate, and varying amounts of the multi-specific binding proteins are added. After 48 hours, the T cells are washed away leaving attached to the plate target cells that were not killed by the T cells. To quantitate the remaining viable cells, CellTiter-Glo® Luminescent Cell Viability Assay (Promega) is used. It is contemplated that the killing rate of B-cell antigen expressing cancer cell induced by CD19-binding multi-specific binding protein will be higher than that induced by similar constructs lacking either a CD19-binding domain or a CD3-binding domain and/or other negative control molecules.

Example 6. Pharmacokinetics of Multi-Specific Binding Proteins with HSA Binding Domain This example is designed to determine the pharmacokinetics of multi-specific binding proteins.

Multi-specific binding proteins containing a domain that binds CD19, a domain that binds CD3, and a domain that binds serum albumin are tested in the cynomolgus monkey in the context of pharmacokinetic (PK) studies to evaluate the serum elimination time of the multi-specific binding protein.

The multi-specific binding proteins are administered as intravenous bolus or intravenous infusion. The multi-specific binding proteins are administered in a dose-linear, pharmacokinetic relevant range of 0.5 μg/kg to 3 μg/kg, 6 μg/kg, 12 μg/kg, and 15 μg/kg, respectively. For purposes of comparability, the serum concentrations of the multi-specific binding proteins are does-normalized and molecular weight-normalized (described in nmol).

For each multi-specific binding protein, a group of at least two to three animals are used. Blood samples are collected and serum is prepared for determination of serum concentrations of the multi-specific binding proteins. Serum multi-specific binding protein levels are measured using an immunoassay. The assay is performed by capturing the multi-specific binding protein via its CD19-binding domain, while an antibody directed against the CD3-binding domain of the multi-specific binding protein is used for detection. The serum concentration-time profiles are used to determine PK parameters using known analytical methods such as those described in Ritschel W A and Kearns G L, 1999, IN: *Handbook Of Basic Pharmacokinetics Including Clinical Applications,* 5th edition, American Pharmaceutical Assoc., Washington, D.C. and softwares such as WinNonlin software (WinNonlin® Professional V. 3.1 WinNonlin™ Copyright 1998-1999. Pharsight Corporation. Mountain View, Calif.).

Alternatively, the serum half-life of the various multi-specific binding proteins containing the serum albumin binding domain is compared to that of control constructs capable of binding CD19 and CD3 but lacking a serum albumin binding domain by including in the experiment another cynomolgus monkey group that receives the control constructs. Additional domains can be included such that the control constructs are similar in size to the multi-specific binding proteins.

It is expected that CD19-binding multi-specific binding protein will have significantly longer serum half-life compared to similar constructs capable of binding CD19 and CD3 but lacking a serum albumin binding domain and/or other negative control molecules.

Example 7. Determination of Antigen Affinity by Flow Cytometry

This example is designed to determine the affinity of a multi-specific binding protein to an antigen.

Various multi-specific binding proteins disclosed herein are tested for their binding affinities to human $CD3^+$ cells and the corresponding B cell surface antigen positive cells, such as human $CD19^+$ cells. The multi-specific binding proteins are also tested for their binding affinities to cynomolgus $CD3^+$ cells and the corresponding B cell surface antigen positive cells, such as cynomolgus $CD19^+$ cells.

$CD3^+$ and $CD19^+$ cells are incubated with 100 µL of serial dilutions of the multi-specific binding protein. After washing three times with FACS buffer the cells are incubated with 0.1 mL of 10 µg/mL mouse monoclonal anti-idiotype antibody in the same buffer for 45 mins on ice. After a second washing cycle, the cells are incubated with 0.1 mL of 15 µg/mL FITC-conjugated goat anti-mouse IgG antibodies under the same conditions as before. As a control, cells are incubated with the anti-His IgG followed by the FITC-conjugated goat anti-mouse IgG antibodies without the multi-specific binding protein. The cells are then washed again and resuspended in 0.2 mL of FACS buffer containing 2 µg/mL propidium iodide (PI) in order to exclude dead cells. The fluorescence of $1 \times 10^4$ living cells is measured using a commercially available flow cytometer and software. Mean fluorescence intensities of the cell samples are calculated using software such as CXP software (Beckman-Coulter, Krefeld, Germany) or Incyte software (Merck Millipore, Schwalbach, Germany). $K_D$ values for one-site binding can be calculated using normalized fluorescence intensity values with known computational equations such as those supplied in the GraphPad Prism software (GraphPad Software, La Jolla Calif. USA). CD3 binding affinity and cross-reactivity are evaluated in titration and flow cytometric experiments on $CD3^+$ Jurkat cells and the cynomolgus $CD3^+$ HSC-F cell line. CD19 binding and cross-reactivity are assessed on the human $CD19^+$ tumor cell lines. The $K_D$ ratio of cross-reactivity can be calculated using the $K_D$ values determined on the CHO cell lines expressing either recombinant human or recombinant cynomolgus antigens.

Example 8. Cytokine Production Induced by Multi-Specific Binding Proteins

This example is designed to determine the ability of a multi-specific binding protein to induce cytokine production from immune cells.

AlphaLISA assays (Perkin Elmer) for TNFα and Interferon γ are used to obtain evidence that T cells are activated by the multi-specific binding proteins of current invention, such as CD19-binding multi-specific binding protein, in the presence of target cells, such as $CD19^+$ B cells. For this assay, primary human T cells and human tumor cells expressing B cell surface antigen are incubated in the presence of the CD19-binding multi-specific binding protein as described under cytotoxicity assays. After 48 hours of incubation, 2 microliter aliquots of the assay supernatants are analyzed according to the manufacturer's instructions. It is contemplated that the TNFα or Interferon γ level induced by CD19-binding multi-specific binding protein is higher than that induced by similar constructs lacking either a CD19-binding domain or a CD3-binding domain and/or other negative control molecules.

Example 9. Antibody Analytics in In Vitro Cytotoxicity and Cytokine Release Studies This example is designed to determine the ability of a multi-specific binding protein to enhance cytotoxicity of T cells and to induce cytokine production from said T cells.

$CD3^+$ T cells purified from a single cryopreserved PBMC donor were incubated with eFluor670-labeled Raji cells at an E:T ratio of 5:1 in the presence of test articles and 15 mg/ml HSA for 48 h at 37° C. Following incubation, cells were pelleted and labeled with Live/Dead fixable stain, while the supernatant was stored for cytokine analysis. Cells were fixed and assessed by flow cytometry. Percentage of live Raji cells was determined by calculating the fraction of eFluor670+ cells that did not label with Live/Dead stain. Concentrations of the cytokines IL-2, IFNγ, and TNFα in the supernatant were evaluated using DuoSet ELISAs from R&D Systems. Four-parameter logistic regression was used to calculate the EC50 for each parameter.

Similarly, $CD3^+$ T cells purified from a single cryopreserved PBMC donor were incubated with eFluor670-labeled Raji cells at an E:T ratio of 0.5:1 in the presence of test articles for 6 d at 37° C., with media and test article re-feeding on day 3. Following incubation, cells were pelleted and labeled with Live/Dead fixable stain. Cells were fixed and assessed by flow cytometry. Percentage of live Raji cells was determined by calculating the fraction of eFluor670+ cells that did not label with Live/Dead stain.

Figure 3A:
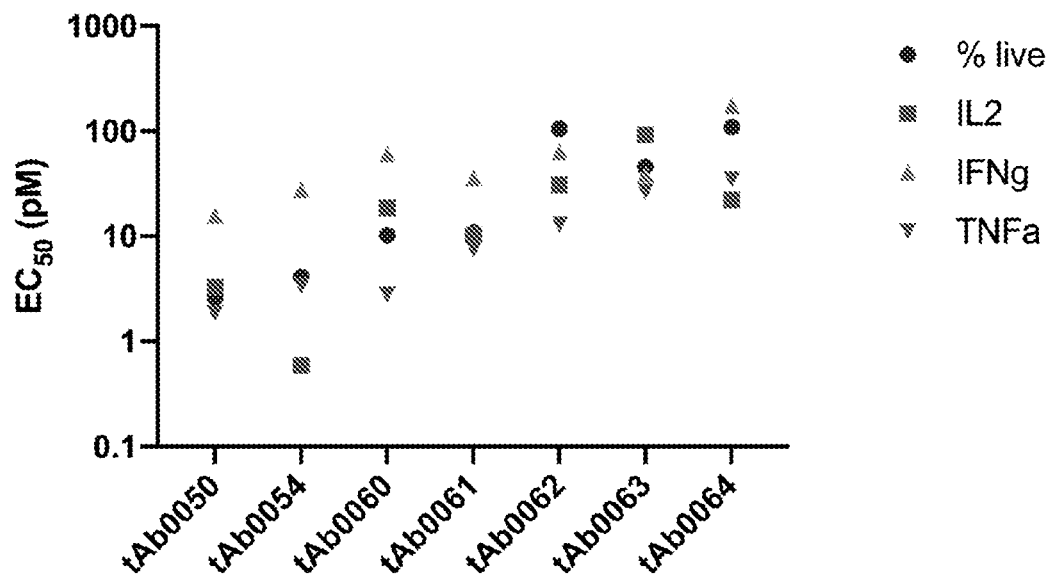
FIG. 3A is a graph showing the $EC_{50}$ values of the indicated multi-specific binding proteins for inducing production of cytokines IL2, IFNγ, and TNFα compared to the $EC_{50}$ values of the same multi-specific binding proteins for inducing cytotoxicity of T cells against Raji cells ("% live") when the numbers of T cells and Raji cells were cultured at a ratio of 5:1.

To assess the efficacy of the multi-specific binding proteins and their safety profiles, the $EC_{50}$ values of the test proteins for mediating T cell cytotoxicity were compared with the $EC_{50}$ values for inducing IL-2, IFNγ, and TNFα production. Potency in mediating T cell cytotoxicity is generally desirable. Production of certain cytokines also facilitates the immune reaction against the CD19-expressing target cells. However, excessive cytokine production could be associated with lower tolerability of the multi-specific binding protein and would be undesirable. As shown in FIG. 3A, a general trend was observed that the multi-specific binding proteins containing the higher-affinity CD3 binder (CNG-CD3-1) showed lower $EC_{50}$ values on all activities than the proteins containing the lower-affinity CD3 binders (CNG-CD3-2 or CNG-CD3-3). The tAb0050, tAb0054, and tAb0060 constructs, which contained a CD3 binder derived from CNG-CD3-1, effected T cell cytotoxicity at $EC_{50}$ values lower than the $EC_{50}$ values for inducing the production of one (in the case of tAb0054) or two (in the cases of tAb0050 and tAb0060) out of the three tested cytokines. The tAb0061, tAb0062, tAb0063, and tAb0064 constructs, which contained CD3 binders derived from CNG-CD3-2 or CNG-CD3-3, effected T cell cytotoxicity at $EC_{50}$ values greater than the $EC_{50}$ values for inducing the production of at least two out of the three tested cytokines. These results suggest that the multi-specific binding proteins containing the higher-affinity CD3 binder (CNG-CD3-1) were generally more potent than the multi-specific binding proteins containing the lower-affinity CD3 binders (CNG-CD3-2 or CNG-CD3-3). Given that their potency in effecting T cell cytotoxicity increased at least proportionally with their ability to induce cytokine production, it is contemplated that these multi-specific binding proteins containing the higher-affinity CD3 binder, relative to the multi-specific binding proteins containing the lower-affinity CD3 binders, could exhibit therapeutic effects at lower doses without eliciting excessive cytokine production.

Figure 3B:
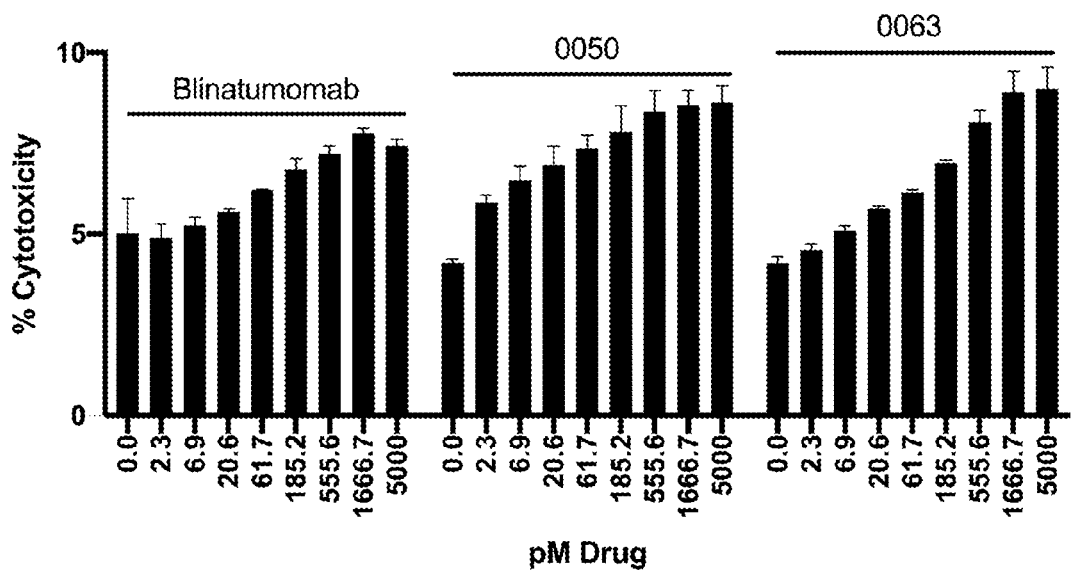
FIG. 3B is a bar graph showing the T cell cytotoxicity percentage mediated by multi-specific binding proteins tAb0050, tAb0063, and control blinatumomab when the numbers of T cells and Raji cells were cultured at a ratio of 0.5:1.
Figure 4A:
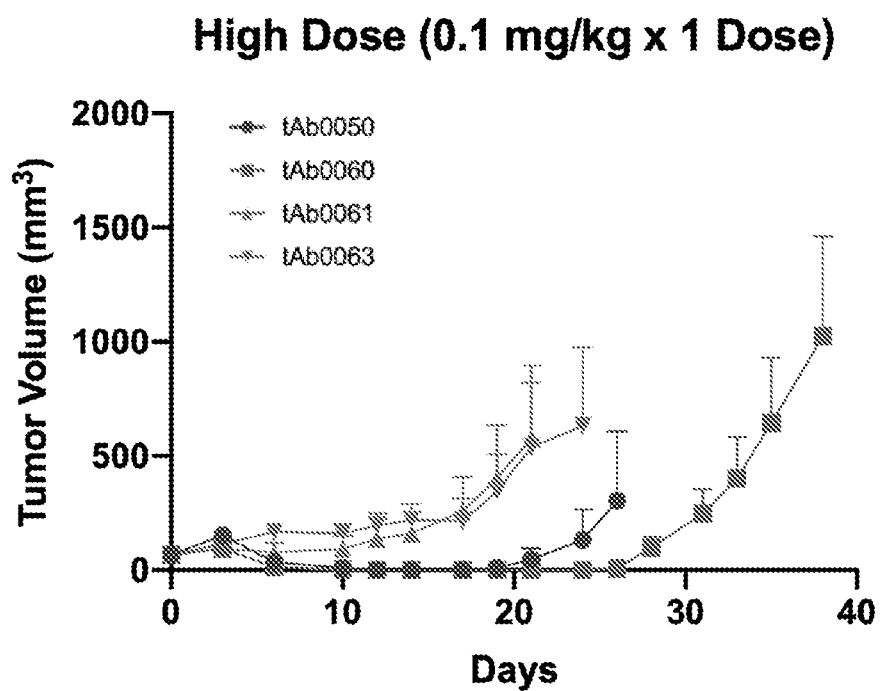
FIGS. 4A-4D depict results of in vivo experiments to assess tumor regression following treatment with multi-specific binding proteins. In one experiment, the mice received high dose treatment (0.1 mg/kg/dose) with test multi-specific binding proteins, and tumor volumes (FIG. 4A) and percent survival (FIG. 4B) were assessed. In another experiment, the mice received low dose treatment (0.01 mg/kg/dose) with test multi-specific binding proteins, and tumor volumes (FIG. 4C) and percent survival (FIG. 4D) were assessed.
Figure 4B:
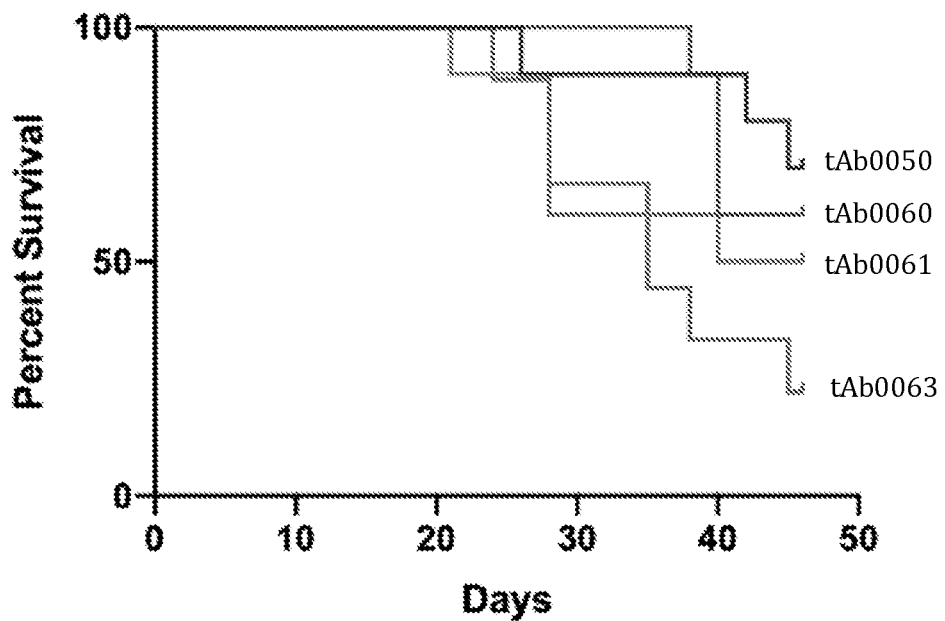
Figure 4C:
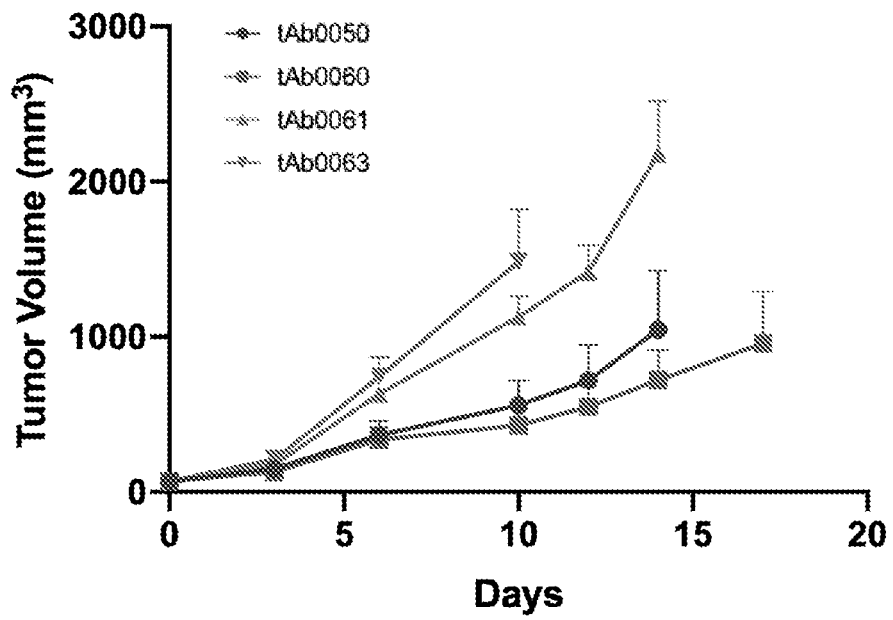
Figure 4D:
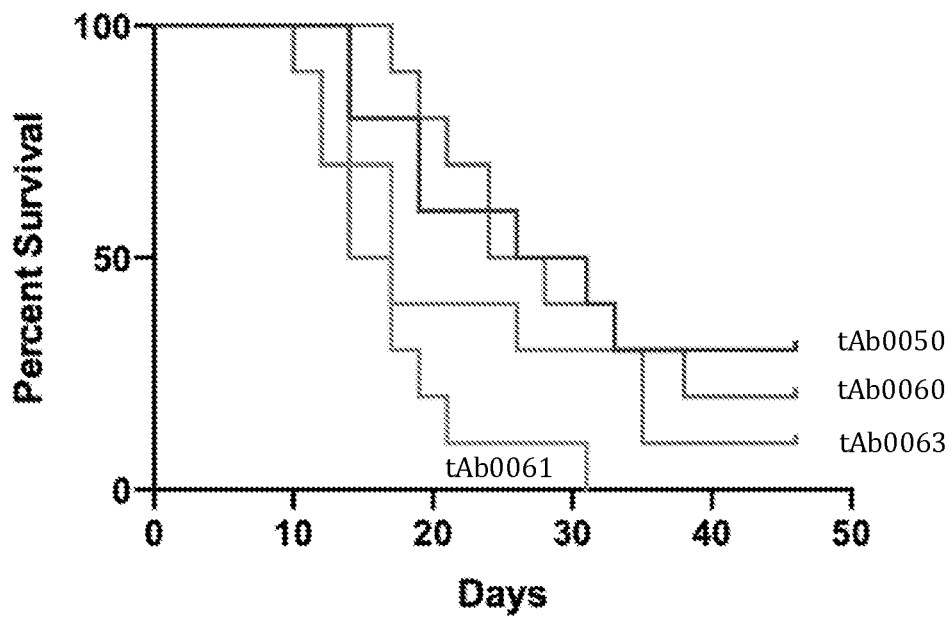
Figure 5A:
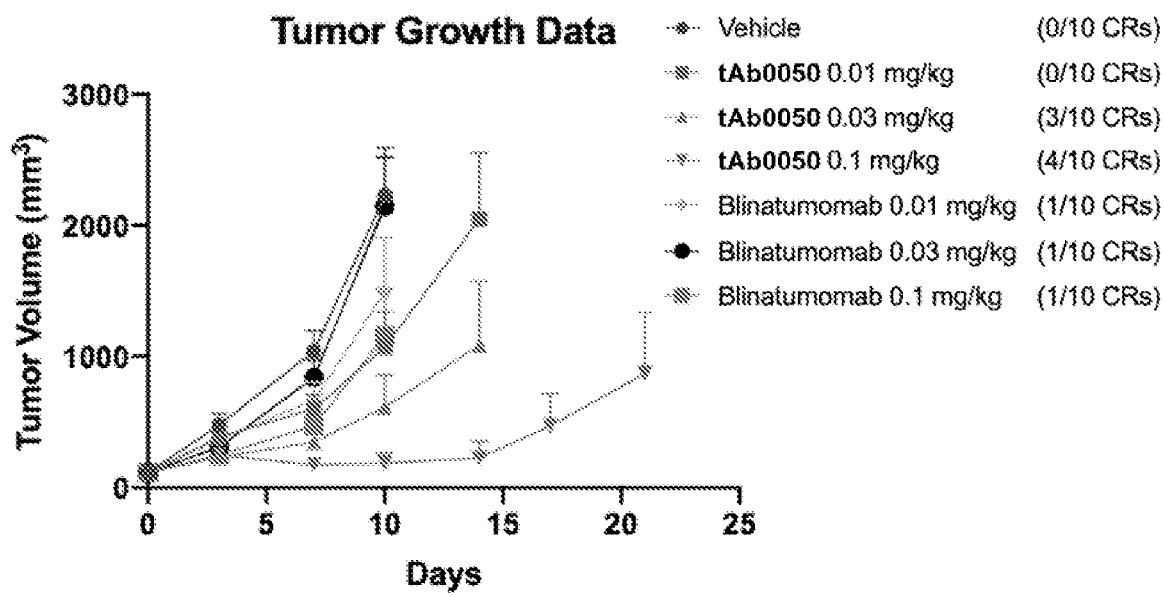
FIGS. 5A-5D depict results of in vivo dose efficacy studies in mice treated with the multi-specific binding protein tAb0050 or blinatumomab. Tumor growth data is shown in FIG. 5A. Percent survival for each treatment is shown for 0.01 mg/kg/dose (FIG. 5B), 0.03 mg/kg/dose (FIG. 5C), and 0.1 mg/kg/dose (FIG. 5D).
Figure 5B:
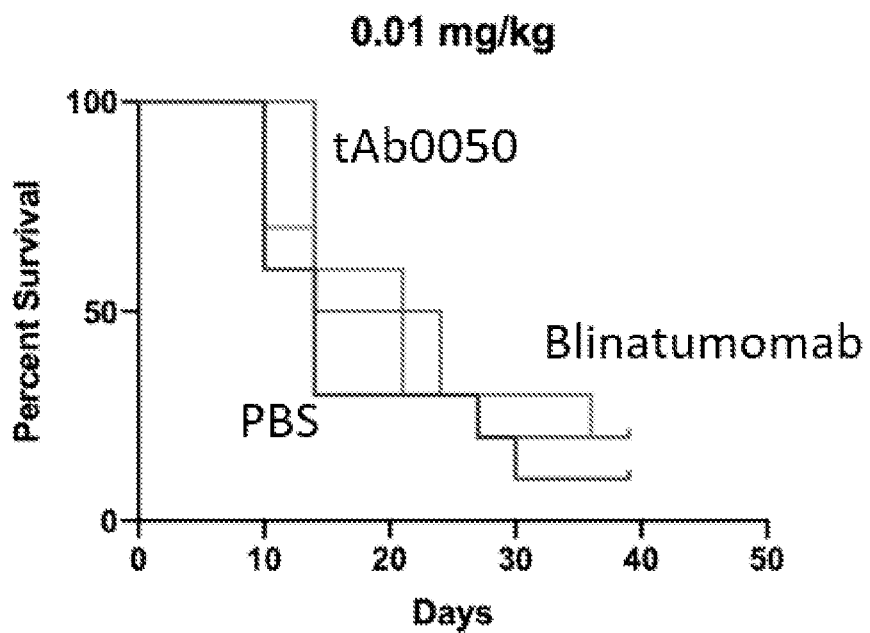
Figure 5C:
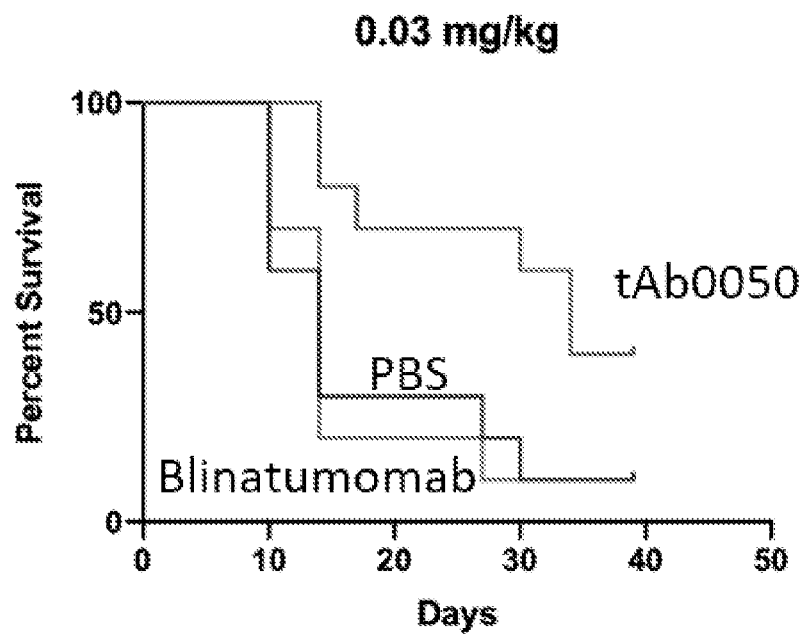
Figure 5D:
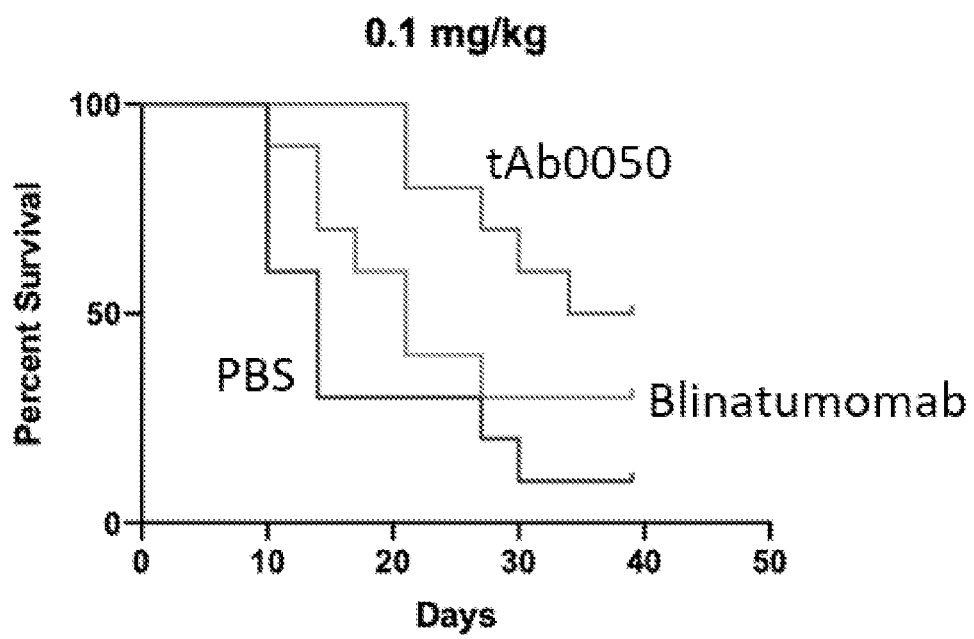

The $EC_{50}$ values for mediating T cell cytotoxicity were also compared between tAb0050, tAb0063, and blinatumomab. As shown in FIG. 3B, tAb0050, which contained a CD3 binder derived from CNG-CD3-1, was more potent in mediating T cell cytotoxicity than tAb0063 and blinatumomab.

Example 10. In Vivo Studies for Efficacy of Multi-Specific Binding Proteins

This example is designed to determine the ability of a multi-specific binding protein to induce tumor regression in vivo in a murine model.

$1 \times 10^6$ HuCELL A20-hCD19 cells in 0.1 ml of PBS were inoculated on the right front flank of CD3ε HuGEMM mice. When mean tumor size reached approximately 68 mm³, mice were randomized. Mice were treated at the indicated dose level intravenously once on the day of randomization. Tumors were subsequently measured 2-3 times per week, and mice were sacrificed if tumor volumes exceeded 3000 mm³. Four-parameter logistic regression was used to calculate the $EC_{50}$ for each parameter.

As shown in FIGS. 4A-4D, at both low dose (0.01 mg/kg, single injection) and high dose (0.1 mg/kg, single injection), treatment with tAb0050 and tAb0060, both containing a CD3 binder derived from CNG-CD3-1 that bound human CD3 with a $K_D$ of 1.6 nM, resulted in similar degree of tumor growth inhibition, and both were more efficacious compared to either tAb0061 or tAb0063, which contained lower-affinity CD3 binders derived from CNG-CD3-2 or CNG-CD3-3. In addition, as shown in Table 15, the complete response rate was higher for both tAb0050 and tAb0060 as compared to tAb0061 or tAb0063. This result indicates that the multi-specific binding proteins containing the higher-affinity CD3 binders were more efficacious in treating CD19-expressing tumors in vivo than the multi-specific binding proteins containing lower-affinity CD3 binders.

TABLE 15

Percentage of mice experiencing complete response in each treatment group.

| Group | % complete response |
|---|---|
| High Dose (0.1 mg/kg × dose) | |
| tAb0050 | 50% |
| tAb0060 | 60% |
| tAb0061 | 30% |
| tAb0063 | 0% |
| Low Dose (0.01 mg/kg × dose) | |
| tAb0050 | 30% |
| tAb0060 | 20% |
| tAb0061 | 0% |
| tAb0063 | 0% |

A similar in vivo study was conducted to compare tAb0050 to blinatumomab at various dose levels. As shown in FIGS. 5A-5D, at both 0.03 mg/kg and 0.1 mg/kg dose levels, the complete response rate was higher for tAb0050 compared to blinatumomab. Taken together, these data demonstrate improved efficacy of tAb0050 in vivo relative to blinatumomab.

INCORPORATION BY REFERENCE

All publications and patents cited throughout the text of this specification (including all patents, patent applications, scientific publications, manufacturer's specifications, instructions, etc.), whether supra or infra, are hereby incorporated by reference in their entirety for all purposes. To the extent the material incorporated by reference contradicts or is inconsistent with this specification, the specification will supersede any such material.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A multi-specific binding protein comprising:
   (a) a first antigen-binding site that binds to human CD19, comprising heavy chain complementarity determining regions (HCDR) and light chain complementarity determining regions (LCDR), wherein HCDR1 comprises the amino acid sequence of SEQ ID NO: 64 or SEQ ID NO: 65, HCDR2 comprises the amino acid sequence of SEQ ID NO: 66, HCDR3 comprises the amino acid sequence of SEQ ID NO: 67 or SEQ ID NO: 68, LCDR1 comprises the amino acid sequence of SEQ ID NO: 69, LCDR2 comprises the amino acid sequence of SEQ ID NO: 70, and LCDR3 comprises the amino acid sequence of SEQ ID NO: 71;
   (b) a second antigen-binding site that binds to human CD3 comprising heavy chain complementarity determining regions (HCDR) and light chain complementarity determining regions (LCDR), wherein HCDR1 comprises the amino acid sequence of SEQ ID NO: 414 or SEQ ID NO: 415, HCDR2 comprises the amino acid sequence of SEQ ID NO: 416, HCDR3 comprises the amino acid sequence of SEQ ID NO: 417 or SEQ ID NO: 418, LCDR1 comprises the amino acid sequence of SEQ ID NO: 419, LCDR2 comprises the amino acid sequence of SEQ ID NO: 420, and LCDR3 comprises the amino acid sequence of SEQ ID NO: 421;
   (c) a third antigen-binding site that binds to human serum albumin comprising heavy chain complementarity determining regions (HCDR) wherein HCDR1 comprises the amino acid sequence of SEQ ID NO: 122 or SEQ ID NO: 123, HCDR2 comprises the amino acid sequence of SEQ ID NO: 124, and HCDR3 comprises the amino acid sequence of SEQ ID NO: 125 or 126; and and wherein the first antigen-binding site and second antigen-binding site comprise a single-chain variable fragment (scFv) and the third antigen-binding site comprises a single-domain antibody (sdAb).

2. The multi-specific binding protein of claim 1, wherein the multi-specific binding protein comprises a single polypeptide chain.

3. The multi-specific binding protein of claim 2, wherein the third antigen-binding site is positioned N-terminal to both the first antigen-binding site and the second antigen-binding site in the polypeptide chain;
   or wherein the third antigen-binding site is positioned N-terminal to the first antigen-binding site, and the first antigen-binding site is positioned N-terminal to the second antigen-binding site in the polypeptide chain;
   or wherein the third antigen-binding site is positioned N-terminal to the second antigen-binding site, and the second antigen-binding site is positioned N-terminal to the first antigen-binding site in the polypeptide chain.

4. The multi-specific binding protein of claim 2, wherein the third antigen-binding site is positioned C-terminal to both the first antigen-binding site and the second antigen-binding site in the polypeptide chain;
   or wherein the first antigen-binding site is positioned N-terminal to the second antigen-binding site, and the second antigen-binding site is positioned N-terminal to the third antigen-binding site in the polypeptide chain;
   or wherein the second antigen-binding site is positioned N-terminal to the first antigen-binding site, and the first antigen-binding site is positioned N-terminal of the third antigen-binding site in the polypeptide chain.

5. The multi-specific binding protein of claim 2, wherein the first antigen-binding site is positioned N-terminal to the third antigen-binding site, and the third antigen-binding site is positioned N-terminal to the second antigen-binding site in the polypeptide chain;
   or wherein the second antigen-binding site is positioned N-terminal to the third antigen-binding site, and the third antigen-binding site is positioned N-terminal binding protein the first antigen-binding site in the polypeptide chain.

6. An isolated polynucleotide encoding the multi-specific binding protein of claim 1.

7. A vector comprising the isolated polynucleotide encoding the multi-specific binding protein of claim 6.

8. A multi-specific binding protein comprising:
   (a) a first antigen-binding site that binds to CD19 comprising a heavy chain variable domain (VH) comprising the amino acid sequence of SEQ ID NO: 62 and a light chain variable domain (VL) comprising the amino acid sequence of SEQ ID NO: 63
   (b) a second antigen-binding site that binds to human CD3 comprising a VH comprising the amino acid sequence of SEQ ID NO: 412 and a VL comprising the amino acid sequence of SEQ ID NO: 413; and
   (c) a third antigen-binding site that binds to human serum albumin (HSA) comprising a VH comprising the amino acid sequence of SEQ ID NO: 121.

9. An isolated polynucleotide encoding the multi-specific binding protein of claim 8.

10. A vector comprising the isolated polynucleotide encoding the multi-specific binding protein of claim 9.

11. A multi-specific binding protein comprising the amino acid sequence of SEQ ID NO: 694.

* * * * *

SEQUENCE LISTING

<160> NUMBER OF SEQ ID NOS: 728

<210> SEQ ID NO 1
<211> LENGTH: 121
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Asp Lys Phe
    50                  55                  60

Gln Glu Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Glu Leu Phe Asp Tyr Trp Gly
            100                 105                 110

Gln Gly Thr Thr Val Thr Val Ser Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Thr
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Ala Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
            100                 105                 110

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Asp Phe Thr Asp Tyr Ile Met His
1               5

<210> SEQ ID NO 4
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 4

Asp Tyr Ile Met His
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ile Asn Pro Tyr Asn Asp Gly Ser Lys Tyr Thr Asp Lys Phe Gln
1               5                   10                  15

Glu

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Arg Gly Thr Tyr Tyr Tyr Gly Pro Glu Leu Phe Asp Tyr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Thr Tyr Tyr Tyr Gly Pro Glu Leu Phe Asp Tyr
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ser Ser Gln Ser Leu Glu Thr Thr Thr Gly Thr Thr Tyr Leu Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

Arg Ala Ser Lys Arg Phe Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Gln Leu Leu Glu Asp Pro Tyr Thr
1               5

<210> SEQ ID NO 11
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Thr
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Ala Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Cys Gly Thr Lys Leu Glu Ile Lys
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Asp Phe Thr Asp Tyr Ile
145                 150                 155                 160

Met His Trp Val Arg Gln Ala Pro Gly Gln Cys Leu Glu Trp Met Gly
                165                 170                 175

Tyr Ile Asn Pro Tyr Asn Asp Gly Ser Lys Tyr Thr Lys Phe Gln
            180                 185                 190

Glu Arg Val Thr Met Thr Ser Asp Thr Ser Ile Ser Thr Ala Tyr Met
        195                 200                 205

Glu Leu Ser Arg Leu Arg Ser Asp Asp Thr Ala Val Tyr Tyr Cys Ala
    210                 215                 220

Arg Gly Thr Tyr Tyr Gly Pro Glu Leu Phe Asp Tyr Trp Gly Gln
225                 230                 235                 240

Gly Thr Thr Val Thr Val Ser Ser
                245

<210> SEQ ID NO 12
<211> LENGTH: 121

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Glu Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
    50                  55                  60

Gln Pro Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
                100                 105                 110

Gln Gly Thr Thr Val Thr Val Ser Ser
                115                 120

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
                20                  25                  30

Thr Gly Thr Thr Tyr Leu Asn Trp Tyr Leu Gln Lys Pro Gly Gln Ser
            35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
                100                 105                 110

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Glu Phe Thr Asp Tyr Ile Met His
1               5

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Ile Asn Pro Tyr Asn Asp Gly Ser Lys Tyr Thr Glu Lys Phe Gln
1               5                   10                  15

Pro

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Arg Gly Thr Tyr Tyr Tyr Gly Pro Gln Leu Phe Asp Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Thr Tyr Tyr Tyr Gly Pro Gln Leu Phe Asp Tyr
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Ser Ser Gln Ser Leu Glu Thr Ser Thr Gly Thr Thr Tyr Leu Asn
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Val Ser Lys Arg Phe Ser
1               5

<210> SEQ ID NO 20
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
            100                 105                 110

Gln Gly Thr Thr Val Thr Val Ser Ser
        115                 120

<210> SEQ ID NO 21
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ala
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Arg Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Ser Phe Gly Gln Gly Thr Lys Leu Glu Ile Lys
            100                 105                 110

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Thr Phe Thr Asp Tyr Ile Met His
1               5

<210> SEQ ID NO 23
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 23

Tyr Ile Asn Pro Tyr Asn Asp Gly Ser Lys Tyr Thr Glu Lys Phe Gln
1               5                   10                  15

Gly

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Ser Ser Gln Ser Leu Glu Thr Ala Thr Gly Thr Thr Tyr Leu Asn
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Val Ser Arg Arg Phe Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Gln Leu Leu Glu Asp Pro Tyr Ser
1               5

<210> SEQ ID NO 27
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
                20                  25                  30

Ile Val His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
        50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
```

```
                    85                  90                  95
Ala Arg Gly Thr Tyr Tyr Tyr Gly Pro Glu Leu Phe Asp Tyr Trp Gly
                100                 105                 110
Gln Gly Thr Thr Val Thr Val Ser Ser
        115                 120
```

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Asp Ile Val Met Thr Gln Thr Pro Leu Ser Leu Ser Val Thr Pro Gly
1               5                   10                  15

Gln Pro Ala Ser Ile Ser Cys Lys Ser Gly Gln Ser Leu Glu Thr Ser
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Arg Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
            100                 105                 110
```

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Tyr Asp Phe Thr Asp Tyr Ile Val His
1               5
```

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Asp Tyr Ile Val His
1               5
```

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

-continued

Lys Ser Gly Gln Ser Leu Glu Thr Ser Thr Gly Thr Thr Tyr Leu Asn
1               5                   10                  15

<210> SEQ ID NO 32
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Glu Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
        50                  55                  60

Glu Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Glu Leu Phe Asp Tyr Trp Gly
            100                 105                 110

Gln Gly Thr Thr Val Thr Val Ser Ser
        115                 120

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Arg Leu Glu Thr Ser
                20                  25                  30

Thr Gly Thr Thr Tyr Leu Asn Trp Tyr Leu Gln Lys Pro Gly Gln Ser
            35                  40                  45

Pro Gln Leu Leu Ile Tyr Arg Val Ser Arg Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Pro Thr Phe Gly Gln Gly Thr Lys Leu Glu Ile Lys
            100                 105                 110

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Ile Asn Pro Tyr Asn Asp Gly Ser Lys Tyr Thr Glu Lys Phe Glu
1               5                   10                  15

Gly

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Ser Ser Gln Arg Leu Glu Thr Ser Thr Gly Thr Thr Tyr Leu Asn
1               5                   10                  15

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Gln Leu Leu Glu Asp Pro Pro Thr
1               5

<210> SEQ ID NO 37
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Glu Tyr Thr Glu Lys Phe
        50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Gln Leu Phe Asp Tyr Trp Gly
            100                 105                 110

Gln Gly Thr Thr Val Thr Val Ser Ser
        115                 120

<210> SEQ ID NO 38
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ala
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
            100                 105                 110

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Ile Asn Pro Tyr Asn Asp Gly Ser Glu Tyr Thr Glu Lys Phe Gln
1               5                   10                  15

Gly

<210> SEQ ID NO 40
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln His Arg Val Thr Met Thr Ser Asp Thr Ser Ile Ser Thr Ala Tyr
65              70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Gln Leu Phe Asp Tyr Trp Gly
            100                 105                 110

Gln Gly Thr Thr Val Thr Val Ser Ser
            115                 120

<210> SEQ ID NO 41
<211> LENGTH: 112
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 41

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
            100                 105                 110

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Ile Asn Pro Tyr Asn Asp Gly Ser Lys Tyr Thr Glu Lys Phe Gln
1               5                   10                  15

His

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Ile Val His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
            100                 105                 110

Gln Gly Thr Thr Val Thr Val Ser Ser
        115                 120
```

```
<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Val
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Pro Thr Phe Gly Gln Gly Thr Lys Leu Glu Ile Lys
            100                 105                 110

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Ser Ser Gln Ser Leu Glu Thr Val Thr Gly Thr Thr Tyr Leu Asn
1               5                   10                  15

<210> SEQ ID NO 46
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Ile Val His Trp Val Arg Gln Ala Pro Gly Gln Gly Leu Glu Trp Met
        35                  40                  45

Gly Tyr Ile Asn Pro Tyr Asn Asp Gly Ser Leu Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Gln Leu Phe Asp Tyr Trp Gly
            100                 105                 110

Gln Gly Thr Thr Val Thr Val Ser Ser
            115                 120
```

<210> SEQ ID NO 47
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Gln Leu Glu Thr Ser
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Ala Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Ser Phe Gly Gln Gly Thr Lys Leu Glu Ile Lys
            100                 105                 110

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Ile Asn Pro Tyr Asn Asp Gly Ser Leu Tyr Thr Glu Lys Phe Gln
1               5                   10                  15

Gly

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ser Ser Gln Gln Leu Glu Thr Ser Thr Gly Thr Thr Tyr Leu Asn
1               5                   10                  15

<210> SEQ ID NO 50
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
            20                  25                  30

```
Thr Gly Thr Thr Tyr Leu Asn Trp Tyr Leu Gln Lys Pro Gly Gln Ser
        35                  40                  45

Pro Gln Leu Leu Ile Tyr Arg Ser Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Pro Thr Phe Gly Gln Gly Thr Lys Leu Glu Ile Lys
            100                 105                 110

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ser Ser Lys Arg Phe Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: T, D or E
<220> FEATURE:
<221> NAME/KEY: MOD_RES
<222> LOCATION: (8)..(8)
<223> OTHER INFORMATION: M or V

<400> SEQUENCE: 52

Tyr Xaa Phe Thr Asp Tyr Ile Xaa His
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: M or V

<400> SEQUENCE: 53

Asp Tyr Ile Xaa His
1               5

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (10)..(10)
<223> OTHER INFORMATION: K, L or E
<220> FEATURE:
<221> NAME/KEY: MOD_RES
<222> LOCATION: (13)..(13)
<223> OTHER INFORMATION: E or D
<220> FEATURE:
<221> NAME/KEY: MOD_RES
<222> LOCATION: (16)..(16)
<223> OTHER INFORMATION: Q or E
<220> FEATURE:
<221> NAME/KEY: MOD_RES
<222> LOCATION: (17)..(17)
<223> OTHER INFORMATION: G, H, E or P

<400> SEQUENCE: 54

Tyr Ile Asn Pro Tyr Asn Asp Gly Ser Xaa Tyr Thr Xaa Lys Phe Xaa
1               5                   10                  15

Xaa

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Q or E

<400> SEQUENCE: 55

Ala Arg Gly Thr Tyr Tyr Tyr Gly Pro Xaa Leu Phe Asp Tyr
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Q or E

<400> SEQUENCE: 56

Gly Thr Tyr Tyr Tyr Gly Pro Xaa Leu Phe Asp Tyr
1               5                   10

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: S or G
<220> FEATURE:
<221> NAME/KEY: MOD_RES
<222> LOCATION: (5)..(5)
<223> OTHER INFORMATION: S, R or Q
<220> FEATURE:
<221> NAME/KEY: MOD_RES
<222> LOCATION: (7)..(7)
<223> OTHER INFORMATION: E or F
```

```
<220> FEATURE:
<221> NAME/KEY: MOD_RES
<222> LOCATION: (9)..(9)
<223> OTHER INFORMATION: S, A, T or V

<400> SEQUENCE: 57

Lys Ser Xaa Gln Xaa Leu Xaa Thr Xaa Thr Gly Thr Thr Tyr Leu Asn
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: V, A or S
<220> FEATURE:
<221> NAME/KEY: MOD_RES
<222> LOCATION: (4)..(4)
<223> OTHER INFORMATION: K or R

<400> SEQUENCE: 58

Arg Xaa Ser Xaa Arg Phe Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Y or P
<220> FEATURE:
<221> NAME/KEY: MOD_RES
<222> LOCATION: (9)..(9)
<223> OTHER INFORMATION: T or S

<400> SEQUENCE: 59

Leu Gln Leu Leu Glu Asp Pro Xaa Xaa
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: V or A
<220> FEATURE:
<221> NAME/KEY: MOD_RES
<222> LOCATION: (4)..(4)
<223> OTHER INFORMATION: K or R

<400> SEQUENCE: 60

Arg Xaa Ser Xaa Arg Phe Ser
1               5

<210> SEQ ID NO 61
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: K or L
<220> FEATURE:
<221> NAME/KEY: MOD_RES
<222> LOCATION: (13)..(13)
<223> OTHER INFORMATION: E or D
<220> FEATURE:
<221> NAME/KEY: MOD_RES
<222> LOCATION: (16)..(16)
<223> OTHER INFORMATION: Q or E
<220> FEATURE:
<221> NAME/KEY: MOD_RES
<222> LOCATION: (17)..(17)
<223> OTHER INFORMATION: G, H or E

<400> SEQUENCE: 61

Tyr Ile Asn Pro Tyr Asn Asp Gly Ser Xaa Tyr Thr Xaa Lys Phe Xaa
1               5                   10                  15

Xaa

<210> SEQ ID NO 62
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
                20                  25                  30

Thr Met Gly Val Gly Trp Ile Arg Gln His Pro Gly Lys Gly Leu Glu
            35                  40                  45

Trp Ile Gly Phe Ile Trp Trp Asp Asp Lys Arg Tyr Asn Pro Asn
        50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 63
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Gly Tyr Met
```

```
                20                  25                  30
His Trp Tyr Gln Gln Lys Pro Gly Gln Ala Pro Arg Leu Leu Ile Tyr
            35                  40                  45

Asp Thr Ser Lys Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys
                100                 105
```

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Gly Ser Ile Ser Thr Ser Thr Met Gly Val Gly
1               5                   10
```

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Thr Ser Thr Met Gly Val Gly
1               5
```

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Phe Ile Trp Trp Asp Asp Asp Lys Arg Tyr Asn Pro Asn Leu Lys Ser
1               5                   10                  15
```

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Ala Arg Met Glu Leu Trp Ser Tyr Tyr Phe Asp Tyr
1               5                   10
```

<210> SEQ ID NO 68
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 68

Met Glu Leu Trp Ser Tyr Tyr Phe Asp Tyr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Ala Ser Ser Ser Val Gly Tyr Met His
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Thr Ser Lys Leu Ala Ser
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Phe Gln Gly Ser Val Tyr Pro Phe Thr
1               5

<210> SEQ ID NO 72
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Gly Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95
```

```
Phe Gly Gln Gly Thr Lys Leu Glu Ile Lys Gly Gly Gly Ser Gly
                100                 105                 110

Gly Gly Gly Ser Gly Gly Gly Ser Gln Val Gln Leu Gln Glu Ser
            115                 120                 125

Gly Pro Gly Leu Val Lys Pro Ser Gln Thr Leu Ser Leu Thr Cys Thr
    130                 135                 140

Val Ser Gly Gly Ser Ile Ser Thr Ser Met Gly Val Gly Trp Ile
145                 150                 155                 160

Arg Gln His Pro Gly Lys Gly Leu Glu Trp Ile Gly Phe Ile Trp Trp
                165                 170                 175

Asp Asp Asp Lys Arg Tyr Asn Pro Asn Leu Lys Ser Arg Val Thr Met
            180                 185                 190

Ser Val Asp Thr Ser Lys Asn Gln Phe Ser Leu Lys Leu Ser Ser Val
            195                 200                 205

Thr Ala Ala Asp Thr Ala Val Tyr Tyr Cys Ala Arg Met Glu Leu Trp
    210                 215                 220

Ser Tyr Tyr Phe Asp Tyr Trp Gly Gln Gly Thr Leu Val Thr Val Ser
225                 230                 235                 240

Ser

<210> SEQ ID NO 73
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Ser Trp Ile Arg Gln His Pro Gly Lys Gly Leu Glu
        35                  40                  45

Trp Ile Gly His Ile Trp Trp Asp Asp Asp Lys Arg Tyr Asn Pro Val
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Pro Trp Gly Gln
            100                 105                 110

Gly Thr Leu Val Thr Val Ser Ser
        115                 120

<210> SEQ ID NO 74
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
```

```
                20                  25                  30
His Trp Tyr Gln Gln Lys Pro Gly Gln Ala Pro Arg Leu Leu Ile Tyr
            35                  40                  45

Asp Thr Ser Lys Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys
            100                 105

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ser Thr Ser Thr Ser Gly Met Gly Val Ser
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Ser Gly Met Gly Val Ser
1               5

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

His Ile Trp Trp Asp Asp Asp Lys Arg Tyr Asn Pro Val Leu Lys Ser
1               5                   10                  15

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Arg Met Glu Leu Trp Ser Tyr Tyr Phe Asp Pro
1               5                   10

<210> SEQ ID NO 79
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 79

Met Glu Leu Trp Ser Tyr Tyr Phe Asp Pro
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Ala Ser Ser Ser Val Ser Tyr Met His
1               5                   10

<210> SEQ ID NO 81
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Thr Met Gly Val Gly Trp Ile Arg Gln His Pro Gly Lys Gly Leu Glu
        35                  40                  45

Trp Ile Gly Phe Ile Trp Trp Asp Asp Lys Arg Tyr Asn Pro Asn
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Glu Tyr Trp Gly Gln
            100                 105                 110

Gly Thr Leu Val Thr Val Ser Ser
        115                 120

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Arg Met Glu Leu Trp Ser Tyr Tyr Phe Glu Tyr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met Glu Leu Trp Ser Tyr Tyr Phe Glu Tyr
1               5                   10

<210> SEQ ID NO 84
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ala Ser Gly
            20                  25                  30

Met Gly Val Gly Trp Ile Arg Gln His Pro Gly Lys Gly Leu Glu Trp
        35                  40                  45

Ile Gly His Ile Trp Trp Asp Asp Lys Arg Tyr Asn Pro Ala Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Glu Leu Trp Ser Tyr Tyr Phe Asp Gly Trp Gly Gln Gly
            100                 105                 110

Thr Leu Val Thr Val Ser Ser
        115

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Ser Ile Ala Ser Gly Met Gly Val Gly
1               5                   10

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Gly Met Gly Val Gly
1               5

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
His Ile Trp Trp Asp Asp Asp Lys Arg Tyr Asn Pro Ala Leu Lys Ser
1               5                   10                  15

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Arg Met Glu Leu Trp Ser Tyr Tyr Phe Asp Gly
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Met Glu Leu Trp Ser Tyr Tyr Phe Asp Gly
1               5                   10

<210> SEQ ID NO 90
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 91
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Ile Val Leu Thr Gln Ser Pro Ala Thr Leu Ser Leu Ser Pro Gly
```

```
            1               5                  10                 15
Glu Arg Ala Thr Leu Ser Cys Ser Ala Ser Ser Ser Val Gly Tyr Met
                    20                  25                 30
His Trp Tyr Gln Gln Lys Pro Gly Gln Ala Pro Arg Leu Leu Ile Tyr
                35                  40                 45
Asp Thr Ser Ser Leu Ala Ser Gly Ile Pro Ala Arg Phe Ser Gly Ser
        50                  55                  60
Gly Ser Gly Thr Asp Phe Thr Leu Thr Ile Ser Ser Leu Glu Pro Glu
65                  70                  75                  80
Asp Phe Ala Val Tyr Tyr Cys Phe Gln Gly Ser Val Tyr Pro Phe Thr
                    85                  90                  95
Phe Gly Gln Gly Thr Lys Leu Glu Ile Lys
                100                 105
```

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Gly Ser Ile Ser Thr Ser Gly Met Gly Val Gly
1               5                   10
```

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

```
Thr Ser Gly Met Gly Val Gly
1               5
```

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

```
Asp Thr Ser Ser Leu Ala Ser
1               5
```

<210> SEQ ID NO 95
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ala Ser Gly
            20                  25                  30
```

```
Met Gly Val Ser Trp Ile Arg Gln His Pro Lys Gly Leu Glu Trp
            35                  40                  45

Ile Gly His Ile Trp Trp Asp Asp Lys Arg Tyr Asn Pro Ala Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Glu Leu Trp Ser Tyr Tyr Phe Asp Pro Trp Gly Gln Gly
                100                 105                 110

Thr Leu Val Thr Val Ser Ser
        115
```

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

```
Gly Ser Ile Ala Ser Gly Met Gly Val Ser
1               5                   10
```

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

```
Ser Gly Met Gly Val Ser
1               5
```

<210> SEQ ID NO 98
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Thr Met Gly Val Gly Trp Ile Arg Gln His Pro Gly Lys Gly Leu Glu
            35                  40                  45

Trp Ile Gly Phe Ile Trp Trp Asp Asp Lys Arg Tyr Asn Pro Asn
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Pro Trp Gly Gln
                100                 105                 110

Gly Thr Leu Val Thr Val Ser Ser
```

<210> SEQ ID NO 99
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Gly Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ser Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys
            100                 105

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asp Thr Ser Lys Leu Ser Ser
1               5

<210> SEQ ID NO 101
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Gly Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Phe Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys
            100                 105

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

```
Asp Thr Ser Lys Leu Ala Phe
1               5
```

<210> SEQ ID NO 103
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Thr Ser
            20                  25                  30

Ser Met Gly Val Gly Trp Ile Arg Gln His Pro Gly Lys Gly Leu Glu
        35                  40                  45

Trp Ile Gly His Ala Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Pro Trp Gly Gln
            100                 105                 110

Gly Thr Leu Val Thr Val Ser Ser
        115                 120
```

<210> SEQ ID NO 104
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Phe Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95
```

Phe Gly Gln Gly Thr Lys Leu Glu Ile Lys
            100                 105

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Val Ser Ile Ser Thr Ser Ser Met Gly Val Gly
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Thr Ser Ser Met Gly Val Gly
1               5

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

His Ala Trp Trp Asp Asp Lys Arg Tyr Asn Pro Ala Leu Lys Ser
1               5                   10                  15

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser Ala Ser Ser Ser Phe Ser Tyr Met His
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G or V
<220> FEATURE:
<221> NAME/KEY: MOD_RES
<222> LOCATION: (3)..(3)
<223> OTHER INFORMATION: I or T
<220> FEATURE:
<221> NAME/KEY: MOD_RES
<222> LOCATION: (4)..(4)
<223> OTHER INFORMATION: S or A

```
<220> FEATURE:
<221> NAME/KEY: MOD_RES
<222> LOCATION: (5)..(5)
<223> OTHER INFORMATION: T or absent
<220> FEATURE:
<221> NAME/KEY: MOD_RES
<222> LOCATION: (7)..(7)
<223> OTHER INFORMATION: G or T
<220> FEATURE:
<221> NAME/KEY: MOD_RES
<222> LOCATION: (11)..(11)
<223> OTHER INFORMATION: G or S

<400> SEQUENCE: 109

Xaa Ser Xaa Xaa Xaa Ser Xaa Met Gly Val Xaa
1               5                   10

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T or absent
<220> FEATURE:
<221> NAME/KEY: MOD_RES
<222> LOCATION: (3)..(3)
<223> OTHER INFORMATION: G or T
<220> FEATURE:
<221> NAME/KEY: MOD_RES
<222> LOCATION: (7)..(7)
<223> OTHER INFORMATION: G or S

<400> SEQUENCE: 110

Xaa Ser Xaa Met Gly Val Xaa
1               5

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H or F
<220> FEATURE:
<221> NAME/KEY: MOD_RES
<222> LOCATION: (2)..(2)
<223> OTHER INFORMATION: I or A
<220> FEATURE:
<221> NAME/KEY: MOD_RES
<222> LOCATION: (13)..(13)
<223> OTHER INFORMATION: A, N or V

<400> SEQUENCE: 111

Xaa Xaa Trp Trp Asp Asp Asp Lys Arg Tyr Asn Pro Xaa Leu Lys Ser
1               5                   10                  15

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (11)..(11)
<223> OTHER INFORMATION: D or E
<220> FEATURE:
<221> NAME/KEY: MOD_RES
<222> LOCATION: (12)..(12)
<223> OTHER INFORMATION: Y, P or G

<400> SEQUENCE: 112

Ala Arg Met Glu Leu Trp Ser Tyr Tyr Phe Xaa Xaa
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D or E
<220> FEATURE:
<221> NAME/KEY: MOD_RES
<222> LOCATION: (10)..(10)
<223> OTHER INFORMATION: Y, P or G

<400> SEQUENCE: 113

Met Glu Leu Trp Ser Tyr Tyr Phe Xaa Xaa
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: V or F
<220> FEATURE:
<221> NAME/KEY: MOD_RES
<222> LOCATION: (7)..(7)
<223> OTHER INFORMATION: S or G

<400> SEQUENCE: 114

Ser Ala Ser Ser Ser Xaa Xaa Tyr Met His
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: K or S
<220> FEATURE:
<221> NAME/KEY: MOD_RES
<222> LOCATION: (6)..(6)
<223> OTHER INFORMATION: A or S
<220> FEATURE:
<221> NAME/KEY: MOD_RES
<222> LOCATION: (7)..(7)
<223> OTHER INFORMATION: S or F

<400> SEQUENCE: 115
```

```
Asp Thr Ser Xaa Leu Xaa Xaa
1               5
```

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G or V
<220> FEATURE:
<221> NAME/KEY: MOD_RES
<222> LOCATION: (4)..(4)
<223> OTHER INFORMATION: S or A
<220> FEATURE:
<221> NAME/KEY: MOD_RES
<222> LOCATION: (5)..(5)
<223> OTHER INFORMATION: T or absent
<220> FEATURE:
<221> NAME/KEY: MOD_RES
<222> LOCATION: (7)..(7)
<223> OTHER INFORMATION: G or T
<220> FEATURE:
<221> NAME/KEY: MOD_RES
<222> LOCATION: (11)..(11)
<223> OTHER INFORMATION: G or S

<400> SEQUENCE: 116

```
Xaa Ser Ile Xaa Xaa Ser Xaa Met Gly Val Xaa
1               5                   10
```

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H or F
<220> FEATURE:
<221> NAME/KEY: MOD_RES
<222> LOCATION: (2)..(2)
<223> OTHER INFORMATION: I or A
<220> FEATURE:
<221> NAME/KEY: MOD_RES
<222> LOCATION: (13)..(13)
<223> OTHER INFORMATION: A or N

<400> SEQUENCE: 117

```
Xaa Xaa Trp Trp Asp Asp Asp Lys Arg Tyr Asn Pro Xaa Leu Lys Ser
1               5                   10                  15
```

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Y or P

<400> SEQUENCE: 118

```
Ala Arg Met Glu Leu Trp Ser Tyr Tyr Phe Asp Xaa
1               5                   10
```

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Y or P

<400> SEQUENCE: 119

```
Met Glu Leu Trp Ser Tyr Tyr Phe Asp Xaa
1               5                   10
```

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: A or S
<220> FEATURE:
<221> NAME/KEY: MOD_RES
<222> LOCATION: (7)..(7)
<223> OTHER INFORMATION: S or F

<400> SEQUENCE: 120

```
Asp Thr Ser Lys Leu Xaa Xaa
1               5
```

<210> SEQ ID NO 121
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser
        115
```

```
<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Phe Thr Phe Ser Ser Phe Gly Met Thr
1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Phe Gly Met Thr
1               5

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Ile Ser Gly Ser Gly Ser Asp Thr Leu Tyr Ala Asp Ser Val Arg
1               5                   10                  15

Gly

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Thr Ile Gly Gly Ser Leu Ser Pro
1               5

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Gly Ser Leu Ser Pro
1               5

<210> SEQ ID NO 127
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 127

Lys Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser
        115

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Phe Thr Phe Ser Ser Phe Gly Met Ser
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Phe Gly Met Ser
1               5

<210> SEQ ID NO 130
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr

```
                65                  70                  75                  80
Leu Gln Met Asn Ser Leu Arg Pro Glu Asp Thr Ala Val Tyr Tyr Cys
                        85                  90                  95
Thr Ile Gly Gly Ser Leu Ser Pro Ser Ser Gln Gly Thr Leu Val Thr
            100                 105                 110

Val Ser Ser
        115

<210> SEQ ID NO 131
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Lys Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe His Ser Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110

Val Ser Ser
        115

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Phe Thr Phe His Ser Phe Gly Met Ser
1               5

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Ile Ser Gly Ser Gly Ser Asp Thr Leu Tyr Ala Asp Ser Val Lys
1               5                   10                  15
Gly

<210> SEQ ID NO 134
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Ile Gly Gly Ser Leu Ser Arg
1               5

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Gly Ser Leu Ser Arg
1               5

<210> SEQ ID NO 136
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Val Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Phe Val Phe Ser Ser Phe Gly Met Ser
1               5

<210> SEQ ID NO 138
<211> LENGTH: 115
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 138

Lys Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Thr Ile Gly Gly Ser Arg Ser Ile Ser Ser Gln Gly Thr Leu Val Thr
            100                 105                 110

Val Ser Ser
        115

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Thr Ile Gly Gly Ser Arg Ser Ile
1               5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Gly Ser Arg Ser Ile
1               5

<210> SEQ ID NO 141
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Lys Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
```

```
                50                  55                  60
Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ser Ile Gly Gly Ser Leu Ile Arg Ser Ser Gln Gly Thr Leu Val Thr
                100                 105                 110

Val Ser Ser
        115

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Ile Gly Gly Ser Leu Ile Arg
1               5

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gly Ser Leu Ile Arg
1               5

<210> SEQ ID NO 144
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Lys Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Gly Ser Phe
                20                  25                  30

Gly Met Ser Trp Val Arg Gln Ala Pro Gly Lys Gly Leu Glu Trp Val
        35                  40                  45

Ser Ser Ile Ser Gly Ser Gly Ala Asp Thr Leu Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Ile Gly Gly Ser Leu Arg Ala Ser Ser Gln Gly Thr Leu Val Thr
                100                 105                 110

Val Ser Ser
        115

<210> SEQ ID NO 145
```

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Phe Thr Phe Gly Ser Phe Gly Met Ser
1               5

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Ile Ser Gly Ser Gly Ala Asp Thr Leu Tyr Ala Asp Ser Val Lys
1               5                   10                  15

Gly

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Thr Ile Gly Gly Ser Leu Arg Ala
1               5

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Gly Ser Leu Arg Ala
1               5

<210> SEQ ID NO 149
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Lys Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Gly Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 150
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Lys Val Gln Leu Val Glu Ser Gly Gly Gly Leu Val Gln Pro Gly Asn
  1               5                  10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Gly Asp Thr Leu Tyr Ala Asp Ser Ala
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ser Ile Ser Gly Ser Gly Gly Asp Thr Leu Tyr Ala Asp Ser Ala Lys
  1               5                  10                  15

Gly

<210> SEQ ID NO 152
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Lys Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
             20                  25                  30
```

```
Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Ile Gly Gly Ser Leu Lys Gln Ser Ser Gln Gly Thr Leu Val Thr
            100                 105                 110

Val Ser Ser
    115

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Ile Ser Gly Ser Gly Ser Asp Thr Leu Tyr Ala Asp Ser Val Glu
1               5                   10                  15

Gly

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Thr Ile Gly Gly Ser Leu Lys Gln
1               5

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Gly Ser Leu Lys Gln
1               5

<210> SEQ ID NO 156
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Lys Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Ser Phe
            20                  25                  30
```

-continued

```
Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Val Ser Lys Ser Ser Arg Gly Thr Leu Val Thr
            100                 105                 110

Val Ser Ser
        115

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Phe Thr Phe Pro Ser Phe Gly Met Ser
1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Thr Ile Gly Gly Ser Val Ser Lys
1               5

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Gly Ser Val Ser Lys
1               5

<210> SEQ ID NO 160
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gly Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
```

```
                35                  40                  45
Ser Ser Ile Ser Gly Thr Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Arg Tyr Ser Ser Gln Gly Thr Leu Val Thr
            100                 105                 110

Val Ser Ser
        115

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Ile Ser Gly Thr Gly Ser Asp Thr Leu Tyr Ala Asp Ser Val Lys
 1               5                  10                  15

Gly

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Thr Ile Gly Gly Ser Leu Arg Tyr
 1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Gly Ser Leu Arg Tyr
 1               5

<210> SEQ ID NO 164
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Lys Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
```

```
                35                  40                  45
Ser Ser Ile Ser Gly Ser Gly Ser Asp Thr Leu Thr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Ile Gly Gly Ser Leu Val Arg Ser Ser Gln Gly Thr Leu Val Thr
            100                 105                 110

Val Ser Ser
        115

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Ile Ser Gly Ser Gly Ser Asp Thr Leu Thr Ala Asp Ser Val Lys
 1               5                  10                  15

Gly

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Thr Ile Gly Gly Ser Leu Val Arg
 1               5

<210> SEQ ID NO 167
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Gly Ser Leu Val Arg
 1               5

<210> SEQ ID NO 168
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Lys Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Gly Trp Val Arg Gln Ala Pro Gly Lys Gly Leu Glu Trp Val
```

```
              35                  40                  45
Ser Ser Ile Ser Gly Ser Gly Ser Asp Thr Leu Tyr Ala Pro Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Phe Ala Gly Ser Leu Ser Arg Ser Ser Gln Gly Thr Leu Val Thr
               100                 105                 110

Val Ser Ser
       115

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Phe Thr Phe Ser Ser Phe Gly Met Gly
1               5

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ser Phe Gly Met Gly
1               5

<210> SEQ ID NO 171
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Ile Ser Gly Ser Gly Ser Asp Thr Leu Tyr Ala Pro Ser Val Lys
1               5                  10                  15

Gly

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Thr Phe Ala Gly Ser Leu Ser Arg
1               5

<210> SEQ ID NO 173
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 173

Ala Gly Ser Leu Ser Arg
1               5

<210> SEQ ID NO 174
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Arg Ala Ser Ser Gln Gly Thr Leu Val Thr
            100                 105                 110

Val Ser Ser
        115

<210> SEQ ID NO 175
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Lys Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Thr Arg Ser Ser Gln Gly Thr Leu Val Thr
            100                 105                 110

Val Ser Ser
        115
```

```
<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Thr Ile Gly Gly Ser Leu Thr Arg
1               5

<210> SEQ ID NO 177
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Gly Ser Leu Thr Arg
1               5

<210> SEQ ID NO 178
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Lys Val Gln Leu Val Glu Ser Gly Gly Leu Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Gly Gly Ser Asp Thr Leu Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Arg Ala Ser Ser Gln Gly Thr Leu Val Thr
            100                 105                 110

Val Ser Ser
        115

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Ile Ser Gly Gly Gly Ser Asp Thr Leu Tyr Ala Asp Ser Val Arg
1               5                   10                  15

Gly
```

<210> SEQ ID NO 180
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 180

Lys Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Ala Leu Tyr Ala Asp Ser Ala
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser
        115

<210> SEQ ID NO 181
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 181

Ser Ile Ser Gly Ser Gly Ser Asp Ala Leu Tyr Ala Asp Ser Ala Lys
1               5                   10                  15

Gly

<210> SEQ ID NO 182
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 182

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys 85                  90                  95
Thr Ile Gly Gly Ser Leu Lys Gln Ser Ser Gln Gly Thr Leu Val Thr
                100                 105                 110

Val Ser Ser
        115

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: S, H, G or P
<220> FEATURE:
<221> NAME/KEY: MOD_RES
<222> LOCATION: (9)..(9)
<223> OTHER INFORMATION: S, T or G

<400> SEQUENCE: 183

Phe Thr Phe Xaa Ser Phe Gly Met Xaa
1               5

<210> SEQ ID NO 184
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: S, T or G

<400> SEQUENCE: 184

Ser Phe Gly Met Xaa
1               5

<210> SEQ ID NO 185
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: S or G
<220> FEATURE:
<221> NAME/KEY: MOD_RES
<222> LOCATION: (7)..(7)
<223> OTHER INFORMATION: S, A or G
<220> FEATURE:
<221> NAME/KEY: MOD_RES
<222> LOCATION: (9)..(9)
<223> OTHER INFORMATION: T or A
<220> FEATURE:
<221> NAME/KEY: MOD_RES
<222> LOCATION: (13)..(13)
<223> OTHER INFORMATION: D or P
<220> FEATURE:
<221> NAME/KEY: MOD_RES
<222> LOCATION: (15)..(15)
<223> OTHER INFORMATION: V or A
<220> FEATURE:
<221> NAME/KEY: MOD_RES
<222> LOCATION: (16)..(16)

-continued

<223> OTHER INFORMATION: K, R or E

<400> SEQUENCE: 185

Ser Ile Ser Gly Xaa Gly Xaa Asp Xaa Leu Tyr Ala Xaa Ser Xaa Xaa
1               5                   10                  15
Gly

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: I or F
<220> FEATURE:
<221> NAME/KEY: MOD_RES
<222> LOCATION: (3)..(3)
<223> OTHER INFORMATION: G or A
<220> FEATURE:
<221> NAME/KEY: MOD_RES
<222> LOCATION: (6)..(6)
<223> OTHER INFORMATION: L or V
<220> FEATURE:
<221> NAME/KEY: MOD_RES
<222> LOCATION: (7)..(7)
<223> OTHER INFORMATION: S, R, K or T
<220> FEATURE:
<221> NAME/KEY: MOD_RES
<222> LOCATION: (8)..(8)
<223> OTHER INFORMATION: R, P, A, Q or K

<400> SEQUENCE: 186

Thr Xaa Xaa Gly Ser Xaa Xaa Xaa
1               5

<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G or A
<220> FEATURE:
<221> NAME/KEY: MOD_RES
<222> LOCATION: (4)..(4)
<223> OTHER INFORMATION: L or V
<220> FEATURE:
<221> NAME/KEY: MOD_RES
<222> LOCATION: (5)..(5)
<223> OTHER INFORMATION: S, R, K or T
<220> FEATURE:
<221> NAME/KEY: MOD_RES
<222> LOCATION: (6)..(6)
<223> OTHER INFORMATION: R, P, A, Q or K

<400> SEQUENCE: 187

Xaa Gly Ser Xaa Xaa Xaa
1               5

<210> SEQ ID NO 188
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: S, H or G
<220> FEATURE:
<221> NAME/KEY: MOD_RES
<222> LOCATION: (9)..(9)
<223> OTHER INFORMATION: S or T

<400> SEQUENCE: 188

Phe Thr Phe Xaa Ser Phe Gly Met Xaa
1               5

<210> SEQ ID NO 189
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: S or T

<400> SEQUENCE: 189

Ser Phe Gly Met Xaa
1               5

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: S or T
<220> FEATURE:
<221> NAME/KEY: MOD_RES
<222> LOCATION: (16)..(16)
<223> OTHER INFORMATION: K or R

<400> SEQUENCE: 190

Ser Ile Ser Gly Xaa Gly Ser Asp Thr Leu Tyr Ala Asp Ser Val Xaa
1               5                   10                  15
Gly

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: S, R or T
<220> FEATURE:
<221> NAME/KEY: MOD_RES
<222> LOCATION: (8)..(8)
<223> OTHER INFORMATION: R, P, Y or A

<400> SEQUENCE: 191

Thr Ile Gly Gly Ser Leu Xaa Xaa
1               5
```

```
<210> SEQ ID NO 192
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: S, R or T
<220> FEATURE:
<221> NAME/KEY: MOD_RES
<222> LOCATION: (6)..(6)
<223> OTHER INFORMATION: R, P, Y or A

<400> SEQUENCE: 192

Gly Gly Ser Leu Xaa Xaa
1               5

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: K or R

<400> SEQUENCE: 193

Ser Ile Ser Gly Ser Gly Ser Asp Thr Leu Tyr Ala Asp Ser Val Xaa
1               5                   10                  15

Gly

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: S, R or T
<220> FEATURE:
<221> NAME/KEY: MOD_RES
<222> LOCATION: (8)..(8)
<223> OTHER INFORMATION: R, P or A

<400> SEQUENCE: 194

Thr Ile Gly Gly Ser Leu Xaa Xaa
1               5

<210> SEQ ID NO 195
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: S, R or T
<220> FEATURE:
<221> NAME/KEY: MOD_RES
```

<222> LOCATION: (6)..(6)
<223> OTHER INFORMATION: R, P or A

<400> SEQUENCE: 195

Gly Gly Ser Leu Xaa Xaa
1               5

<210> SEQ ID NO 196
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 197
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser
        115                 120

-continued

```
<210> SEQ ID NO 198
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

<210> SEQ ID NO 199
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ser Tyr Val Met His
1               5

<210> SEQ ID NO 200
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Trp Ile Gly Tyr Ile Asn Pro Tyr Asn Asp Gly Thr Lys Tyr
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Thr Tyr Tyr Tyr Gly Thr Arg Val Phe Asp Tyr
1               5                   10

<210> SEQ ID NO 202
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 202

Arg Ser Ser Lys Ser Leu Gln Asn Val Asn Gly Asn Thr Tyr Leu Tyr
1               5                   10                  15

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Arg Met Ser Asn Leu Asn Ser
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Met Gln His Leu Glu Tyr Pro Ile Thr
1               5

<210> SEQ ID NO 205
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Ser Val Thr Val Ser Ser
        115                 120

<210> SEQ ID NO 206
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Asp Ile Leu Leu Thr Gln Thr Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Tyr Trp Met Asn
1               5

<210> SEQ ID NO 208
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gln Ile Trp Pro Gly Asp Gly Asp Thr Asn Tyr Asn Gly Lys Phe Lys
1               5                   10                  15

Gly

<210> SEQ ID NO 209
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Arg Glu Thr Thr Thr Val Gly Arg Tyr Tyr Tyr Ala Met Asp Tyr
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Lys Ala Ser Gln Ser Val Asp Tyr Asp Gly Asp Ser Tyr Leu Asn
1               5                   10                  15

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Asp Ala Ser Asn Leu Val Ser
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gln Gln Ser Thr Glu Asp Pro Trp Thr
1               5

<210> SEQ ID NO 213
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Ala Phe Ser Ser Tyr
            20                  25                  30

Trp Met Asn Trp Val Arg Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Arg Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Ser Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 214
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Asp Ile Gln Leu Thr Gln Ser Pro Ser Ser Leu Ser Ala Ser Val Gly
1               5                   10                  15

```
Asp Arg Val Thr Ile Thr Cys Lys Ala Ser Gln Ser Val Asp Tyr Asp
            20                  25                  30

Gly Asp Ser Tyr Leu Asn Trp Tyr Gln Gln Ile Pro Gly Lys Ala Pro
        35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Tyr Thr Phe Thr Ile Ser
 65                  70                  75                  80

Ser Leu Gln Pro Glu Asp Ile Ala Thr Tyr His Cys Gln Gln Ser Thr
                85                  90                  95

Glu Asp Pro Trp Thr Phe Gly Gly Gly Thr Lys Leu Gln Ile Lys Arg
            100                 105                 110

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gln Ile Trp Pro Gly Asp Gly Asp Thr Asn Tyr Asn Gly Lys Phe Lys
1               5                   10                  15

Gly

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Arg Glu Thr Thr Thr Val Gly Arg Tyr Tyr Tyr Ala Met Asp Tyr
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Lys Ala Ser Gln Ser Val Asp Tyr Asp Gly Asp Ser Tyr Leu Asn
1               5                   10                  15

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Asp Ala Ser Asn Leu Val Ser
1               5

<210> SEQ ID NO 219
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gln Gln Ser Thr Glu Asp Pro Trp Thr
1               5

<210> SEQ ID NO 220
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gln Val Gln Leu Glu Gln Pro Gly Ala Glu Val Val Lys Pro Gly Ala
1               5                   10                  15

Ser Val Lys Val Ser Cys Lys Thr Ser Gly Tyr Thr Phe Thr Ser Asn
            20                  25                  30

Trp Met His Trp Val Lys Gln Thr Pro Gly Lys Gly Leu Glu Trp Ile
        35                  40                  45

Gly Glu Ile Asp Pro Ser Asp Ser Tyr Thr Asn Tyr Asn Gln Lys Phe
    50                  55                  60

Asp Gly Lys Ala Lys Leu Thr Val Asp Lys Ser Ser Ser Thr Ala Tyr
65                  70                  75                  80

Met Glu Val Ser Asp Leu Thr Ala Glu Asp Ser Ala Thr Tyr Tyr Cys
                85                  90                  95

Ala Arg Gly Ser Asn Pro Tyr Tyr Tyr Ala Met Asp Tyr Trp Gly Gln
            100                 105                 110

Gly Thr Ser Val Thr Val Ser Ser
        115                 120

<210> SEQ ID NO 221
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Ile Val Leu Thr Gln Ser Pro Ala Thr Leu Ser Ala Ser Pro Gly
1               5                   10                  15

Glu Lys Ala Thr Met Thr Cys Ser Ala Ser Ser Gly Val Asn Tyr Met
            20                  25                  30

His Trp Tyr Gln Gln Lys Pro Gly Thr Ser Pro Lys Arg Trp Ile Tyr
        35                  40                  45

Asp Thr Asp Lys Thr Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys
            100
```

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ser Asn Trp Met His
1               5

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Glu Ile Asp Pro Ser Asp Ser Tyr Thr Asn
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Ser Asn Pro Tyr Tyr Tyr Ala Met Asp Tyr
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ser Ala Ser Ser Gly Val Asn Tyr Met His
1               5                   10

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Asp Thr Asp Lys Thr Ala Ser
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

His Gln Arg Gly Ser Tyr Thr
1               5

<210> SEQ ID NO 228
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Ser
            20                  25                  30

Trp Ile Gly Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Thr Met Ile Trp Gly Val Ile Ile Asp Phe Trp Gly
            100                 105                 110

Gln Gly Thr Leu Val Thr Val Ser Ser
        115                 120

<210> SEQ ID NO 229
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105

<210> SEQ ID NO 230
<211> LENGTH: 5
<212> TYPE: PRT
<213> ORGANISM: Artificial Sequence
<220> FEATURE:
<223> OTHER INFORMATION: Description of Artificial Sequence: Synthetic

```
                          peptide

<400> SEQUENCE: 230

Ser Ser Trp Ile Gly
1               5

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ile Ile Tyr Pro Asp Asp Ser Asp Thr Arg Tyr Ser Pro Ser Phe Gln
1               5                   10                  15

Gly

<210> SEQ ID NO 232
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

His Val Thr Met Ile Trp Gly Val Ile Ile Asp Phe
1               5                   10

<210> SEQ ID NO 233
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Arg Ala Ser Gln Gly Ile Ser Ser Ala Leu Ala
1               5                   10

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asp Ala Ser Ser Leu Glu Ser
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gln Gln Phe Asn Ser Tyr Pro Phe Thr
1               5
```

```
<210> SEQ ID NO 236
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser
            20                  25                  30

Trp Ile Gly Trp Val Arg Gln Met Pro Gly Lys Gly Leu Glu Trp Met
            35                  40                  45

Gly Ile Ile Tyr Pro Asp Asp Ser Asp Thr Arg Tyr Ser Pro Ser Phe
50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Thr Met Ile Trp Gly Val Ile Ile Asp Phe Trp Gly
            100                 105                 110

Gln Gly Thr Leu Val Thr Val Ser Ser
        115                 120

<210> SEQ ID NO 237
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105

<210> SEQ ID NO 238
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ser Ser Trp Ile Gly
```

```
1               5

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ile Ile Tyr Pro Asp Asp Ser Asp Thr Arg Tyr Ser Pro Ser Phe Gln
1               5                   10                  15

Gly

<210> SEQ ID NO 240
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

His Val Thr Met Ile Trp Gly Val Ile Ile Asp Phe
1               5                   10

<210> SEQ ID NO 241
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Arg Ala Ser Gln Gly Ile Ser Ser Ala Leu Ala
1               5                   10

<210> SEQ ID NO 242
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Asp Ala Ser Ser Leu Glu Ser
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gln Gln Phe Asn Ser Tyr Pro Tyr Thr
1               5

<210> SEQ ID NO 244
<211> LENGTH: 119
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 244

Gln Val Gln Leu Val Gln Ser Gly Ala Glu Val Lys Lys Pro Gly Ser
1               5                   10                  15

Ser Val Lys Val Ser Cys Lys Asp Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Gln Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Ala Asp Trp Leu Asp Pro Trp Gly Gln Gly
            100                 105                 110

Thr Leu Val Thr Val Ser Ser
            115

<210> SEQ ID NO 245
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Arg
                85                  90                  95

Phe Thr Phe Gly Pro Gly Thr Lys Val Asp Ile Lys
            100                 105

<210> SEQ ID NO 246
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ser Tyr Ala Ile Ser
1               5

<210> SEQ ID NO 247
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Ile Ile Pro Ile Phe Gly Thr Thr Asn Tyr Ala Gln Gln Phe Gln
1               5                   10                  15

Gly

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Glu Ala Val Ala Ala Asp Trp Leu Asp Pro
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Arg Ala Ser Gln Ser Val Ser Ser Tyr Leu Ala
1               5                   10

<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gly Ala Ser Ser Arg Ala Thr
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gln Gln Tyr Gly Ser Ser Arg Phe Thr
1               5

<210> SEQ ID NO 252
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252
```

-continued

```
Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Tyr Ser Ser Gly Trp Asp Ser Tyr Tyr Gly Met Gly
            100                 105                 110

Val Trp Gly Gln Gly Thr Thr Val Thr Val Ser Ser
        115                 120
```

<210> SEQ ID NO 253
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105
```

<210> SEQ ID NO 254
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

```
Ser Tyr Trp Ile Ala
1               5
```

<210> SEQ ID NO 255
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 255

Ile Ile Tyr Pro Gly Asp Ser Asp Thr Arg Tyr Ser Pro Ser Phe Gln
1               5                   10                  15

Gly

<210> SEQ ID NO 256
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gln Gly Tyr Ser Ser Gly Trp Asp Ser Tyr Tyr Gly Met Gly Val
1               5                   10                  15

<210> SEQ ID NO 257
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Arg Ala Ser Gln Gly Ile Ser Ser Ala Leu Ala
1               5                   10

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Asp Ala Ser Ser Leu Glu Ser
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gln Gln Phe Asn Ser Tyr Pro Tyr Thr
1               5

<210> SEQ ID NO 260
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                   20                  25                  30
Thr Ile Asn Trp Val Arg Gln Ala Pro Gly Gln Gly Leu Glu Trp Met
                35                  40                  45

Gly Gly Ile Ile Pro Ile Phe Gly Ile Pro Asn Tyr Ala Gln Lys Phe
        50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ala Glu Asp Thr Ala Val Tyr Tyr Cys
                85                  90                  95

Ala Arg Ala Ser Gly Gly Ser Ala Asp Tyr Ser Tyr Gly Met Asp Val
            100                 105                 110

Trp Gly Gln Gly Thr Ala Val Thr Val Ser Ser
            115                 120
```

<210> SEQ ID NO 261
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 261

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Arg Tyr Pro Tyr
                85                  90                  95

Thr Phe Gly Gln Gly Thr Lys Leu Glu Ile Lys
            100                 105
```

<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 262

```
Ser Tyr Thr Ile Asn
1               5
```

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 263

```
Gly Ile Ile Pro Ile Phe Gly Ile Pro Asn Tyr Ala Gln Lys Phe Gln
1               5                   10                  15
```

Gly

<210> SEQ ID NO 264
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ala Ser Gly Gly Ser Ala Asp Tyr Ser Tyr Gly Met Asp Val
1               5                   10

<210> SEQ ID NO 265
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Arg Ala Ser Gln Gly Ile Ser Ser Trp Leu Ala
1               5                   10

<210> SEQ ID NO 266
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ala Ala Ser Ser Leu Gln Ser
1               5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gln Gln Tyr Lys Arg Tyr Pro Tyr Thr
1               5

<210> SEQ ID NO 268
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Glu Val Gln Leu Val Gln Ser Gly Ala Glu Val Lys Lys Pro Gly Glu
1               5                   10                  15

Ser Leu Asn Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
            50                  55                  60

Gln Gly Gln Val Thr Ile Ser Ala Asp Lys Ser Ile Asn Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Val Ser Met Ile Trp Gly Val Ile Met Asp Val Trp Gly
            100                 105                 110

Gln Gly Thr Thr Val Thr Val Ser Ser
            115                 120

<210> SEQ ID NO 269
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
            20                  25                  30

Leu Ala Trp Tyr Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Trp
                 85                  90                  95

Thr Phe Gly Gln Gly Thr Lys Val Glu Ile Lys
            100                 105

<210> SEQ ID NO 270
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ser Tyr Trp Ile Gly
 1               5

<210> SEQ ID NO 271
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ile Ile Tyr Pro Gly Asp Ser Asp Thr Arg Tyr Ser Pro Ser Phe Gln
 1               5                  10                  15

Gly

<210> SEQ ID NO 272

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gly Val Ser Met Ile Trp Gly Val Ile Met Asp Val
1               5                   10

<210> SEQ ID NO 273
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Arg Ala Ser Gln Gly Ile Ser Ser Ala Leu Ala
1               5                   10

<210> SEQ ID NO 274
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Asp Ala Ser Ser Leu Glu Ser
1               5

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gln Gln Phe Asn Ser Tyr Pro Trp Thr
1               5

<210> SEQ ID NO 276
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Glu Val Gln Leu Val Gln Ser Gly Ala Glu Val Lys Lys Pro Gly Glu
1               5                   10                  15

Ser Leu Gln Ile Ser Cys Lys Gly Ser Gly Tyr Thr Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Gly Leu Lys Ala Ser Asp Thr Ala Met Tyr Tyr Cys
            85                  90                  95

Ala Arg Gln Gly Tyr Ser Ser Gly Trp Arg Ser Tyr Tyr Gly Met Gly
            100                 105                 110

Val Trp Gly Gln Gly Thr Thr Val Thr Val Ser Ser
            115                 120

<210> SEQ ID NO 277
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
            85                  90                  95

Thr Phe Gly Gln Gly Thr Lys Leu Glu Ile Lys
            100                 105

<210> SEQ ID NO 278
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Asn Tyr Trp Ile Ala
1               5

<210> SEQ ID NO 279
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ile Ile Tyr Pro Gly Asp Ser Asp Thr Arg Tyr Ser Pro Ser Phe Gln
1               5                   10                  15

Gly

<210> SEQ ID NO 280
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 280

Gln Gly Tyr Ser Ser Gly Trp Arg Ser Tyr Tyr Gly Met Gly Val
1               5                   10                  15

<210> SEQ ID NO 281
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Arg Ala Ser Gln Gly Ile Ser Ser Ala Leu Ala
1               5                   10

<210> SEQ ID NO 282
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Thr Val
                20                  25                  30

Glu Gly Val Asn Ala Leu Lys Asp Glu Ile Leu Lys Ala
            35                  40                  45

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Gln Gln Phe Asn Ser Tyr Pro His Thr
1               5

<210> SEQ ID NO 284
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Glu Val Gln Leu Val Gln Ser Gly Ala Glu Val Lys Lys Pro Gly Glu
1               5                   10                  15

Ser Leu Gln Ile Ser Cys Lys Gly Ser Gly Tyr Thr Phe Thr Asn Tyr
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr

```
                65                  70                  75                  80
Leu Gln Trp Ser Gly Leu Lys Ala Ser Asp Thr Ala Met Tyr Tyr Cys
                    85                  90                  95

Ala Arg Gln Gly Tyr Ser Ser Gly Trp Arg Ser Tyr Tyr Gly Met Gly
                100                 105                 110

Val Trp Gly Gln Gly Thr Thr Val Thr Val Ser Ser
        115                 120

<210> SEQ ID NO 285
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Thr Phe Gly Gln Gly Thr Lys Leu Glu Ile Lys
            100                 105

<210> SEQ ID NO 286
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Asn Tyr Trp Ile Ala
1               5

<210> SEQ ID NO 287
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ile Ile Tyr Pro Gly Asp Ser Asp Thr Arg Tyr Ser Pro Ser Phe Gln
1               5                   10                  15

Gly

<210> SEQ ID NO 288
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 288

Gln Gly Tyr Ser Ser Gly Trp Arg Ser Tyr Tyr Gly Met Gly Val
1               5                   10                  15

<210> SEQ ID NO 289
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Arg Ala Ser Gln Gly Ile Ser Ser Ala Leu Ala
1               5                   10

<210> SEQ ID NO 290
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Asp Ala Ser Ser Leu Glu Ser
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gln Gln Phe Asn Ser Tyr Pro His Thr
1               5

<210> SEQ ID NO 292
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gly Ser Gly Ser Gly Ser Gly Ser Gly Ser Gly Ser Gly Ser Gly Ser
1               5                   10                  15

Gly Ser Gly Ser
            20

<210> SEQ ID NO 293
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gly Gly Ser Gly Gly Ser Gly Gly Ser Gly Gly Ser Gly Gly Ser Gly

```
                1               5                   10                  15
Gly Ser Gly Gly Ser Gly Gly Ser Gly Gly Ser Gly Gly Ser
                        20                  25                  30

<210> SEQ ID NO 294
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Gly Gly Gly Ser Gly Gly Gly Ser Gly Gly Ser Gly Gly Gly Ser
1               5                   10                  15

Gly Gly Gly Ser Gly Gly Gly Ser Gly Gly Gly Ser Gly Gly Gly Ser
                        20                  25                  30

Gly Gly Gly Ser Gly Gly Gly Ser
                35                  40

<210> SEQ ID NO 295
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
                        20                  25                  30

Gly Gly Ser Gly Gly Gly Ser Gly
                35                  40

<210> SEQ ID NO 296
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Gly Gly Ser Gly Gly Gly Gly Ser Gly Gly Gly Gly Ser Gly Gly Gly
1               5                   10                  15

Gly Ser Gly Gly Gly Gly Ser Gly Gly Gly Ser Gly Gly Gly Gly
                        20                  25                  30

Ser Gly Gly Gly Gly Ser Gly Gly Gly Ser Gly Gly Gly Gly Ser
                    35                  40                  45

Gly Gly
    50

<210> SEQ ID NO 297
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297
```

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Ser Gly Gly
                20                  25                  30

Gly Gly Ser Gly Gly Gly Gly Ser Gly Gly Gly Ser Gly Gly Gly
        35                  40                  45

Gly Ser
    50
```

<210> SEQ ID NO 298
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 299
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 299

```
Gly Gly Gly Gly Ser Gly Gly Gly Gly Ser Gly Gly Gly Gly Ser
1               5                   10                  15
```

<210> SEQ ID NO 300
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 300

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Ser Gly Gly Gly
                20                  25                  30

Gly Gly Ser Gly Gly Gly Gly Ser Gly Gly Gly Ser Gly Gly Gly Gly
        35                  40                  45

Gly Ser Gly Gly Gly Gly Ser Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100
```

<210> SEQ ID NO 301
<211> LENGTH: 100
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 301

```
Gly Gly Ser Gly Gly Gly Ser Gly Gly Gly Ser Gly Gly Gly Ser Gly Gly
1               5                   10                  15
Gly Ser Gly Gly Gly Ser Gly Gly Gly Ser Gly Gly Gly Gly
            20                  25                  30
Ser Gly Gly Gly Gly Ser Gly Gly Gly Gly Ser Gly Gly Gly Ser
            35                  40                  45
Gly Gly Gly Gly Ser Gly Gly Gly Gly Ser Gly Gly Gly Gly Ser Gly
    50                  55                  60
Gly Gly Ser Gly Gly Gly Ser Gly Gly Gly Ser Gly Gly
65                  70                  75                  80
Gly Gly Ser Gly Gly Gly Ser Gly Gly Gly Ser Gly Gly
            85                  90                  95
Gly Ser Gly Gly
        100
```

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 302

```
Gly Gly Gly Gly Ser Gly Gly Gly Ser
1               5
```

<210> SEQ ID NO 303
<211> LENGTH: 642
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 303

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Ile Met His Trp Val Arg Gln Ala Pro Gly Gln Gly Leu Glu Trp Met
        35                  40                  45
Gly Tyr Ile Asn Pro Tyr Asn Asp Gly Ser Lys Tyr Thr Glu Lys Phe
    50                  55                  60
Gln Gly Arg Val Thr Met Thr Ser Asp Thr Ser Ile Ser Thr Ala Tyr
65                  70                  75                  80
Met Glu Leu Ser Arg Leu Arg Ser Asp Asp Thr Ala Val Tyr Tyr Cys
            85                  90                  95
Ala Arg Gly Thr Tyr Tyr Tyr Gly Pro Gln Leu Phe Asp Tyr Trp Gly
            100                 105                 110
Gln Gly Thr Thr Val Thr Val Ser Ser Gly Gly Gly Gly Ser Gly Gly
        115                 120                 125
Gly Gly Ser Gly Gly Gly Gly Ser Asp Ile Val Met Thr Gln Thr Pro
    130                 135                 140
```

-continued

```
Leu Ser Leu Ser Val Thr Pro Gly Gln Pro Ala Ser Ile Ser Cys Lys
145                 150                 155                 160

Ser Ser Gln Ser Leu Glu Thr Ser Thr Gly Thr Thr Tyr Leu Asn Trp
            165                 170                 175

Tyr Leu Gln Lys Pro Gly Gln Ser Pro Gln Leu Leu Ile Tyr Arg Val
        180                 185                 190

Ser Lys Arg Phe Ser Gly Val Pro Asp Arg Phe Ser Gly Ser Gly Ser
    195                 200                 205

Gly Thr Asp Phe Thr Leu Lys Ile Ser Arg Val Glu Ala Glu Asp Val
210                 215                 220

Gly Val Tyr Tyr Cys Leu Gln Leu Leu Glu Asp Pro Tyr Thr Phe Gly
225                 230                 235                 240

Gln Gly Thr Lys Leu Glu Ile Lys Gly Gly Gly Ser Gly Gly Gly Gly
            245                 250                 255

Ser Asp Ile Val Met Thr Gln Ser Pro Asp Ser Leu Ala Val Ser Leu
        260                 265                 270

Gly Glu Arg Ala Thr Ile Asn Cys Lys Ser Ser Gln Ser Leu Leu Asn
    275                 280                 285

Ala Arg Thr Gly Lys Asn Tyr Leu Ala Trp Tyr Gln Gln Lys Pro Gly
290                 295                 300

Gln Pro Pro Lys Leu Leu Ile Tyr Trp Ala Ser Thr Arg Glu Ser Gly
305                 310                 315                 320

Val Pro Asp Arg Phe Ser Gly Ser Gly Ser Gly Thr Asp Phe Thr Leu
            325                 330                 335

Thr Ile Ser Ser Leu Gln Ala Glu Asp Val Ala Val Tyr Tyr Cys Lys
        340                 345                 350

Gln Ser Tyr Ser Arg Arg Thr Phe Gly Gly Gly Thr Lys Val Glu Ile
    355                 360                 365

Lys Gly Gly Gly Gly Ser Gly Gly Gly Gly Ser Gly Gly Gly Gly Ser
370                 375                 380

Gly Gly Gly Gly Ser Gln Val Gln Leu Val Gln Ser Gly Ala Glu Val
385                 390                 395                 400

Lys Lys Pro Gly Ala Ser Val Lys Val Ser Cys Lys Ala Ser Gly Phe
            405                 410                 415

Asn Ile Lys Asp Tyr Tyr Met His Trp Val Arg Gln Ala Pro Gly Gln
        420                 425                 430

Arg Leu Glu Trp Met Gly Trp Ile Asp Leu Glu Asn Ala Asn Thr Ile
    435                 440                 445

Tyr Asp Ala Lys Phe Gln Gly Arg Val Thr Ile Thr Arg Asp Thr Ser
450                 455                 460

Ala Ser Thr Ala Tyr Met Glu Leu Ser Ser Leu Arg Ser Glu Asp Thr
465                 470                 475                 480

Ala Val Tyr Tyr Cys Ala Arg Asp Ala Tyr Gly Arg Tyr Phe Tyr Asp
            485                 490                 495

Val Trp Gly Gln Gly Thr Leu Val Thr Val Ser Ser Gly Gly Gly Gly
        500                 505                 510

Ser Gly Gly Gly Ser Glu Val Gln Leu Val Glu Ser Gly Gly Gly Leu
    515                 520                 525

Val Gln Pro Gly Asn Ser Leu Arg Leu Ser Cys Ala Ala Ser Gly Phe
530                 535                 540

Thr Phe Ser Ser Phe Gly Met Ser Trp Val Arg Gln Ala Pro Gly Lys
545                 550                 555                 560
```

Gly Leu Glu Trp Val Ser Ser Ile Ser Gly Ser Gly Ser Asp Thr Leu
                565                 570                 575

Tyr Ala Asp Ser Val Lys Gly Arg Phe Thr Ile Ser Arg Asp Asn Ala
            580                 585                 590

Lys Thr Thr Leu Tyr Leu Gln Met Asn Ser Leu Arg Pro Glu Asp Thr
            595                 600                 605

Ala Val Tyr Tyr Cys Thr Ile Gly Gly Ser Leu Ser Arg Ser Ser Gln
610                 615                 620

Gly Thr Leu Val Thr Val Ser Ser His His His His His His His His
625                 630                 635                 640

His His

<210> SEQ ID NO 304
<211> LENGTH: 642
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Ser Gly Gly Gly Gly Ser Gly
        115                 120                 125

Gly Gly Gly Ser Gln Val Gln Leu Val Gln Ser Gly Ala Glu Val Lys
130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser Gly Gly Gly Gly Ser
                245                 250                 255

Gly Gly Gly Ser Gln Val Gln Leu Val Gln Ser Gly Ala Glu Val Lys
            260                 265                 270

```
Lys Pro Gly Ala Ser Val Lys Val Ser Cys Lys Ala Ser Gly Tyr Thr
            275                 280                 285

Phe Thr Asp Tyr Ile Met His Trp Val Arg Gln Ala Pro Gly Gln Gly
            290                 295                 300

Leu Glu Trp Met Gly Tyr Ile Asn Pro Tyr Asn Asp Gly Ser Lys Tyr
305                 310                 315                 320

Thr Glu Lys Phe Gln Gly Arg Val Thr Met Thr Ser Asp Thr Ser Ile
                325                 330                 335

Ser Thr Ala Tyr Met Glu Leu Ser Arg Leu Arg Ser Asp Asp Thr Ala
            340                 345                 350

Val Tyr Tyr Cys Ala Arg Gly Thr Tyr Tyr Gly Pro Gln Leu Phe
            355                 360                 365

Asp Tyr Trp Gly Gln Gly Thr Thr Val Thr Val Ser Ser Gly Gly Gly
            370                 375                 380

Gly Ser Gly Gly Gly Gly Ser Gly Gly Gly Gly Ser Asp Ile Val Met
385                 390                 395                 400

Thr Gln Thr Pro Leu Ser Leu Ser Val Thr Pro Gly Gln Pro Ala Ser
                405                 410                 415

Ile Ser Cys Lys Ser Ser Gln Ser Leu Glu Thr Ser Thr Gly Thr Thr
            420                 425                 430

Tyr Leu Asn Trp Tyr Leu Gln Lys Pro Gly Gln Ser Pro Gln Leu Leu
            435                 440                 445

Ile Tyr Arg Val Ser Lys Arg Phe Ser Gly Val Pro Asp Arg Phe Ser
            450                 455                 460

Gly Ser Gly Ser Gly Thr Asp Phe Thr Leu Lys Ile Ser Arg Val Glu
465                 470                 475                 480

Ala Glu Asp Val Gly Val Tyr Tyr Cys Leu Gln Leu Leu Glu Asp Pro
                485                 490                 495

Tyr Thr Phe Gly Gln Gly Thr Lys Leu Glu Ile Lys Gly Gly Gly Gly
            500                 505                 510

Ser Gly Gly Gly Ser Glu Val Gln Leu Val Glu Ser Gly Gly Gly Leu
            515                 520                 525

Val Gln Pro Gly Asn Ser Leu Arg Leu Ser Cys Ala Ala Ser Gly Phe
530                 535                 540

Thr Phe Ser Ser Phe Gly Met Ser Trp Val Arg Gln Ala Pro Gly Lys
545                 550                 555                 560

Gly Leu Glu Trp Val Ser Ser Ile Ser Gly Ser Gly Ser Asp Thr Leu
                565                 570                 575

Tyr Ala Asp Ser Val Lys Gly Arg Phe Thr Ile Ser Arg Asp Asn Ala
            580                 585                 590

Lys Thr Thr Leu Tyr Leu Gln Met Asn Ser Leu Arg Pro Glu Asp Thr
            595                 600                 605

Ala Val Tyr Tyr Cys Thr Ile Gly Gly Ser Leu Ser Arg Ser Ser Gln
            610                 615                 620

Gly Thr Leu Val Thr Val Ser Ser His His His His His His
625                 630                 635                 640

His His
```

<210> SEQ ID NO 305
<211> LENGTH: 642
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 305

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Ser Gly Gly Gly Ser Gly
        115                 120                 125

Gly Gly Gly Ser Gln Val Gln Leu Val Gln Ser Gly Ala Glu Val Lys
130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Asn Ser Leu Arg Leu Ser Cys Ala Ala Ser Gly Phe Thr
        275                 280                 285

Phe Ser Ser Phe Gly Met Ser Trp Val Arg Gln Ala Pro Gly Lys Gly
290                 295                 300

Leu Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
                325                 330                 335

Thr Thr Leu Tyr Leu Gln Met Asn Ser Leu Arg Pro Glu Asp Thr Ala
            340                 345                 350

Val Tyr Tyr Cys Thr Ile Gly Gly Ser Leu Ser Arg Ser Ser Gln Gly
        355                 360                 365

Thr Leu Val Thr Val Ser Ser Gly Gly Gly Gly Ser Gly Gly Gly Ser
370                 375                 380

Gln Val Gln Leu Val Gln Ser Gly Ala Glu Val Lys Lys Pro Gly Ala
385                 390                 395                 400

Ser Val Lys Val Ser Cys Lys Ala Ser Gly Tyr Thr Phe Thr Asp Tyr

```
            405                 410                 415
Ile Met His Trp Val Arg Gln Ala Pro Gly Gln Gly Leu Glu Trp Met
            420                 425                 430

Gly Tyr Ile Asn Pro Tyr Asn Asp Gly Ser Lys Tyr Thr Glu Lys Phe
            435                 440                 445

Gln Gly Arg Val Thr Met Thr Ser Asp Thr Ser Ile Ser Thr Ala Tyr
450                 455                 460

Met Glu Leu Ser Arg Leu Arg Ser Asp Asp Thr Ala Val Tyr Tyr Cys
465                 470                 475                 480

Ala Arg Gly Thr Tyr Tyr Tyr Gly Pro Gln Leu Phe Asp Tyr Trp Gly
                485                 490                 495

Gln Gly Thr Thr Val Thr Val Ser Ser Gly Gly Gly Ser Gly Gly
            500                 505                 510

Gly Gly Ser Gly Gly Gly Ser Asp Ile Val Met Thr Gln Thr Pro
            515                 520                 525

Leu Ser Leu Ser Val Thr Pro Gly Gln Pro Ala Ser Ile Ser Cys Lys
530                 535                 540

Ser Ser Gln Ser Leu Glu Thr Ser Thr Gly Thr Thr Tyr Leu Asn Trp
545                 550                 555                 560

Tyr Leu Gln Lys Pro Gly Gln Ser Pro Gln Leu Leu Ile Tyr Arg Val
                565                 570                 575

Ser Lys Arg Phe Ser Gly Val Pro Asp Arg Phe Ser Gly Ser Gly Ser
                580                 585                 590

Gly Thr Asp Phe Thr Leu Lys Ile Ser Arg Val Glu Ala Glu Asp Val
                595                 600                 605

Gly Val Tyr Tyr Cys Leu Gln Leu Leu Glu Asp Pro Tyr Thr Phe Gly
            610                 615                 620

Gln Gly Thr Lys Leu Glu Ile Lys His His His His His His His
625                 630                 635                 640

His His

<210> SEQ ID NO 306
<211> LENGTH: 642
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Asp Ile Val Met
```

|     |     |     |     | 115 |     |     |     | 120 |     |     |     | 125 |     |     |
| --- | --- | --- | --- | --- | --- | --- | --- | --- | --- | --- | --- | --- | --- | --- |
| Thr | Gln | Ser | Pro | Asp | Ser | Leu | Ala | Val | Ser | Leu | Gly | Glu | Arg | Ala | Thr |
|     |     |     |     |     |     |     |     |     |     |     |     |     |     |     |
| 130 |     |     |     | 135 |     |     |     | 140 |     |     |     |     |     |     |
| Ile | Asn | Cys | Lys | Ser | Ser | Gln | Ser | Leu | Leu | Asn | Ala | Arg | Thr | Gly | Lys |
| 145 |     |     |     | 150 |     |     |     | 155 |     |     |     |     |     |     | 160 |
| Asn | Tyr | Leu | Ala | Trp | Tyr | Gln | Gln | Lys | Pro | Gly | Gln | Pro | Pro | Lys | Leu |
|     |     |     |     | 165 |     |     |     | 170 |     |     |     | 175 |     |     |     |
| Leu | Ile | Tyr | Trp | Ala | Ser | Thr | Arg | Glu | Ser | Gly | Val | Pro | Asp | Arg | Phe |
|     |     |     | 180 |     |     |     | 185 |     |     |     | 190 |     |     |     |     |
| Ser | Gly | Ser | Gly | Ser | Gly | Thr | Asp | Phe | Thr | Leu | Thr | Ile | Ser | Ser | Leu |
|     | 195 |     |     |     |     | 200 |     |     |     | 205 |     |     |     |     |     |
| Gln | Ala | Glu | Asp | Val | Ala | Val | Tyr | Tyr | Cys | Lys | Gln | Ser | Tyr | Ser | Arg |
| 210 |     |     |     |     | 215 |     |     |     | 220 |     |     |     |     |     |     |
| Arg | Thr | Phe | Gly | Gly | Gly | Thr | Lys | Val | Glu | Ile | Lys | Gly | Gly | Gly | Gly |
| 225 |     |     |     |     | 230 |     |     |     | 235 |     |     |     |     |     | 240 |
| Ser | Gly | Gly | Gly | Gly | Ser | Gly | Gly | Gly | Ser | Gly | Gly | Gly | Gly | Ser |     |
|     |     |     |     | 245 |     |     |     | 250 |     |     |     | 255 |     |     |     |
| Gln | Val | Gln | Leu | Val | Gln | Ser | Gly | Ala | Glu | Val | Lys | Lys | Pro | Gly | Ala |
|     | 260 |     |     |     |     | 265 |     |     |     | 270 |     |     |     |     |     |
| Ser | Val | Lys | Val | Ser | Cys | Lys | Ala | Ser | Gly | Phe | Asn | Ile | Lys | Asp | Tyr |
|     | 275 |     |     |     | 280 |     |     |     | 285 |     |     |     |     |     |     |
| Tyr | Met | His | Trp | Val | Arg | Gln | Ala | Pro | Gly | Gln | Arg | Leu | Glu | Trp | Met |
| 290 |     |     |     |     | 295 |     |     |     | 300 |     |     |     |     |     |     |
| Gly | Trp | Ile | Asp | Leu | Glu | Asn | Ala | Asn | Thr | Ile | Tyr | Asp | Ala | Lys | Phe |
| 305 |     |     |     | 310 |     |     |     | 315 |     |     |     |     |     |     | 320 |
| Gln | Gly | Arg | Val | Thr | Ile | Thr | Arg | Asp | Thr | Ser | Ala | Ser | Thr | Ala | Tyr |
|     |     |     |     | 325 |     |     |     | 330 |     |     |     | 335 |     |     |     |
| Met | Glu | Leu | Ser | Ser | Leu | Arg | Ser | Glu | Asp | Thr | Ala | Val | Tyr | Tyr | Cys |
|     |     |     | 340 |     |     |     | 345 |     |     |     | 350 |     |     |     |     |
| Ala | Arg | Asp | Ala | Tyr | Gly | Arg | Tyr | Phe | Tyr | Asp | Val | Trp | Gly | Gln | Gly |
|     |     |     | 355 |     |     |     | 360 |     |     |     | 365 |     |     |     |     |
| Thr | Leu | Val | Thr | Val | Ser | Ser | Gly | Gly | Gly | Gly | Ser | Gly | Gly | Gly | Ser |
|     | 370 |     |     |     |     | 375 |     |     |     | 380 |     |     |     |     |     |
| Gln | Val | Gln | Leu | Val | Gln | Ser | Gly | Ala | Glu | Val | Lys | Lys | Pro | Gly | Ala |
| 385 |     |     |     |     | 390 |     |     |     | 395 |     |     |     |     |     | 400 |
| Ser | Val | Lys | Val | Ser | Cys | Lys | Ala | Ser | Gly | Tyr | Thr | Phe | Thr | Asp | Tyr |
|     |     |     |     | 405 |     |     |     | 410 |     |     |     | 415 |     |     |     |
| Ile | Met | His | Trp | Val | Arg | Gln | Ala | Pro | Gly | Gln | Gly | Leu | Glu | Trp | Met |
|     |     |     | 420 |     |     |     | 425 |     |     |     | 430 |     |     |     |     |
| Gly | Tyr | Ile | Asn | Pro | Tyr | Asn | Asp | Gly | Ser | Lys | Tyr | Thr | Glu | Lys | Phe |
|     | 435 |     |     |     |     | 440 |     |     |     | 445 |     |     |     |     |     |
| Gln | Gly | Arg | Val | Thr | Met | Thr | Ser | Asp | Thr | Ser | Ile | Ser | Thr | Ala | Tyr |
|     | 450 |     |     |     |     | 455 |     |     |     | 460 |     |     |     |     |     |
| Met | Glu | Leu | Ser | Arg | Leu | Arg | Ser | Asp | Asp | Thr | Ala | Val | Tyr | Tyr | Cys |
| 465 |     |     |     |     | 470 |     |     |     | 475 |     |     |     |     |     | 480 |
| Ala | Arg | Gly | Thr | Tyr | Tyr | Tyr | Gly | Pro | Gln | Leu | Phe | Asp | Tyr | Trp | Gly |
|     |     |     |     | 485 |     |     |     | 490 |     |     |     | 495 |     |     |     |
| Gln | Gly | Thr | Thr | Val | Thr | Val | Ser | Gly | Gly | Gly | Gly | Ser | Gly | Gly |     |
|     |     |     | 500 |     |     |     | 505 |     |     |     | 510 |     |     |     |     |
| Gly | Gly | Ser | Gly | Gly | Gly | Gly | Ser | Asp | Ile | Val | Met | Thr | Gln | Thr | Pro |
|     |     |     | 515 |     |     |     | 520 |     |     |     | 525 |     |     |     |     |
| Leu | Ser | Leu | Ser | Val | Thr | Pro | Gly | Gln | Pro | Ala | Ser | Ile | Ser | Cys | Lys |
| 530 |     |     |     |     | 535 |     |     |     | 540 |     |     |     |     |     |     |

Ser Ser Gln Ser Leu Glu Thr Ser Thr Gly Thr Thr Tyr Leu Asn Trp
545                 550                 555                 560

Tyr Leu Gln Lys Pro Gly Gln Ser Pro Gln Leu Leu Ile Tyr Arg Val
                565                 570                 575

Ser Lys Arg Phe Ser Gly Val Pro Asp Arg Phe Ser Gly Ser Gly Ser
            580                 585                 590

Gly Thr Asp Phe Thr Leu Lys Ile Ser Arg Val Glu Ala Glu Asp Val
        595                 600                 605

Gly Val Tyr Tyr Cys Leu Gln Leu Leu Glu Asp Pro Tyr Thr Phe Gly
    610                 615                 620

Gln Gly Thr Lys Leu Glu Ile Lys His His His His His His His His
625                 630                 635                 640

His His

<210> SEQ ID NO 307
<211> LENGTH: 642
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gln Val Gln Leu
        115                 120                 125

Val Gln Ser Gly Ala Glu Val Lys Lys Pro Gly Ala Ser Val Lys Val
    130                 135                 140

Ser Cys Lys Ala Ser Gly Tyr Thr Phe Thr Asp Tyr Ile Met His Trp
145                 150                 155                 160

Val Arg Gln Ala Pro Gly Gln Gly Leu Glu Trp Met Gly Tyr Ile Asn
                165                 170                 175

Pro Tyr Asn Asp Gly Ser Lys Tyr Thr Glu Lys Phe Gln Gly Arg Val
            180                 185                 190

Thr Met Thr Ser Asp Thr Ser Ile Ser Thr Ala Tyr Met Glu Leu Ser
        195                 200                 205

Arg Leu Arg Ser Asp Asp Thr Ala Val Tyr Tyr Cys Ala Arg Gly Thr
    210                 215                 220

Tyr Tyr Tyr Gly Pro Gln Leu Phe Asp Tyr Trp Gly Gln Gly Thr Thr
225                 230                 235                 240

Val Thr Val Ser Ser Gly Gly Gly Gly Ser Gly Gly Gly Gly Ser Gly
                245                 250                 255

-continued

Gly Gly Gly Ser Asp Ile Val Met Thr Gln Thr Pro Leu Ser Leu Ser
            260                 265                 270

Val Thr Pro Gly Gln Pro Ala Ser Ile Ser Cys Lys Ser Ser Gln Ser
        275                 280                 285

Leu Glu Thr Ser Thr Gly Thr Thr Tyr Leu Asn Trp Tyr Leu Gln Lys
    290                 295                 300

Pro Gly Gln Ser Pro Gln Leu Leu Ile Tyr Arg Val Ser Lys Arg Phe
305                 310                 315                 320

Ser Gly Val Pro Asp Arg Phe Ser Gly Ser Gly Ser Gly Thr Asp Phe
                325                 330                 335

Thr Leu Lys Ile Ser Arg Val Glu Ala Glu Asp Val Gly Val Tyr Tyr
            340                 345                 350

Cys Leu Gln Leu Leu Glu Asp Pro Tyr Thr Phe Gly Gln Gly Thr Lys
        355                 360                 365

Leu Glu Ile Lys Gly Gly Gly Gly Ser Gly Gly Gly Ser Asp Ile Val
    370                 375                 380

Met Thr Gln Ser Pro Asp Ser Leu Ala Val Ser Leu Gly Glu Arg Ala
385                 390                 395                 400

Thr Ile Asn Cys Lys Ser Ser Gln Ser Leu Leu Asn Ala Arg Thr Gly
                405                 410                 415

Lys Asn Tyr Leu Ala Trp Tyr Gln Gln Lys Pro Gly Gln Pro Pro Lys
            420                 425                 430

Leu Leu Ile Tyr Trp Ala Ser Thr Arg Glu Ser Gly Val Pro Asp Arg
        435                 440                 445

Phe Ser Gly Ser Gly Ser Gly Thr Asp Phe Thr Leu Thr Ile Ser Ser
    450                 455                 460

Leu Gln Ala Glu Asp Val Ala Val Tyr Tyr Cys Lys Gln Ser Tyr Ser
465                 470                 475                 480

Arg Arg Thr Phe Gly Gly Gly Thr Lys Val Glu Ile Lys Gly Gly Gly
                485                 490                 495

Gly Ser Gly Gly Gly Gly Ser Gly Gly Gly Gly Ser Gly Gly Gly Gly
            500                 505                 510

Ser Gln Val Gln Leu Val Gln Ser Gly Ala Glu Val Lys Lys Pro Gly
        515                 520                 525

Ala Ser Val Lys Val Ser Cys Lys Ala Ser Gly Phe Asn Ile Lys Asp
    530                 535                 540

Tyr Tyr Met His Trp Val Arg Gln Ala Pro Gly Gln Arg Leu Glu Trp
545                 550                 555                 560

Met Gly Trp Ile Asp Leu Glu Asn Ala Asn Thr Ile Tyr Asp Ala Lys
                565                 570                 575

Phe Gln Gly Arg Val Thr Ile Thr Arg Asp Thr Ser Ala Ser Thr Ala
            580                 585                 590

Tyr Met Glu Leu Ser Ser Leu Arg Ser Glu Asp Thr Ala Val Tyr Tyr
        595                 600                 605

Cys Ala Arg Asp Ala Tyr Gly Arg Phe Tyr Asp Val Trp Gly Gln
    610                 615                 620

Gly Thr Leu Val Thr Val Ser Ser His His His His His His
625                 630                 635                 640

His His

<210> SEQ ID NO 308
<211> LENGTH: 636
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 308

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Ala
130                 135                 140

Thr Leu Ser Leu Ser Pro Gly Glu Arg Ala Thr Leu Ser Cys Ser Ala
145                 150                 155                 160

Ser Ser Ser Val Ser Tyr Met His Trp Tyr Gln Gln Lys Pro Gly Gln
                165                 170                 175

Ala Pro Arg Leu Leu Ile Tyr Asp Thr Ser Lys Leu Ala Ser Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Phe Ala Val Tyr Tyr Cys Phe Gln
    210                 215                 220

Gly Ser Val Tyr Pro Phe Thr Phe Gly Gln Gly Thr Lys Leu Glu Ile
225                 230                 235                 240

Lys Arg Gly Gly Gly Gly Ser Gly Gly Gly Ser Asp Ile Val Met Thr
                245                 250                 255

Gln Ser Pro Asp Ser Leu Ala Val Ser Leu Gly Glu Arg Ala Thr Ile
            260                 265                 270

Asn Cys Lys Ser Ser Gln Ser Leu Leu Asn Ala Arg Thr Gly Lys Asn
        275                 280                 285

Tyr Leu Ala Trp Tyr Gln Gln Lys Pro Gly Gln Pro Pro Lys Leu Leu
    290                 295                 300

Ile Tyr Trp Ala Ser Thr Arg Glu Ser Gly Val Pro Asp Arg Phe Ser
305                 310                 315                 320

Gly Ser Gly Ser Gly Thr Asp Phe Thr Leu Thr Ile Ser Ser Leu Gln
                325                 330                 335

Ala Glu Asp Val Ala Val Tyr Tyr Cys Lys Gln Ser Tyr Ser Arg Arg
            340                 345                 350

Thr Phe Gly Gly Gly Thr Lys Val Glu Ile Lys Gly Gly Gly Gly Ser
        355                 360                 365

Gly Gly Gly Gly Ser Gly Gly Gly Ser Gly Gly Gly Gly Ser Gln
370                 375                 380

Val Gln Leu Val Gln Ser Gly Ala Glu Val Lys Lys Pro Gly Ala Ser
385                 390                 395                 400

Val Lys Val Ser Cys Lys Ala Ser Gly Phe Asn Ile Lys Asp Tyr Tyr
            405                 410                 415

Met His Trp Val Arg Gln Ala Pro Gly Gln Arg Leu Glu Trp Met Gly
        420                 425                 430

Trp Ile Asp Leu Glu Asn Ala Asn Thr Ile Tyr Asp Ala Lys Phe Gln
    435                 440                 445

Gly Arg Val Thr Ile Thr Arg Asp Thr Ser Ala Ser Thr Ala Tyr Met
450                 455                 460

Glu Leu Ser Ser Leu Arg Ser Glu Asp Thr Ala Val Tyr Tyr Cys Ala
465                 470                 475                 480

Arg Asp Ala Tyr Gly Arg Tyr Phe Tyr Asp Val Trp Gly Gln Gly Thr
                485                 490                 495

Leu Val Thr Val Ser Ser Gly Gly Gly Ser Gly Gly Gly Ser Glu
            500                 505                 510

Val Gln Leu Val Glu Ser Gly Gly Gly Leu Val Gln Pro Gly Asn Ser
        515                 520                 525

Leu Arg Leu Ser Cys Ala Ala Ser Gly Phe Thr Phe Ser Ser Phe Gly
    530                 535                 540

Met Ser Trp Val Arg Gln Ala Pro Gly Lys Gly Leu Glu Trp Val Ser
545                 550                 555                 560

Ser Ile Ser Gly Ser Gly Ser Asp Thr Leu Tyr Ala Asp Ser Val Lys
                565                 570                 575

Gly Arg Phe Thr Ile Ser Arg Asp Asn Ala Lys Thr Thr Leu Tyr Leu
            580                 585                 590

Gln Met Asn Ser Leu Arg Pro Glu Asp Thr Ala Val Tyr Tyr Cys Thr
        595                 600                 605

Ile Gly Gly Ser Leu Ser Arg Ser Ser Gln Gly Thr Leu Val Thr Val
    610                 615                 620

Ser Ser His His His His His His His His
625                 630                 635

<210> SEQ ID NO 309
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Glu Ile Val Leu Thr Gln Ser Pro Ala
            130                 135                 140

Thr Leu Ser Leu Ser Pro Gly Glu Arg Ala Thr Leu Ser Cys Ser Ala
145                 150                 155                 160

Ser Ser Ser Val Ser Tyr Met His Trp Tyr Gln Gln Lys Pro Gly Gln
                165                 170                 175

Ala Pro Arg Leu Leu Ile Tyr Asp Thr Ser Lys Leu Ala Ser Gly Ile
            180                 185                 190

Pro Ala Arg Phe Ser Gly Ser Gly Ser Gly Thr Asp Phe Thr Leu Thr
            195                 200                 205

Ile Ser Ser Leu Glu Pro Glu Asp Phe Ala Val Tyr Tyr Cys Phe Gln
210                 215                 220

Gly Ser Val Tyr Pro Phe Thr Phe Gly Gln Gly Thr Lys Leu Glu Ile
225                 230                 235                 240

Lys Arg Gly Gly Gly Gly Ser Gly Gly Gly Ser Glu Val Gln Leu Val
            245                 250                 255

Glu Ser Gly Gly Gly Leu Val Gln Pro Gly Asn Ser Leu Arg Leu Ser
            260                 265                 270

Cys Ala Ala Ser Gly Phe Thr Phe Ser Ser Phe Gly Met Ser Trp Val
            275                 280                 285

Arg Gln Ala Pro Gly Lys Gly Leu Glu Trp Val Ser Ser Ile Ser Gly
            290                 295                 300

Ser Gly Ser Asp Thr Leu Tyr Ala Asp Ser Val Lys Gly Arg Phe Thr
305                 310                 315                 320

Ile Ser Arg Asp Asn Ala Lys Thr Thr Leu Tyr Leu Gln Met Asn Ser
                325                 330                 335

Leu Arg Pro Glu Asp Thr Ala Val Tyr Tyr Cys Thr Ile Gly Gly Ser
            340                 345                 350

Leu Ser Arg Ser Ser Gln Gly Thr Leu Val Thr Val Ser Ser Gly Gly
            355                 360                 365

Gly Gly Ser Gly Gly Gly Ser Asp Ile Val Met Thr Gln Ser Pro Asp
370                 375                 380

Ser Leu Ala Val Ser Leu Gly Glu Arg Ala Thr Ile Asn Cys Lys Ser
385                 390                 395                 400

Ser Gln Ser Leu Leu Asn Ala Arg Thr Gly Lys Asn Tyr Leu Ala Trp
            405                 410                 415

Tyr Gln Gln Lys Pro Gly Gln Pro Pro Lys Leu Leu Ile Tyr Trp Ala
            420                 425                 430

Ser Thr Arg Glu Ser Gly Val Pro Asp Arg Phe Ser Gly Ser Gly Ser
            435                 440                 445

Gly Thr Asp Phe Thr Leu Thr Ile Ser Ser Leu Gln Ala Glu Asp Val
            450                 455                 460

Ala Val Tyr Tyr Cys Lys Gln Ser Tyr Ser Arg Arg Thr Phe Gly Gly
465                 470                 475                 480

Gly Thr Lys Val Glu Ile Lys Gly Gly Gly Gly Ser Gly Gly Gly Gly
            485                 490                 495

Ser Gly Gly Gly Gly Ser Gly Gly Gly Ser Gln Val Gln Leu Val
            500                 505                 510

Gln Ser Gly Ala Glu Val Lys Lys Pro Gly Ala Ser Val Lys Val Ser
            515                 520                 525

```
Cys Lys Ala Ser Gly Phe Asn Ile Lys Asp Tyr Tyr Met His Trp Val
    530                 535                 540

Arg Gln Ala Pro Gly Gln Arg Leu Glu Trp Met Gly Trp Ile Asp Leu
545                 550                 555                 560

Glu Asn Ala Asn Thr Ile Tyr Asp Ala Lys Phe Gln Gly Arg Val Thr
                565                 570                 575

Ile Thr Arg Asp Thr Ser Ala Ser Thr Ala Tyr Met Glu Leu Ser Ser
                580                 585                 590

Leu Arg Ser Glu Asp Thr Ala Val Tyr Tyr Cys Ala Arg Asp Ala Tyr
        595                 600                 605

Gly Arg Tyr Phe Tyr Asp Val Trp Gly Gln Gly Thr Leu Val Thr Val
        610                 615                 620

Ser Ser His His His His His His His His
625                 630                 635

<210> SEQ ID NO 310
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Gln Val Gln Leu Val Gln Ser Gly Ala Glu Val Lys
    130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser Gly Gly Gly Gly Ser
                245                 250                 255
```

Gly Gly Gly Ser Gln Val Gln Leu Gln Glu Ser Gly Pro Gly Leu Val
            260                 265                 270

Lys Pro Ser Gln Thr Leu Ser Leu Thr Cys Thr Val Ser Gly Gly Ser
            275                 280                 285

Ile Ser Thr Ser Gly Met Gly Val Gly Trp Ile Arg Gln His Pro Gly
        290                 295                 300

Lys Gly Leu Glu Trp Ile Gly His Ile Trp Trp Asp Asp Lys Arg
305             310                 315                 320

Tyr Asn Pro Ala Leu Lys Ser Arg Val Thr Ile Ser Val Asp Thr Ser
                325                 330                 335

Lys Asn Gln Phe Ser Leu Lys Leu Ser Ser Val Thr Ala Ala Asp Thr
            340                 345                 350

Ala Val Tyr Tyr Cys Ala Arg Met Glu Leu Trp Ser Tyr Tyr Phe Asp
            355                 360                 365

Tyr Trp Gly Gln Gly Thr Leu Val Thr Val Ser Ser Gly Gly Gly Gly
370                 375                 380

Ser Gly Gly Gly Gly Ser Gly Gly Gly Gly Ser Glu Ile Val Leu Thr
385                 390                 395                 400

Gln Ser Pro Ala Thr Leu Ser Leu Ser Pro Gly Glu Arg Ala Thr Leu
            405                 410                 415

Ser Cys Ser Ala Ser Ser Val Ser Tyr Met His Trp Tyr Gln Gln
            420                 425                 430

Lys Pro Gly Gln Ala Pro Arg Leu Leu Ile Tyr Asp Thr Ser Lys Leu
            435                 440                 445

Ala Ser Gly Ile Pro Ala Arg Phe Ser Gly Ser Gly Ser Gly Thr Asp
450                 455                 460

Phe Thr Leu Thr Ile Ser Ser Leu Glu Pro Glu Asp Phe Ala Val Tyr
465                 470                 475                 480

Tyr Cys Phe Gln Gly Ser Val Tyr Pro Phe Thr Phe Gly Gln Gly Thr
                485                 490                 495

Lys Leu Glu Ile Lys Arg Gly Gly Gly Ser Gly Gly Gly Ser Glu
            500                 505                 510

Val Gln Leu Val Glu Ser Gly Gly Gly Leu Val Gln Pro Gly Asn Ser
            515                 520                 525

Leu Arg Leu Ser Cys Ala Ala Ser Gly Phe Thr Phe Ser Ser Phe Gly
            530                 535                 540

Met Ser Trp Val Arg Gln Ala Pro Gly Lys Gly Leu Glu Trp Val Ser
545                 550                 555                 560

Ser Ile Ser Gly Ser Gly Ser Asp Thr Leu Tyr Ala Asp Ser Val Lys
                565                 570                 575

Gly Arg Phe Thr Ile Ser Arg Asp Asn Ala Lys Thr Thr Leu Tyr Leu
            580                 585                 590

Gln Met Asn Ser Leu Arg Pro Glu Asp Thr Ala Val Tyr Tyr Cys Thr
            595                 600                 605

Ile Gly Gly Ser Leu Ser Arg Ser Ser Gln Gly Thr Leu Val Thr Val
        610                 615                 620

Ser Ser His His His His His His His His
625                 630                 635

<210> SEQ ID NO 311
<211> LENGTH: 636
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 311

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Gln Val Gln Leu Val Gln Ser Gly Ala Glu Val Lys
    130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Gly Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Asn Ser Leu Arg Leu Ser Cys Ala Ala Ser Gly Phe Thr
        275                 280                 285

Phe Ser Ser Phe Gly Met Ser Trp Val Arg Gln Ala Pro Gly Lys Gly
    290                 295                 300

Leu Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
                325                 330                 335

Thr Thr Leu Tyr Leu Gln Met Asn Ser Leu Arg Pro Glu Asp Thr Ala
            340                 345                 350

Val Tyr Tyr Cys Thr Ile Gly Gly Ser Leu Ser Arg Ser Ser Gln Gly
        355                 360                 365

Thr Leu Val Thr Val Ser Ser Gly Gly Gly Ser Gly Gly Gly Ser
    370                 375                 380

Gln Val Gln Leu Gln Glu Ser Gly Pro Gly Leu Val Lys Pro Ser Gln
385                 390                 395                 400
```

```
Thr Leu Ser Leu Thr Cys Thr Val Ser Gly Gly Ser Ile Ser Thr Ser
                405                 410                 415

Gly Met Gly Val Gly Trp Ile Arg Gln His Pro Lys Gly Leu Glu
        420                 425                 430

Trp Ile Gly His Ile Trp Trp Asp Asp Lys Arg Tyr Asn Pro Ala
            435                 440                 445

Leu Lys Ser Arg Val Thr Ile Ser Val Asp Thr Ser Lys Asn Gln Phe
450                 455                 460

Ser Leu Lys Leu Ser Ser Val Thr Ala Ala Asp Thr Ala Val Tyr Tyr
465                 470                 475                 480

Cys Ala Arg Met Glu Leu Trp Ser Tyr Tyr Phe Asp Tyr Trp Gly Gln
                485                 490                 495

Gly Thr Leu Val Thr Val Ser Ser Gly Gly Gly Gly Ser Gly Gly Gly
                500                 505                 510

Gly Ser Gly Gly Gly Gly Ser Glu Ile Val Leu Thr Gln Ser Pro Ala
                515                 520                 525

Thr Leu Ser Leu Ser Pro Gly Glu Arg Ala Thr Leu Ser Cys Ser Ala
530                 535                 540

Ser Ser Ser Val Ser Tyr Met His Trp Tyr Gln Gln Lys Pro Gly Gln
545                 550                 555                 560

Ala Pro Arg Leu Leu Ile Tyr Asp Thr Ser Lys Leu Ala Ser Gly Ile
                565                 570                 575

Pro Ala Arg Phe Ser Gly Ser Gly Ser Gly Thr Asp Phe Thr Leu Thr
                580                 585                 590

Ile Ser Ser Leu Glu Pro Glu Asp Phe Ala Val Tyr Tyr Cys Phe Gln
                595                 600                 605

Gly Ser Val Tyr Pro Phe Thr Phe Gly Gln Gly Thr Lys Leu Glu Ile
                610                 615                 620

Lys Arg His His His His His His His His His
625                 630                 635

<210> SEQ ID NO 312
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
                100                 105                 110

Val Ser Ser Gly Gly Gly Gly Ser Gly Gly Gly Ser Asp Ile Val Met
```

-continued

```
                115                 120                 125
Thr Gln Ser Pro Asp Ser Leu Ala Val Ser Leu Gly Glu Arg Ala Thr
130                 135                 140
Ile Asn Cys Lys Ser Ser Gln Ser Leu Leu Asn Ala Arg Thr Gly Lys
145                 150                 155                 160
Asn Tyr Leu Ala Trp Tyr Gln Gln Lys Pro Gly Gln Pro Pro Lys Leu
                165                 170                 175
Leu Ile Tyr Trp Ala Ser Thr Arg Glu Ser Gly Val Pro Asp Arg Phe
            180                 185                 190
Ser Gly Ser Gly Ser Gly Thr Asp Phe Thr Leu Thr Ile Ser Ser Leu
        195                 200                 205
Gln Ala Glu Asp Val Ala Val Tyr Tyr Cys Lys Gln Ser Tyr Ser Arg
210                 215                 220
Arg Thr Phe Gly Gly Gly Thr Lys Val Glu Ile Lys Gly Gly Gly Gly
225                 230                 235                 240
Ser Gly Gly Gly Gly Ser Gly Gly Gly Gly Ser Gly Gly Gly Gly Ser
                245                 250                 255
Gln Val Gln Leu Val Gln Ser Gly Ala Glu Val Lys Lys Pro Gly Ala
            260                 265                 270
Ser Val Lys Val Ser Cys Lys Ala Ser Gly Phe Asn Ile Lys Asp Tyr
        275                 280                 285
Tyr Met His Trp Val Arg Gln Ala Pro Gly Gln Arg Leu Glu Trp Met
290                 295                 300
Gly Trp Ile Asp Leu Glu Asn Ala Asn Thr Ile Tyr Asp Ala Lys Phe
305                 310                 315                 320
Gln Gly Arg Val Thr Ile Thr Arg Asp Thr Ser Ala Ser Thr Ala Tyr
                325                 330                 335
Met Glu Leu Ser Ser Leu Arg Ser Glu Asp Thr Ala Val Tyr Tyr Cys
            340                 345                 350
Ala Arg Asp Ala Tyr Gly Arg Tyr Phe Tyr Asp Val Trp Gly Gln Gly
        355                 360                 365
Thr Leu Val Thr Val Ser Ser Gly Gly Gly Gly Ser Gly Gly Gly Ser
370                 375                 380
Gln Val Gln Leu Gln Glu Ser Gly Pro Gly Leu Val Lys Pro Ser Gln
385                 390                 395                 400
Thr Leu Ser Leu Thr Cys Thr Val Ser Gly Ser Ile Ser Thr Ser Ser
                405                 410                 415
Gly Met Gly Val Gly Trp Ile Arg Gln His Pro Gly Lys Gly Leu Glu
            420                 425                 430
Trp Ile Gly His Ile Trp Trp Asp Asp Asp Lys Arg Tyr Asn Pro Ala
        435                 440                 445
Leu Lys Ser Arg Val Thr Ile Ser Val Asp Thr Ser Lys Asn Gln Phe
450                 455                 460
Ser Leu Lys Leu Ser Ser Val Thr Ala Ala Asp Thr Ala Val Tyr Tyr
465                 470                 475                 480
Cys Ala Arg Met Glu Leu Trp Ser Tyr Tyr Phe Asp Tyr Trp Gly Gln
                485                 490                 495
Gly Thr Leu Val Thr Val Ser Ser Gly Gly Gly Gly Ser Gly Gly Gly
            500                 505                 510
Gly Ser Gly Gly Gly Gly Ser Glu Ile Val Leu Thr Gln Ser Pro Ala
        515                 520                 525
Thr Leu Ser Leu Ser Pro Gly Glu Arg Ala Thr Leu Ser Cys Ser Ala
530                 535                 540
```

```
Ser Ser Ser Val Ser Tyr Met His Trp Tyr Gln Gln Lys Pro Gly Gln
545                 550                 555                 560

Ala Pro Arg Leu Leu Ile Tyr Asp Thr Ser Lys Leu Ala Ser Gly Ile
            565                 570                 575

Pro Ala Arg Phe Ser Gly Ser Gly Ser Gly Thr Asp Phe Thr Leu Thr
            580                 585                 590

Ile Ser Ser Leu Glu Pro Glu Asp Phe Ala Val Tyr Tyr Cys Phe Gln
        595                 600                 605

Gly Ser Val Tyr Pro Phe Thr Phe Gly Gln Gly Thr Lys Leu Glu Ile
        610                 615                 620

Lys Arg His His His His His His His His
625                 630                 635
```

<210> SEQ ID NO 313
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gln Val Gln Leu
        115                 120                 125

Gln Glu Ser Gly Pro Gly Leu Val Lys Pro Ser Gln Thr Leu Ser Leu
    130                 135                 140

Thr Cys Thr Val Ser Gly Gly Ser Ile Ser Thr Ser Gly Met Gly Val
145                 150                 155                 160

Gly Trp Ile Arg Gln His Pro Gly Lys Gly Leu Glu Trp Ile Gly His
                165                 170                 175

Ile Trp Trp Asp Asp Asp Lys Arg Tyr Asn Pro Ala Leu Lys Ser Arg
            180                 185                 190

Val Thr Ile Ser Val Asp Thr Ser Lys Asn Gln Phe Ser Leu Lys Leu
        195                 200                 205

Ser Ser Val Thr Ala Ala Asp Thr Ala Val Tyr Tyr Cys Ala Arg Met
    210                 215                 220

Glu Leu Trp Ser Tyr Tyr Phe Asp Tyr Trp Gly Gln Gly Thr Leu Val
225                 230                 235                 240

Thr Val Ser Ser Gly Gly Gly Gly Ser Gly Gly Gly Gly Ser Gly Gly
                245                 250                 255

Gly Gly Ser Glu Ile Val Leu Thr Gln Ser Pro Ala Thr Leu Ser Leu
```

```
            260                 265                 270
Ser Pro Gly Glu Arg Ala Thr Leu Ser Cys Ser Ala Ser Ser Ser Val
        275                 280                 285

Ser Tyr Met His Trp Tyr Gln Gln Lys Pro Gly Gln Ala Pro Arg Leu
    290                 295                 300

Leu Ile Tyr Asp Thr Ser Lys Leu Ala Ser Gly Ile Pro Ala Arg Phe
305                 310                 315                 320

Ser Gly Ser Gly Ser Gly Thr Asp Phe Thr Leu Thr Ile Ser Ser Leu
                325                 330                 335

Glu Pro Glu Asp Phe Ala Val Tyr Tyr Cys Phe Gln Gly Ser Val Tyr
            340                 345                 350

Pro Phe Thr Phe Gly Gln Gly Thr Lys Leu Glu Ile Lys Arg Gly Gly
        355                 360                 365

Gly Gly Ser Gly Gly Gly Ser Asp Ile Val Met Thr Gln Ser Pro Asp
    370                 375                 380

Ser Leu Ala Val Ser Leu Gly Glu Arg Ala Thr Ile Asn Cys Lys Ser
385                 390                 395                 400

Ser Gln Ser Leu Leu Asn Ala Arg Thr Gly Lys Asn Tyr Leu Ala Trp
                405                 410                 415

Tyr Gln Gln Lys Pro Gly Gln Pro Pro Lys Leu Leu Ile Tyr Trp Ala
            420                 425                 430

Ser Thr Arg Glu Ser Gly Val Pro Asp Arg Phe Ser Gly Ser Gly Ser
        435                 440                 445

Gly Thr Asp Phe Thr Leu Thr Ile Ser Ser Leu Gln Ala Glu Asp Val
    450                 455                 460

Ala Val Tyr Tyr Cys Lys Gln Ser Tyr Ser Arg Arg Thr Phe Gly Gly
465                 470                 475                 480

Gly Thr Lys Val Glu Ile Lys Gly Gly Gly Ser Gly Gly Gly Gly
                485                 490                 495

Ser Gly Gly Gly Gly Ser Gly Gly Gly Ser Gln Val Gln Leu Val
        500                 505                 510

Gln Ser Gly Ala Glu Val Lys Lys Pro Gly Ala Ser Val Lys Val Ser
    515                 520                 525

Cys Lys Ala Ser Gly Phe Asn Ile Lys Asp Tyr Tyr Met His Trp Val
530                 535                 540

Arg Gln Ala Pro Gly Gln Arg Leu Glu Trp Met Gly Trp Ile Asp Leu
545                 550                 555                 560

Glu Asn Ala Asn Thr Ile Tyr Asp Ala Lys Phe Gln Gly Arg Val Thr
                565                 570                 575

Ile Thr Arg Asp Thr Ser Ala Ser Thr Ala Tyr Met Glu Leu Ser Ser
            580                 585                 590

Leu Arg Ser Glu Asp Thr Ala Val Tyr Tyr Cys Ala Arg Asp Ala Tyr
        595                 600                 605

Gly Arg Tyr Phe Tyr Asp Val Trp Gly Gln Gly Thr Leu Val Thr Val
    610                 615                 620

Ser Ser His His His His His His His His
625                 630                 635

<210> SEQ ID NO 314
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 314

```
Glu Val Gln Leu Val Glu Ser Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Ile Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Gln Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Ala Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Ser Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Ala Ser Ser Thr Gly Ala Val Thr Ser Gly Asn Tyr Pro Asn
            165                 170                 175

Trp Val Gln Gln Lys Pro Gly Gln Ala Pro Arg Gly Leu Ile Gly Gly
        180                 185                 190

Thr Lys Phe Leu Val Pro Gly Thr Pro Ala Arg Phe Ser Gly Ser Leu
    195                 200                 205

Leu Gly Gly Lys Ala Ala Leu Thr Leu Ser Gly Val Gln Pro Glu Asp
    210                 215                 220

Glu Ala Glu Tyr Tyr Cys Thr Leu Trp Tyr Ser Asn Arg Trp Val Phe
225                 230                 235                 240

Gly Gly Gly Thr Lys Leu Thr Val Leu Gly Gly Gly Ser Gly Gly
                245                 250                 255

Gly Ser Glu Val Gln Leu Val Glu Ser Gly Gly Leu Val Gln Pro
        260                 265                 270

Gly Asn Ser Leu Arg Leu Ser Cys Ala Ala Ser Gly Phe Thr Phe Ser
    275                 280                 285

Ser Phe Gly Met Ser Trp Val Arg Gln Ala Pro Gly Lys Gly Leu Glu
    290                 295                 300

Trp Val Ser Ser Ile Ser Gly Ser Gly Ser Asp Thr Leu Tyr Ala Asp
305                 310                 315                 320

Ser Val Lys Gly Arg Phe Thr Ile Ser Arg Asp Asn Ala Lys Thr Thr
            325                 330                 335

Leu Tyr Leu Gln Met Asn Ser Leu Arg Pro Glu Asp Thr Ala Val Tyr
        340                 345                 350

Tyr Cys Thr Ile Gly Gly Ser Leu Ser Arg Ser Ser Gln Gly Thr Leu
    355                 360                 365

Val Thr Val Ser Ser Gly Gly Gly Ser Gly Gly Ser Gln Val
    370                 375                 380

Gln Leu Gln Glu Ser Gly Pro Gly Leu Val Lys Pro Ser Gln Thr Leu
385                 390                 395                 400

Ser Leu Thr Cys Thr Val Ser Gly Gly Ser Ile Ser Thr Ser Gly Met
```

405                 410                 415
Gly Val Gly Trp Ile Arg Gln His Pro Gly Lys Gly Leu Glu Trp Ile
            420                 425                 430

Gly His Ile Trp Trp Asp Asp Lys Arg Tyr Asn Pro Ala Leu Lys
        435                 440                 445

Ser Arg Val Thr Ile Ser Val Asp Thr Ser Lys Asn Gln Phe Ser Leu
450                 455                 460

Lys Leu Ser Ser Val Thr Ala Ala Asp Thr Ala Val Tyr Tyr Cys Ala
465                 470                 475                 480

Arg Met Glu Leu Trp Ser Tyr Tyr Phe Asp Tyr Trp Gly Gln Gly Thr
            485                 490                 495

Leu Val Thr Val Ser Ser Gly Gly Gly Gly Ser Gly Gly Gly Gly Ser
            500                 505                 510

Gly Gly Gly Gly Ser Glu Ile Val Leu Thr Gln Ser Pro Ala Thr Leu
            515                 520                 525

Ser Leu Ser Pro Gly Glu Arg Ala Thr Leu Ser Cys Ser Ala Ser Ser
530                 535                 540

Ser Val Ser Tyr Met His Trp Tyr Gln Gln Lys Pro Gly Gln Ala Pro
545                 550                 555                 560

Arg Leu Leu Ile Tyr Asp Thr Ser Lys Leu Ala Ser Gly Ile Pro Ala
            565                 570                 575

Arg Phe Ser Gly Ser Gly Ser Gly Thr Asp Phe Thr Leu Thr Ile Ser
            580                 585                 590

Ser Leu Glu Pro Glu Asp Phe Ala Val Tyr Tyr Cys Phe Gln Gly Ser
            595                 600                 605

Val Tyr Pro Phe Thr Phe Gly Gln Gly Thr Lys Leu Glu Ile Lys Arg
            610                 615                 620

His His His His His His His His His
625                 630

<210> SEQ ID NO 315
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Val Ser Gly Ile Tyr Asn Leu His Gly Phe Asp Ile Trp
            100                 105                 110

Gly Gln Gly Thr Leu Val Thr Val Ser Ser
        115                 120

<210> SEQ ID NO 316
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Phe Gly Ser Pro
                85                  90                  95

Phe Thr Phe Gly Gln Gly Thr Lys Val Glu Ile Lys
            100                 105

<210> SEQ ID NO 317
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gly Tyr Ser Phe Thr Ser Tyr Trp
1               5

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Ile Tyr Pro Gly Asp Ser Asp Thr
1               5

<210> SEQ ID NO 319
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Ala Arg Gly Val Ser Gly Ile Tyr Asn Leu His Gly Phe Asp Ile
1               5                   10                  15

<210> SEQ ID NO 320
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 320

Gln Ser Ile Ser Ser Tyr
1               5

<210> SEQ ID NO 321
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Ala Ala Ser
1

<210> SEQ ID NO 322
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln Gln Gly Arg Phe Gly Ser Pro Phe Thr
1               5                   10

<210> SEQ ID NO 323
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Ser Arg Leu Asp Tyr Trp Gly Gln Gly Thr Leu
            100                 105                 110

Val Thr Val Ser Ser
        115

<210> SEQ ID NO 324
<211> LENGTH: 113
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 324

Gln Thr Val Val Thr Gln Glu Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Thr Gly Thr Lys Leu Thr Val Leu Gly Ser
            100                 105                 110

Arg

<210> SEQ ID NO 325
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Leu Ser Gln Ile Asp Ser Trp Gly Gln Gly Thr Leu
            100                 105                 110

Val Thr Val Ser Ser
        115

<210> SEQ ID NO 326
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Arg Gln Leu Pro Gly Thr Ala Pro Lys Leu Leu
            35                  40                  45

Ile Tyr Glu Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Arg Ala Gly Val Phe Gly Thr Gly Thr Lys Val Thr Val Leu
            100                 105                 110

<210> SEQ ID NO 327
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Ala Pro Gly Lys Gly Leu Glu Trp Met
            35                  40                  45

Gly Leu Val Asp Pro Glu Asp Gly Glu Thr Ile Tyr Ala Glu Lys Phe
 50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Ile Tyr Ser Arg Pro Leu Gly Tyr Trp Gly Gln Gly Thr
            100                 105                 110

Leu Val Thr Val Ser Ser
        115

<210> SEQ ID NO 328
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly His Val Val Phe Gly Gly Thr Lys Leu Thr Val Leu
            100                 105                 110

<210> SEQ ID NO 329
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Asp Gly Lys His Phe Trp Gln Gln Tyr Asp Ala Trp Gly
            100                 105                 110

Gln Gly Thr Leu Val Thr Val Ser Ser
        115                 120

<210> SEQ ID NO 330
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser His
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110

<210> SEQ ID NO 331
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Asn Ile Asp Tyr Trp Gly Gln Gly Thr Leu Val Thr Val
            100                 105                 110

Ser Ser

<210> SEQ ID NO 332
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Asp Ile Gln Leu Thr Gln Ser Pro Ser Ser Leu Ser Ala Tyr Val Gly
1               5                   10                  15

Asp Arg Val Thr Ile Thr Cys Arg Ala Ser Gln Gly Ile Thr Asn Ser
            20                  25                  30

Leu Ala Trp Tyr Gln Gln Lys Pro Gly Lys Ala Pro Lys Leu Leu Leu
        35                  40                  45

His Ala Ala Ser Arg Leu Glu Ser Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Glu Asp Phe Ala Val Tyr Tyr Cys Gln His Tyr Leu Gly Thr Pro Tyr
                85                  90                  95

Ser Phe Gly Gln Gly Thr Lys Val Glu Ile Lys
            100                 105

<210> SEQ ID NO 333
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Glu Val Gln Leu Val Gln Ser Gly Ala Glu Val Lys Arg Pro Gly Glu
1               5                   10                  15

Ser Leu Thr Ile Ser Cys Lys Gly Ser Glu Tyr Ser Phe Ala Ser Tyr
            20                  25                  30

Trp Ile Thr Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

```
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Ile Tyr Tyr Cys
                 85                  90                  95

Ala Arg Pro Phe Gln Tyr Asp Tyr Gly Gly Tyr Ser Ala Phe Asp
            100                 105                 110

Ile Trp Gly Gln Gly Thr Met Val Thr Val Ser Ser
        115                 120

<210> SEQ ID NO 334
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Glu Ile Val Leu Thr Gln Ser Pro Ser Ser Leu Ser Ala Ser Val Gly
  1               5                  10                  15

Asp Arg Val Thr Ile Ser Cys Arg Ala Ser Gln Ser Val Ser Arg Phe
             20                  25                  30

Leu Asn Trp Tyr Gln Gln Lys Pro Gly Lys Ala Pro Lys Leu Leu Ile
         35                  40                  45

Tyr Gly Val Ser Thr Leu Glu Arg Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Glu Ser Tyr Ile Ile Pro Leu
                 85                  90                  95

Thr Phe Gly Gly Gly Thr Lys Leu Glu Ile Lys
            100                 105

<210> SEQ ID NO 335
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Gln Met Gln Leu Val Gln Ser Gly Ala Glu Val Lys Lys Ala Gly Ser
  1               5                  10                  15

Ser Val Lys Val Ser Cys Glu Thr Ser Gly Gly Thr Phe Ser Ser Ser
             20                  25                  30

Ser Val Asn Trp Val Arg Gln Ala Pro Gly Gln Gly Leu Glu Trp Met
         35                  40                  45

Gly Gly Ile Ile Pro Ile Val Gly Thr Pro Asn Tyr Ala Gln Lys Phe
 50                  55                  60

Gln Asp Arg Val Thr Ile Thr Ala Val Glu Ser Thr Phe Thr Ala Tyr
 65                  70                  75                  80

Met Glu Leu Ser Gly Leu Arg Ser Glu Asp Thr Ala Val Tyr Tyr Cys
                 85                  90                  95

Ala Arg Gly Gly Tyr Arg Asp Tyr Met Asp Val Trp Gly Arg Gly Thr
            100                 105                 110

Thr Val Thr Val Ser Ser
            115
```

<210> SEQ ID NO 336
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Glu Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu Asp Ser
            20                  25                  30

Asn Gly Phe Asn Ser Leu Asp Trp Tyr Leu Gln Lys Pro Gly Gln Ser
        35                  40                  45

Pro Gln Leu Leu Ile His Leu Gly Ser Asp Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Leu Gln Ile Pro Thr Phe Gly Gln Gly Thr Lys Val Glu Ile Lys
            100                 105                 110

<210> SEQ ID NO 337
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Ala Glu Phe Asp Tyr Trp Gly Gln Gly Thr Leu
            100                 105                 110

Val Thr Val Ser Ser
        115

<210> SEQ ID NO 338
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

-continued

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu
            100                 105                 110

<210> SEQ ID NO 339
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Ile Ser Asp Asp Tyr Tyr Gly Ser Gly Ser Tyr Asp Asn
            100                 105                 110

Trp Gly Gln Gly Thr Leu Val Thr Val Ser Ser
        115                 120

<210> SEQ ID NO 340
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Ser Tyr Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
50                  55                  60

```
Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Glu Asp
                 85                  90                  95

Val Phe Gly Pro Gly Thr Lys Val Thr Val Leu
            100                 105

<210> SEQ ID NO 341
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Arg Gly Met Gly Tyr Ala Phe Asp Ile Trp Gly Gln Gly Thr
            100                 105                 110

Met Val Thr Val Ser Ser
        115

<210> SEQ ID NO 342
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Gly Gly Thr Lys Val Glu Ile Lys
            100                 105

<210> SEQ ID NO 343
<211> LENGTH: 114
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Gln Leu Gln Leu Gln Glu Ser Gly Pro Gly Leu Val Lys Pro Ser Glu
1               5                   10                  15

Thr Leu Ser Leu Thr Cys Ser Val Ser Gly Val Ser Met Ser Glu Asn
            20                  25                  30

Tyr Trp Ser Trp Ile Arg Gln Pro Pro Gly Lys Arg Leu Glu Trp Ile
        35                  40                  45

Gly Cys Ala His Tyr Thr Gly Asp Thr His Tyr Asn Pro Ser Leu Lys
    50                  55                  60

Gly Arg Val Thr Ile Ser Leu Asp Thr Ser Met Asn Gln Phe Ser Leu
65                  70                  75                  80

Arg Leu Asn Ser Val Thr Ala Ala Asp Thr Ala Val Tyr Tyr Cys Ala
                85                  90                  95

Ser Tyr His Pro Phe Asn Tyr Trp Gly Gln Gly Thr Leu Val Thr Val
            100                 105                 110

Ser Ser

<210> SEQ ID NO 344
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Tyr
            20                  25                  30

Leu Ala Trp Tyr Gln Gln Lys Pro Gly Lys Ala Pro Lys Leu Leu Ile
        35                  40                  45

Tyr Pro Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Leu Phe Gly
                85                  90                  95

Gln Gly Thr Arg Leu Glu Ile Lys
            100

<210> SEQ ID NO 345
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Glu Val Gln Leu Val Gln Ser Gly Ala Glu Val Arg Arg Pro Gly Ala
1               5                   10                  15

Thr Val Lys Ile Ser Cys Lys Val Ser Gly Tyr Thr Phe Asn Asp Phe
            20                  25                  30
```

```
Tyr Leu His Trp Val Arg Gln Ala Pro Gly Lys Gly Leu Glu Trp Met
            35                  40                  45

Gly Arg Ile Asp Pro Glu Asp Gly Lys Thr Arg Tyr Ala Glu Lys Phe
        50                  55                  60

Gln Gly Arg Leu Thr Ile Thr Ala Asp Thr Ser Thr Asp Thr Leu Tyr
65                  70                  75                  80

Met Gln Leu Gly Gly Leu Thr Ser Asp Thr Ala Val Tyr Tyr Cys
                85                  90                  95

Thr Thr Asp Trp Gly Tyr Ser Ser Leu Arg Glu Glu Asp Ile Trp
                100                 105                 110

Tyr Asp Cys Trp Gly Gln Gly Thr Leu Val Thr Val Ser Ser
            115                 120                 125

<210> SEQ ID NO 346
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Thr Lys
                20                  25                  30

Thr Val Asn Trp Tyr Gln Val Leu Pro Gly Thr Ala Pro Lys Leu Leu
            35                  40                  45

Ile Tyr Ser Asn Tyr Arg Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Asp Asp Glu Ala Asp Tyr Tyr Cys Ala Leu Trp Asp Ser Leu
                85                  90                  95

Asp Gly Tyr Val Phe Gly Thr Gly Thr Lys Val Thr Val Leu
                100                 105                 110

<210> SEQ ID NO 347
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Asp Tyr Gly Tyr Gly Asp Tyr Gly Asp Ala Phe Asp Ile Trp
            100                 105                 110

Gly Gln Gly Thr Met Val Thr Val Ser Ser
            115                 120

<210> SEQ ID NO 348
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu
            100                 105

<210> SEQ ID NO 349
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Val Gly Thr Ile Tyr Ser Met Gln Tyr Asp Val Trp Gly
            100                 105                 110

Gln Gly Thr Leu Val Thr Val Ser Ser
        115                 120

<210> SEQ ID NO 350
<211> LENGTH: 108
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 350

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Arg Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Ser Cys Gln Val Trp Asp Ser Ser Asp His
                85                  90                  95

Tyr Val Phe Gly Pro Gly Thr Lys Val Thr Val Leu
            100                 105

<210> SEQ ID NO 351
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Val Trp Gly Trp Gln Gly Gly Met Tyr Pro Arg Ser Asn
            100                 105                 110

Trp Trp Tyr Asn Met Asp Ser Trp Gly Gln Gly Thr Leu Val Thr Val
        115                 120                 125

Ser Ser
    130

<210> SEQ ID NO 352
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Leu Pro Val Leu Thr Gln Pro Pro Ser Val Ser Val Ala Pro Gly Lys
1               5                   10                  15
```

```
Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp Tyr
                85                  90                  95

Val Val Phe Gly Gly Gly Thr Lys Leu Thr Val Leu
            100                 105

<210> SEQ ID NO 353
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Ser Ser Thr Trp Asp Ser Met Tyr Met Asp Tyr Trp Gly
            100                 105                 110

Gln Gly Thr Leu Val Thr Val Ser Ser
        115                 120

<210> SEQ ID NO 354
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Gln Ala Val Leu Thr Gln Pro Pro Ser Val Ser Glu Ala Pro Arg Gln
1               5                   10                  15

Arg Val Thr Ile Ser Cys Ser Gly Ser Ser Ser Asn Val Gly Asn Asn
            20                  25                  30

Ala Val Asn Trp Tyr Gln Gln Val Pro Gly Lys Ala Pro Lys Leu Leu
        35                  40                  45

Ile Tyr Tyr Asp Asp Leu Leu Ser Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80
```

Ser Glu Asp Glu Ala Asp Tyr Tyr Cys Ala Ala Trp Asp Asp Ser Leu
            85                  90                  95

Asn Gly Pro Val Phe Gly Gly Thr Lys Leu Thr Val Leu
            100                 105                 110

<210> SEQ ID NO 355
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Thr Tyr Ser Met Asp Ser Tyr Tyr Phe Asp Ser Trp Gly
            100                 105                 110

Gln Gly Thr Leu Val Thr Val Ser Ser
        115                 120

<210> SEQ ID NO 356
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Glu Ser Val
            20                  25                  30

His Trp Tyr Gln Gln Lys Pro Gly Gln Ala Pro Met Val Val Ile Tyr
        35                  40                  45

Tyr Asp Ser Asn Arg Pro Ser Gly Ile Pro Glu Arg Phe Ser Gly Ser
    50                  55                  60

Asn Ser Gly Asn Thr Ala Thr Leu Thr Val Ser Arg Val Glu Ala Glu
65                  70                  75                  80

Asp Glu Ala Asp Tyr Tyr Cys Gln Val Trp Asn Ser Ser Ser Asp His
                85                  90                  95

Arg Gly Val Phe Gly Gly Gly Thr Lys Leu Thr Val
            100                 105

<210> SEQ ID NO 357
<211> LENGTH: 121
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 357

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Phe Asn Pro Tyr Asn Asp Gly Thr Glu Tyr Asn Glu Lys Phe
    50                  55                  60

Lys Ala Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Pro Tyr Tyr Tyr Gly Ser Ser Pro Phe Asp Tyr Trp Gly
            100                 105                 110

Gln Gly Thr Thr Leu Thr Val Ser Ser
            115                 120

<210> SEQ ID NO 358
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 358

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Tyr Thr Phe Gly Gly Gly Thr Lys Leu Glu Ile Lys
            100                 105                 110

<210> SEQ ID NO 359
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 359

Gly Tyr Thr Phe Thr Asn Tyr Val Ile His
1               5                   10

<210> SEQ ID NO 360
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 360

Tyr Phe Asn Pro Tyr Asn Asp Gly Thr Glu Tyr Asn Glu Lys Phe Lys
1               5                   10                  15

Ala

<210> SEQ ID NO 361
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Gly Pro Tyr Tyr Tyr Gly Ser Ser Pro Phe Asp Tyr
1               5                   10

<210> SEQ ID NO 362
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Arg Ser Ser Gln Ser Leu Glu Asn Ser Asn Gly Asn Thr Tyr Leu Asn
1               5                   10                  15

<210> SEQ ID NO 363
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Arg Val Ser Asn Arg Phe Ser
1               5

<210> SEQ ID NO 364
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Arg Val Ser Asn Arg Phe Ser
1               5

<210> SEQ ID NO 365
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365
```

-continued

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Thr Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Asp Thr Lys Tyr Asn Gly Lys Phe
50                  55                  60

Lys Gly Lys Ala Ser Leu Thr Ala Asp Lys Ser Ser Thr Ala Tyr
65                  70                  75                  80

Met Gln Leu Ile Ser Leu Thr Ser Glu Asp Ser Ala Val Tyr Phe Cys
            85                  90                  95

Ala Arg Arg Tyr Phe Arg Tyr Asp Tyr Trp Tyr Ser Asp Val Trp Gly
            100                 105                 110

Ala Gly Thr Thr Val Thr Val Thr Ser
        115                 120

<210> SEQ ID NO 366
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ala Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys His Gln Gly Asn Thr Leu Pro Leu
            85                  90                  95

Thr Phe Gly Ala Gly Thr Lys Leu Glu Leu Lys
            100                 105

<210> SEQ ID NO 367
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gly Tyr Ala Phe Ser Thr Tyr Trp Met Asn
1               5                   10

<210> SEQ ID NO 368
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 368

Gln Ile Tyr Pro Gly Asp Asp Thr Lys Tyr Asn Gly Lys Phe Lys
1               5                   10                  15

Gly

<210> SEQ ID NO 369
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Arg Tyr Phe Arg Tyr Asp Tyr Trp Tyr Ser Asp Val
1               5                   10

<210> SEQ ID NO 370
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Arg Ala Ser Gln Asp Ile Ser Asn Tyr Leu Asn
1               5                   10

<210> SEQ ID NO 371
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Tyr Thr Ser Arg Leu His Ser
1               5

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

His Gln Gly Asn Thr Leu Pro Leu Thr
1               5

<210> SEQ ID NO 373
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
                20                  25                  30
```

```
Asn Met Tyr Trp Val Lys Gln Ser His Gly Lys Ser Leu Glu Trp Ile
         35                  40                  45

Gly Tyr Ile Asp Pro Tyr Asn Gly Asp Thr Thr Tyr Asn Gln Lys Phe
     50                  55                  60

Lys Gly Lys Ala Thr Leu Thr Val Asp Lys Ser Ser Ser Thr Ala Tyr
 65                  70                  75                  80

Met His Leu Asn Ser Leu Thr Ser Glu Asp Ser Ala Val Tyr Tyr Cys
                 85                  90                  95

Leu Thr Thr Ala Tyr Ala Met Asp Tyr Trp Gly Gln Gly Thr Ser Val
             100                 105                 110

Thr Val Ser Ser
        115
```

<210> SEQ ID NO 374
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

```
Gln Ile Val Leu Thr Gln Ser Pro Ala Ile Met Ser Ala Ser Leu Gly
 1               5                  10                  15

Glu Glu Ile Thr Leu Thr Cys Ser Ala Ser Ser Thr Val Asn Tyr Met
             20                  25                  30

His Trp Tyr Gln Gln Lys Ser Gly Thr Ser Pro Lys Leu Leu Ile Tyr
         35                  40                  45

Ser Thr Ser Asn Leu Ala Ser Gly Val Pro Ser Arg Phe Ser Gly Ser
     50                  55                  60

Gly Ser Gly Thr Phe Tyr Ser Leu Thr Ile Arg Ser Val Glu Ala Glu
 65                  70                  75                  80

Asp Ala Ala Asp Tyr Tyr Cys His Gln Trp Ser Tyr Pro Tyr Thr
                 85                  90                  95

Phe Gly Gly Gly Thr Lys Leu Glu Ile Lys
            100                 105
```

<210> SEQ ID NO 375
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

```
Gly Tyr Ala Phe Thr Ser Tyr Asn Met Tyr
 1               5                  10
```

<210> SEQ ID NO 376
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

```
Tyr Ile Asp Pro Tyr Asn Gly Asp Thr Thr Tyr Asn Gln Lys Phe Lys
 1               5                  10                  15
```

```
Gly

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Thr Ala Tyr Ala Met Asp Tyr
1               5

<210> SEQ ID NO 378
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ser Ala Ser Ser Thr Val Asn Tyr Met His
1               5                   10

<210> SEQ ID NO 379
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ser Thr Ser Asn Leu Ala Ser
1               5

<210> SEQ ID NO 380
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

His Gln Trp Ser Ser Tyr Pro Tyr Thr
1               5

<210> SEQ ID NO 381
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Val Ile His Trp Val Arg Gln Ala Pro Gly Gln Gly Leu Glu Trp Met
            35                  40                  45

Gly Tyr Phe Asn Pro Tyr Asn Asp Gly Thr Glu Tyr Asn Glu Lys Phe
```

```
                50                  55                  60
Lys Ala Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Pro Tyr Tyr Tyr Gly Ser Ser Pro Phe Asp Tyr Trp Gly
                100                 105                 110

Gln Gly Thr Thr Val Thr Val Ser Ser
            115                 120
```

<210> SEQ ID NO 382
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

```
Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Glu Asn Ser
                20                  25                  30

Asn His Asn Thr Tyr Ile Asn Trp Tyr Leu Gln Lys Pro Gly Gln Ser
             35                  40                  45

Pro Gln Leu Leu Ile Tyr Arg Val Ser Lys Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys His Gln Val
                 85                  90                  95

Thr His Val Pro Tyr Thr Phe Gly Gln Gly Thr Lys Leu Glu Ile Lys
                100                 105                 110
```

<210> SEQ ID NO 383
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

```
Gly Tyr Thr Phe Thr Asn Tyr Val Ile His
 1               5                  10
```

<210> SEQ ID NO 384
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

```
Tyr Phe Asn Pro Tyr Asn Asp Gly Thr Glu Tyr Asn Glu Lys Phe Lys
 1               5                  10                  15

Ala
```

<210> SEQ ID NO 385
<211> LENGTH: 12

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Gly Pro Tyr Tyr Tyr Gly Ser Ser Pro Phe Asp Tyr
1               5                   10

<210> SEQ ID NO 386
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Arg Ser Ser Gln Ser Leu Glu Asn Ser Asn His Asn Thr Tyr Ile Asn
1               5                   10                  15

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

His Gln Val Thr His Val Pro Tyr Thr
1               5

<210> SEQ ID NO 388
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Thr Tyr
                20                  25                  30

Trp Met Asn Trp Val Arg Gln Ala Pro Gly Gln Gly Leu Glu Trp Met
            35                  40                  45

Gly Gln Ile Tyr Pro Gly Asp Asp Asp Thr Lys Tyr Ser Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Phe Arg Tyr Asp Tyr Trp Tyr Ser Asp Val Trp Gly
                100                 105                 110

Gln Gly Thr Thr Val Thr Val Ser Ser
            115                 120

<210> SEQ ID NO 389
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys His Gln Gly Asn Thr Leu Pro Leu
                85                  90                  95

Thr Phe Gly Gln Gly Thr Lys Leu Glu Ile Lys
            100                 105

<210> SEQ ID NO 390
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Gly Tyr Ala Phe Ser Thr Tyr Trp Met Asn
1               5                   10

<210> SEQ ID NO 391
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Gln Ile Tyr Pro Gly Asp Asp Asp Thr Lys Tyr Ser Gly Lys Phe Lys
1               5                   10                  15

Gly

<210> SEQ ID NO 392
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Arg Tyr Phe Arg Tyr Asp Tyr Trp Tyr Ser Asp Val
1               5                   10

<210> SEQ ID NO 393
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Arg Ala Ser Gln Asp Ile Ser Asn Tyr Leu Asn
1               5                   10

<210> SEQ ID NO 394
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Tyr Thr Ser Arg Leu His Ser
1               5

<210> SEQ ID NO 395
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

His Gln Gly Asn Thr Leu Pro Leu Thr
1               5

<210> SEQ ID NO 396
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Ala Phe Thr Ser Tyr
            20                  25                  30

Asn Met Tyr Trp Val Arg Gln Ala Arg Gly Gln Arg Leu Glu Trp Ile
        35                  40                  45

Gly Tyr Ile Asp Pro Tyr Asn Ala Asp Thr Thr Tyr Asn Gln Lys Phe
    50                  55                  60

Lys Gly Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Leu Thr Thr Ala Tyr Ala Met Asp Tyr Trp Gly Gln Gly Thr Leu Val
            100                 105                 110

Thr Val Ser Ser
        115

<210> SEQ ID NO 397
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

```
Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Thr Val Asn Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Trp Ser Ser Tyr Pro Tyr Thr
                85                  90                  95

Phe Gly Gln Gly Thr Lys Leu Glu Ile Lys
            100                 105
```

<210> SEQ ID NO 398
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

```
Gly Tyr Ala Phe Thr Ser Tyr Asn Met Tyr
1               5                   10
```

<210> SEQ ID NO 399
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

```
Tyr Ile Asp Pro Tyr Asn Ala Asp Thr Thr Tyr Asn Gln Lys Phe Lys
1               5                   10                  15

Gly
```

<210> SEQ ID NO 400
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

```
Thr Ala Tyr Ala Met Asp Tyr
1               5
```

<210> SEQ ID NO 401
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

```
Ser Ala Ser Ser Thr Val Asn Tyr Met His
1               5                   10
```

<210> SEQ ID NO 402
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Ser Thr Ser Asn Leu Ala Ser
1               5

<210> SEQ ID NO 403
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

His Gln Trp Ser Ser Tyr Pro Tyr Thr
1               5

<210> SEQ ID NO 404
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Gln Val Lys Leu Glu Glu Ser Gly Gly Glu Leu Val Gln Pro Gly Gly
1               5                   10                  15

Pro Leu Arg Leu Ser Cys Ala Ala Ser Gly Asn Ile Phe Ser Ile Asn
            20                  25                  30

Arg Met Gly Trp Tyr Arg Gln Ala Pro Gly Lys Gln Arg Ala Phe Val
        35                  40                  45

Ala Ser Ile Thr Val Arg Gly Ile Thr Asn Tyr Ala Asp Ser Val Lys
    50                  55                  60

Gly Arg Phe Thr Ile Ser Val Asp Lys Ser Lys Asn Thr Ile Tyr Leu
65                  70                  75                  80

Gln Met Asn Ala Leu Lys Pro Glu Asp Thr Ala Val Tyr Tyr Cys Asn
                85                  90                  95

Ala Val Ser Ser Asn Arg Asp Pro Asp Tyr Trp Gly Gln Gly Thr Gln
            100                 105                 110

Val Thr Val Ser Ser
        115

<210> SEQ ID NO 405
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Ile Asn Arg Met Gly
1               5

```
<210> SEQ ID NO 406
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Ser Ile Thr Val Arg Gly Ile Thr Asn Tyr Ala Asp Ser Val Lys Gly
1               5                   10                  15

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Val Ser Ser Asn Arg Asp Pro Asp Tyr
1               5

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: T or V
<220> FEATURE:
<221> NAME/KEY: MOD_RES
<222> LOCATION: (4)..(4)
<223> OTHER INFORMATION: S, H, G or P
<220> FEATURE:
<221> NAME/KEY: MOD_RES
<222> LOCATION: (9)..(9)
<223> OTHER INFORMATION: S, T or G

<400> SEQUENCE: 408

Phe Xaa Phe Xaa Ser Phe Gly Met Xaa
1               5

<210> SEQ ID NO 409
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: S, T or G
<220> FEATURE:
<221> NAME/KEY: MOD_RES
<222> LOCATION: (7)..(7)
<223> OTHER INFORMATION: S, A or G
<220> FEATURE:
<221> NAME/KEY: MOD_RES
<222> LOCATION: (9)..(9)
<223> OTHER INFORMATION: T or A
<220> FEATURE:
<221> NAME/KEY: MOD_RES
<222> LOCATION: (11)..(11)
<223> OTHER INFORMATION: Y or T
<220> FEATURE:
<221> NAME/KEY: MOD_RES
```

```
<222> LOCATION: (13)..(13)
<223> OTHER INFORMATION: D or P
<220> FEATURE:
<221> NAME/KEY: MOD_RES
<222> LOCATION: (15)..(15)
<223> OTHER INFORMATION: V or A
<220> FEATURE:
<221> NAME/KEY: MOD_RES
<222> LOCATION: (16)..(16)
<223> OTHER INFORMATION: K, R or E

<400> SEQUENCE: 409

Ser Ile Ser Gly Xaa Gly Xaa Asp Xaa Leu Xaa Ala Xaa Ser Xaa Xaa
1               5                   10                  15
Gly

<210> SEQ ID NO 410
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T or S
<220> FEATURE:
<221> NAME/KEY: MOD_RES
<222> LOCATION: (2)..(2)
<223> OTHER INFORMATION: I or F
<220> FEATURE:
<221> NAME/KEY: MOD_RES
<222> LOCATION: (3)..(3)
<223> OTHER INFORMATION: G or A
<220> FEATURE:
<221> NAME/KEY: MOD_RES
<222> LOCATION: (6)..(6)
<223> OTHER INFORMATION: L, R or V
<220> FEATURE:
<221> NAME/KEY: MOD_RES
<222> LOCATION: (7)..(7)
<223> OTHER INFORMATION: S, I, R, K, V or T
<220> FEATURE:
<221> NAME/KEY: MOD_RES
<222> LOCATION: (8)..(8)
<223> OTHER INFORMATION: R, P, I, A, Q, K or Y

<400> SEQUENCE: 410

Xaa Xaa Xaa Gly Ser Xaa Xaa Xaa
1               5

<210> SEQ ID NO 411
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G or A
<220> FEATURE:
<221> NAME/KEY: MOD_RES
<222> LOCATION: (4)..(4)
<223> OTHER INFORMATION: L, R or V
<220> FEATURE:
<221> NAME/KEY: MOD_RES
<222> LOCATION: (5)..(5)
<223> OTHER INFORMATION: S, I, R, K, V or T
<220> FEATURE:
<221> NAME/KEY: MOD_RES
<222> LOCATION: (6)..(6)
```

<223> OTHER INFORMATION: R, P, I, A, Q, K or Y

<400> SEQUENCE: 411

Xaa Gly Ser Xaa Xaa Xaa
1               5

<210> SEQ ID NO 412
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Ala Asn Thr Ile Tyr Asp Ala Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Tyr Gly Arg Tyr Phe Tyr Asp Val Trp Gly Gln Gly
            100                 105                 110

Thr Leu Val Thr Val Ser Ser
        115

<210> SEQ ID NO 413
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

<210> SEQ ID NO 414
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 414

Phe Asn Ile Lys Asp Tyr Tyr Met His
1               5

<210> SEQ ID NO 415
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Asp Tyr Tyr Met His
1               5

<210> SEQ ID NO 416
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Trp Ile Asp Leu Glu Asn Ala Asn Thr Ile Tyr Asp Ala Lys Phe Gln
1               5                   10                  15

Gly

<210> SEQ ID NO 417
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Ala Arg Asp Ala Tyr Gly Arg Tyr Phe Tyr Asp Val
1               5                   10

<210> SEQ ID NO 418
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Asp Ala Tyr Gly Arg Tyr Phe Tyr Asp Val
1               5                   10

<210> SEQ ID NO 419
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Lys Ser Ser Gln Ser Leu Leu Asn Ala Arg Thr Gly Lys Asn Tyr Leu
```

-continued

```
1               5                   10                  15

Ala

<210> SEQ ID NO 420
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Trp Ala Ser Thr Arg Glu Ser
1               5

<210> SEQ ID NO 421
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Lys Gln Ser Tyr Ser Arg Arg Thr
1               5

<210> SEQ ID NO 422
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
                20                  25                  30

Arg Thr Gly Lys Asn Tyr Leu Ala Trp Tyr Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Gln Val Gln Leu Val Gln Ser Gly Ala Glu Val Lys
    130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190
```

```
Asp Ala Lys Phe Gln Gly Arg Val Thr Ile Thr Arg Asp Thr Ser Ala
            195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser
                245                 250

<210> SEQ ID NO 423
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Cys Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Gln Val Gln Leu Val Gln Ser Gly Ala Glu Val Lys
    130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Cys
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser
                245                 250

<210> SEQ ID NO 424
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 424

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Ala Asn Thr Ile Tyr Asp Ala Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Tyr Gly Arg Tyr Phe Tyr Asp Val Trp Gly Gln Gly
            100                 105                 110

Thr Leu Val Thr Val Ser Ser
        115

<210> SEQ ID NO 425
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Ala Arg Asp Gln Tyr Gly Arg Tyr Phe Tyr Asp Val
1               5                   10

<210> SEQ ID NO 426
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Asp Gln Tyr Gly Arg Tyr Phe Tyr Asp Val
1               5                   10

<210> SEQ ID NO 427
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr

```
                65                  70                  75                  80
Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
                100                 105                 110

Gly Gly Gly Gly Ser Gly Gly Gly Gly Ser Gly Gly Gly Gly Ser Gly
                115                 120                 125

Gly Gly Gly Ser Gln Val Gln Leu Val Gln Ser Gly Ala Glu Val Lys
            130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
                180                 185                 190

Asp Ala Lys Phe Gln Gly Arg Val Thr Ile Thr Arg Asp Thr Ser Ala
                195                 200                 205

Ser Thr Ala Tyr Met Glu Leu Ser Ser Leu Arg Ser Glu Asp Thr Ala
            210                 215                 220

Val Tyr Tyr Cys Ala Arg Asp Gln Tyr Gly Arg Tyr Phe Tyr Asp Val
225                 230                 235                 240

Trp Gly Gln Gly Thr Leu Val Thr Val Ser Ser
                245                 250

<210> SEQ ID NO 428
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
                20                  25                  30

Arg Thr Gly Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Cys Gly Thr Lys Val Glu Ile Lys
                100                 105                 110

Gly Gly Gly Gly Ser Gly Gly Gly Gly Ser Gly Gly Gly Gly Ser Gly
                115                 120                 125

Gly Gly Gly Ser Gln Val Gln Leu Val Gln Ser Gly Ala Glu Val Lys
            130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Cys
                165                 170                 175
```

Leu Glu Trp Met Gly Trp Ile Asp Leu Glu Asn Ala Asn Thr Ile Tyr
                180                 185                 190

Asp Ala Lys Phe Gln Gly Arg Val Thr Ile Thr Arg Asp Thr Ser Ala
            195                 200                 205

Ser Thr Ala Tyr Met Glu Leu Ser Ser Leu Arg Ser Glu Asp Thr Ala
        210                 215                 220

Val Tyr Tyr Cys Ala Arg Asp Gln Tyr Gly Arg Tyr Phe Tyr Asp Val
225                 230                 235                 240

Trp Gly Gln Gly Thr Leu Val Thr Val Ser Ser
                245                 250

<210> SEQ ID NO 429
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Glu Gly Asn Thr Ile Tyr Asp Ala Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Tyr Gly Arg Tyr Phe Tyr Asp Val Trp Gly Gln Gly
            100                 105                 110

Thr Leu Val Thr Val Ser Ser
        115

<210> SEQ ID NO 430
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

```
Ser Tyr Ser Leu Arg Thr Phe Gly Gly Gly Thr Lys Val Glu Ile Lys
            100                 105                 110
```

```
<210> SEQ ID NO 431
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Trp Ile Asp Leu Glu Glu Gly Asn Thr Ile Tyr Asp Ala Lys Phe Gln
1               5                   10                  15

Gly
```

```
<210> SEQ ID NO 432
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Lys Gln Ser Tyr Ser Leu Arg Thr
1               5
```

```
<210> SEQ ID NO 433
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
                20                  25                  30

Arg Thr Gly Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Gly Gly Thr Lys Val Glu Ile Lys
            100                 105                 110

Gly Gly Gly Gly Ser Gly Gly Gly Ser Gly Gly Gly Ser
            115                 120                 125

Gly Gly Gly Ser Gln Val Gln Leu Val Gln Ser Gly Ala Glu Val Lys
        130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Glu Gly Asn Thr Ile Tyr
            180                 185                 190
```

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser
                245                 250

<210> SEQ ID NO 434
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Cys Gly Thr Lys Val Glu Ile Lys
            100                 105                 110

Gly Gly Gly Gly Ser Gly Gly Gly Ser Gly Gly Gly Ser
        115                 120                 125

Gly Gly Gly Ser Gln Val Gln Leu Val Gln Ser Gly Ala Glu Val Lys
130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Cys
                165                 170                 175

Leu Glu Trp Met Gly Trp Ile Asp Leu Glu Glu Gly Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser
                245                 250

<210> SEQ ID NO 435
<211> LENGTH: 119
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 435

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Ala Asn Thr Ile Tyr Asp Ala Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Tyr Gly Arg Tyr Phe Tyr Asp Leu Trp Gly Gln Gly
            100                 105                 110

Thr Leu Val Thr Val Ser Ser
        115

<210> SEQ ID NO 436
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Glu Ser
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

<210> SEQ ID NO 437
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Phe Asn Ile Lys Asp Tyr Tyr Met His
1               5

<210> SEQ ID NO 438
<211> LENGTH: 17
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 438

Trp Ile Asp Leu Glu Asn Ala Asn Thr Ile Tyr Asp Ala Lys Phe Gln
1               5                   10                  15

Gly

<210> SEQ ID NO 439
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Ala Arg Asp Val Tyr Gly Arg Tyr Phe Tyr Asp Leu
1               5                   10

<210> SEQ ID NO 440
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Lys Ser Ser Gln Ser Leu Leu Asn Ala Arg Thr Gly Lys Asn Tyr Leu
1               5                   10                  15

Ala

<210> SEQ ID NO 441
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Trp Ala Ser Thr Arg Glu Ser
1               5

<210> SEQ ID NO 442
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Lys Gln Ser Tyr Ser Arg Arg Thr
1               5

<210> SEQ ID NO 443
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
            35                  40                  45

Gly Trp Ile Asp Leu Glu Asn Ala Asn Thr Ile Tyr Asp Ala Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Ala Tyr Gly Gly Tyr Phe Tyr Asp Val Trp Gly Gln Gly
            100                 105                 110

Thr Leu Val Thr Val Ser Ser
        115

<210> SEQ ID NO 444
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Gly Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
            85                  90                  95

Ser Tyr Ser Arg Arg Thr Phe Gly Cys Gly Thr Lys Val Glu Ile Lys
            100                 105                 110

<210> SEQ ID NO 445
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Phe Asn Ile Lys Asp Tyr Tyr Met His
1               5

<210> SEQ ID NO 446
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 446

Trp Ile Asp Leu Glu Asn Ala Asn Thr Ile Tyr Asp Ala Lys Phe Gln
1               5                   10                  15
Gly

<210> SEQ ID NO 447
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Ala Arg Asp Ala Tyr Gly Gly Tyr Phe Tyr Asp Val
1               5                   10

<210> SEQ ID NO 448
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Lys Ser Ser Gln Ser Leu Leu Asn Ala Arg Thr Gly Lys Asn Tyr Leu
1               5                   10                  15
Ala

<210> SEQ ID NO 449
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Trp Ala Ser Thr Arg Glu Ser
1               5

<210> SEQ ID NO 450
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Lys Gln Ser Tyr Ser Arg Arg Thr
1               5

<210> SEQ ID NO 451
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Ser Thr
65                  70                  75                  80

Leu Tyr Leu Gln Met Glu Ser Leu Arg Ala Glu Asp Thr Ala Val Tyr
                85                  90                  95

Tyr Cys Val Arg His Gly Asn Phe Gly Asn Tyr Ala Val Ser Trp Phe
            100                 105                 110

Ala His Trp Gly Gln Gly Thr Leu Val Thr Val Ser Ser
        115                 120                 125

<210> SEQ ID NO 452
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Gln Thr Val Val Thr Gln Glu Pro Ser Leu Ser Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Thr Pro Gly Gln Ala Pro Arg Gly
        35                  40                  45

Leu Ile Gly Gly Thr Asp Lys Arg Ala Pro Gly Val Pro Asp Arg Phe
    50                  55                  60

Ser Gly Ser Leu Leu Gly Asp Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 453
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Phe Thr Phe Asp Thr Tyr Ala Met Asn
1               5

<210> SEQ ID NO 454
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

-continued

```
Arg Ile Arg Ser Lys Tyr Asn Asn Tyr Ala Thr Tyr Tyr Ala Asp Ser
1               5                   10                  15

Val Lys Asp

<210> SEQ ID NO 455
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Val Arg His Gly Asn Phe Gly Asn Tyr Ala Val Ser Trp Phe Ala His
1               5                   10                  15

<210> SEQ ID NO 456
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Gly Ser Ser Thr Gly Ala Val Thr Thr Ser Asn Tyr Ala Asn
1               5                   10

<210> SEQ ID NO 457
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Gly Thr Asp Lys Arg Ala Pro
1               5

<210> SEQ ID NO 458
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Ala Leu Trp Tyr Ser Asn His Trp Val
1               5

<210> SEQ ID NO 459
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Tyr
            20                  25                  30

Ala Met Asn Trp Val Arg Gln Ala Pro Gly Lys Gly Leu Glu Trp Val
```

35                  40                  45
Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Thr
65                  70                  75                  80

Leu Tyr Leu Gln Met Glu Ser Leu Arg Ala Glu Asp Thr Ala Val Tyr
                85                  90                  95

Tyr Cys Val Arg His Gly Ser Phe Gly Asn His Ile Val Ser Trp Phe
            100                 105                 110

Ala His Trp Gly Gln Gly Thr Leu Val Thr Val Ser Ser
        115                 120                 125

<210> SEQ ID NO 460
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Gln Thr Val Val Thr Gln Glu Pro Ser Leu Ser Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Thr Pro Gly Gln Ala Pro Arg Gly
        35                  40                  45

Leu Ile Gly Gly Thr Asp Lys Arg Ala Pro Gly Val Pro Asp Arg Phe
    50                  55                  60

Ser Gly Ser Leu Leu Gly Asp Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 461
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Phe Thr Phe Asp Thr Tyr Ala Met Asn
1               5

<210> SEQ ID NO 462
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Arg Ile Arg Ser Lys Tyr Asn Asn Tyr Ala Thr Tyr Tyr Ala Asp Ser
1               5                   10                  15

Val Lys Asp

```
<210> SEQ ID NO 463
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Val Arg His Gly Ser Phe Gly Asn His Ile Val Ser Trp Phe Ala His
1               5                   10                  15

<210> SEQ ID NO 464
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Gly Ser Ser Thr Gly Ala Val Thr Thr Ser Asn Tyr Ala Asn
1               5                   10

<210> SEQ ID NO 465
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Gly Thr Asp Lys Arg Ala Pro
1               5

<210> SEQ ID NO 466
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Ala Leu Trp Tyr Ser Asn His Trp Val
1               5

<210> SEQ ID NO 467
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Ala Lys Phe
    50                  55                  60
```

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Arg Tyr Phe Tyr Asp Val Trp Gly Gln Gly
            100                 105                 110

Thr Leu Val Thr Val Ser Ser
        115

<210> SEQ ID NO 468
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

<210> SEQ ID NO 469
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Ala Asn Thr Ile Tyr Asp Ala Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Tyr Gly Arg Tyr Leu Tyr Asp Val Trp Gly Gln Gly
            100                 105                 110

Thr Leu Val Thr Val Ser Ser
        115

```
<210> SEQ ID NO 470
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Asn
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

<210> SEQ ID NO 471
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Pro Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Tyr Gly Arg Tyr Phe Tyr Asp Val Trp Gly Gln Gly
            100                 105                 110

Thr Leu Val Thr Val Ser Ser
        115

<210> SEQ ID NO 472
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Asp Ile Val Met Thr Gln Ser Pro Asp Ser Leu Ala Val Ser Leu Gly
```

```
                1               5                  10                 15
            Glu Arg Ala Thr Ile Asn Cys Arg Ser Ser Gln Ser Leu Leu Asn Ser
                            20                  25                  30

Arg Thr Arg Lys Asn Tyr Leu Ala Trp Tyr Gln Gln Lys Pro Gly Gln
                            35                  40                  45

Pro Pro Lys Leu Leu Ile Tyr Trp Ala Ser Thr Arg Glu Ser Gly Val
                50                  55                  60

Pro Asp Arg Phe Ser Gly Ser Gly Ser Gly Thr Asp Phe Thr Leu Thr
            65                  70                  75                  80

Ile Ser Ser Leu Gln Ala Glu Asp Val Ala Val Tyr Tyr Cys Lys Gln
                            85                  90                  95

Ser Tyr Ser Arg Arg Thr Phe Gly Gly Gly Thr Lys Val Glu Ile Lys
                            100                 105                 110

<210> SEQ ID NO 473
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Asp Ile Val Met Thr Gln Ser Pro Asp Ser Leu Ala Val Ser Leu Gly
            1               5                  10                 15

Glu Arg Ala Thr Ile Asn Cys Lys Ser Ser Gln Ser Leu Leu Asn Gly
                            20                  25                  30

Arg Thr Arg Lys Asn Tyr Leu Ala Trp Tyr Gln Gln Lys Pro Gly Gln
                            35                  40                  45

Pro Pro Lys Leu Leu Ile Tyr Trp Ala Ser Thr Arg Glu Ser Gly Val
                50                  55                  60

Pro Asp Arg Phe Ser Gly Ser Gly Thr Gly Thr Asp Phe Thr Leu Thr
            65                  70                  75                  80

Ile Ser Ser Leu Gln Ala Glu Asp Val Ala Val Tyr Tyr Cys Lys Gln
                            85                  90                  95

Ser Tyr Ser Arg Arg Thr Phe Gly Gly Gly Thr Lys Val Glu Ile Lys
                            100                 105                 110

<210> SEQ ID NO 474
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Gln Val Gln Leu Val Gln Ser Gly Ala Glu Val Lys Lys Pro Gly Ala
            1               5                  10                 15

Ser Val Lys Val Ser Cys Lys Ala Ser Gly Phe Asn Ile Lys Asp Tyr
                            20                  25                  30

Tyr Met His Trp Val Arg Gln Ala Pro Gly Gln Arg Leu Glu Trp Met
                            35                  40                  45

Gly Trp Ile Asp Leu Glu Asn Ala Asn Thr Ile Tyr Asp Ala Lys Phe
                50                  55                  60

Gln Gly Arg Val Thr Ile Thr Arg Asp Thr Ser Ala Ser Thr Ala Tyr
            65                  70                  75                  80

Met Glu Leu Ser Ser Leu Arg Ser Glu Asp Thr Ala Val Tyr Tyr Cys
```

```
                85                  90                  95
Ala Arg Asp Asn Tyr Gly Gly Tyr Phe Tyr Asp Val Trp Gly Gln Gly
            100                 105                 110
Thr Leu Val Thr Val Ser Ser
        115

<210> SEQ ID NO 475
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Asp Ile Val Met Thr Gln Ser Pro Asp Ser Leu Ala Val Pro Leu Gly
1               5                   10                  15
Glu Arg Ala Thr Ile Asn Cys Lys Ser Gln Ser Leu Leu Asn Ser
            20                  25                  30
Arg Thr Arg Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Lys Gln
                85                  90                  95
Ser Tyr Ser Arg Arg Thr Phe Gly Gly Gly Thr Lys Val Glu Ile Lys
            100                 105                 110

<210> SEQ ID NO 476
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Gln Val Gln Leu Val Gln Ser Gly Ala Glu Val Lys Lys Pro Gly Ala
1               5                   10                  15
Ser Val Lys Val Ser Cys Lys Ala Ser Gly Phe Asn Ile Lys Asp Tyr
            20                  25                  30
Tyr Met His Trp Val Arg Gln Ala Pro Gly Gln Arg Leu Glu Trp Met
        35                  40                  45
Gly Trp Ile Asp Leu Glu Asn Gly Asn Thr Ile Tyr Asp Pro Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Gly Tyr Gly Arg Tyr Phe Tyr Asp Val Trp Gly Gln Gly
            100                 105                 110
Thr Leu Val Thr Val Ser Ser
        115

<210> SEQ ID NO 477
<211> LENGTH: 112
<212> TYPE: PRT
```

<213> ORGANISM: Artificial Sequence
<220> FEATURE:
<223> OTHER INFORMATION: Description of Artificial Sequence: Synthetic
     polypeptide

<400> SEQUENCE: 477

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Gly Gly Thr Lys Val Glu Ile Lys
            100                 105                 110
```

<210> SEQ ID NO 478
<211> LENGTH: 119
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 478

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Pro Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Arg Tyr Phe Phe Asp Val Trp Gly Gln Gly
            100                 105                 110

Thr Leu Val Thr Val Ser Ser
        115
```

<210> SEQ ID NO 479
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 479

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30
```

```
Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Tyr Asn Leu Arg Thr Phe Gly Gly Gly Thr Lys Val Glu Ile Lys
                100                 105                 110

<210> SEQ ID NO 480
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Tyr
                20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Pro Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Tyr Gly Arg Tyr Phe Tyr Asp Val Trp Gly Gln Gly
                100                 105                 110

Thr Leu Val Thr Val Ser Ser
        115

<210> SEQ ID NO 481
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 481

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95
```

Ser Tyr Phe Arg Arg Ala Phe Gly Gly Gly Thr Lys Val Glu Ile Lys
              100                 105                 110

<210> SEQ ID NO 482
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Pro Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Arg Tyr Tyr Asp Val Trp Gly Gln Gly
            100                 105                 110

Thr Leu Val Thr Val Ser Ser
        115

<210> SEQ ID NO 483
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 484
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 484

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Gln Pro Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Gly Tyr Gly Arg Tyr Phe Tyr Asp Val Trp Gly Gln Gly
                100                 105                 110

Thr Leu Val Thr Val Ser Ser
            115

<210> SEQ ID NO 485
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 485

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
            85                  90                  95

Ser Tyr Ser Leu Arg Thr Phe Gly Gly Gly Thr Lys Val Glu Ile Lys
                100                 105                 110

<210> SEQ ID NO 486
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 486

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Pro Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Gly Arg Tyr Phe Tyr Asp Tyr Trp Gly Gln Gly
                100                 105                 110

Thr Leu Val Thr Val Ser Ser
            115

<210> SEQ ID NO 487
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 487

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Glu Ser
                20                  25                  30

Arg Thr Gly Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Tyr Ser Leu Arg Thr Phe Gly Gly Gly Thr Lys Val Glu Ile Lys
                100                 105                 110

<210> SEQ ID NO 488
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 488

Asp Ile Lys Leu Gln Gln Ser Gly Ala Glu Leu Ala Arg Pro Gly Ala
 1               5                  10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
 50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

```
Thr Thr Leu Thr Val Ser Ser Val Glu
        115                 120
```

```
<210> SEQ ID NO 489
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 489

Val Asp Asp Ile Gln Leu Thr Gln Ser Pro Ala Ile Met Ser Ala Ser
1               5                   10                  15

Pro Gly Glu Lys Val Thr Met Thr Cys Arg Ala Ser Ser Ser Val Ser
            20                  25                  30

Tyr Met Asn Trp Tyr Gln Gln Lys Ser Gly Thr Ser Pro Lys Arg Trp
        35                  40                  45

Ile Tyr Asp Thr Ser Lys Val Ala Ser Gly Val Pro Tyr Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Asn Pro
                85                  90                  95

Leu Thr Phe Gly Ala Gly Thr Lys Leu Glu Leu Lys
            100                 105
```

```
<210> SEQ ID NO 490
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175
```

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
            195                 200                 205

Leu Thr Ile Ser Ser Met Glu Ala Glu Asp Ala Ala Thr Tyr Tyr Cys
        210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 491
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Lys Phe Ser Gly Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser
        115

<210> SEQ ID NO 492
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 492

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys

<210> SEQ ID NO 493
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Gly Tyr Gly Met His
1               5

<210> SEQ ID NO 494
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Val Ile Trp Tyr Asp Gly Ser Lys Lys Tyr Tyr Val Asp Ser Val Lys
1               5                   10                  15

Gly

<210> SEQ ID NO 495
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Gln Met Gly Tyr Trp His Phe Asp Leu
1               5

<210> SEQ ID NO 496
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Arg Ala Ser Gln Ser Val Ser Ser Tyr Leu Ala
1               5                   10

<210> SEQ ID NO 497
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Asp Ala Ser Asn Arg Ala Thr
1               5

<210> SEQ ID NO 498
<211> LENGTH: 10
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 498

Gln Gln Arg Ser Asn Trp Pro Pro Leu Thr
1               5                   10

<210> SEQ ID NO 499
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 499

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Pro Met Ala Trp Val Arg Gln Ala Pro Gly Lys Gly Leu Glu Trp Val
        35                  40                  45

Ser Thr Ile Ser Thr Ser Gly Gly Arg Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Gln Tyr Ser Gly Gly Phe Asp Tyr Trp Gly Gln Gly
            100                 105                 110

Thr Leu Val Thr Val Ser Ser
        115

<210> SEQ ID NO 500
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

Asp Phe Met Leu Thr Gln Pro His Ser Val Ser Glu Ser Pro Gly Lys
1               5                   10                  15

Thr Val Ile Ile Ser Cys Trp Tyr Gln Gln Arg Pro Gly Arg Ala Pro
            20                  25                  30

Thr Thr Val Ile Phe Gly Val Pro Asp Arg Phe Ser Gly Ser Ile Asp
        35                  40                  45

Arg Ser Ser Asn Ser Ala Ser Leu Thr Ile Ser Gly Leu Gln Thr Glu
    50                  55                  60

Asp Glu Ala Asp Tyr Tyr Cys Phe Gly Gly Gly Thr Lys Leu Thr Val
65                  70                  75                  80

Leu Gly Gln Pro Lys Ala Ala Pro Ser Val Thr Leu Phe Pro Pro Ser
                85                  90                  95

Ser Glu Glu Leu Gln
            100

<210> SEQ ID NO 501
<211> LENGTH: 119
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Pro Met Ala Trp Val Arg Gln Ala Pro Gly Lys Gly Leu Glu Trp Val
        35                  40                  45

Ser Thr Ile Ser Thr Ser Gly Gly Arg Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Gln Tyr Ser Gly Gly Phe Asp Tyr Trp Gly Gln Gly
            100                 105                 110

Thr Leu Val Thr Val Ser Ser
            115

<210> SEQ ID NO 502
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 502

Asp Ile Gln Leu Thr Gln Pro Asn Ser Val Ser Thr Ser Leu Gly Ser
1               5                   10                  15

Thr Val Lys Leu Ser Cys Thr Leu Ser Ser Gly Asn Ile Glu Asn Asn
            20                  25                  30

Tyr Val His Trp Tyr Gln Leu Tyr Glu Gly Arg Ser Pro Thr Thr Met
        35                  40                  45

Ile Tyr Asp Asp Asp Lys Arg Pro Asp Gly Val Pro Asp Arg Phe Ser
    50                  55                  60

Gly Ser Ile Asp Arg Ser Ser Asn Ser Ala Phe Leu Thr Ile His Asn
65                  70                  75                  80

Val Ala Ile Glu Asp Glu Ala Ile Tyr Phe Cys His Ser Tyr Val Ser
                85                  90                  95

Ser Phe Asn Val Phe Gly Gly Gly Thr Lys Leu Thr Val Leu Arg
            100                 105                 110

<210> SEQ ID NO 503
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 503

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
```

```
            20                  25                  30
Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
            115

<210> SEQ ID NO 504
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 504

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
    50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 505
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 505

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
```

85                  90                  95
Ala Arg Tyr Tyr Asp Asp His Tyr Cys Leu Asp Tyr Trp Gly Gln Gly
                100                 105                 110

Thr Thr Val Thr Val Ser Ser Gly Glu Gly Thr Ser Thr Gly Ser Gly
            115                 120                 125

Gly Ser Gly Gly Ser Gly Gly Ala Asp Asp Ile Val Leu Thr Gln Ser
        130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
                180                 185                 190

Gly Val Pro Ala Arg Phe Ser Gly Ser Gly Ser Gly Thr Asp Tyr Ser
                195                 200                 205

Leu Thr Ile Asn Ser Leu Glu Ala Glu Asp Ala Ala Thr Tyr Tyr Cys
            210                 215                 220

Gln Gln Trp Ser Ser Asn Pro Leu Thr Phe Gly Gly Gly Thr Lys Val
225                 230                 235                 240

Glu Ile Lys

<210> SEQ ID NO 506
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 506

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
                100                 105                 110

Thr Pro Val Thr Val Ser Ser
        115

<210> SEQ ID NO 507
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Asp Asp Ile Gln Met Thr Gln Ser Pro Ser Ser Leu Ser Ala Ser Val
1               5                   10                  15

```
Gly Asp Arg Val Thr Ile Thr Cys Ser Ala Ser Ser Val Ser Tyr
            20                  25                  30

Met Asn Trp Tyr Gln Gln Thr Pro Gly Lys Ala Pro Lys Arg Trp Ile
        35                  40                  45

Tyr Asp Thr Ser Lys Leu Ala Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Trp Ser Ser Asn Pro Phe
                85                  90                  95

Thr Phe Gly Gln Gly Thr Lys Leu Gln Ile Thr
            100                 105

<210> SEQ ID NO 508
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

Gln Val Gln Leu Val Gln Ser Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115

<210> SEQ ID NO 509
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80
```

```
Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105
```

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

```
<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531
```

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 600

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 601
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 601

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 602
<211> LENGTH: 123
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 602

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly His Tyr Tyr Tyr Gly Met Asp Val
            100                 105                 110

Trp Gly Gln Gly Thr Thr Val Thr Val Ala Ser
        115                 120

<210> SEQ ID NO 603
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 603

Ala Glu Ile Val Met Thr Gln Ser Pro Ala Thr Leu Ser Val Ser Pro
1               5                   10                  15

Gly Glu Arg Ala Thr Leu Ser Cys Arg Ala Ser Gln Ser Val Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln His Tyr Ile Asn Trp Pro
                85                  90                  95

Leu Thr Phe Gly Gly Gly Thr Lys Val Glu Ile Lys
            100                 105

<210> SEQ ID NO 604
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 604

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Thr Tyr
            20                  25                  30

Tyr Ile His Trp Val Arg Gln Ala Pro Gly Gln Gly Leu Glu Trp Met
        35                  40                  45

Gly Trp Ile Phe Pro Gly Asn Asp Asn Ile Lys Tyr Ser Glu Lys Phe
            50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ile Asp Ser Val Ser Ile Tyr Tyr Phe Asp Tyr Trp Gly Gln Gly
            100                 105                 110

Thr Leu Val Thr Val Ser Ser
        115

<210> SEQ ID NO 605
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 605

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Pro Pro Lys Leu Leu Ile Tyr Trp Ala Ser Thr Arg Lys Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Thr Gln
                 85                  90                  95

Ser Phe Ile Leu Arg Thr Phe Gly Gly Gly Thr Lys Val Glu Ile Lys
            100                 105                 110

<210> SEQ ID NO 606
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Gly Tyr Ser Phe Thr Thr Tyr Tyr Ile His
 1               5                  10

<210> SEQ ID NO 607
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Trp Ile Phe Pro Gly Asn Asp Asn Ile Lys Tyr Ser Glu Lys Phe Lys
 1               5                  10                  15

Gly

```
<210> SEQ ID NO 608
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Asp Ser Val Ser Ile Tyr Tyr Phe Asp Tyr
1               5                   10

<210> SEQ ID NO 609
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Lys Ser Ser Gln Ser Leu Leu Asn Ser Arg Thr Arg Lys Asn Tyr Leu
1               5                   10                  15

Ala

<210> SEQ ID NO 610
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Trp Ala Ser Thr Arg Lys Ser
1               5

<210> SEQ ID NO 611
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Thr Gln Ser Phe Ile Leu Arg Thr
1               5

<210> SEQ ID NO 612
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 612

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ala Phe Thr Asp Tyr
            20                  25                  30

Tyr Ile His Trp Val Arg Gln Ala Pro Gly Gln Gly Leu Glu Trp Met
        35                  40                  45

Gly Trp Ile Ser Pro Gly Asn Val Asn Thr Lys Tyr Asn Glu Asn Phe
    50                  55                  60
```

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Ser Leu Tyr Tyr Phe Asp Tyr Trp Gly Gln Gly
            100                 105                 110

Thr Leu Val Thr Val Ser Ser
        115

<210> SEQ ID NO 613
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 613

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Pro Pro Lys Leu Leu Ile Tyr Trp Ala Ser Thr Arg Gln Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Thr Gln
                 85                  90                  95

Ser His Thr Leu Arg Thr Phe Gly Gly Gly Thr Lys Val Glu Ile Lys
            100                 105                 110

<210> SEQ ID NO 614
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Gly Phe Ala Phe Thr Asp Tyr Tyr Ile His
 1               5                  10

<210> SEQ ID NO 615
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Trp Ile Ser Pro Gly Asn Val Asn Thr Lys Tyr Asn Glu Asn Phe Lys
 1               5                  10                  15

Gly

<210> SEQ ID NO 616
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 616

Asp Gly Tyr Ser Leu Tyr Tyr Phe Asp Tyr
1               5                   10

<210> SEQ ID NO 617
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Lys Ser Ser Gln Ser Leu Leu Asn Ser Arg Thr Arg Lys Asn Tyr Leu
1               5                   10                  15

Ala

<210> SEQ ID NO 618
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Trp Ala Ser Thr Arg Gln Ser
1               5

<210> SEQ ID NO 619
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Thr Gln Ser His Thr Leu Arg Thr
1               5

<210> SEQ ID NO 620
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 620

Met Ala Glu Ser Gly Gly Gly Ser Val Gln Thr Gly Gly Ser Leu Arg
1               5                   10                  15

Leu Ser Cys Ala Tyr Thr Ala Ser Ser Val Cys Met Ala Trp Phe Arg
                20                  25                  30

Gln Ala Pro Gly Lys Glu Arg Glu Gly Val Ala Val Thr Arg Glu Gly
            35                  40                  45

Leu Thr Lys Thr Gly Tyr Ala Asp Ser Val Lys Gly Arg Phe Ala Ile
        50                  55                  60

Ser Gln Asp Tyr Ala Lys Lys Thr Leu Tyr Leu Gln Met Ser Ser Leu
65                  70                  75                  80
```

```
Lys Pro Glu Asp Thr Ala Arg Tyr Tyr Cys Ala Ala Arg Pro Thr Ser
                85                  90                  95

Pro Cys Thr Val Asp Gly Glu Leu Leu Ala Ser Thr Tyr Asn Tyr Trp
            100                 105                 110

Gly Gln Gly Thr Gln Val Thr Val
        115                 120

<210> SEQ ID NO 621
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 621

Met Ala Glu Ser Gly Gly Gly Ser Val Gln Thr Gly Gly Ser Leu Arg
1               5                   10                  15

Leu Ser Cys Ala Tyr Thr Ala Ser Ser Val Cys Met Ala Trp Phe Arg
            20                  25                  30

Gln Ala Pro Gly Lys Glu Arg Glu Gly Val Ala Val Thr Arg Glu Gly
        35                  40                  45

Leu Thr Lys Thr Gly Tyr Ala Asp Ser Val Lys Gly Arg Phe Ala Ile
    50                  55                  60

Ser Gln Asp Tyr Ala Lys Lys Thr Leu Tyr Leu Gln Met Ser Ser Leu
65                  70                  75                  80

Lys Pro Glu Asp Thr Ala Arg Tyr Tyr Cys Ala Ala Arg Pro Thr Ser
                85                  90                  95

Pro Cys Thr Val Asp Gly Glu Leu Leu Ala Ser Thr Tyr Asp Tyr Trp
            100                 105                 110

Gly Gln Gly Thr Gln Val Thr Val
        115                 120

<210> SEQ ID NO 622
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 622

Met Ala Glu Ser Gly Gly Gly Ser Val Gln Thr Gly Gly Ser Leu Arg
1               5                   10                  15

Leu Ser Cys Ala Tyr Thr Ala Ser Ser Val Cys Met Ala Trp Phe Arg
            20                  25                  30

Gln Ala Pro Gly Lys Glu Arg Glu Gly Val Ala Val Thr Arg Glu Gly
        35                  40                  45

Leu Thr Gln Thr Gly Tyr Ala Asp Ser Val Lys Gly Arg Phe Ala Ile
    50                  55                  60

Ser Gln Asp Tyr Ala Lys Lys Thr Leu Tyr Leu Gln Met Ser Ser Leu
65                  70                  75                  80

Lys Pro Glu Asp Thr Ala Arg Tyr Tyr Cys Ala Ala Arg Pro Thr Ser
                85                  90                  95

Pro Cys Thr Val Asp Gly Glu Leu Leu Ala Ser Thr Tyr Asn Tyr Trp
            100                 105                 110

Gly Gln Gly Thr Gln Val Thr Val
        115                 120
```

```
<210> SEQ ID NO 623
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 623

Met Ala Glu Ser Gly Gly Gly Ser Val Gln Thr Gly Gly Ser Leu Arg
1               5                   10                  15

Leu Ser Cys Ala Tyr Thr Ala Ser Ser Val Cys Met Ala Trp Phe Arg
            20                  25                  30

Gln Ala Pro Gly Lys Glu Arg Glu Gly Val Ala Val Thr Arg Glu Gly
        35                  40                  45

Leu Thr Gln Thr Gly Tyr Ala Asp Ser Val Lys Gly Arg Phe Ala Ile
    50                  55                  60

Ser Gln Asp Tyr Ala Lys Lys Thr Leu Tyr Leu Gln Met Ser Ser Leu
65                  70                  75                  80

Lys Pro Glu Asp Thr Ala Arg Tyr Tyr Cys Ala Ala Arg Pro Thr Ser
                85                  90                  95

Pro Cys Thr Val Asp Gly Glu Leu Leu Ala Ser Thr Tyr Asp Tyr Trp
            100                 105                 110

Gly Gln Gly Thr Gln Val Thr Val
        115                 120

<210> SEQ ID NO 624
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 624

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 625
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 625

Phe Thr Phe Arg Ser Phe Gly Met Ser
1               5

<210> SEQ ID NO 626
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 626

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 627
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 627

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 628
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Phe Thr Phe Arg Ser Phe Gly Met Ser
1               5

<210> SEQ ID NO 629
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 629

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 630
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Phe Thr Phe Arg Ser Phe Gly Met Ser
1               5

<210> SEQ ID NO 631
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 631

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45
```

```
Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 632
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Phe Thr Phe Arg Ser Phe Gly Met Ser
 1               5

<210> SEQ ID NO 633
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 633

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 634
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 634

Glu Val Gln Leu Val Glu Ser Gly Gly Gly Leu Val Gln Pro Gly Asn
 1               5                  10                  15
```

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 635
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 635

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 636
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Phe Thr Phe Arg Ser Phe Gly Met Ser
1               5

<210> SEQ ID NO 637
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 637

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 638
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 638

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 639
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Phe Thr Phe Arg Ser Phe Gly Met Ser
1               5

<210> SEQ ID NO 640
<211> LENGTH: 116
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 640

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
            85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 641
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 641

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Ser Gln Gly Thr Leu Val Thr
            100                 105                 110

Val Ser Ser
        115

<210> SEQ ID NO 642
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 642

Glu Val Gln Leu Val Glu Ser Gly Gly Gly Val Val Gln Pro Gly Asn
1               5                   10                  15

-continued

```
Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115
```

<210> SEQ ID NO 643
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 643

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
        115
```

<210> SEQ ID NO 644
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 644

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60
```

```
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser Ala Ala Ala
        115

<210> SEQ ID NO 645
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 645

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 646
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 646

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110
```

Val Ser Ser Gly Gly
        115

<210> SEQ ID NO 647
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 647

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
        115

<210> SEQ ID NO 648
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 648

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 649
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 649

Phe Thr Phe Arg Ser Phe Gly Met Ser
1               5

<210> SEQ ID NO 650
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 650

Ala Val Gln Leu Val Asp Ser Gly Gly Gly Leu Val Gln Pro Gly Gly
1               5                   10                  15

Ser Leu Arg Leu Ser Cys Ala Ala Ser Gly Phe Ser Phe Gly Ser Phe
            20                  25                  30

Gly Met Ser Trp Val Arg Gln Tyr Pro Gly Lys Glu Pro Glu Trp Val
        35                  40                  45

Ser Ser Ile Asn Gly Arg Gly Asp Asp Thr Arg Tyr Ala Asp Ser Val
    50                  55                  60

Lys Gly Arg Phe Ser Ile Ser Arg Asp Asn Ala Lys Asn Thr Leu Tyr
65                  70                  75                  80

Leu Gln Met Asn Ser Leu Lys Pro Glu Asp Thr Ala Glu Tyr Tyr Cys
                85                  90                  95

Thr Ile Gly Arg Ser Val Ser Arg Ser Arg Thr Gln Gly Thr Gln Val
            100                 105                 110

Thr Val Ser Ser
        115

<210> SEQ ID NO 651
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Phe Ser Phe Gly Ser Phe Gly Met Ser
1               5

<210> SEQ ID NO 652
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Ser Ile Asn Gly Arg Gly Asp Asp Thr Arg Tyr Ala Asp Ser Val Lys
1               5                   10                  15

Gly

<210> SEQ ID NO 653
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 653

Gly Arg Ser Val Ser Arg Ser
1               5

<210> SEQ ID NO 654
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 654

Ala Val Gln Leu Val Glu Ser Gly Gly Gly Leu Val Gln Pro Gly Gly
1               5                   10                  15

Ser Leu Arg Leu Thr Cys Thr Ala Ser Gly Phe Thr Phe Arg Ser Phe
            20                  25                  30

Gly Met Ser Trp Val Arg Gln Ala Pro Gly Lys Asp Gln Glu Trp Val
        35                  40                  45

Ser Ala Ile Ser Ala Asp Ser Ser Thr Lys Asn Tyr Ala Asp Ser Val
    50                  55                  60

Lys Gly Arg Phe Thr Ile Ser Arg Asp Asn Ala Lys Lys Met Leu Tyr
65                  70                  75                  80

Leu Glu Met Asn Ser Leu Lys Pro Glu Asp Thr Ala Val Tyr Tyr Cys
                85                  90                  95

Val Ile Gly Arg Gly Ser Pro Ser Pro Gly Thr Gln Val Thr Val
            100                 105                 110

Ser Ser

<210> SEQ ID NO 655
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Phe Thr Phe Arg Ser Phe Gly Met Ser
1               5

<210> SEQ ID NO 656
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Ala Ile Ser Ala Asp Ser Ser Thr Lys Asn Tyr Ala Asp Ser Val Lys
1               5                   10                  15

Gly

<210> SEQ ID NO 657
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 657

Gly Arg Gly Ser Pro
1               5

<210> SEQ ID NO 658
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 658

Gln Val Gln Leu Ala Glu Ser Gly Gly Gly Leu Val Gln Pro Gly Gly
1               5                   10                  15

Ser Leu Arg Leu Thr Cys Thr Ala Ser Gly Phe Thr Phe Gly Ser Phe
                20                  25                  30

Gly Met Ser Trp Val Arg Gln Ala Pro Gly Glu Gly Leu Glu Trp Val
            35                  40                  45

Ser Ala Ile Ser Ala Asp Ser Ser Asp Lys Arg Tyr Ala Asp Ser Val
        50                  55                  60

Lys Gly Arg Phe Thr Ile Ser Arg Asp Asn Ala Lys Lys Met Leu Tyr
65                  70                  75                  80

Leu Glu Met Asn Ser Leu Lys Ser Glu Asp Thr Ala Val Tyr Tyr Cys
                85                  90                  95

Val Ile Gly Arg Gly Ser Pro Ala Ser Gln Gly Thr Gln Val Thr Val
            100                 105                 110

Ser Ser

<210> SEQ ID NO 659
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Ala Ile Ser Ala Asp Ser Ser Asp Lys Arg Tyr Ala Asp Ser Val Lys
1               5                   10                  15

Gly

<210> SEQ ID NO 660
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Gly Arg Gly Ser Pro
1               5

<210> SEQ ID NO 661
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 661

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Val Ala Pro Gly Lys Gly Leu Glu Arg Ile
        35                  40                  45

Ser Arg Asp Ile Ser Thr Gly Gly Tyr Ser Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Leu Tyr Tyr
                85                  90                  95

Cys Ala Lys Asp Arg Glu Ala Gln Val Asp Thr Leu Asp Phe Asp Tyr
            100                 105                 110

Arg Gly Gln Gly Thr Gln Val Thr Val Ser Ser
        115                 120

<210> SEQ ID NO 662
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Phe Thr Phe Ser Asn Tyr Trp Met Tyr
1               5

<210> SEQ ID NO 663
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Asn Tyr Trp Met Tyr
1               5

<210> SEQ ID NO 664
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Arg Asp Ile Ser Thr Gly Gly Tyr Ser Tyr Tyr Ala Asp Ser Val
1               5                   10                  15

Lys Gly

<210> SEQ ID NO 665
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 665

Asp Arg Glu Ala Gln Val Asp Thr Leu Asp Phe Asp Tyr
1               5                   10

<210> SEQ ID NO 666
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 666

Ala Val Gln Leu Val Glu Ser Gly Gly Gly Leu Val Gln Gly Gly
1               5                   10                  15

Ser Leu Arg Leu Ala Cys Ala Ala Ser Glu Arg Ile Phe Asp Leu Asn
                20                  25                  30

Leu Met Gly Trp Tyr Arg Gln Gly Pro Gly Asn Glu Arg Glu Leu Val
            35                  40                  45

Ala Thr Cys Ile Thr Val Gly Asp Ser Thr Asn Tyr Ala Asp Ser Val
        50                  55                  60

Lys Gly Arg Phe Thr Ile Ser Met Asp Tyr Thr Lys Gln Thr Val Tyr
65                  70                  75                  80

Leu His Met Asn Ser Leu Arg Pro Glu Asp Thr Gly Leu Tyr Tyr Cys
                85                  90                  95

Lys Ile Arg Arg Thr Trp His Ser Glu Leu Trp Gly Gln Gly Thr Gln
            100                 105                 110

Val Thr Val Ser Ser
        115

<210> SEQ ID NO 667
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Ser Glu Arg Ile Phe Asp Leu Asn Leu Met Gly
1               5                   10

<210> SEQ ID NO 668
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Leu Asn Leu Met Gly
1               5

<210> SEQ ID NO 669
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 669

Thr Cys Ile Thr Val Gly Asp Ser Thr Asn Tyr Ala Asp Ser Val Lys
1               5                   10                  15

Gly

<210> SEQ ID NO 670
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Arg Arg Thr Trp His Ser Glu Leu
1               5

<210> SEQ ID NO 671
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 671

Glu Val Gln Leu Val Glu Ser Gly Gly Gly Leu Val Gln Gly Gly
1               5                   10                  15

Ser Leu Arg Leu Ala Cys Ala Ala Ser Glu Arg Ile Trp Asp Ile Asn
            20                  25                  30

Leu Leu Gly Trp Tyr Arg Gln Gly Pro Gly Asn Glu Arg Glu Leu Val
        35                  40                  45

Ala Thr Ile Thr Val Gly Asp Ser Thr Ser Tyr Ala Asp Ser Val Lys
    50                  55                  60

Gly Arg Phe Thr Ile Ser Arg Asp Tyr Asp Lys Asn Thr Leu Tyr Leu
65                  70                  75                  80

Gln Met Asn Ser Leu Arg Pro Glu Asp Thr Gly Leu Tyr Tyr Cys Lys
                85                  90                  95

Ile Arg Arg Thr Trp His Ser Glu Leu Trp Gly Gln Gly Thr Gln Val
            100                 105                 110

Thr Val Ser Ser
        115

<210> SEQ ID NO 672
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Ser Glu Arg Ile Trp Asp Ile Asn Leu Leu Gly
1               5                   10

<210> SEQ ID NO 673
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 673

Ile Asn Leu Leu Gly
1               5

<210> SEQ ID NO 674
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Thr Ile Thr Val Gly Asp Ser Thr Ser Tyr Ala Asp Ser Val Lys Gly
1               5                   10                  15

<210> SEQ ID NO 675
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Arg Arg Thr Trp His Ser Glu Leu
1               5

<210> SEQ ID NO 676
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 676

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser
        115

<210> SEQ ID NO 677
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677
```

```
Gly Phe Thr Phe Ser Lys Phe Gly Met Ser
1               5                  10
```

<210> SEQ ID NO 678
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

```
Ser Ile Ser Gly Ser Gly Arg Asp Thr Leu Tyr Ala Glu Ser Val Lys
1               5                   10                  15
```

<210> SEQ ID NO 679
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

```
Gly Gly Ser Leu Ser Val
1               5
```

<210> SEQ ID NO 680
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 680

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 681
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

```
Gly Phe Thr Phe Ser Arg Phe Gly Met Ser
1               5                   10
```

```
<210> SEQ ID NO 682
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

Ser Ile Ser Gly Ser Gly Ser Asp Thr Leu Tyr Ala Glu Ser Val Lys
1               5                   10                  15

<210> SEQ ID NO 683
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 683

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Thr Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 684
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 684

Ser Ile Ser Gly Ser Gly Thr Asp Thr Leu Tyr Ala Glu Ser Val Lys
1               5                   10                  15

<210> SEQ ID NO 685
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 685

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
```

```
                   20                  25                  30

Trp Met Ser Trp Val Arg Gln Ala Pro Gly Lys Gly Leu Glu Trp Val
            35                  40                  45

Ser Ser Ile Asp Phe Met Gly Pro His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Arg Thr Ser Met Leu Pro Met Lys Gly Lys Phe Asp Tyr
            100                 105                 110

Trp Gly Gln Gly Thr Leu Val Thr Val Ser Ser
        115                 120
```

<210> SEQ ID NO 686
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 686

```
Glu Val Gln Leu Leu Glu Ser Gly Gly Gly Leu Val Gln Pro Gly Gly
 1               5                  10                  15

Ser Leu Arg Leu Ser Cys Thr Ala Ser Gly Phe Thr Phe Asp Glu Tyr
                20                  25                  30

Asn Met Ser Trp Val Arg Gln Ala Pro Gly Lys Gly Leu Glu Trp Val
            35                  40                  45

Ser Thr Ile Leu Pro His Gly Asp Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gln Asp Pro Leu Tyr Arg Phe Asp Tyr Trp Gly Gln Gly Thr
            100                 105                 110

Leu Val Thr Val Ser Ser
        115
```

<210> SEQ ID NO 687
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 687

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Lys Ile Ala Thr Tyr
                20                  25                  30

Leu Asn Trp Tyr Gln Gln Lys Pro Gly Lys Ala Pro Lys Leu Leu Ile
            35                  40                  45

Tyr Arg Ser Ser Ser Leu Gln Ser Ala Val Pro Ser Arg Phe Ser Gly
 50                  55                  60

Ser Gly Ser Gly Thr Val Phe Thr Leu Thr Ile Ser Ser Leu Gln Pro
```

```
            65                  70                  75                  80
Glu Asp Phe Ala Thr Tyr Tyr Cys Gln Gln Thr Tyr Ala Val Pro Pro
                85                  90                  95
Thr Phe Gly Gln Gly Thr Lys Val Glu Ile Lys Arg
            100                 105
```

<210> SEQ ID NO 688
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 688

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Arg Asn Ser Pro Leu Gln Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Thr Tyr Arg Val Pro Pro
                85                  90                  95
Thr Phe Gly Gln Gly Thr Lys Val Glu Ile Lys Arg
            100                 105
```

<210> SEQ ID NO 689
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 689

```
Gln Val Gln Leu Gln Glu Ser Gly Gly Gly Leu Val Gln Pro Gly Gly
1               5                   10                  15
Ser Leu Arg Leu Ser Cys Glu Ala Ser Gly Phe Thr Phe Ser Arg Phe
            20                  25                  30
Gly Met Thr Trp Val Arg Gln Ala Pro Gly Lys Gly Val Glu Trp Val
        35                  40                  45
Ser Gly Ile Ser Ser Leu Gly Asp Ser Thr Leu Tyr Ala Asp Ser Val
50                  55                  60
Lys Gly Arg Phe Thr Ile Ser Arg Asp Asn Ala Lys Asn Thr Leu Tyr
65                  70                  75                  80
Leu Gln Met Asn Ser Leu Lys Pro Glu Asp Thr Ala Val Tyr Tyr Cys
                85                  90                  95
Thr Ile Gly Gly Ser Leu Asn Pro Gly Gly Gln Gly Thr Gln Val Thr
            100                 105                 110
Val Ser Ser
        115
```

<210> SEQ ID NO 690
<211> LENGTH: 121
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 690

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 691
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 691

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys Arg Thr
            100                 105                 110

<210> SEQ ID NO 692
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 692

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

```
Ala Ile Asn Trp Val Arg Gln Ala Pro Gly Lys Gly Leu Glu Trp Ile
         35                  40                  45

Gly Ile Ile Trp Ala Ser Gly Thr Thr Phe Tyr Ala Thr Trp Ala Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
             85                  90                  95

Arg Thr Val Pro Gly Tyr Ser Thr Ala Pro Tyr Phe Asp Leu Trp Gly
                100                 105                 110

Gln Gly Thr Leu Val Thr Val Ser Ser
            115                 120

<210> SEQ ID NO 693
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 693

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
         35                  40                  45

Ile Tyr Glu Ala Ser Lys Leu Thr Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gly Gly Gly Tyr Ser Ser Ile
             85                  90                  95

Ser Asp Thr Thr Phe Gly Gly Gly Thr Lys Val Glu Ile Lys Arg Thr
                100                 105                 110

<210> SEQ ID NO 694
<211> LENGTH: 625
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 694

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95
```

```
Thr Ile Gly Gly Ser Leu Ser Pro Ser Ser Gln Gly Thr Leu Val Thr
                100                 105                 110

Val Ser Ser Gly Gly Gly Gly Ser Gly Gly Gly Ser Glu Ile Val Leu
                115                 120                 125

Thr Gln Ser Pro Ala Thr Leu Ser Leu Ser Pro Gly Glu Arg Ala Thr
    130                 135                 140

Leu Ser Cys Ser Ala Ser Ser Ser Val Gly Tyr Met His Trp Tyr Gln
145                 150                 155                 160

Gln Lys Pro Gly Gln Ala Pro Arg Leu Leu Ile Tyr Asp Thr Ser Lys
                165                 170                 175

Leu Ala Ser Gly Ile Pro Ala Arg Phe Ser Gly Ser Gly Ser Gly Thr
                180                 185                 190

Asp Phe Thr Leu Thr Ile Ser Ser Leu Glu Pro Glu Asp Phe Ala Val
            195                 200                 205

Tyr Tyr Cys Phe Gln Gly Ser Val Tyr Pro Phe Thr Phe Gly Gln Gly
210                 215                 220

Thr Lys Leu Glu Ile Lys Gly Gly Gly Gly Ser Gly Gly Gly Gly Ser
225                 230                 235                 240

Gly Gly Gly Gly Ser Gln Val Gln Leu Gln Glu Ser Gly Pro Gly Leu
                245                 250                 255

Val Lys Pro Ser Gln Thr Leu Ser Leu Thr Cys Thr Val Ser Gly Gly
                260                 265                 270

Ser Ile Ser Thr Ser Thr Met Gly Val Gly Trp Ile Arg Gln His Pro
                275                 280                 285

Gly Lys Gly Leu Glu Trp Ile Gly Phe Ile Trp Trp Asp Asp Asp Lys
                290                 295                 300

Arg Tyr Asn Pro Asn Leu Lys Ser Arg Val Thr Met Ser Val Asp Thr
305                 310                 315                 320

Ser Lys Asn Gln Phe Ser Leu Lys Leu Ser Ser Val Thr Ala Ala Asp
                325                 330                 335

Thr Ala Val Tyr Tyr Cys Ala Arg Met Glu Leu Trp Ser Tyr Tyr Phe
                340                 345                 350

Asp Tyr Trp Gly Gln Gly Thr Leu Val Thr Val Ser Ser Gly Gly Gly
                355                 360                 365

Gly Ser Gly Gly Gly Ser Asp Ile Val Met Thr Gln Ser Pro Asp Ser
    370                 375                 380

Leu Ala Val Ser Leu Gly Glu Arg Ala Thr Ile Asn Cys Lys Ser Ser
385                 390                 395                 400

Gln Ser Leu Leu Asn Ala Arg Thr Gly Lys Asn Tyr Leu Ala Trp Tyr
                405                 410                 415

Gln Gln Lys Pro Gly Gln Pro Pro Lys Leu Leu Ile Tyr Trp Ala Ser
                420                 425                 430

Thr Arg Glu Ser Gly Val Pro Asp Arg Phe Ser Gly Ser Gly Ser Gly
        435                 440                 445

Thr Asp Phe Thr Leu Thr Ile Ser Ser Leu Gln Ala Glu Asp Val Ala
    450                 455                 460

Val Tyr Tyr Cys Lys Gln Ser Tyr Ser Arg Arg Thr Phe Gly Gly Gly
465                 470                 475                 480

Thr Lys Val Glu Ile Lys Gly Gly Gly Gly Ser Gly Gly Gly Gly Ser
                485                 490                 495

Gly Gly Gly Gly Ser Gly Gly Gly Ser Gln Val Gln Leu Val Gln
                500                 505                 510
```

```
Ser Gly Ala Glu Val Lys Lys Pro Gly Ala Ser Val Lys Val Ser Cys
            515                 520                 525

Lys Ala Ser Gly Phe Asn Ile Lys Asp Tyr Tyr Met His Trp Val Arg
530                 535                 540

Gln Ala Pro Gly Gln Arg Leu Glu Trp Met Gly Trp Ile Asp Leu Glu
545                 550                 555                 560

Asn Ala Asn Thr Ile Tyr Asp Ala Lys Phe Gln Gly Arg Val Thr Ile
                565                 570                 575

Thr Arg Asp Thr Ser Ala Ser Thr Ala Tyr Met Glu Leu Ser Ser Leu
            580                 585                 590

Arg Ser Glu Asp Thr Ala Val Tyr Tyr Cys Ala Arg Asp Ala Tyr Gly
    595                 600                 605

Arg Tyr Phe Tyr Asp Val Trp Gly Gln Gly Thr Leu Val Thr Val Ser
        610                 615                 620

Ser
625

<210> SEQ ID NO 695
<211> LENGTH: 625
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 695

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser Gly Gly Gly Gly Ser Gly Gly Gly Ser Asp Ile Val Met
        115                 120                 125

Thr Gln Ser Pro Asp Ser Leu Ala Val Ser Leu Gly Glu Arg Ala Thr
    130                 135                 140

Ile Asn Cys Lys Ser Ser Gln Ser Leu Leu Asn Ala Arg Thr Gly Lys
145                 150                 155                 160

Asn Tyr Leu Ala Trp Tyr Gln Gln Lys Pro Gly Gln Pro Pro Lys Leu
                165                 170                 175

Leu Ile Tyr Trp Ala Ser Thr Arg Glu Ser Gly Val Pro Asp Arg Phe
            180                 185                 190

Ser Gly Ser Gly Ser Gly Thr Asp Phe Thr Leu Thr Ile Ser Ser Leu
        195                 200                 205

Gln Ala Glu Asp Val Ala Val Tyr Tyr Cys Lys Gln Ser Tyr Ser Arg
    210                 215                 220

Arg Thr Phe Gly Gly Gly Thr Lys Val Glu Ile Lys Gly Gly Gly Gly
225                 230                 235                 240
```

```
Ser Gly Gly Gly Gly Ser Gly Gly Gly Ser Gly Gly Gly Ser
            245                 250                 255

Gln Val Gln Leu Val Gln Ser Gly Ala Glu Val Lys Lys Pro Gly Ala
            260                 265                 270

Ser Val Lys Val Ser Cys Lys Ala Ser Gly Phe Asn Ile Lys Asp Tyr
            275                 280                 285

Tyr Met His Trp Val Arg Gln Ala Pro Gly Gln Arg Leu Glu Trp Met
            290                 295                 300

Gly Trp Ile Asp Leu Glu Asn Ala Asn Thr Ile Tyr Asp Ala Lys Phe
305                 310                 315                 320

Gln Gly Arg Val Thr Ile Thr Arg Asp Thr Ser Ala Ser Thr Ala Tyr
            325                 330                 335

Met Glu Leu Ser Ser Leu Arg Ser Glu Asp Thr Ala Val Tyr Tyr Cys
            340                 345                 350

Ala Arg Asp Ala Tyr Gly Arg Tyr Phe Tyr Asp Val Trp Gly Gln Gly
            355                 360                 365

Thr Leu Val Thr Val Ser Ser Gly Gly Gly Ser Gly Gly Gly Ser
            370                 375                 380

Glu Ile Val Leu Thr Gln Ser Pro Ala Thr Leu Ser Leu Ser Pro Gly
385                 390                 395                 400

Glu Arg Ala Thr Leu Ser Cys Ser Ala Ser Ser Val Gly Tyr Met
            405                 410                 415

His Trp Tyr Gln Gln Lys Pro Gly Gln Ala Pro Arg Leu Leu Ile Tyr
            420                 425                 430

Asp Thr Ser Lys Leu Ala Ser Gly Ile Pro Ala Arg Phe Ser Gly Ser
            435                 440                 445

Gly Ser Gly Thr Asp Phe Thr Leu Thr Ile Ser Ser Leu Glu Pro Glu
            450                 455                 460

Asp Phe Ala Val Tyr Tyr Cys Phe Gln Gly Ser Val Tyr Pro Phe Thr
465                 470                 475                 480

Phe Gly Gln Gly Thr Lys Leu Glu Ile Lys Gly Gly Gly Ser Gly
            485                 490                 495

Gly Gly Gly Ser Gly Gly Gly Ser Gln Val Gln Leu Gln Glu Ser
            500                 505                 510

Gly Pro Gly Leu Val Lys Pro Ser Gln Thr Leu Ser Leu Thr Cys Thr
            515                 520                 525

Val Ser Gly Gly Ser Ile Ser Thr Ser Thr Met Gly Val Gly Trp Ile
530                 535                 540

Arg Gln His Pro Gly Lys Gly Leu Glu Trp Ile Gly Phe Ile Trp Trp
545                 550                 555                 560

Asp Asp Asp Lys Arg Tyr Asn Pro Asn Leu Lys Ser Arg Val Thr Met
            565                 570                 575

Ser Val Asp Thr Ser Lys Asn Gln Phe Ser Leu Lys Leu Ser Ser Val
            580                 585                 590

Thr Ala Ala Asp Thr Ala Val Tyr Tyr Cys Ala Arg Met Glu Leu Trp
            595                 600                 605

Ser Tyr Tyr Phe Asp Tyr Trp Gly Gln Gly Thr Leu Val Thr Val Ser
            610                 615                 620

Ser
625

<210> SEQ ID NO 696
<211> LENGTH: 625
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 696

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Gly Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys Gly Gly Gly Gly Ser Gly
            100                 105                 110

Gly Gly Gly Ser Gly Gly Gly Gly Ser Gln Val Gln Leu Gln Glu Ser
        115                 120                 125

Gly Pro Gly Leu Val Lys Pro Ser Gln Thr Leu Ser Leu Thr Cys Thr
    130                 135                 140

Val Ser Gly Gly Ser Ile Ser Thr Ser Thr Met Gly Val Gly Trp Ile
145                 150                 155                 160

Arg Gln His Pro Gly Lys Gly Leu Glu Trp Ile Gly Phe Ile Trp Trp
                165                 170                 175

Asp Asp Asp Lys Arg Tyr Asn Pro Asn Leu Lys Ser Arg Val Thr Met
            180                 185                 190

Ser Val Asp Thr Ser Lys Asn Gln Phe Ser Leu Lys Leu Ser Ser Val
        195                 200                 205

Thr Ala Ala Asp Thr Ala Val Tyr Tyr Cys Ala Arg Met Glu Leu Trp
    210                 215                 220

Ser Tyr Tyr Phe Asp Tyr Trp Gly Gln Gly Thr Leu Val Thr Val Ser
225                 230                 235                 240

Ser Gly Gly Gly Gly Ser Gly Gly Gly Ser Lys Val Gln Leu Val Glu
                245                 250                 255

Ser Gly Gly Gly Leu Val Gln Pro Gly Gly Ser Leu Arg Leu Ser Cys
            260                 265                 270

Ala Ala Ser Gly Phe Thr Phe Ser Ser Phe Gly Met Thr Trp Val Arg
        275                 280                 285

Gln Ala Pro Gly Lys Gly Leu Glu Trp Val Ser Ser Ile Ser Gly Ser
    290                 295                 300

Gly Ser Asp Thr Leu Tyr Ala Asp Ser Val Arg Gly Arg Phe Thr Ile
305                 310                 315                 320

Ser Arg Asp Asn Ser Lys Asn Thr Leu Tyr Leu Gln Met Asn Ser Leu
                325                 330                 335

Arg Ala Glu Asp Thr Ala Val Tyr Tyr Cys Thr Ile Gly Gly Ser Leu
            340                 345                 350

Ser Pro Ser Ser Gln Gly Thr Leu Val Thr Val Ser Ser Gly Gly Gly
        355                 360                 365

Gly Ser Gly Gly Gly Ser Asp Ile Val Met Thr Gln Ser Pro Asp Ser
    370                 375                 380

```
Leu Ala Val Ser Leu Gly Glu Arg Ala Thr Ile Asn Cys Lys Ser Ser
385                 390                 395                 400

Gln Ser Leu Leu Asn Ala Arg Thr Gly Lys Asn Tyr Leu Ala Trp Tyr
            405                 410                 415

Gln Gln Lys Pro Gly Gln Pro Pro Lys Leu Leu Ile Tyr Trp Ala Ser
        420                 425                 430

Thr Arg Glu Ser Gly Val Pro Asp Arg Phe Ser Gly Ser Gly Ser Gly
    435                 440                 445

Thr Asp Phe Thr Leu Thr Ile Ser Ser Leu Gln Ala Glu Asp Val Ala
450                 455                 460

Val Tyr Tyr Cys Lys Gln Ser Tyr Ser Arg Arg Thr Phe Gly Gly Gly
465                 470                 475                 480

Thr Lys Val Glu Ile Lys Gly Gly Gly Ser Gly Gly Gly Gly Ser
                485                 490                 495

Gly Gly Gly Gly Ser Gly Gly Gly Ser Gln Val Gln Leu Val Gln
                500                 505                 510

Ser Gly Ala Glu Val Lys Lys Pro Gly Ala Ser Val Lys Val Ser Cys
            515                 520                 525

Lys Ala Ser Gly Phe Asn Ile Lys Asp Tyr Tyr Met His Trp Val Arg
        530                 535                 540

Gln Ala Pro Gly Gln Arg Leu Glu Trp Met Gly Trp Ile Asp Leu Glu
545                 550                 555                 560

Asn Ala Asn Thr Ile Tyr Asp Ala Lys Phe Gln Gly Arg Val Thr Ile
                565                 570                 575

Thr Arg Asp Thr Ser Ala Ser Thr Ala Tyr Met Glu Leu Ser Ser Leu
            580                 585                 590

Arg Ser Glu Asp Thr Ala Val Tyr Tyr Cys Ala Arg Asp Ala Tyr Gly
        595                 600                 605

Arg Tyr Phe Tyr Asp Val Trp Gly Gln Gly Thr Leu Val Thr Val Ser
    610                 615                 620

Ser
625

<210> SEQ ID NO 697
<211> LENGTH: 625
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 697

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
```

-continued

```
            100                 105                 110
Gly Gly Gly Gly Ser Gly Gly Gly Ser Gly Gly Gly Ser Gly
        115                 120                 125
Gly Gly Gly Ser Gln Val Gln Leu Val Gln Ser Gly Ala Glu Val Lys
        130                 135                 140
Lys Pro Gly Ala Ser Val Lys Val Ser Cys Lys Ala Ser Gly Phe Asn
145                 150                 155                 160
Ile Lys Asp Tyr Tyr Met His Trp Val Arg Gln Ala Pro Gly Gln Arg
                165                 170                 175
Leu Glu Trp Met Gly Trp Ile Asp Leu Glu Asn Ala Asn Thr Ile Tyr
            180                 185                 190
Asp Ala Lys Phe Gln Gly Arg Val Thr Ile Thr Arg Asp Thr Ser Ala
            195                 200                 205
Ser Thr Ala Tyr Met Glu Leu Ser Ser Leu Arg Ser Glu Asp Thr Ala
210                 215                 220
Val Tyr Tyr Cys Ala Arg Asp Ala Tyr Gly Arg Tyr Phe Tyr Asp Val
225                 230                 235                 240
Trp Gly Gln Gly Thr Leu Val Thr Val Ser Ser Gly Gly Gly Gly Ser
                245                 250                 255
Gly Gly Gly Ser Lys Val Gln Leu Val Glu Ser Gly Gly Gly Leu Val
                260                 265                 270
Gln Pro Gly Gly Ser Leu Arg Leu Ser Cys Ala Ala Ser Gly Phe Thr
            275                 280                 285
Phe Ser Ser Phe Gly Met Thr Trp Val Arg Gln Ala Pro Gly Lys Gly
        290                 295                 300
Leu Glu Trp Val Ser Ser Ile Ser Gly Ser Gly Ser Asp Thr Leu Tyr
305                 310                 315                 320
Ala Asp Ser Val Arg Gly Arg Phe Thr Ile Ser Arg Asp Asn Ser Lys
                325                 330                 335
Asn Thr Leu Tyr Leu Gln Met Asn Ser Leu Arg Ala Glu Asp Thr Ala
            340                 345                 350
Val Tyr Tyr Cys Thr Ile Gly Gly Ser Leu Ser Pro Ser Ser Gln Gly
                355                 360                 365
Thr Leu Val Thr Val Ser Ser Gly Gly Gly Ser Gly Gly Gly Ser
            370                 375                 380
Glu Ile Val Leu Thr Gln Ser Pro Ala Thr Leu Ser Leu Ser Pro Gly
385                 390                 395                 400
Glu Arg Ala Thr Leu Ser Cys Ser Ala Ser Ser Val Gly Tyr Met
                405                 410                 415
His Trp Tyr Gln Gln Lys Pro Gly Gln Ala Pro Arg Leu Leu Ile Tyr
                420                 425                 430
Asp Thr Ser Lys Leu Ala Ser Gly Ile Pro Ala Arg Phe Ser Gly Ser
            435                 440                 445
Gly Ser Gly Thr Asp Phe Thr Leu Thr Ile Ser Ser Leu Glu Pro Glu
        450                 455                 460
Asp Phe Ala Val Tyr Tyr Cys Phe Gln Gly Ser Val Tyr Pro Phe Thr
465                 470                 475                 480
Phe Gly Gln Gly Thr Lys Leu Glu Ile Lys Gly Gly Gly Gly Ser Gly
                485                 490                 495
Gly Gly Gly Ser Gly Gly Gly Gly Ser Gln Val Gln Leu Gln Glu Ser
            500                 505                 510
Gly Pro Gly Leu Val Lys Pro Ser Gln Thr Leu Ser Leu Thr Cys Thr
        515                 520                 525
```

```
Val Ser Gly Gly Ser Ile Ser Thr Ser Thr Met Gly Val Gly Trp Ile
        530                 535                 540

Arg Gln His Pro Gly Lys Gly Leu Glu Trp Ile Gly Phe Ile Trp Trp
545                 550                 555                 560

Asp Asp Asp Lys Arg Tyr Asn Pro Asn Leu Lys Ser Arg Val Thr Met
                565                 570                 575

Ser Val Asp Thr Ser Lys Asn Gln Phe Ser Leu Lys Leu Ser Ser Val
        580                 585                 590

Thr Ala Ala Asp Thr Ala Val Tyr Tyr Cys Ala Arg Met Glu Leu Trp
        595                 600                 605

Ser Tyr Tyr Phe Asp Tyr Trp Gly Gln Gly Thr Leu Val Thr Val Ser
        610                 615                 620

Ser
625

<210> SEQ ID NO 698
<211> LENGTH: 625
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 698

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Gly Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys Gly Gly Gly Gly Ser Gly
            100                 105                 110

Gly Gly Gly Ser Gly Gly Gly Gly Ser Gln Val Gln Leu Gln Glu Ser
        115                 120                 125

Gly Pro Gly Leu Val Lys Pro Ser Gln Thr Leu Ser Leu Thr Cys Thr
    130                 135                 140

Val Ser Gly Gly Ser Ile Ser Thr Ser Thr Met Gly Val Gly Trp Ile
145                 150                 155                 160

Arg Gln His Pro Gly Lys Gly Leu Glu Trp Ile Gly Phe Ile Trp Trp
                165                 170                 175

Asp Asp Asp Lys Arg Tyr Asn Pro Asn Leu Lys Ser Arg Val Thr Met
            180                 185                 190

Ser Val Asp Thr Ser Lys Asn Gln Phe Ser Leu Lys Leu Ser Ser Val
        195                 200                 205

Thr Ala Ala Asp Thr Ala Val Tyr Tyr Cys Ala Arg Met Glu Leu Trp
    210                 215                 220

Ser Tyr Tyr Phe Asp Tyr Trp Gly Gln Gly Thr Leu Val Thr Val Ser
225                 230                 235                 240

Ser Gly Gly Gly Gly Ser Gly Gly Gly Ser Asp Ile Val Met Thr Gln
```

-continued

```
                245                 250                 255
Ser Pro Asp Ser Leu Ala Val Ser Leu Gly Glu Arg Ala Thr Ile Asn
            260                 265                 270

Cys Lys Ser Ser Gln Ser Leu Leu Asn Ala Arg Thr Gly Lys Asn Tyr
        275                 280                 285

Leu Ala Trp Tyr Gln Gln Lys Pro Gly Gln Pro Pro Lys Leu Leu Ile
    290                 295                 300

Tyr Trp Ala Ser Thr Arg Glu Ser Gly Val Pro Asp Arg Phe Ser Gly
305                 310                 315                 320

Ser Gly Ser Gly Thr Asp Phe Thr Leu Thr Ile Ser Ser Leu Gln Ala
                325                 330                 335

Glu Asp Val Ala Val Tyr Tyr Cys Lys Gln Ser Tyr Ser Arg Arg Thr
            340                 345                 350

Phe Gly Gly Gly Thr Lys Val Glu Ile Lys Gly Gly Gly Gly Ser Gly
        355                 360                 365

Gly Gly Gly Ser Gly Gly Gly Ser Gly Gly Gly Ser Gln Val
    370                 375                 380

Gln Leu Val Gln Ser Gly Ala Glu Val Lys Lys Pro Gly Ala Ser Val
385                 390                 395                 400

Lys Val Ser Cys Lys Ala Ser Gly Phe Asn Ile Lys Asp Tyr Tyr Met
                405                 410                 415

His Trp Val Arg Gln Ala Pro Gly Gln Arg Leu Glu Trp Met Gly Trp
            420                 425                 430

Ile Asp Leu Glu Asn Ala Asn Thr Ile Tyr Asp Ala Lys Phe Gln Gly
        435                 440                 445

Arg Val Thr Ile Thr Arg Asp Thr Ser Ala Ser Thr Ala Tyr Met Glu
    450                 455                 460

Leu Ser Ser Leu Arg Ser Glu Asp Thr Ala Val Tyr Tyr Cys Ala Arg
465                 470                 475                 480

Asp Ala Tyr Gly Arg Tyr Phe Tyr Asp Val Trp Gly Gln Gly Thr Leu
                485                 490                 495

Val Thr Val Ser Ser Gly Gly Gly Gly Ser Gly Gly Gly Ser Lys Val
            500                 505                 510

Gln Leu Val Glu Ser Gly Gly Gly Leu Val Gln Pro Gly Gly Ser Leu
        515                 520                 525

Arg Leu Ser Cys Ala Ala Ser Gly Phe Thr Phe Ser Ser Phe Gly Met
    530                 535                 540

Thr Trp Val Arg Gln Ala Pro Gly Lys Gly Leu Glu Trp Val Ser Ser
545                 550                 555                 560

Ile Ser Gly Ser Gly Ser Asp Thr Leu Tyr Ala Asp Ser Val Arg Gly
                565                 570                 575

Arg Phe Thr Ile Ser Arg Asp Asn Ser Lys Asn Thr Leu Tyr Leu Gln
            580                 585                 590

Met Asn Ser Leu Arg Ala Glu Asp Thr Ala Val Tyr Tyr Cys Thr Ile
        595                 600                 605

Gly Gly Ser Leu Ser Pro Ser Ser Gln Gly Thr Leu Val Thr Val Ser
    610                 615                 620

Ser
625

<210> SEQ ID NO 699
<211> LENGTH: 625
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 699

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Ser Gly Gly Gly Ser
            115                 120                 125

Gly Gly Gly Ser Gln Val Gln Leu Val Gln Ser Gly Ala Glu Val Lys
130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Gly Gly Gly Gly Ser
                245                 250                 255

Gly Gly Gly Ser Glu Ile Val Leu Thr Gln Ser Pro Ala Thr Leu Ser
            260                 265                 270

Leu Ser Pro Gly Glu Arg Ala Thr Leu Ser Cys Ser Ala Ser Ser Ser
        275                 280                 285

Val Gly Tyr Met His Trp Tyr Gln Gln Lys Pro Gly Gln Ala Pro Arg
290                 295                 300

Leu Leu Ile Tyr Asp Thr Ser Lys Leu Ala Ser Gly Ile Pro Ala Arg
305                 310                 315                 320

Phe Ser Gly Ser Gly Ser Gly Thr Asp Phe Thr Leu Thr Ile Ser Ser
                325                 330                 335

Leu Glu Pro Glu Asp Phe Ala Val Tyr Tyr Cys Phe Gln Gly Ser Val
            340                 345                 350

Tyr Pro Phe Thr Phe Gly Gln Gly Thr Lys Leu Glu Ile Lys Gly Gly
        355                 360                 365

Gly Gly Ser Gly Gly Gly Gly Ser Gly Gly Gly Gly Ser Gln Val Gln
370                 375                 380

Leu Gln Glu Ser Gly Pro Gly Leu Val Lys Pro Ser Gln Thr Leu Ser
```

```
                385                 390                 395                 400
Leu Thr Cys Thr Val Ser Gly Gly Ser Ile Ser Thr Ser Thr Met Gly
                405                 410                 415

Val Gly Trp Ile Arg Gln His Pro Lys Gly Leu Glu Trp Ile Gly
                420                 425                 430

Phe Ile Trp Trp Asp Asp Lys Arg Tyr Asn Pro Asn Leu Lys Ser
                435                 440                 445

Arg Val Thr Met Ser Val Asp Thr Ser Lys Asn Gln Phe Ser Leu Lys
            450                 455                 460

Leu Ser Ser Val Thr Ala Ala Asp Thr Ala Val Tyr Tyr Cys Ala Arg
465                 470                 475                 480

Met Glu Leu Trp Ser Tyr Tyr Phe Asp Tyr Trp Gly Gln Gly Thr Leu
                485                 490                 495

Val Thr Val Ser Ser Gly Gly Gly Gly Ser Gly Gly Gly Ser Lys Val
                500                 505                 510

Gln Leu Val Glu Ser Gly Gly Gly Leu Val Gln Pro Gly Gly Ser Leu
            515                 520                 525

Arg Leu Ser Cys Ala Ala Ser Gly Phe Thr Phe Ser Ser Phe Gly Met
            530                 535                 540

Thr Trp Val Arg Gln Ala Pro Gly Lys Gly Leu Glu Trp Val Ser Ser
545                 550                 555                 560

Ile Ser Gly Ser Gly Ser Asp Thr Leu Tyr Ala Asp Ser Val Arg Gly
                565                 570                 575

Arg Phe Thr Ile Ser Arg Asp Asn Ser Lys Asn Thr Leu Tyr Leu Gln
                580                 585                 590

Met Asn Ser Leu Arg Ala Glu Asp Thr Ala Val Tyr Tyr Cys Thr Ile
                595                 600                 605

Gly Gly Ser Leu Ser Pro Ser Gln Gly Thr Leu Val Thr Val Ser
            610                 615                 620

Ser
625

<210> SEQ ID NO 700
<211> LENGTH: 632
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 700

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Gln Gly Thr Leu Val Thr
            100                 105                 110
```

-continued

```
Val Ser Ser Gly Gly Gly Ser Gly Gly Ser Asp Ile Val Met
        115                 120             125

Thr Gln Thr Pro Leu Ser Leu Ser Val Thr Pro Gly Gln Pro Ala Ser
130                 135                 140

Ile Ser Cys Lys Ser Ser Gln Ser Leu Glu Thr Thr Gly Thr Thr
145                 150                 155                 160

Tyr Leu Asn Trp Tyr Leu Gln Lys Pro Gly Gln Ser Pro Gln Leu Leu
                165                 170                 175

Ile Tyr Arg Ala Ser Lys Arg Phe Ser Gly Val Pro Asp Arg Phe Ser
            180                 185                 190

Gly Ser Gly Ser Gly Thr Asp Phe Thr Leu Lys Ile Ser Arg Val Glu
        195                 200                 205

Ala Glu Asp Val Gly Val Tyr Tyr Cys Leu Gln Leu Leu Glu Asp Pro
    210                 215                 220

Tyr Thr Phe Gly Cys Gly Thr Lys Leu Glu Ile Lys Gly Gly Gly Gly
225                 230                 235                 240

Ser Gly Gly Gly Gly Ser Gly Gly Gly Ser Gln Val Gln Leu Val
                245                 250                 255

Gln Ser Gly Ala Glu Val Lys Lys Pro Gly Ala Ser Val Lys Val Ser
        260                 265                 270

Cys Lys Ala Ser Gly Tyr Asp Phe Thr Asp Tyr Ile Met His Trp Val
    275                 280                 285

Arg Gln Ala Pro Gly Gln Cys Leu Glu Trp Met Gly Tyr Ile Asn Pro
290                 295                 300

Tyr Asn Asp Gly Ser Lys Tyr Thr Asp Lys Phe Gln Glu Arg Val Thr
305                 310                 315                 320

Met Thr Ser Asp Thr Ser Ile Ser Thr Ala Tyr Met Glu Leu Ser Arg
                325                 330                 335

Leu Arg Ser Asp Asp Thr Ala Val Tyr Tyr Cys Ala Arg Gly Thr Tyr
            340                 345                 350

Tyr Tyr Gly Pro Glu Leu Phe Asp Tyr Trp Gly Gln Gly Thr Thr Val
        355                 360                 365

Thr Val Ser Ser Gly Gly Gly Gly Ser Gly Gly Gly Ser Asp Ile Val
    370                 375                 380

Met Thr Gln Ser Pro Asp Ser Leu Ala Val Ser Leu Gly Glu Arg Ala
385                 390                 395                 400

Thr Ile Asn Cys Lys Ser Ser Gln Ser Leu Leu Asn Ala Arg Thr Gly
                405                 410                 415

Lys Asn Tyr Leu Ala Trp Tyr Gln Gln Lys Pro Gly Gln Pro Pro Lys
            420                 425                 430

Leu Leu Ile Tyr Trp Ala Ser Thr Arg Glu Ser Gly Val Pro Asp Arg
        435                 440                 445

Phe Ser Gly Ser Gly Ser Gly Thr Asp Phe Thr Leu Thr Ile Ser Ser
    450                 455                 460

Leu Gln Ala Glu Asp Val Ala Val Tyr Tyr Cys Lys Gln Ser Tyr Ser
465                 470                 475                 480

Arg Arg Thr Phe Gly Gly Gly Thr Lys Val Glu Ile Lys Gly Gly Gly
                485                 490                 495

Gly Ser Gly Gly Gly Gly Ser Gly Gly Gly Ser Gly Gly Gly Gly
            500                 505                 510

Ser Gln Val Gln Leu Val Gln Ser Gly Ala Glu Val Lys Lys Pro Gly
        515                 520                 525

Ala Ser Val Lys Val Ser Cys Lys Ala Ser Gly Phe Asn Ile Lys Asp
```

-continued

```
                530               535               540
Tyr Tyr Met His Trp Val Arg Gln Ala Pro Gly Gln Arg Leu Glu Trp
545                 550               555               560

Met Gly Trp Ile Asp Leu Glu Asn Ala Asn Thr Ile Tyr Asp Ala Lys
                565               570               575

Phe Gln Gly Arg Val Thr Ile Thr Arg Asp Thr Ser Ala Ser Thr Ala
                580               585               590

Tyr Met Glu Leu Ser Ser Leu Arg Ser Glu Asp Thr Ala Val Tyr Tyr
                595               600               605

Cys Ala Arg Asp Ala Tyr Gly Arg Tyr Phe Tyr Asp Val Trp Gly Gln
            610               615               620

Gly Thr Leu Val Thr Val Ser Ser
625                 630

<210> SEQ ID NO 701
<211> LENGTH: 632
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 701

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Gly Met Thr Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser Gly Gly Gly Gly Ser Gly Gly Gly Ser Asp Ile Val Met
        115                 120                 125

Thr Gln Ser Pro Asp Ser Leu Ala Val Ser Leu Gly Glu Arg Ala Thr
130                 135                 140

Ile Asn Cys Lys Ser Ser Gln Ser Leu Leu Asn Ala Arg Thr Gly Lys
145                 150                 155                 160

Asn Tyr Leu Ala Trp Tyr Gln Gln Lys Pro Gly Gln Pro Pro Lys Leu
                165                 170                 175

Leu Ile Tyr Trp Ala Ser Thr Arg Glu Ser Gly Val Pro Asp Arg Phe
            180                 185                 190

Ser Gly Ser Gly Ser Gly Thr Asp Phe Thr Leu Thr Ile Ser Ser Leu
        195                 200                 205

Gln Ala Glu Asp Val Ala Val Tyr Tyr Cys Lys Gln Ser Tyr Ser Arg
    210                 215                 220

Arg Thr Phe Gly Gly Gly Thr Lys Val Glu Ile Lys Gly Gly Gly Gly
225                 230                 235                 240

Ser Gly Gly Gly Gly Ser Gly Gly Gly Gly Ser Gly Gly Gly Gly Ser
                245                 250                 255
```

Gln Val Gln Leu Val Gln Ser Gly Ala Glu Val Lys Lys Pro Gly Ala
            260                 265                 270

Ser Val Lys Val Ser Cys Lys Ala Ser Gly Phe Asn Ile Lys Asp Tyr
        275                 280                 285

Tyr Met His Trp Val Arg Gln Ala Pro Gly Gln Arg Leu Glu Trp Met
290                 295                 300

Gly Trp Ile Asp Leu Glu Asn Ala Asn Thr Ile Tyr Asp Ala Lys Phe
305                 310                 315                 320

Gln Gly Arg Val Thr Ile Thr Arg Asp Thr Ser Ala Ser Thr Ala Tyr
                325                 330                 335

Met Glu Leu Ser Ser Leu Arg Ser Glu Asp Thr Ala Val Tyr Tyr Cys
            340                 345                 350

Ala Arg Asp Ala Tyr Gly Arg Tyr Phe Tyr Asp Val Trp Gly Gln Gly
                355                 360                 365

Thr Leu Val Thr Val Ser Ser Gly Gly Gly Ser Gly Gly Gly Ser
            370                 375                 380

Asp Ile Val Met Thr Gln Thr Pro Leu Ser Leu Ser Val Thr Pro Gly
385                 390                 395                 400

Gln Pro Ala Ser Ile Ser Cys Lys Ser Ser Gln Ser Leu Glu Thr Thr
                405                 410                 415

Thr Gly Thr Thr Tyr Leu Asn Trp Tyr Leu Gln Lys Pro Gly Gln Ser
            420                 425                 430

Pro Gln Leu Leu Ile Tyr Arg Ala Ser Lys Arg Phe Ser Gly Val Pro
                435                 440                 445

Asp Arg Phe Ser Gly Ser Gly Ser Gly Thr Asp Phe Thr Leu Lys Ile
450                 455                 460

Ser Arg Val Glu Ala Glu Asp Val Gly Val Tyr Tyr Cys Leu Gln Leu
465                 470                 475                 480

Leu Glu Asp Pro Tyr Thr Phe Gly Cys Gly Thr Lys Leu Glu Ile Lys
                485                 490                 495

Gly Gly Gly Gly Ser Gly Gly Gly Ser Gly Gly Gly Ser Gln
                500                 505                 510

Val Gln Leu Val Gln Ser Gly Ala Glu Val Lys Lys Pro Gly Ala Ser
        515                 520                 525

Val Lys Val Ser Cys Lys Ala Ser Gly Tyr Asp Phe Thr Asp Tyr Ile
    530                 535                 540

Met His Trp Val Arg Gln Ala Pro Gly Gln Cys Leu Glu Trp Met Gly
545                 550                 555                 560

Tyr Ile Asn Pro Tyr Asn Asp Gly Ser Lys Tyr Thr Asp Lys Phe Gln
                565                 570                 575

Glu Arg Val Thr Met Thr Ser Asp Thr Ser Ile Ser Thr Ala Tyr Met
            580                 585                 590

Glu Leu Ser Arg Leu Arg Ser Asp Asp Thr Ala Val Tyr Tyr Cys Ala
                595                 600                 605

Arg Gly Thr Tyr Tyr Gly Pro Glu Leu Phe Asp Tyr Trp Gly Gln
            610                 615                 620

Gly Thr Thr Val Thr Val Ser Ser
625                 630

<210> SEQ ID NO 702
<211> LENGTH: 632
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 702

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Ser Gly Gly Gly Gly Ser Gly
            115                 120                 125

Gly Gly Gly Ser Gln Val Gln Leu Val Gln Ser Gly Ala Glu Val Lys
130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser Gly Gly Gly Gly Ser
                245                 250                 255

Gly Gly Gly Ser Lys Val Gln Leu Val Glu Ser Gly Gly Gly Leu Val
            260                 265                 270

Gln Pro Gly Gly Ser Leu Arg Leu Ser Cys Ala Ala Ser Gly Phe Thr
        275                 280                 285

Phe Ser Ser Phe Gly Met Thr Trp Val Arg Gln Ala Pro Gly Lys Gly
290                 295                 300

Leu Glu Trp Val Ser Ser Ile Ser Gly Ser Gly Ser Asp Thr Leu Tyr
305                 310                 315                 320

Ala Asp Ser Val Arg Gly Arg Phe Thr Ile Ser Arg Asp Asn Ser Lys
                325                 330                 335

Asn Thr Leu Tyr Leu Gln Met Asn Ser Leu Arg Ala Glu Asp Thr Ala
            340                 345                 350

Val Tyr Tyr Cys Thr Ile Gly Gly Ser Leu Ser Pro Ser Ser Gln Gly
        355                 360                 365

Thr Leu Val Thr Val Ser Ser Gly Gly Gly Ser Gly Gly Gly Ser
370                 375                 380

Asp Ile Val Met Thr Gln Thr Pro Leu Ser Leu Ser Val Thr Pro Gly
385                 390                 395                 400

Gln Pro Ala Ser Ile Ser Cys Lys Ser Ser Gln Ser Leu Glu Thr Thr
                    405                 410                 415

Thr Gly Thr Thr Tyr Leu Asn Trp Tyr Leu Gln Lys Pro Gly Gln Ser
            420                 425                 430

Pro Gln Leu Leu Ile Tyr Arg Ala Ser Lys Arg Phe Ser Gly Val Pro
        435                 440                 445

Asp Arg Phe Ser Gly Ser Gly Ser Gly Thr Asp Phe Thr Leu Lys Ile
    450                 455                 460

Ser Arg Val Glu Ala Glu Asp Val Gly Val Tyr Tyr Cys Leu Gln Leu
465                 470                 475                 480

Leu Glu Asp Pro Tyr Thr Phe Gly Cys Gly Thr Lys Leu Glu Ile Lys
                485                 490                 495

Gly Gly Gly Gly Ser Gly Gly Gly Ser Gly Gly Gly Gly Ser Gln
                500                 505                 510

Val Gln Leu Val Gln Ser Gly Ala Glu Val Lys Lys Pro Gly Ala Ser
            515                 520                 525

Val Lys Val Ser Cys Lys Ala Ser Gly Tyr Asp Phe Thr Asp Tyr Ile
        530                 535                 540

Met His Trp Val Arg Gln Ala Pro Gly Gln Cys Leu Glu Trp Met Gly
545                 550                 555                 560

Tyr Ile Asn Pro Tyr Asn Asp Gly Ser Lys Tyr Thr Asp Lys Phe Gln
                565                 570                 575

Glu Arg Val Thr Met Thr Ser Asp Thr Ser Ile Ser Thr Ala Tyr Met
            580                 585                 590

Glu Leu Ser Arg Leu Arg Ser Asp Asp Thr Ala Val Tyr Tyr Cys Ala
        595                 600                 605

Arg Gly Thr Tyr Tyr Tyr Gly Pro Glu Leu Phe Asp Tyr Trp Gly Gln
    610                 615                 620

Gly Thr Thr Val Thr Val Ser Ser
625                 630

<210> SEQ ID NO 703
<211> LENGTH: 632
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 703

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Thr
                20                  25                  30

Thr Gly Thr Thr Tyr Leu Asn Trp Tyr Leu Gln Lys Pro Gly Gln Ser
            35                  40                  45

Pro Gln Leu Leu Ile Tyr Arg Ala Ser Lys Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Cys Gly Thr Lys Leu Glu Ile Lys
            100                 105                 110

Gly Gly Gly Gly Ser Gly Gly Gly Ser Gly Gly Gly Gly Ser Gln
        115                 120                 125

-continued

Val Gln Leu Val Gln Ser Gly Ala Glu Val Lys Lys Pro Gly Ala Ser
130                 135                 140

Val Lys Val Ser Cys Lys Ala Ser Gly Tyr Asp Phe Thr Asp Tyr Ile
145                 150                 155                 160

Met His Trp Val Arg Gln Ala Pro Gly Gln Cys Leu Glu Trp Met Gly
                165                 170                 175

Tyr Ile Asn Pro Tyr Asn Asp Gly Ser Lys Tyr Thr Asp Lys Phe Gln
                180                 185                 190

Glu Arg Val Thr Met Thr Ser Asp Thr Ser Ile Ser Thr Ala Tyr Met
                195                 200                 205

Glu Leu Ser Arg Leu Arg Ser Asp Asp Thr Ala Val Tyr Tyr Cys Ala
210                 215                 220

Arg Gly Thr Tyr Tyr Gly Pro Glu Leu Phe Asp Tyr Trp Gly Gln Gly
225                 230                 235                 240

Thr Thr Val Thr Val Ser Ser Gly Gly Gly Gly Ser Gly Gly Gly Gly
                245                 250                 255

Ser Asp Ile Val Met Thr Gln Ser Pro Asp Ser Leu Ala Val Ser Leu
                260                 265                 270

Gly Glu Arg Ala Thr Ile Asn Cys Lys Ser Ser Gln Ser Leu Leu Asn
                275                 280                 285

Ala Arg Thr Gly Lys Asn Tyr Leu Ala Trp Tyr Gln Gln Lys Pro Gly
                290                 295                 300

Gln Pro Pro Lys Leu Leu Ile Tyr Trp Ala Ser Thr Arg Glu Ser Gly
305                 310                 315                 320

Val Pro Asp Arg Phe Ser Gly Ser Gly Ser Gly Thr Asp Phe Thr Leu
                325                 330                 335

Thr Ile Ser Ser Leu Gln Ala Glu Asp Val Ala Val Tyr Tyr Cys Lys
                340                 345                 350

Gln Ser Tyr Ser Arg Arg Thr Phe Gly Gly Gly Thr Lys Val Glu Ile
                355                 360                 365

Lys Gly Gly Gly Gly Ser Gly Gly Gly Gly Ser Gly Gly Gly Gly Ser
                370                 375                 380

Gly Gly Gly Gly Ser Gln Val Gln Leu Val Gln Ser Gly Ala Glu Val
385                 390                 395                 400

Lys Lys Pro Gly Ala Ser Val Lys Val Ser Cys Lys Ala Ser Gly Phe
                405                 410                 415

Asn Ile Lys Asp Tyr Tyr Met His Trp Val Arg Gln Ala Pro Gly Gln
                420                 425                 430

Arg Leu Glu Trp Met Gly Trp Ile Asp Leu Glu Asn Ala Asn Thr Ile
                435                 440                 445

Tyr Asp Ala Lys Phe Gln Gly Arg Val Thr Ile Thr Arg Asp Thr Ser
450                 455                 460

Ala Ser Thr Ala Tyr Met Glu Leu Ser Ser Leu Arg Ser Glu Asp Thr
465                 470                 475                 480

Ala Val Tyr Tyr Cys Ala Arg Asp Ala Tyr Gly Arg Tyr Phe Tyr Asp
                485                 490                 495

Val Trp Gly Gln Gly Thr Leu Val Thr Val Ser Ser Gly Gly Gly Gly
                500                 505                 510

Ser Gly Gly Gly Ser Lys Val Gln Leu Val Glu Ser Gly Gly Gly Leu
                515                 520                 525

Val Gln Pro Gly Gly Ser Leu Arg Leu Ser Cys Ala Ala Ser Gly Phe
530                 535                 540

```
Thr Phe Ser Ser Phe Gly Met Thr Trp Val Arg Gln Ala Pro Gly Lys
545                 550                 555                 560

Gly Leu Glu Trp Val Ser Ser Ile Ser Gly Ser Gly Ser Asp Thr Leu
                565                 570                 575

Tyr Ala Asp Ser Val Arg Gly Arg Phe Thr Ile Ser Arg Asp Asn Ser
            580                 585                 590

Lys Asn Thr Leu Tyr Leu Gln Met Asn Ser Leu Arg Ala Glu Asp Thr
        595                 600                 605

Ala Val Tyr Tyr Cys Thr Ile Gly Gly Ser Leu Ser Pro Ser Ser Gln
    610                 615                 620

Gly Thr Leu Val Thr Val Ser Ser
625                 630
```

<210> SEQ ID NO 704
<211> LENGTH: 625
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 704

```
Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser Gly Gly Gly Gly Ser Gly Gly Gly Ser Glu Ile Val Leu
        115                 120                 125

Thr Gln Ser Pro Ala Thr Leu Ser Leu Ser Pro Gly Glu Arg Ala Thr
    130                 135                 140

Leu Ser Cys Ser Ala Ser Ser Val Gly Tyr Met His Trp Tyr Gln
145                 150                 155                 160

Gln Lys Pro Gly Gln Ala Pro Arg Leu Leu Ile Tyr Asp Thr Ser Lys
                165                 170                 175

Leu Ala Ser Gly Ile Pro Ala Arg Phe Ser Gly Ser Gly Ser Gly Thr
            180                 185                 190

Asp Phe Thr Leu Thr Ile Ser Ser Leu Glu Pro Glu Asp Phe Ala Val
        195                 200                 205

Tyr Tyr Cys Phe Gln Gly Ser Val Tyr Pro Phe Thr Phe Gly Gln Gly
    210                 215                 220

Thr Lys Leu Glu Ile Lys Gly Gly Gly Ser Gly Gly Gly Gly Ser
225                 230                 235                 240

Gly Gly Gly Gly Ser Gln Val Gln Leu Gln Glu Ser Gly Pro Gly Leu
                245                 250                 255

Val Lys Pro Ser Gln Thr Leu Ser Leu Thr Cys Thr Val Ser Gly Gly
            260                 265                 270
```

```
Ser Ile Ser Thr Ser Thr Met Gly Val Gly Trp Ile Arg Gln His Pro
            275                 280                 285

Gly Lys Gly Leu Glu Trp Ile Gly Phe Ile Trp Trp Asp Asp Asp Lys
        290                 295                 300

Arg Tyr Asn Pro Asn Leu Lys Ser Arg Val Thr Met Ser Val Asp Thr
305                 310                 315                 320

Ser Lys Asn Gln Phe Ser Leu Lys Leu Ser Ser Val Thr Ala Ala Asp
                325                 330                 335

Thr Ala Val Tyr Tyr Cys Ala Arg Met Glu Leu Trp Ser Tyr Tyr Phe
                340                 345                 350

Asp Tyr Trp Gly Gln Gly Thr Leu Val Thr Val Ser Ser Gly Gly Gly
            355                 360                 365

Gly Ser Gly Gly Gly Ser Asp Ile Val Met Thr Gln Ser Pro Asp Ser
    370                 375                 380

Leu Ala Val Ser Leu Gly Glu Arg Ala Thr Ile Asn Cys Lys Ser Ser
385                 390                 395                 400

Gln Ser Leu Leu Asn Ala Arg Thr Gly Lys Asn Tyr Leu Ala Trp Tyr
                405                 410                 415

Gln Gln Lys Pro Gly Gln Pro Pro Lys Leu Leu Ile Tyr Trp Ala Ser
            420                 425                 430

Thr Arg Glu Ser Gly Val Pro Asp Arg Phe Ser Gly Ser Gly Ser Gly
        435                 440                 445

Thr Asp Phe Thr Leu Thr Ile Ser Ser Leu Gln Ala Glu Asp Val Ala
    450                 455                 460

Val Tyr Tyr Cys Lys Gln Ser Tyr Ser Arg Arg Thr Phe Gly Cys Gly
465                 470                 475                 480

Thr Lys Val Glu Ile Lys Gly Gly Gly Gly Ser Gly Gly Gly Gly Ser
                485                 490                 495

Gly Gly Gly Gly Ser Gly Gly Gly Ser Gln Val Gln Leu Val Gln
            500                 505                 510

Ser Gly Ala Glu Val Lys Lys Pro Gly Ala Ser Val Lys Val Ser Cys
    515                 520                 525

Lys Ala Ser Gly Phe Asn Ile Lys Asp Tyr Tyr Met His Trp Val Arg
530                 535                 540

Gln Ala Pro Gly Gln Cys Leu Glu Trp Met Gly Trp Ile Asp Leu Glu
            545                 550                 555                 560

Asn Ala Asn Thr Ile Tyr Asp Ala Lys Phe Gln Gly Arg Val Thr Ile
                565                 570                 575

Thr Arg Asp Thr Ser Ala Ser Thr Ala Tyr Met Glu Leu Ser Ser Leu
            580                 585                 590

Arg Ser Glu Asp Thr Ala Val Tyr Tyr Cys Ala Arg Asp Ala Tyr Gly
        595                 600                 605

Arg Tyr Phe Tyr Asp Val Trp Gly Gln Gly Thr Leu Val Thr Val Ser
    610                 615                 620

Ser
625

<210> SEQ ID NO 705
<211> LENGTH: 625
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 705

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser Gly Gly Gly Gly Ser Gly Gly Gly Ser Glu Ile Val Leu
        115                 120                 125

Thr Gln Ser Pro Ala Thr Leu Ser Leu Ser Pro Gly Glu Arg Ala Thr
    130                 135                 140

Leu Ser Cys Ser Ala Ser Ser Ser Val Gly Tyr Met His Trp Tyr Gln
145                 150                 155                 160

Gln Lys Pro Gly Gln Ala Pro Arg Leu Leu Ile Tyr Asp Thr Ser Lys
                165                 170                 175

Leu Ala Ser Gly Ile Pro Ala Arg Phe Ser Gly Ser Gly Ser Gly Thr
            180                 185                 190

Asp Phe Thr Leu Thr Ile Ser Ser Leu Glu Pro Glu Asp Phe Ala Val
        195                 200                 205

Tyr Tyr Cys Phe Gln Gly Ser Val Tyr Pro Phe Thr Phe Gly Gln Gly
    210                 215                 220

Thr Lys Leu Glu Ile Lys Gly Gly Gly Ser Gly Gly Gly Gly Ser
225                 230                 235                 240

Gly Gly Gly Gly Ser Gln Val Gln Leu Gln Glu Ser Gly Pro Gly Leu
                245                 250                 255

Val Lys Pro Ser Gln Thr Leu Ser Leu Thr Cys Thr Val Ser Gly Gly
            260                 265                 270

Ser Ile Ser Thr Ser Thr Met Gly Val Gly Trp Ile Arg Gln His Pro
        275                 280                 285

Gly Lys Gly Leu Glu Trp Ile Gly Phe Ile Trp Trp Asp Asp Asp Lys
    290                 295                 300

Arg Tyr Asn Pro Asn Leu Lys Ser Arg Val Thr Met Ser Val Asp Thr
305                 310                 315                 320

Ser Lys Asn Gln Phe Ser Leu Lys Leu Ser Ser Val Thr Ala Ala Asp
                325                 330                 335

Thr Ala Val Tyr Tyr Cys Ala Arg Met Glu Leu Trp Ser Tyr Tyr Phe
            340                 345                 350

Asp Tyr Trp Gly Gln Gly Thr Leu Val Thr Val Ser Ser Gly Gly Gly
        355                 360                 365

Gly Ser Gly Gly Gly Ser Asp Ile Val Met Thr Gln Ser Pro Asp Ser
    370                 375                 380

Leu Ala Val Ser Leu Gly Glu Arg Ala Thr Ile Asn Cys Lys Ser Ser
385                 390                 395                 400

Gln Ser Leu Leu Asn Ala Arg Thr Gly Lys Asn Tyr Leu Ala Trp Tyr
                405                 410                 415
```

```
Gln Gln Lys Pro Gly Gln Pro Pro Lys Leu Leu Ile Tyr Trp Ala Ser
            420                 425                 430

Thr Arg Glu Ser Gly Val Pro Asp Arg Phe Ser Gly Ser Gly
        435                 440                 445

Thr Asp Phe Thr Leu Thr Ile Ser Ser Leu Gln Ala Glu Asp Val Ala
        450                 455                 460

Val Tyr Tyr Cys Lys Gln Ser Tyr Ser Arg Arg Thr Phe Gly Gly
465                 470                 475                 480

Thr Lys Val Glu Ile Lys Gly Gly Gly Gly Gly Gly Ser
                485                 490                 495

Gly Gly Gly Gly Ser Gly Gly Gly Ser Gln Val Gln Leu Val Gln
            500                 505                 510

Ser Gly Ala Glu Val Lys Lys Pro Gly Ala Ser Val Lys Val Ser Cys
            515                 520                 525

Lys Ala Ser Gly Phe Asn Ile Lys Asp Tyr Tyr Met His Trp Val Arg
            530                 535                 540

Gln Ala Pro Gly Gln Arg Leu Glu Trp Met Gly Trp Ile Asp Leu Glu
545                 550                 555                 560

Asn Ala Asn Thr Ile Tyr Asp Ala Lys Phe Gln Gly Arg Val Thr Ile
                565                 570                 575

Thr Arg Asp Thr Ser Ala Ser Thr Ala Tyr Met Glu Leu Ser Ser Leu
            580                 585                 590

Arg Ser Glu Asp Thr Ala Val Tyr Tyr Cys Ala Arg Asp Gln Tyr Gly
            595                 600                 605

Arg Tyr Phe Tyr Asp Val Trp Gly Gln Gly Thr Leu Val Thr Val Ser
            610                 615                 620

Ser
625

<210> SEQ ID NO 706
<211> LENGTH: 625
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 706

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Gln Gly Thr Leu Val Thr
            100                 105                 110

Val Ser Ser Gly Gly Gly Gly Ser Gly Gly Gly Ser Glu Ile Val Leu
        115                 120                 125

Thr Gln Ser Pro Ala Thr Leu Ser Leu Ser Pro Gly Glu Arg Ala Thr
```

```
                130                 135                 140
Leu Ser Cys Ser Ala Ser Ser Val Gly Tyr Met His Trp Tyr Gln
145                 150                 155                 160

Gln Lys Pro Gly Gln Ala Pro Arg Leu Leu Ile Tyr Asp Thr Ser Lys
                165                 170                 175

Leu Ala Ser Gly Ile Pro Ala Arg Phe Ser Gly Ser Gly Ser Gly Thr
                180                 185                 190

Asp Phe Thr Leu Thr Ile Ser Ser Leu Glu Pro Glu Asp Phe Ala Val
                195                 200                 205

Tyr Tyr Cys Phe Gln Gly Ser Val Tyr Pro Phe Thr Phe Gly Gln Gly
                210                 215                 220

Thr Lys Leu Glu Ile Lys Gly Gly Gly Ser Gly Gly Gly Gly Ser
225                 230                 235                 240

Gly Gly Gly Gly Ser Gln Val Gln Leu Gln Glu Ser Gly Pro Gly Leu
                245                 250                 255

Val Lys Pro Ser Gln Thr Leu Ser Leu Thr Cys Thr Val Ser Gly Gly
                260                 265                 270

Ser Ile Ser Thr Ser Thr Met Gly Val Gly Trp Ile Arg Gln His Pro
                275                 280                 285

Gly Lys Gly Leu Glu Trp Ile Gly Phe Ile Trp Trp Asp Asp Asp Lys
                290                 295                 300

Arg Tyr Asn Pro Asn Leu Lys Ser Arg Val Thr Met Ser Val Asp Thr
305                 310                 315                 320

Ser Lys Asn Gln Phe Ser Leu Lys Leu Ser Ser Val Thr Ala Ala Asp
                325                 330                 335

Thr Ala Val Tyr Tyr Cys Ala Arg Met Glu Leu Trp Ser Tyr Tyr Phe
                340                 345                 350

Asp Tyr Trp Gly Gln Gly Thr Leu Val Thr Val Ser Ser Gly Gly Gly
                355                 360                 365

Gly Ser Gly Gly Gly Ser Asp Ile Val Met Thr Gln Ser Pro Asp Ser
370                 375                 380

Leu Ala Val Ser Leu Gly Glu Arg Ala Thr Ile Asn Cys Lys Ser Ser
385                 390                 395                 400

Gln Ser Leu Leu Asn Ala Arg Thr Gly Lys Asn Tyr Leu Ala Trp Tyr
                405                 410                 415

Gln Gln Lys Pro Gly Gln Pro Pro Lys Leu Leu Ile Tyr Trp Ala Ser
                420                 425                 430

Thr Arg Glu Ser Gly Val Pro Asp Arg Phe Ser Gly Ser Gly Ser Gly
                435                 440                 445

Thr Asp Phe Thr Leu Thr Ile Ser Ser Leu Gln Ala Glu Asp Val Ala
                450                 455                 460

Val Tyr Tyr Cys Lys Gln Ser Tyr Ser Arg Arg Thr Phe Gly Cys Gly
465                 470                 475                 480

Thr Lys Val Glu Ile Lys Gly Gly Gly Ser Gly Gly Gly Gly Ser
                485                 490                 495

Gly Gly Gly Gly Ser Gly Gly Gly Ser Gln Val Gln Leu Val Gln
                500                 505                 510

Ser Gly Ala Glu Val Lys Lys Pro Gly Ala Ser Val Lys Val Ser Cys
                515                 520                 525

Lys Ala Ser Gly Phe Asn Ile Lys Asp Tyr Tyr Met His Trp Val Arg
                530                 535                 540

Gln Ala Pro Gly Gln Cys Leu Glu Trp Met Gly Trp Ile Asp Leu Glu
545                 550                 555                 560
```

```
Asn Ala Asn Thr Ile Tyr Asp Ala Lys Phe Gln Gly Arg Val Thr Ile
                565                 570                 575

Thr Arg Asp Thr Ser Ala Ser Thr Ala Tyr Met Glu Leu Ser Ser Leu
            580                 585                 590

Arg Ser Glu Asp Thr Ala Val Tyr Tyr Cys Ala Arg Asp Gln Tyr Gly
        595                 600                 605

Arg Tyr Phe Tyr Asp Val Trp Gly Gln Gly Thr Leu Val Thr Val Ser
    610                 615                 620

Ser
625

<210> SEQ ID NO 707
<211> LENGTH: 625
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 707

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser Gly Gly Gly Gly Ser Gly Gly Gly Ser Glu Ile Val Leu
        115                 120                 125

Thr Gln Ser Pro Ala Thr Leu Ser Leu Ser Pro Gly Glu Arg Ala Thr
    130                 135                 140

Leu Ser Cys Ser Ala Ser Ser Val Gly Tyr Met His Trp Tyr Gln
145                 150                 155                 160

Gln Lys Pro Gly Gln Ala Pro Arg Leu Leu Ile Tyr Asp Thr Ser Lys
                165                 170                 175

Leu Ala Ser Gly Ile Pro Ala Arg Phe Ser Gly Ser Gly Ser Gly Thr
            180                 185                 190

Asp Phe Thr Leu Thr Ile Ser Ser Leu Glu Pro Glu Asp Phe Ala Val
        195                 200                 205

Tyr Tyr Cys Phe Gln Gly Ser Val Tyr Pro Phe Thr Phe Gly Gln Gly
    210                 215                 220

Thr Lys Leu Glu Ile Lys Gly Gly Gly Ser Gly Gly Gly Gly Ser
225                 230                 235                 240

Gly Gly Gly Gly Ser Gln Val Gln Leu Gln Glu Ser Gly Pro Gly Leu
                245                 250                 255

Val Lys Pro Ser Gln Thr Leu Ser Leu Thr Cys Thr Val Ser Gly Gly
            260                 265                 270

Ser Ile Ser Thr Ser Thr Met Gly Val Gly Trp Ile Arg Gln His Pro
```

Gly Lys Gly Leu Glu Trp Ile Gly Phe Ile Trp Trp Asp Asp Asp Lys
            275                 280                 285
                290                 295                 300

Arg Tyr Asn Pro Asn Leu Lys Ser Arg Val Thr Met Ser Val Asp Thr
305                 310                 315                 320

Ser Lys Asn Gln Phe Ser Leu Lys Leu Ser Ser Val Thr Ala Ala Asp
                325                 330                 335

Thr Ala Val Tyr Tyr Cys Ala Arg Met Glu Leu Trp Ser Tyr Tyr Phe
            340                 345                 350

Asp Tyr Trp Gly Gln Gly Thr Leu Val Thr Val Ser Ser Gly Gly Gly
                355                 360                 365

Gly Ser Gly Gly Gly Ser Asp Ile Val Met Thr Gln Ser Pro Asp Ser
            370                 375                 380

Leu Ala Val Ser Leu Gly Glu Arg Ala Thr Ile Asn Cys Lys Ser Ser
385                 390                 395                 400

Gln Ser Leu Leu Asn Ala Arg Thr Gly Lys Asn Tyr Leu Ala Trp Tyr
                405                 410                 415

Gln Gln Lys Pro Gly Gln Pro Pro Lys Leu Leu Ile Tyr Trp Ala Ser
            420                 425                 430

Thr Arg Glu Ser Gly Val Pro Asp Arg Phe Ser Gly Ser Gly Ser Gly
                435                 440                 445

Thr Asp Phe Thr Leu Thr Ile Ser Ser Leu Gln Ala Glu Asp Val Ala
450                 455                 460

Val Tyr Tyr Cys Lys Gln Ser Tyr Ser Leu Arg Thr Phe Gly Gly Gly
465                 470                 475                 480

Thr Lys Val Glu Ile Lys Gly Gly Gly Ser Gly Gly Gly Gly Ser
                485                 490                 495

Gly Gly Gly Gly Ser Gly Gly Gly Ser Gln Val Gln Leu Val Gln
            500                 505                 510

Ser Gly Ala Glu Val Lys Lys Pro Gly Ala Ser Val Lys Val Ser Cys
            515                 520                 525

Lys Ala Ser Gly Phe Asn Ile Lys Asp Tyr Tyr Met His Trp Val Arg
530                 535                 540

Gln Ala Pro Gly Gln Arg Leu Glu Trp Met Gly Trp Ile Asp Leu Glu
545                 550                 555                 560

Glu Gly Asn Thr Ile Tyr Asp Ala Lys Phe Gln Gly Arg Val Thr Ile
                565                 570                 575

Thr Arg Asp Thr Ser Ala Ser Thr Ala Tyr Met Glu Leu Ser Ser Leu
            580                 585                 590

Arg Ser Glu Asp Thr Ala Val Tyr Tyr Cys Ala Arg Asp Ala Tyr Gly
            595                 600                 605

Arg Tyr Phe Tyr Asp Val Trp Gly Gln Gly Thr Leu Val Thr Val Ser
        610                 615                 620

Ser
625

<210> SEQ ID NO 708
<211> LENGTH: 625
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 708

-continued

```
Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser Gly Gly Gly Gly Ser Gly Gly Gly Ser Glu Ile Val Leu
            115                 120                 125

Thr Gln Ser Pro Ala Thr Leu Ser Leu Ser Pro Gly Glu Arg Ala Thr
130                 135                 140

Leu Ser Cys Ser Ala Ser Ser Ser Val Gly Tyr Met His Trp Tyr Gln
145                 150                 155                 160

Gln Lys Pro Gly Gln Ala Pro Arg Leu Leu Ile Tyr Asp Thr Ser Lys
                165                 170                 175

Leu Ala Ser Gly Ile Pro Ala Arg Phe Ser Gly Ser Gly Ser Gly Thr
            180                 185                 190

Asp Phe Thr Leu Thr Ile Ser Ser Leu Glu Pro Glu Asp Phe Ala Val
            195                 200                 205

Tyr Tyr Cys Phe Gln Gly Ser Val Tyr Pro Phe Thr Phe Gly Gln Gly
210                 215                 220

Thr Lys Leu Glu Ile Lys Gly Gly Gly Gly Ser Gly Gly Gly Gly Ser
225                 230                 235                 240

Gly Gly Gly Gly Ser Gln Val Gln Leu Gln Glu Ser Gly Pro Gly Leu
                245                 250                 255

Val Lys Pro Ser Gln Thr Leu Ser Leu Thr Cys Thr Val Ser Gly Gly
            260                 265                 270

Ser Ile Ser Thr Ser Thr Met Gly Val Gly Trp Ile Arg Gln His Pro
            275                 280                 285

Gly Lys Gly Leu Glu Trp Ile Gly Phe Ile Trp Trp Asp Asp Asp Lys
290                 295                 300

Arg Tyr Asn Pro Asn Leu Lys Ser Arg Val Thr Met Ser Val Asp Thr
305                 310                 315                 320

Ser Lys Asn Gln Phe Ser Leu Lys Leu Ser Ser Val Thr Ala Ala Asp
                325                 330                 335

Thr Ala Val Tyr Tyr Cys Ala Arg Met Glu Leu Trp Ser Tyr Tyr Phe
            340                 345                 350

Asp Tyr Trp Gly Gln Gly Thr Leu Val Thr Val Ser Ser Gly Gly Gly
            355                 360                 365

Gly Ser Gly Gly Gly Ser Asp Ile Val Met Thr Gln Ser Pro Asp Ser
370                 375                 380

Leu Ala Val Ser Leu Gly Glu Arg Ala Thr Ile Asn Cys Lys Ser Ser
385                 390                 395                 400

Gln Ser Leu Leu Asn Ala Arg Thr Gly Lys Asn Tyr Leu Ala Trp Tyr
                405                 410                 415

Gln Gln Lys Pro Gly Gln Pro Pro Lys Leu Leu Ile Tyr Trp Ala Ser
```

```
            420                 425                 430
Thr Arg Glu Ser Gly Val Pro Asp Arg Phe Ser Gly Ser Gly Ser Gly
            435                 440                 445

Thr Asp Phe Thr Leu Thr Ile Ser Ser Leu Gln Ala Glu Asp Val Ala
450                 455                 460

Val Tyr Tyr Cys Lys Gln Ser Tyr Ser Leu Arg Thr Phe Gly Cys Gly
465                 470                 475                 480

Thr Lys Val Glu Ile Lys Gly Gly Gly Ser Gly Gly Gly Gly Gly Ser
                485                 490                 495

Gly Gly Gly Gly Ser Gly Gly Gly Ser Gln Val Gln Leu Val Gln
                500                 505                 510

Ser Gly Ala Glu Val Lys Lys Pro Gly Ala Ser Val Lys Val Ser Cys
            515                 520                 525

Lys Ala Ser Gly Phe Asn Ile Lys Asp Tyr Tyr Met His Trp Val Arg
            530                 535                 540

Gln Ala Pro Gly Gln Cys Leu Glu Trp Met Gly Trp Ile Asp Leu Glu
545                 550                 555                 560

Glu Gly Asn Thr Ile Tyr Asp Ala Lys Phe Gln Gly Arg Val Thr Ile
                565                 570                 575

Thr Arg Asp Thr Ser Ala Ser Thr Ala Tyr Met Glu Leu Ser Ser Leu
            580                 585                 590

Arg Ser Glu Asp Thr Ala Val Tyr Tyr Cys Ala Arg Asp Ala Tyr Gly
            595                 600                 605

Arg Tyr Phe Tyr Asp Val Trp Gly Gln Gly Thr Leu Val Thr Val Ser
            610                 615                 620

Ser
625

<210> SEQ ID NO 709
<211> LENGTH: 632
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 709

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser Gly Gly Gly Gly Ser Gly Gly Gly Ser Asp Ile Val Met
        115                 120                 125

Thr Gln Thr Pro Leu Ser Leu Ser Val Thr Pro Gly Gln Pro Ala Ser
    130                 135                 140
```

-continued

Ile Ser Cys Lys Ser Ser Gln Ser Leu Glu Thr Thr Thr Gly Thr Thr
145                 150                 155                 160

Tyr Leu Asn Trp Tyr Leu Gln Lys Pro Gly Gln Ser Pro Gln Leu Leu
            165                 170                 175

Ile Tyr Arg Ala Ser Lys Arg Phe Ser Gly Val Pro Asp Arg Phe Ser
        180                 185                 190

Gly Ser Gly Ser Gly Thr Asp Phe Thr Leu Lys Ile Ser Arg Val Glu
    195                 200                 205

Ala Glu Asp Val Gly Val Tyr Tyr Cys Leu Gln Leu Leu Glu Asp Pro
210                 215                 220

Tyr Thr Phe Gly Cys Gly Thr Lys Leu Glu Ile Lys Gly Gly Gly Gly
225                 230                 235                 240

Ser Gly Gly Gly Gly Ser Gly Gly Gly Ser Gln Val Gln Leu Val
            245                 250                 255

Gln Ser Gly Ala Glu Val Lys Lys Pro Gly Ala Ser Val Lys Val Ser
        260                 265                 270

Cys Lys Ala Ser Gly Tyr Asp Phe Thr Asp Tyr Ile Met His Trp Val
        275                 280                 285

Arg Gln Ala Pro Gly Gln Cys Leu Glu Trp Met Gly Tyr Ile Asn Pro
    290                 295                 300

Tyr Asn Asp Gly Ser Lys Tyr Thr Asp Lys Phe Gln Glu Arg Val Thr
305                 310                 315                 320

Met Thr Ser Asp Thr Ser Ile Ser Thr Ala Tyr Met Glu Leu Ser Arg
            325                 330                 335

Leu Arg Ser Asp Asp Thr Ala Val Tyr Tyr Cys Ala Arg Gly Thr Tyr
        340                 345                 350

Tyr Tyr Gly Pro Glu Leu Phe Asp Tyr Trp Gly Gln Gly Thr Thr Val
    355                 360                 365

Thr Val Ser Ser Gly Gly Gly Gly Ser Gly Gly Gly Ser Asp Ile Val
370                 375                 380

Met Thr Gln Ser Pro Asp Ser Leu Ala Val Ser Leu Gly Glu Arg Ala
385                 390                 395                 400

Thr Ile Asn Cys Lys Ser Ser Gln Ser Leu Leu Asn Ala Arg Thr Gly
            405                 410                 415

Lys Asn Tyr Leu Ala Trp Tyr Gln Gln Lys Pro Gly Gln Pro Pro Lys
        420                 425                 430

Leu Leu Ile Tyr Trp Ala Ser Thr Arg Glu Ser Gly Val Pro Asp Arg
    435                 440                 445

Phe Ser Gly Ser Gly Ser Gly Thr Asp Phe Thr Leu Thr Ile Ser Ser
450                 455                 460

Leu Gln Ala Glu Asp Val Ala Val Tyr Tyr Cys Lys Gln Ser Tyr Ser
465                 470                 475                 480

Arg Arg Thr Phe Gly Gly Gly Thr Lys Val Glu Ile Lys Gly Gly Gly
            485                 490                 495

Gly Ser Gly Gly Gly Gly Ser Gly Gly Gly Ser Gly Gly Gly Gly
        500                 505                 510

Ser Gln Val Gln Leu Val Gln Ser Gly Ala Glu Val Lys Lys Pro Gly
    515                 520                 525

Ala Ser Val Lys Val Ser Cys Lys Ala Ser Gly Phe Asn Ile Lys Asp
530                 535                 540

Tyr Tyr Met His Trp Val Arg Gln Ala Pro Gly Gln Arg Leu Glu Trp
545                 550                 555                 560

Met Gly Trp Ile Asp Leu Glu Asn Ala Asn Thr Ile Tyr Asp Ala Lys

```
                    565                 570                 575
Phe Gln Gly Arg Val Thr Ile Thr Arg Asp Thr Ser Ala Ser Thr Ala
                580                 585                 590

Tyr Met Glu Leu Ser Ser Leu Arg Ser Glu Asp Thr Ala Val Tyr Tyr
            595                 600                 605

Cys Ala Arg Asp Gln Tyr Gly Arg Tyr Phe Tyr Asp Val Trp Gly Gln
610                 615                 620

Gly Thr Leu Val Thr Val Ser Ser
625                 630

<210> SEQ ID NO 710
<211> LENGTH: 632
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 710

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Thr Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ile Gly Gly Ser Leu Ser Pro Ser Ser Gln Gly Thr Leu Val Thr
            100                 105                 110

Val Ser Ser Gly Gly Gly Gly Ser Gly Gly Gly Ser Asp Ile Val Met
        115                 120                 125

Thr Gln Thr Pro Leu Ser Leu Ser Val Thr Pro Gly Gln Pro Ala Ser
    130                 135                 140

Ile Ser Cys Lys Ser Ser Gln Ser Leu Glu Thr Thr Gly Thr Thr
145                 150                 155                 160

Tyr Leu Asn Trp Tyr Leu Gln Lys Pro Gly Gln Ser Pro Gln Leu Leu
                165                 170                 175

Ile Tyr Arg Ala Ser Lys Arg Phe Ser Gly Val Pro Asp Arg Phe Ser
            180                 185                 190

Gly Ser Gly Ser Gly Thr Asp Phe Thr Leu Lys Ile Ser Arg Val Glu
        195                 200                 205

Ala Glu Asp Val Gly Val Tyr Tyr Cys Leu Gln Leu Leu Glu Asp Pro
    210                 215                 220

Tyr Thr Phe Gly Cys Gly Thr Lys Leu Glu Ile Lys Gly Gly Gly Gly
225                 230                 235                 240

Ser Gly Gly Gly Gly Ser Gly Gly Gly Ser Gln Val Gln Leu Val
                245                 250                 255

Gln Ser Gly Ala Glu Val Lys Lys Pro Gly Ala Ser Val Lys Val Ser
            260                 265                 270

Cys Lys Ala Ser Gly Tyr Asp Phe Thr Asp Tyr Ile Met His Trp Val
        275                 280                 285
```

```
Arg Gln Ala Pro Gly Gln Cys Leu Glu Trp Met Gly Tyr Ile Asn Pro
    290                 295                 300
Tyr Asn Asp Gly Ser Lys Tyr Thr Asp Lys Phe Gln Glu Arg Val Thr
305                 310                 315                 320
Met Thr Ser Asp Thr Ser Ile Ser Thr Ala Tyr Met Glu Leu Ser Arg
                325                 330                 335
Leu Arg Ser Asp Asp Thr Ala Val Tyr Tyr Cys Ala Arg Gly Thr Tyr
                340                 345                 350
Tyr Tyr Gly Pro Glu Leu Phe Asp Tyr Trp Gly Gln Gly Thr Thr Val
                355                 360                 365
Thr Val Ser Ser Gly Gly Gly Ser Gly Gly Ser Asp Ile Val
370                 375                 380
Met Thr Gln Ser Pro Asp Ser Leu Ala Val Ser Leu Gly Glu Arg Ala
385                 390                 395                 400
Thr Ile Asn Cys Lys Ser Ser Gln Ser Leu Leu Asn Ala Arg Thr Gly
                405                 410                 415
Lys Asn Tyr Leu Ala Trp Tyr Gln Gln Lys Pro Gly Gln Pro Pro Lys
                420                 425                 430
Leu Leu Ile Tyr Trp Ala Ser Thr Arg Glu Ser Gly Val Pro Asp Arg
                435                 440                 445
Phe Ser Gly Ser Gly Ser Gly Thr Asp Phe Thr Leu Thr Ile Ser Ser
                450                 455                 460
Leu Gln Ala Glu Asp Val Ala Val Tyr Tyr Cys Lys Gln Ser Tyr Ser
465                 470                 475                 480
Leu Arg Thr Phe Gly Gly Gly Thr Lys Val Glu Ile Lys Gly Gly Gly
                485                 490                 495
Gly Ser Gly Gly Gly Gly Ser Gly Gly Gly Gly Ser Gly Gly Gly Gly
                500                 505                 510
Ser Gln Val Gln Leu Val Gln Ser Gly Ala Glu Val Lys Lys Pro Gly
                515                 520                 525
Ala Ser Val Lys Val Ser Cys Lys Ala Ser Gly Phe Asn Ile Lys Asp
                530                 535                 540
Tyr Tyr Met His Trp Val Arg Gln Ala Pro Gly Gln Arg Leu Glu Trp
545                 550                 555                 560
Met Gly Trp Ile Asp Leu Glu Glu Gly Asn Thr Ile Tyr Asp Ala Lys
                565                 570                 575
Phe Gln Gly Arg Val Thr Ile Thr Arg Asp Thr Ser Ala Ser Thr Ala
                580                 585                 590
Tyr Met Glu Leu Ser Ser Leu Arg Ser Glu Asp Thr Ala Val Tyr Tyr
                595                 600                 605
Cys Ala Arg Asp Ala Tyr Gly Arg Tyr Phe Tyr Asp Val Trp Gly Gln
                610                 615                 620
Gly Thr Leu Val Thr Val Ser Ser
625                 630

<210> SEQ ID NO 711
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

His His His His His His His His His His
1               5                   10
```

<210> SEQ ID NO 712
<211> LENGTH: 703
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 712

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Thr Met Gly Val Gly Trp Ile Arg Gln His Pro Gly Lys Gly Leu Glu
        35                  40                  45

Trp Ile Gly Phe Ile Trp Trp Asp Asp Lys Arg Tyr Asn Pro Asn
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
```

```
                355                 360                 365
Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Gly Asp Ile Val Met Thr Gln Ser Pro Asp Ser Leu Ala
    450                 455                 460

Val Ser Leu Gly Glu Arg Ala Thr Ile Asn Cys Lys Ser Ser Gln Ser
465                 470                 475                 480

Leu Leu Asn Ala Arg Thr Gly Lys Asn Tyr Leu Ala Trp Tyr Gln Gln
                485                 490                 495

Lys Pro Gly Gln Pro Pro Lys Leu Leu Ile Tyr Trp Ala Ser Thr Arg
            500                 505                 510

Glu Ser Gly Val Pro Asp Arg Phe Ser Gly Ser Gly Ser Gly Thr Asp
        515                 520                 525

Phe Thr Leu Thr Ile Ser Ser Leu Gln Ala Glu Asp Val Ala Val Tyr
    530                 535                 540

Tyr Cys Lys Gln Ser Tyr Ser Arg Arg Thr Phe Gly Gly Gly Thr Lys
545                 550                 555                 560

Val Glu Ile Lys Gly Gly Gly Gly Ser Gly Gly Gly Gly Ser Gly Gly
                565                 570                 575

Gly Gly Ser Gly Gly Gly Gly Ser Gln Val Gln Leu Val Gln Ser Gly
            580                 585                 590

Ala Glu Val Lys Lys Pro Gly Ala Ser Val Lys Val Ser Cys Lys Ala
        595                 600                 605

Ser Gly Phe Asn Ile Lys Asp Tyr Tyr Met His Trp Val Arg Gln Ala
    610                 615                 620

Pro Gly Gln Arg Leu Glu Trp Met Gly Trp Ile Asp Leu Glu Asn Ala
625                 630                 635                 640

Asn Thr Ile Tyr Asp Ala Lys Phe Gln Gly Arg Val Thr Ile Thr Arg
                645                 650                 655

Asp Thr Ser Ala Ser Thr Ala Tyr Met Glu Leu Ser Ser Leu Arg Ser
            660                 665                 670

Glu Asp Thr Ala Val Tyr Tyr Cys Ala Arg Asp Ala Tyr Gly Arg Tyr
        675                 680                 685

Phe Tyr Asp Val Trp Gly Gln Gly Thr Leu Val Thr Val Ser Ser
    690                 695                 700

<210> SEQ ID NO 713
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 713

Glu Ile Val Leu Thr Gln Ser Pro Ala Thr Leu Ser Leu Ser Pro Gly
1               5                   10                  15
```

Glu Arg Ala Thr Leu Ser Cys Ser Ala Ser Ser Val Gly Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 714
<211> LENGTH: 703
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 714

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Thr Met Gly Val Gly Trp Ile Arg Gln His Pro Gly Lys Gly Leu Glu
        35                  40                  45

Trp Ile Gly Phe Ile Trp Trp Asp Asp Lys Arg Tyr Asn Pro Asn
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Ser Gly Asp Ile Val Met Thr Gln Ser Pro Asp Ser Leu Ala
450                 455                 460

Val Ser Leu Gly Glu Arg Ala Thr Ile Asn Cys Lys Ser Ser Gln Ser
465                 470                 475                 480

Leu Leu Asn Ala Arg Thr Gly Lys Asn Tyr Leu Ala Trp Tyr Gln Gln
                485                 490                 495

Lys Pro Gly Gln Pro Pro Lys Leu Leu Ile Tyr Trp Ala Ser Thr Arg
            500                 505                 510

Glu Ser Gly Val Pro Asp Arg Phe Ser Gly Ser Gly Ser Gly Thr Asp
            515                 520                 525

Phe Thr Leu Thr Ile Ser Ser Leu Gln Ala Glu Asp Val Ala Val Tyr
            530                 535                 540

Tyr Cys Lys Gln Ser Tyr Ser Arg Arg Thr Phe Gly Gly Gly Thr Lys
545                 550                 555                 560

Val Glu Ile Lys Gly Gly Gly Gly Ser Gly Gly Gly Gly Ser Gly Gly
                565                 570                 575
```

```
Gly Gly Ser Gly Gly Gly Ser Gln Val Gln Leu Val Gln Ser Gly
                580                 585                 590

Ala Glu Val Lys Lys Pro Gly Ala Ser Val Lys Val Ser Cys Lys Ala
            595                 600                 605

Ser Gly Phe Asn Ile Lys Asp Tyr Tyr Met His Trp Val Arg Gln Ala
        610                 615                 620

Pro Gly Gln Arg Leu Glu Trp Met Gly Trp Ile Asp Leu Glu Asn Ala
625                 630                 635                 640

Asn Thr Ile Tyr Asp Ala Lys Phe Gln Gly Arg Val Thr Ile Thr Arg
                645                 650                 655

Asp Thr Ser Ala Ser Thr Ala Tyr Met Glu Leu Ser Ser Leu Arg Ser
            660                 665                 670

Glu Asp Thr Ala Val Tyr Tyr Cys Ala Arg Asp Gln Tyr Gly Arg Tyr
        675                 680                 685

Phe Tyr Asp Val Trp Gly Gln Gly Thr Leu Val Thr Val Ser Ser
    690                 695                 700
```

<210> SEQ ID NO 715
<211> LENGTH: 703
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 715

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Thr Met Gly Val Gly Trp Ile Arg Gln His Pro Gly Lys Gly Leu Glu
        35                  40                  45

Trp Ile Gly Phe Ile Trp Trp Asp Asp Asp Lys Arg Tyr Asn Pro Asn
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Gly Asp Ile Val Met Thr Gln Ser Pro Asp Ser Leu Ala
    450                 455                 460

Val Ser Leu Gly Glu Arg Ala Thr Ile Asn Cys Lys Ser Ser Gln Ser
465                 470                 475                 480

Leu Leu Asn Ala Arg Thr Gly Lys Asn Tyr Leu Ala Trp Tyr Gln Gln
                485                 490                 495

Lys Pro Gly Gln Pro Pro Lys Leu Leu Ile Tyr Trp Ala Ser Thr Arg
            500                 505                 510

Glu Ser Gly Val Pro Asp Arg Phe Ser Gly Ser Gly Ser Gly Thr Asp
        515                 520                 525

Phe Thr Leu Thr Ile Ser Ser Leu Gln Ala Glu Asp Val Ala Val Tyr
    530                 535                 540

Tyr Cys Lys Gln Ser Tyr Ser Leu Arg Thr Phe Gly Gly Gly Thr Lys
545                 550                 555                 560

Val Glu Ile Lys Gly Gly Gly Gly Ser Gly Gly Gly Gly Ser Gly Gly
                565                 570                 575

Gly Gly Ser Gly Gly Gly Gly Ser Gln Val Gln Leu Val Gln Ser Gly
            580                 585                 590

Ala Glu Val Lys Lys Pro Gly Ala Ser Val Lys Val Ser Cys Lys Ala
        595                 600                 605

Ser Gly Phe Asn Ile Lys Asp Tyr Tyr Met His Trp Val Arg Gln Ala
    610                 615                 620

Pro Gly Gln Arg Leu Glu Trp Met Gly Trp Ile Asp Leu Glu Glu Gly
625                 630                 635                 640

Asn Thr Ile Tyr Asp Ala Lys Phe Gln Gly Arg Val Thr Ile Thr Arg
                645                 650                 655
```

```
Asp Thr Ser Ala Ser Thr Ala Tyr Met Glu Leu Ser Ser Leu Arg Ser
            660                 665                 670

Glu Asp Thr Ala Val Tyr Tyr Cys Ala Arg Asp Ala Tyr Gly Arg Tyr
            675                 680                 685

Phe Tyr Asp Val Trp Gly Gln Gly Thr Leu Val Thr Val Ser Ser
            690                 695                 700

<210> SEQ ID NO 716
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 716

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Thr Met Gly Val Gly Trp Ile Arg Gln His Pro Gly Lys Gly Leu Glu
            35                  40                  45

Trp Ile Gly Phe Ile Trp Trp Asp Asp Lys Arg Tyr Asn Pro Asn
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 717
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 717

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Gly Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Gly Ser Gly Gly Gly Gly Ser Gly
```

```
                210                 215                 220

Gly Gly Gly Ser Asp Ile Val Met Thr Gln Ser Pro Asp Ser Leu Ala
225                 230                 235                 240

Val Ser Leu Gly Glu Arg Ala Thr Ile Asn Cys Lys Ser Ser Gln Ser
                245                 250                 255

Leu Leu Asn Ala Arg Thr Gly Lys Asn Tyr Leu Ala Trp Tyr Gln Gln
                260                 265                 270

Lys Pro Gly Gln Pro Pro Lys Leu Leu Ile Tyr Trp Ala Ser Thr Arg
                275                 280                 285

Glu Ser Gly Val Pro Asp Arg Phe Ser Gly Ser Gly Ser Gly Thr Asp
                290                 295                 300

Phe Thr Leu Thr Ile Ser Ser Leu Gln Ala Glu Asp Val Ala Val Tyr
305                 310                 315                 320

Tyr Cys Lys Gln Ser Tyr Ser Arg Arg Thr Phe Gly Gly Gly Thr Lys
                325                 330                 335

Val Glu Ile Lys Gly Gly Gly Gly Ser Gly Gly Gly Gly Ser Gly Gly
                340                 345                 350

Gly Gly Ser Gly Gly Gly Gly Ser Gln Val Gln Leu Val Gln Ser Gly
                355                 360                 365

Ala Glu Val Lys Lys Pro Gly Ala Ser Val Lys Val Ser Cys Lys Ala
                370                 375                 380

Ser Gly Phe Asn Ile Lys Asp Tyr Tyr Met His Trp Val Arg Gln Ala
385                 390                 395                 400

Pro Gly Gln Arg Leu Glu Trp Met Gly Trp Ile Asp Leu Glu Asn Ala
                405                 410                 415

Asn Thr Ile Tyr Asp Ala Lys Phe Gln Gly Arg Val Thr Ile Thr Arg
                420                 425                 430

Asp Thr Ser Ala Ser Thr Ala Tyr Met Glu Leu Ser Ser Leu Arg Ser
                435                 440                 445

Glu Asp Thr Ala Val Tyr Tyr Cys Ala Arg Asp Ala Tyr Gly Arg Tyr
                450                 455                 460

Phe Tyr Asp Val Trp Gly Gln Gly Thr Leu Val Thr Val Ser Ser
465                 470                 475

<210> SEQ ID NO 718
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 718

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Gly Tyr Met
                20                  25                  30

His Trp Tyr Gln Gln Lys Pro Gly Gln Ala Pro Arg Leu Leu Ile Tyr
                35                  40                  45

Asp Thr Ser Lys Leu Ala Ser Gly Ile Pro Ala Arg Phe Ser Gly Ser
                50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95
```

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Ser Gly Gly Gly Ser Gly
    210                 215                 220

Gly Gly Gly Ser Asp Ile Val Met Thr Gln Ser Pro Asp Ser Leu Ala
225                 230                 235                 240

Val Ser Leu Gly Glu Arg Ala Thr Ile Asn Cys Lys Ser Ser Gln Ser
                245                 250                 255

Leu Leu Asn Ala Arg Thr Gly Lys Asn Tyr Leu Ala Trp Tyr Gln Gln
            260                 265                 270

Lys Pro Gly Gln Pro Pro Lys Leu Leu Ile Tyr Trp Ala Ser Thr Arg
        275                 280                 285

Glu Ser Gly Val Pro Asp Arg Phe Ser Gly Ser Gly Ser Gly Thr Asp
    290                 295                 300

Phe Thr Leu Thr Ile Ser Ser Leu Gln Ala Glu Asp Val Ala Val Tyr
305                 310                 315                 320

Tyr Cys Lys Gln Ser Tyr Ser Arg Arg Thr Phe Gly Gly Gly Thr Lys
                325                 330                 335

Val Glu Ile Lys Gly Gly Gly Gly Ser Gly Gly Gly Ser Gly Gly
            340                 345                 350

Gly Gly Ser Gly Gly Gly Ser Gln Val Gln Leu Val Gln Ser Gly
        355                 360                 365

Ala Glu Val Lys Lys Pro Gly Ala Ser Val Lys Val Ser Cys Lys Ala
    370                 375                 380

Ser Gly Phe Asn Ile Lys Asp Tyr Tyr Met His Trp Val Arg Gln Ala
385                 390                 395                 400

Pro Gly Gln Arg Leu Glu Trp Met Gly Trp Ile Asp Leu Glu Asn Ala
                405                 410                 415

Asn Thr Ile Tyr Asp Ala Lys Phe Gln Gly Arg Val Thr Ile Thr Arg
            420                 425                 430

Asp Thr Ser Ala Ser Thr Ala Tyr Met Glu Leu Ser Ser Leu Arg Ser
        435                 440                 445

Glu Asp Thr Ala Val Tyr Tyr Cys Ala Arg Asp Gln Tyr Gly Arg Tyr
    450                 455                 460

Phe Tyr Asp Val Trp Gly Gln Gly Thr Leu Val Thr Val Ser Ser
465                 470                 475

<210> SEQ ID NO 719
<211> LENGTH: 479
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 719

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Gly Tyr Met
            20                  25                  30

His Trp Tyr Gln Gln Lys Pro Gly Gln Ala Pro Arg Leu Leu Ile Tyr
            35                  40                  45

Asp Thr Ser Lys Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Ser Gly Gly Gly Ser Gly
210                 215                 220

Gly Gly Gly Ser Asp Ile Val Met Thr Gln Ser Pro Asp Ser Leu Ala
225                 230                 235                 240

Val Ser Leu Gly Glu Arg Ala Thr Ile Asn Cys Lys Ser Ser Gln Ser
                245                 250                 255

Leu Leu Asn Ala Arg Thr Gly Lys Asn Tyr Leu Ala Trp Tyr Gln Gln
            260                 265                 270

Lys Pro Gly Gln Pro Pro Lys Leu Leu Ile Tyr Trp Ala Ser Thr Arg
        275                 280                 285

Glu Ser Gly Val Pro Asp Arg Phe Ser Gly Ser Gly Ser Gly Thr Asp
290                 295                 300

Phe Thr Leu Thr Ile Ser Ser Leu Gln Ala Glu Asp Val Ala Val Tyr
305                 310                 315                 320

Tyr Cys Lys Gln Ser Tyr Ser Leu Arg Thr Phe Gly Gly Gly Thr Lys
                325                 330                 335

Val Glu Ile Lys Gly Gly Gly Gly Ser Gly Gly Gly Gly Ser Gly Gly
            340                 345                 350

Gly Gly Ser Gly Gly Gly Gly Ser Gln Val Gln Leu Val Gln Ser Gly
        355                 360                 365

Ala Glu Val Lys Lys Pro Gly Ala Ser Val Lys Val Ser Cys Lys Ala
370                 375                 380

Ser Gly Phe Asn Ile Lys Asp Tyr Tyr Met His Trp Val Arg Gln Ala
385                 390                 395                 400

```
Pro Gly Gln Arg Leu Glu Trp Met Gly Trp Ile Asp Leu Glu Glu Gly
            405                 410                 415

Asn Thr Ile Tyr Asp Ala Lys Phe Gln Gly Arg Val Thr Ile Thr Arg
        420                 425                 430

Asp Thr Ser Ala Ser Thr Ala Tyr Met Glu Leu Ser Ser Leu Arg Ser
    435                 440                 445

Glu Asp Thr Ala Val Tyr Tyr Cys Ala Arg Asp Ala Tyr Gly Arg Tyr
450                 455                 460

Phe Tyr Asp Val Trp Gly Gln Gly Thr Leu Val Thr Val Ser Ser
465                 470                 475

<210> SEQ ID NO 720
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 720

Gly Phe Thr Phe Ser Ser Phe Gly Met Ser
1               5                   10

<210> SEQ ID NO 721
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-20 "Gly Ser"
      repeating units

<400> SEQUENCE: 721

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser
        35                  40

<210> SEQ ID NO 722
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(60)
<223> OTHER INFORMATION: This sequence may encompass 1-20 "Gly Gly Ser"
      repeating units

<400> SEQUENCE: 722

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45
```

Gly Gly Ser Gly Gly Ser Gly Ser Gly Gly Ser
          50              55              60

<210> SEQ ID NO 723
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(80)
<223> OTHER INFORMATION: This sequence may encompass 1-20 "Gly Gly Gly
      Ser" repeating units

<400> SEQUENCE: 723

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80

<210> SEQ ID NO 724
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(80)
<223> OTHER INFORMATION: This sequence may encompass 1-20 "Gly Gly Ser
      Gly" repeating units

<400> SEQUENCE: 724

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly Gly Gly Ser Gly Gly Gly Ser Gly
        35                  40                  45

Gly Gly Ser Gly Gly Gly Ser Gly Gly Gly Ser Gly Gly Gly Ser Gly
    50                  55                  60

Gly Gly Ser Gly Gly Gly Ser Gly Gly Gly Ser Gly Gly Gly Ser Gly
65                  70                  75                  80

<210> SEQ ID NO 725
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This sequence may encompass 1-20 "Gly Gly Ser
      Gly Gly" repeating units

```
<400> SEQUENCE: 725

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
                20                  25                  30

Ser Gly Gly Gly Ser Gly Gly Gly Ser Gly Gly Gly Ser Gly Gly Ser
            35                  40                  45

Gly Gly Gly Gly Ser Gly Gly Gly Ser Gly Gly Gly Ser Gly Gly Gly
        50                  55                  60

Gly Gly Gly Ser Gly Gly Gly Ser Gly Gly Gly Ser Gly Gly Gly Gly
65                  70                  75                  80

Gly Gly Ser Gly Gly Gly Ser Gly Gly Gly Ser Gly Gly Gly Gly Gly
                85                  90                  95

Gly Ser Gly Gly
        100

<210> SEQ ID NO 726
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This sequence may encompass 1-20 "Gly Gly Gly
      Gly Ser" repeating units

<400> SEQUENCE: 726

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly Ser Gly Gly Gly Gly Ser Gly Gly Gly Gly
        50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
        100

<210> SEQ ID NO 727
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 727

His His His His His His
1               5

<210> SEQ ID NO 728
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 728

Asp Ala Ser Ser Leu Glu Ser
1               5
```